United States Patent
Wu et al.

(10) Patent No.: US 11,078,202 B2
(45) Date of Patent: *Aug. 3, 2021

(54) β-LACTAMASE INHIBITOR AND USE THEREOF

(71) Applicant: SUZHOU SINOVENT PHARMACEUTICALS CO., LTD.

(72) Inventors: Yuchuan Wu, Beijing (CN); Shaoqiang Huang, Beijing (CN); Xi Chen, Beijing (CN); Yonghan Hu, Beijing (CN); Xiao Liu, Beijing (CN)

(73) Assignee: SUZHOU SINOVENT PHARMACEUTICALS CO., LTD., Jiangsu Province (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/998,577

(22) Filed: Aug. 20, 2020

(65) Prior Publication Data

US 2021/0032260 A1 Feb. 4, 2021

Related U.S. Application Data

(63) Continuation of application No. 16/964,416, filed as application No. PCT/CN2019/073000 on Jan. 24, 2019.

(30) Foreign Application Priority Data

Jan. 25, 2018 (WO) ............... PCT/CN2018/074185

(51) Int. Cl.
*C07D 471/08* (2006.01)
*A61K 45/06* (2006.01)

(52) U.S. Cl.
CPC ............ *C07D 471/08* (2013.01); *A61K 45/06* (2013.01)

(58) Field of Classification Search
None
See application file for complete search history.

(56) References Cited

U.S. PATENT DOCUMENTS

2021/0032260 A1 2/2021 Wu

FOREIGN PATENT DOCUMENTS

| CN | 101918407 A | 12/2010 |
|---|---|---|
| CN | 103649088 A | 3/2014 |
| CN | 104334555 A | 2/2015 |
| WO | 2014/141132 A1 | 9/2014 |
| WO | WO 2014/141132 | 9/2014 |
| WO | 2015/150890 A1 | 10/2015 |
| WO | WO 2015/150890 A1 | 10/2015 |

OTHER PUBLICATIONS

International Search Report and Written Opinion in related PCT Application No. PCT/CN2019/073000, dated Apr. 24, 2019 (3 pages).
U.S. Appl. No. 16/964,416, filed Jul. 23, 2020, Yuchan Wu.

*Primary Examiner* — Brian J Davis
(74) *Attorney, Agent, or Firm* — Lathrop GPM LLP; Brian C. Trinque

(57) ABSTRACT

Provided are a β-lactamase inhibitor of formula (I), or an ester, a stereoisomer or a pharmaceutically acceptable salt thereof, and a method of preparing the same. Further provided is a pharmaceutical composition comprising the β-lactamase inhibitor of formula (I), or the ester, the stereoisomer or pharmaceutically acceptable salt thereof. In addition, the present invention relates to a method for treating diseases caused by bacterial infection, which comprises administering the β-lactamase inhibitor of formula (I), or the ester, the stereoisomer or the pharmaceutically acceptable salt thereof to a patient or a subject in need.

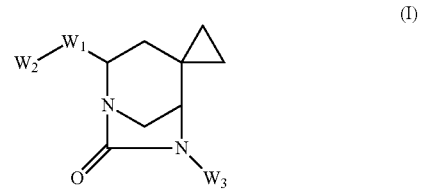

(I)

19 Claims, No Drawings

β-LACTAMASE INHIBITOR AND USE THEREOF

CROSS REFERENCED TO RELATED APPLICATIONS

This application is a continuation of Ser. No. 16/964,416, filed Jul. 23, 2020, which application is a 35 U.S.C. § 371 filing of International Application No. PCT/CN2019/073000, filed Jan. 24, 2019, which application claims the benefit of PCT/CN2018/074185, filed Jan. 25, 2018.

TECHNICAL FIELD

The present invention relates to a β-lactamase inhibitor and a preparation method thereof. The present invention also relates to a pharmaceutical composition comprising the β-lactamase inhibitor and use thereof.

BACKGROUND

β-lactam antibiotics are the first antibiotics introduced clinically. The development of β-lactam antibiotics has been accelerated since the successful application of penicillin G as the first β-lactam antibiotic in the clinic practice. β-lactam antibiotics with different structure are developed and widely applied clinically, and good results are achieved. However, bacterial cells can produce β-lactamases which inactivate the antibiotics, resulting in bacteria resistance to β-lactam antibiotics. β-lactamases are enzymes that catalyze the hydrolysis of β-lactam rings, which inactivates the antibacterial activity of β-lactam antibiotics and allows bacteria to develop resistance to β-lactam antibiotics. β-lactamases can be divided into class A, B, C, D, etc. according to the amino acid sequence differences in the molecular structure. Class A β-lactamases preferably hydrolyze penicillin antibiotics. Class B β-lactamases can hydrolyze various β-lactam antibiotics, including carbapenems. Class C β-lactamases can more effectively hydrolyze cephalosporin antibiotics. Class D β-lactamases more tend to hydrolyze oxacillin and o-cloxacillin. Bacteria, particularly gram-negative bacteria, often develop resistance to β-lactam antibiotics by synthesizing β-lactamases as mediators.

Inhibition of β-lactamases may delay or inhibit the degradation of β-lactam antibiotics and restore the susceptibility of bacteria that develop resistance to β-lactam antibiotics. At present, the hydrolytic activity of β-lactamases to β-lactam antibiotics can be inactivated by combining β-lactamase inhibitors with β-lactam antibiotics clinically, so that the susceptibility of bacteria to β-lactam antibiotics is enhanced, and drug resistance is reduced or overcome. The prior art discloses various β-lactamase inhibitors, for example, diazaspiro[bicyclo[3.2.1]octane-based compounds disclosed in WO2013149121 A1, WO2014141132A1, US20130296290A1, WO2013030735A1, WO2015110963A1, WO2015150890A1, WO2015159265A1, WO2015173663, WO2015173665A1, and WO2017055922A1. Furthermore, various β-lactamase inhibitors are commercially available, such as Clavulanic Acid, Tazobactam, Avibactam, and Relebactam. However, the inhibitory effect of such β-lactamase inhibitors on β-lactamases has not been quite satisfactory. Therefore, there is currently an urgent need for novel β-lactamase inhibitors to be able to treat infections caused by β-lactam antibiotic resistant bacteria in combination with β-lactam antibiotics.

SUMMARY

The present invention provides a compound as shown in formula (I), or an ester thereof, a stereoisomer thereof, and a pharmaceutically acceptable salt thereof:

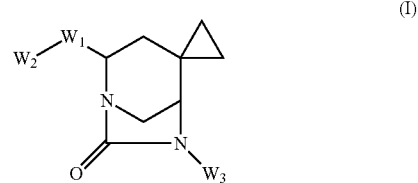

wherein $W_1$ is selected from an optionally substituted 5- or 6-membered heteroaromatic ring containing O, N, and/or S, and —C(O)—; and, (i) when $W_1$ is the optionally substituted 5- or 6-membered heteroaromatic ring containing O, N, and/or S, $W_1$ is optionally substituted with $C_1$-$C_{12}$ alkyl, $W_2$ is selected from:
a. H
b.

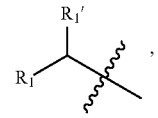

wherein $R_1$ is selected from

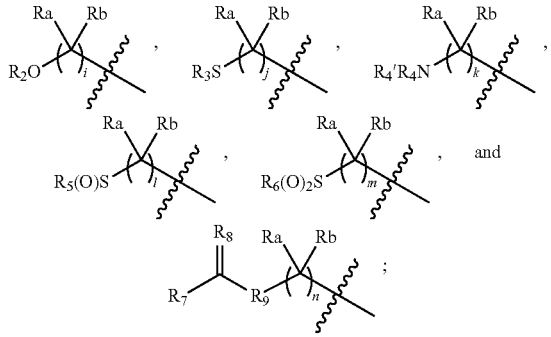

wherein $R_2$, $R_3$, $R_4$, $R_4'$, $R_5$, and $R_6$ are each independently selected from H, $C_1$-$C_{12}$ alkyl, amino $C_1$-$C_{12}$ alkyl, $C_1$-$C_{12}$ alkylamino $C_1$-$C_{12}$ alkyl,

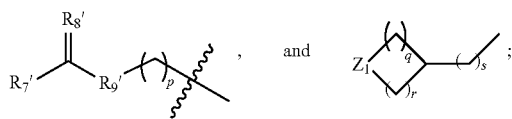

$R_a$ and $R_b$ are each independently selected from H, $C_1$-$C_{12}$ alkyl, OH, —O$C_1$-$C_{12}$ alkyl, —NH$_2$, —NH$C_1$-$C_{12}$ alkyl, —N($C_1$-$C_{12}$ alkyl)$_2$, —SH, —S$C_1$-$C_{12}$ alkyl, —S(O)$C_1$-$C_{12}$ alkyl, —S(O$_2$)$C_1$-$C_{12}$ alkyl, and —SO$_3$H; $R_7$ and $R_7'$ are each independently selected from —NH$_2$, —NH$C_1$-$C_{12}$ alkyl, —N($C_1$-$C_{12}$ alkyl)$_2$, —O$C_1$-$C_{12}$ alkyl, and —S$C_1$-$C_{12}$ alkyl; $R_8$ and $R_8'$ are each independently selected from NH, —N$C_1$-$C_{12}$ alkyl, O, and S; $R_9$ and $R_9'$ are each independently selected from —NH—, —N($C_1$-$C_{12}$ alkyl)-, —O—, and —S—; $Z_1$ is selected from $CR_{10}R_{11}$ and $NR_{12}$; $R_{10}$, $R_{11}$ and $R_{12}$ are each independently selected from H, $NH_2$,

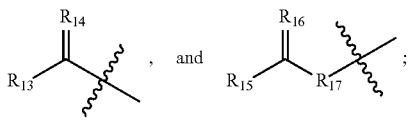

wherein $R_{13}$ and $R_{15}$ are each independently selected from —$NH_2$, —$NHC_1$-$C_{12}$ alkyl, —N($C_1$-$C_{12}$ alkyl)$_2$, —O$C_1$-$C_{12}$ alkyl, and —S$C_1$-$C_{12}$ alkyl; $R_{14}$ and $R_{16}$ are each independently selected from NH, —NH$C_1$-$C_{12}$ alkyl, O, and S; $R_{17}$ is selected from —NH—, —N($C_1$-$C_{12}$ alkyl)-, —O—, and —S—; i, j, k, l, m, n, p, q, r, and s are each independently selected from 0, 1, 2, 3, 4, 5, and 6, provided that q and r are not both 0; $R_1'$ is selected from H, $C_1$-$C_{12}$ alkyl, $C_3$-$C_8$ cycloalkyl, OH, —O$C_1$-$C_{12}$ alkyl, —$NH_2$, —NH$C_1$-$C_{12}$ alkyl, —N($C_1$-$C_{12}$ alkyl)$_2$, —SH, —S$C_1$-$C_{12}$ alkyl, —S(O)$C_1$-$C_{12}$ alkyl, —S($O_2$)$C_1$-$C_{12}$ alkyl, and —S$O_3$H;

c.

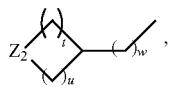

wherein $Z_2$ is selected from $CR_{18}R_{19}$, and $NR_{20}$; $R_{18}$, $R_{19}$ and $R_{20}$ are each independently selected from H, $NH_2$, and

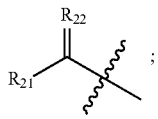

wherein $R_{21}$ is selected from —$NH_2$, —NH$C_1$-$C_{12}$ alkyl, —N($C_1$-$C_{12}$ alkyl)$_2$, —O$C_1$-$C_{12}$ alkyl, —S$C_1$-$C_{12}$ alkyl; $R_{22}$ is selected from NH, —NH$C_1$-$C_{12}$ alkyl, O, and S; t, u and w are each independently selected from 1, 2, 3, 4, 5, and 6, provided that t and u are not both 0;

d.

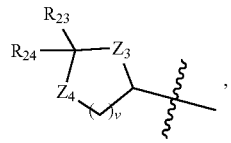

wherein $Z_3$ and $Z_4$ are each independently selected from —$NR_{25}$—, and —O—; $R_{23}$ and $R_{24}$ are each independently selected from H and $C_1$-$C_{12}$ alkyl, or $R_{23}$ and $R_{24}$ together form =O or =NH; $R_{25}$ is selected from H, amino $C_1$-$C_{12}$ alkyl, and $C_1$-$C_{12}$ alkylamino $C_1$-$C_{12}$ alkyl;

(ii) when $W_1$ is —C(O)—, $W_2$ is selected from —$OR_{26}$, and —$NHR_{27}$; wherein $R_{26}$ and $R_{27}$ are each independently selected from H, $C_1$-$C_{12}$ alkyl, and

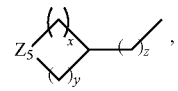

wherein $Z_5$ is selected from $CR_{28}R_{29}$, and $NR_{30}$, $R_{28}$, $R_{29}$ and $R_{30}$ are each independently selected from H, $NH_2$, and

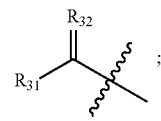

$R_{31}$ is selected from —$NH_2$, —NH$C_1$-$C_{12}$ alkyl, —N($C_1$-$C_{12}$ alkyl)$_2$, —O$C_1$-$C_{12}$ alkyl, and —S$C_1$-$C_{12}$ alkyl; $R_{32}$ is selected from NH, N$C_1$-$C_{12}$ alkyl, O, and S; and x, y and z are each independently selected from 1, 2, 3, 4, 5, and 6, provided that x and y are not both 0;

$W_3$ is selected from —$SO_3$M, —$OSO_3$M, —$OSO_2NH_2$, —$OPO_3$M, —$OCR_{33}R_{34}CO_2$M, —$OCR_{35}R_{36}SO_3$M, and —$OCR_{37}R_{38}PO_3$M; wherein M is selected from H and a pharmaceutically acceptable cation; $R_{33}$, $R_{34}$, $R_{35}$, $R_{36}$, $R_{37}$ and $R_{38}$ are independently selected from H, $C_1$-$C_{12}$ alkyl, and halogen.

In another aspect, the present invention provides a preparation method for the compound as shown in formula (I) or the pharmaceutically acceptable salt thereof.

In yet another aspect, the present invention provides a pharmaceutical composition comprising the compound as shown in formula (I) or the pharmaceutically acceptable salt thereof and one or more β-lactam antibiotics.

In still yet another aspect, the present invention provides a method for treating a disease caused by a bacterial infection, which comprises administering the compound as shown in formula (I) described herein in combination with one or more β-lactam antibiotics to a patient or subject in need.

DETAILED DESCRIPTION

Definitions

As used herein, the term "alkyl" refers to straight or branched chain saturated hydrocarbyl having 1-20 carbon atoms. Preferably, the alkyl has 1-12 carbon atoms. More preferably, the alkyl has 1-6 carbon atoms. Most preferably, the alkyl has 1-4 carbon atoms. Examples of alkyl include, but are not limited to, methyl, ethyl, 1-propyl (n-propyl), 2-propyl (isopropyl), 1-butyl (n-butyl), 2-methyl-1-propyl (isobutyl), 2-butyl (sec-butyl), 2-methyl-2-propyl (tert-butyl), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, 1-nonyl, 1-decyl, and the like.

As used herein, the term "amino" refers to —$NH_2$.

As used herein, the term "halogen" refers to fluorine, chlorine, bromine, and iodine.

As used herein, the term "aminoalkyl" refers to an alkyl in which one or more hydrogens are substituted with amino.

As used herein, the term "cycloalkyl" refers to a monovalent saturated carbocyclic group. Preferably, cycloalkyl is a 3-8 membered monocyclic group. More preferably, cycloalkyl is a 3-6 membered monocyclic group. Examples of cycloalkyl include, but are not limited to, cyclopropyl, cyclobutyl, cyclopentyl, cyclohexyl, and the like.

As used herein, the term "heteroaryl" refers to a 5- or 6-membered monovalent aromatic group containing 1-3 heteroatoms independently selected from nitrogen, oxygen, and sulfur. Examples of heteroaryl include a furan ring, a pyrrole ring, a pyrazole ring, an imidazole ring, a triazole ring, a thiophene ring, a thiazole ring, an isothiazole ring, an oxazole ring, an isoxazole ring, a 1,2,4-oxadiazole ring, a 1,3,4-oxadiazole ring, a pyridine ring, pyrimidyl, a triazine ring, a pyrazine ring, a tetrazole ring, a pyridazine ring, and a thiadiazole ring. Heteroaryl is optionally independently substituted with one or more substituents described herein.

As used herein, the term "optionally substituted" means that a given structure or group is not substituted, or that a given structure or group is substituted with one or more specific substituents. Unless otherwise stated, optional substitution may occur at any position of the substituted group.

As used herein, the term "ester" refers to an ester formed by esterification of —OSO$_3$— or COOH (if present) in the compound as shown in formula (I) with an alcohol. When hydroxyl is present in the compound as shown in formula (I), the ester refers to an ester formed by esterification with an organic acid, an inorganic acid, or the like. The ester can undergo hydrolysis under an acidic or alkaline condition to form the corresponding acid or alcohol.

As used herein, the term "stereoisomer" refers to a compound having same chemical composition and connectivity but different orientations of atoms in space, wherein the orientations cannot be rotationally interchanged through a single bond. The stereoisomer includes a "diastereoisomer" and an "enantiomer". The "diastereoisomer" refers to a stereoisomer having two or more chiral centers and whose molecules are not mirror images of each other. Diastereoisomers have different physical properties, such as melting points, boiling points, spectral properties, and reactivity. Mixtures of diastereoisomers can be separated in high resolution analytical procedures such as crystallization, electrophoresis, and chromatography. The "enantiomer" refers to two stereoisomers that are non-overlapping mirror images of each other.

As used herein, the term "pharmaceutically acceptable salt" refers to a pharmaceutically acceptable organic or inorganic salt of the compound of the present invention. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisate, fumarate, gluconate, glucuronate, saccharate, formate, benzoate, glutamate, methanesulfonate, ethanesulfonate, benzenesulfonate, p-toluenesulfonate, pamoate, ammonium salts (e.g., primary amine salts, secondary amine salts, tertiary amine salts, and quaternary ammonium salts), and metal salts (e.g., sodium salts, potassium salts, calcium salts, magnesium salts, manganese salts, iron salts, zinc salts, copper salts, lithium salts, and aluminum salts).

As used herein, the term "pharmaceutically acceptable" means that the substance or composition must be compatible chemically and/or toxicologically with the other ingredients comprising a preparation, and/or the mammal being treated therewith.

As used herein, the term "treating" refers to therapeutic treatments and prophylactic or preventative or protective measures, which aim to prevent or slow down (alleviate) an undesired pathological change or disorder. For purposes of the present invention, beneficial or desired clinical results include, but are not limited to, alleviation of symptoms, reduction in disease severity, delay or slowing of disease progression, amelioration or palliation of the disease state, and remission (whether partial or total), whether detectable or undetectable.

As used herein, the term "therapeutically effective amount" means that an amount of a compound of the present invention that (i) treats or prevents a disease or disorder described herein, (ii) alleviates or eliminates one or more diseases or disorders described herein, or (iii) prevents or delays the onset of one or more symptoms of a disease or disorder described herein.

In one embodiment, the present invention claims protection for a compound as shown in formula (Ia) or an ester, solvate, stereoisomer, and pharmaceutically acceptable salt thereof:

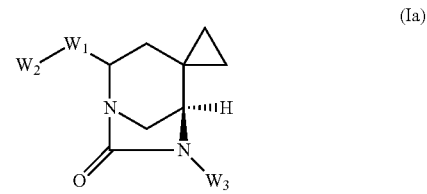

(Ia)

wherein $W_1$, $W_2$, and $W_3$ are as defined in formula (I).

In one preferred embodiment, $W_1$ is selected from an optionally substituted 5- or 6-membered heteroaromatic ring containing O, N, and/or S;

$W_2$ is selected from:
a. H
b.

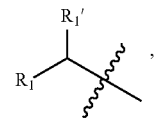

wherein $R_1$ is selected from

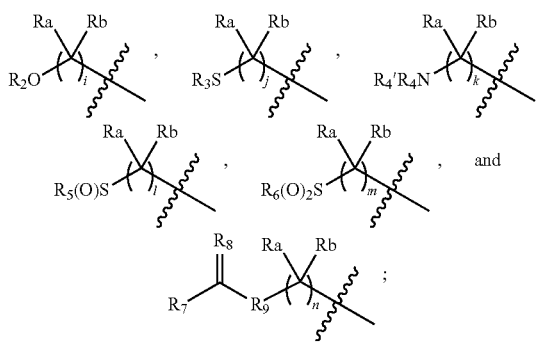

wherein $R_2$, $R_3$, $R_4$, $R_4'$, $R_5$, and $R_6$ are each independently selected from H, $C_1$-$C_{12}$ alkyl, amino $C_1$-$C_{12}$ alkyl, $C_1$-$C_{12}$ alkylamino $C_1$-$C_{12}$ alkyl,

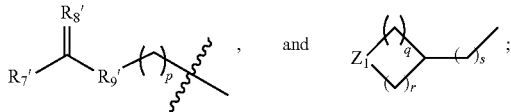

$R_a$ and $R_b$ are each independently selected from H, $C_1$-$C_{12}$ alkyl, OH, —$OC_1$-$C_{12}$ alkyl, —$NH_2$, —$NHC_1$-$C_{12}$ alkyl, —$N(C_1$-$C_{12}$ alkyl$)_2$, —SH, —$SC_1$-$C_{12}$ alkyl, —$S(O)C_1$-$C_{12}$ alkyl, —$S(O_2)C_1$-$C_{12}$ alkyl, and —$SO_3H$; $R_7$ and $R_7'$ are each independently selected from —$NH_2$, —$NHC_1$-$C_{12}$ alkyl, —$N(C_1$-$C_{12}$ alkyl$)_2$, —$OC_1$-$C_{12}$ alkyl, and —$SC_1$-$C_{12}$ alkyl; $R_8$ and $R_8'$ are each independently selected from NH, —$NC_1$-$C_{12}$ alkyl, O, and S; $R_9$ and $R_9'$ are each independently selected from —NH—, —$N(C_1$-$C_{12}$ alkyl)-, —O—, and —S—; $Z_1$ is selected from $CR_{10}R_{11}$ and $NR_{12}$; $R_{10}$, $R_{11}$ and $R_{12}$ are each independently selected from H, $NH_2$,

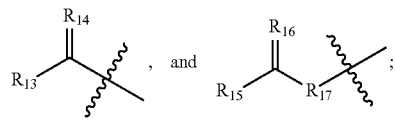

wherein $R_{13}$ and $R_{15}$ are each independently selected from —$NH_2$, —$NHC_1$-$C_{12}$ alkyl, —$N(C_1$-$C_{12}$ alkyl$)_2$, —$OC_1$-$C_{12}$ alkyl, and —$SC_1$-$C_{12}$ alkyl; $R_{14}$ and $R_{16}$ are each independently selected from NH, —$NHC_1$-$C_{12}$ alkyl, O, and S; $R_{17}$ is selected from —NH—, —$N(C_1$-$C_{12}$ alkyl)-, —O—, and —S—; i, j, k, l, m, n, p, q, r, and s are each independently selected from 0, 1, 2, 3, 4, 5, and 6, provided that q and r are not both 0;
$R_1'$ is selected from H, $C_1$-$C_{12}$ alkyl, $C_3$-$C_8$ cycloalkyl, OH, —$OC_1$-$C_{12}$ alkyl, —$NH_2$, —$NHC_1$-$C_{12}$ alkyl, —$N(C_1$-$C_{12}$ alkyl$)_2$, —SH, —$SC_1$-$C_{12}$ alkyl, —$S(O)C_1$-$C_{12}$ alkyl, —$S(O_2)C_1$-$C_{12}$ alkyl, and —$SO_3H$;
c.

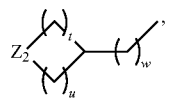

wherein $Z_2$ is selected from $CR_{18}R_{19}$, and $NR_{20}$; $R_{18}$, $R_{19}$ and $R_{20}$ are each independently selected from H, $NH_2$, and

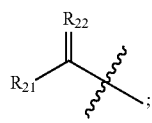

wherein $R_{21}$ is selected from —$NH_2$, —$NHC_1$-$C_{12}$ alkyl, —$N(C_1$-$C_{12}$ alkyl$)_2$, —$OC_1$-$C_{12}$ alkyl, —$SC_1$-$C_{12}$ alkyl; $R_{22}$ is selected from NH, —$NHC_1$-$C_{12}$ alkyl, O, and S; t, u and w are each independently selected from 1, 2, 3, 4, 5, and 6, provided that t and u are not both 0;
d.

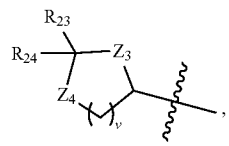

wherein $Z_3$ and $Z_4$ are each independently selected from —$NR_{25}$—, and —O—, $R_{23}$ and $R_{24}$ are each independently selected from H and $C_1$-$C_{12}$ alkyl, or $R_{23}$ and $R_{24}$ together form =O or =NH; and $R_{25}$ is selected from H, amino $C_1$-$C_{12}$ alkyl, and $C_1$-$C_{12}$ alkylamino $C_1$-$C_{12}$ alkyl.

Preferably, $W_1$ is

wherein X is selected from O, S, and NH; Y and Z are each independently selected from CH and N; and $W_1$ is optionally substituted with $C_1$-$C_{12}$ alkyl.

More preferably, $W_1$ is selected from a furan ring, a pyrrole ring, a pyrazole ring, an imidazole ring, a triazole ring, a thiophene ring, a thiazole ring, an isothiazole ring, an oxazole ring, an isoxazole ring, a 1,2,4-oxadiazole ring, a 1,3,4-oxadiazole ring, a pyridine ring, pyrimidyl, a triazine ring, a pyrazine ring, a tetrazole ring, a pyridazine ring, and a thiadiazole ring.

Most preferably, $W_1$ is selected from

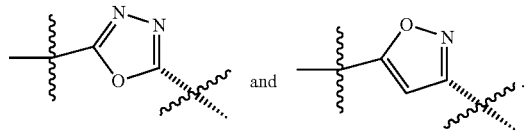

M is selected from H, sodium ion, potassium ion, calcium ion, magnesium ion, $NH_4^+$, and $N(C_1$-$C_{12}$ alkyl$)_4^+$.

In another preferred embodiment, $W_1$ is —C(O)—;
$W_2$ is selected from —$OR_{26}$, and —$NHR_{27}$, wherein $R_{26}$ and $R_{27}$ are each independently selected from H, $C_1$-$C_{12}$ alkyl, and

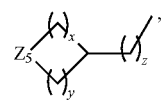

wherein $Z_5$ is selected from $CR_{28}R_{29}$, and $NR_{30}$, $R_{28}$, $R_{29}$, and $R_{30}$ are each independently selected from H, $NH_2$, and

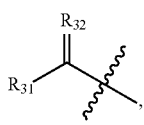

wherein $R_{31}$ is selected from —NH$_2$, —NHC$_1$-C$_{12}$ alkyl, —N(C$_1$-C$_{12}$ alkyl)$_2$, —OC$_1$-C$_{12}$ alkyl, and —SC$_1$-C$_{12}$ alkyl; $R_{32}$ is selected from NH, NC$_1$-C$_{12}$ alkyl, O, and S; and x, y and z are each independently selected from 1, 2, 3, 4, 5, and 6, provided that x and y are not both 0.

Preferred compounds of the present invention are shown below:

(1R,4S)-4-(1,3,4-oxadiazol-2-yl)-6-oxo-5,7-diazaspiro[bicyclo[3.2.1]octane-2,1'-cyclopropan]-7-yl sulfate;

(1R,4S)-4-(5-(aminomethyl)-1,3,4-oxadiazol-2-yl)-6-oxo-5,7-diazaspiro[bicycle [3.2.1]octane-2,1'-cyclopropan]-7-yl sulfate;

(1R,4S)-4-(5-(guanidinomethyl)-1,3,4-oxadiazol-2-yl)-6-oxo-5,7-diazaspiro[bicycle [3.2.1]octane-2,1'-cyclopropan]-7-yl sulfate;

(1R,4S)-4-(5-(2-aminoethyl)-1,3,4-oxadiazol-2-yl)-6-oxo-5,7-diazaspiro[bicycle[3.2.1]octane-2,1'-cyclopropan]-7-yl sulfate;

(1R,4S)-4-(5-(2-guanidinoethyl)-1,3,4-oxadiazol-2-yl)-6-oxo-5,7-diazaspiro[bicycle [3.2.1]octane-2,1'-cyclopropan]-7-yl sulfate;

sodium (1R,4S)-4-(5-(3-aminopropyl)-1,3,4-oxadiazol-2-yl)-6-oxo-5,7-diazaspiro [bicycle[3.2.1]octane-2,1'-cyclopropan]-7-yl sulfate;

(1R,4S)-4-(5-(4-aminobutyl)-1,3,4-oxadiazol-2-yl)-6-oxo-5,7-diazaspiro[bicycle[3.2.1] octane-2,1'-cyclopropan]-7-yl sulfate;

(1R,4S)-4-(5-(2-iminoimidazolidin-4-yl)-1,3,4-oxadiazol-2-yl)-6-oxo-5,7-diazaspiro [bicyclo[3.2.1]octane-2,1'-cyclopropan]-7-yl sulfate;

(1R,4S)-4-(5-(2-amino-1-hydroxyethyl)-1,3,4-oxadiazol-2-yl)-6-oxo-5,7-diazaspiro [bicyclo[3.2.1]octane-2,1'-cyclopropan]-7-yl sulfate;

(1R,4S)-4-(5-(2-guanidyl-1-hydroxyethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-((R)-2-guanidyl-1-hydroxyethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-((S)-2-guanidyl-1-hydroxyethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(1-(guanidinomethyl)cyclopropyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-((azetidin-3-ylamino)methyl)-1,3,4-oxadiazol-2-yl)-6-oxo-5,7-diazaspiro [bicyclo[3.2.1]octane-2,1'-cyclopropan]-7-yl sulfate;

(1R,4S)-4-(isoxazol-3-yl)-6-oxo-5,7-diazaspiro[bicyclo[3.2.1]octane-2,1'-cyclopropan]-7-yl sulfate;

(1R,4S)-4-(5-(guanidinomethyl)isoxazol-3-yl)-6-oxo-5,7-diazaspiro[bicyclo[3.2.1] octane-2,1'-cyclopropan]-7-yl sulfate;

(1R,4S)-4-(5-((1-methylguanidino)methyl)isoxazol-3-yl)-6-oxo-5,7-diazaspiro[bicycle [3.2.1]octane-2,1'-cyclopropan]-7-yl sulfate;

(1R,4S)-4-(5-(aminomethyl)-isoxazol-3-yl)-6-oxo-5,7-diazaspiro[bicyclo[3.2.1]octane-2,1'-cyclopropan]-7-yl sulfate;

(1R,4S)-4-(5-((methylamino)methyl)isoxazol-3-yl)-6-oxo-5,7-diazaspiro[bicycle[3.2.1] octane-2,1'-cyclopropan]-7-yl sulfate;

(1R,4S)-4-(5-(2-guanidinoethyl)isoxazol-3-yl)-6-oxo-5,7-diazaspiro[bicyclo[3.2.1] octane-2,1'-cyclopropan]-7-yl sulfate;

(1R,4S)-4-(5-(2-(1-methylguanidino)ethyl)isoxazol-3-yl)-6-oxo-5,7-diazaspiro[bicycle [3.2.1]octane-2,1'-cyclopropan]-7-yl sulfate;

(1R,4S)-4-(5-(2-guanidyl-1-hydroxyethyl)isoxazol-3-yl)-6-oxo-5,7-diazaspiro[bicycle [3.2.1]octane-2,1'-cyclopropan]-7-yl sulfate;

(1R,4S)-4-(5-((S)-2-guanidyl-1-hydroxyethyl)isoxazol-3-yl)-6-oxo-5,7-diazaspiro [bicyclo[3.2.1]octane-2,1'-cyclopropan]-7-yl sulfate;

(1R,4S)-4-(5-((R)-2-guanidyl-1-hydroxyethyl)isoxazol-3-yl)-6-oxo-5,7-diazaspiro [bicyclo[3.2.1]octane-2,1'-cyclopropan]-7-yl sulfate;

(1R,4S)-4-(5-(2-aminoethyl)isoxazol-3-yl)-6-oxo-5,7-diazaspiro[bicyclo[3.2.1]octane-2,1'-cyclopropan]-7-yl sulfate;

(1R,4S)-4-(5-(2-(methylamino)ethyl)isoxazol-3-yl)-6-oxo-5,7-diazaspiro[bicycle[3.2.1] octane-2,1'-cyclopropan]-7-yl sulfate;

(1R,4S)-6-oxo-4-(5-(piperidin-4-yl)isoxazol-3-yl)-5,7-diazaspiro[bicyclo[3.2.1]octane-2,1'-cyclopropan]-7-yl sulfate;

(1R,4S)-6-oxo-4-(5-(piperidin-3-yl)isoxazol-3-yl)-5,7-diazaspiro[bicyclo[3.2.1]octane-2,1'-cyclopropan]-7-yl sulfate;

(1R,4S)-6-oxo-4-(5-(pyrrolidin-3-yl)isoxazol-3-yl)-5,7-diazaspiro[bicyclo[3.2.1]octane-2,1'-cyclopropan]-7-yl sulfate;

(1R,4S)-6-oxo-4-(5-(2-(piperidin-4-ylamino)ethyl)isoxazol-3-yl)-5,7-diazaspiro[bicycle [3.2.1]octane-2,1'-cyclopropan]-7-yl sulfate;

(1R,4S)-4-(5-(2-((1-amidinopiperidin-4-yl)amino)ethyl)isoxazol-3-yl)-6-oxo-5,7-diazaspiro[bicyclo[3.2.1]octane-2,1'-cyclopropan]-7-yl sulfate;

(1R,4S)-4-(5-((1S,3R)-3-aminocyclobutyl)-1,3,4-oxadiazol-2-yl)-6-oxo-5,7-diazaspiro [bicyclo[3.2.1]octane-2,1'-cyclopropan]-7-yl sulfate;

(1R,4S)-4-(5-((1R,3S)-3-aminocyclopentyl)-1,3,4-oxadiazol-2-yl)-6-oxo-5,7-diazaspiro [bicyclo[3.2.1]octane-2,1'-cyclopropan]-7-yl sulfate;

(1R,4S)-4-(5-((1R,3S)-3-aminocyclopentyl)-1,3,4-oxadiazol-2-yl)-6-oxo-5,7-diazaspiro [bicyclo[3.2.1]octane-2,1'-cyclopropan]-7-yl sulfate;

(1R,4S)-4-(5-((1R,3R)-3-aminocyclopentyl)-1,3,4-oxadiazol-2-yl)-6-oxo-5,7-diazaspiro [bicyclo[3.2.1]octane-2,1'-cyclopropan]-7-yl sulfate;

(1R,4S)-4-(5-(((1R,3R)-3-aminocyclobutyl)methyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(((1S,3S)-3-aminocyclobutyl)methyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-((1-aminocyclopropyl)methyl)-1,3,4-oxadiazol-2-yl)-6-oxo-5,7-diazaspiro [bicyclo[3.2.1]octane-2,1'-cyclopropan]-7-yl sulfate;

(1R,4S)-4-(5-((1-(methylamino)cyclopropyl)methyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(azetidin-3-ylmethyl)-1,3,4-oxadiazol-2-yl)-6-oxo-5,7-diazaspiro[bicycle [3.2.1] octane-2,1'-cyclopropan]-7-yl sulfate;

(1R,4S)-4-(5-(2-(methylamino)ethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-((azetidin-3-ylamino)methyl)isoxazol-3-yl)-6-oxo-5,7-diazaspiro[bicycle [3.2.1] octane-2,1'-cyclopropan]-7-yl sulfate;

(1R,4S)-4-(5-(azetidin-3-ylmethyl)isoxazol-3-yl)-6-oxo-5,7-diazaspiro[bicycle[3.2.1] octane-2,1'-cyclopropan]-7-yl sulfate;

(1R,4S)-4-(5-((azetidin-3-yloxy)methyl)isoxazol-3-yl)-6-oxo-5,7-diazaspiro[bicycle [3.2.1] octane-2,1'-cyclopropan]-7-yl sulfate;

(1R,4S)-4-(5-(((1-amidinoazetidin-3-yl)amino)methyl)isoxazol-3-yl)-6-oxo-5,7-diazaspiro[bicyclo[3.2.1]octane-2,1'-cyclopropan]-7-yl sulfate;

(1R,4S)-4-(5-(3-aminocyclobutyl)isoxazol-3-yl)-6-oxo-5,7-diazaspiro[bicyclo[3.2.1] octane-2,1'-cyclopropan]-7-yl sulfate;

(1R,4S)-4-(5-((1S,3S)-3-aminocyclobutyl)isoxazol-3-yl)-6-oxo-5,7-diazaspiro[bicycle [3.2.1] octane-2,1'-cyclopropan]-7-yl sulfate;

(1R,4S)-4-(5-((1R,3R)-3-aminocyclobutyl)isoxazol-3-yl)-6-oxo-5,7-diazaspiro[bicycle [3.2.1] octane-2,1'-cyclopropan]-7-yl sulfate;

(1R,4S)-4-(5-(2-((2-guanidinoethyl)amino)ethyl)isoxazol-3-yl)-6-oxo-5,7-diazaspiro [bicyclo[3.2.1]octane-2,1'-cyclopropan]-7-yl sulfate;

(1R,4S)-6-oxo-4-(piperidin-4-ylaminoformyl)-5,7-diazaspiro[bicyclo[3.2.1]octane-2,1'-cyclopropan]-7-yl sulfate;

(1R,4S)-6-oxo-4-(pyrrolidin-3-ylaminoformyl)-5,7-diazaspiro[bicyclo[3.2.1]octane-2,1'-cyclopropan]-7-yl sulfate;

(1R,4S)-4-(azetidin-3-ylaminoformyl)-6-oxo-5,7-diazaspiro[bicyclo[3.2.1]octane-2,1'-cyclopropan]-7-yl sulfate;

(1R,4S)-4-(5-((S)-1-hydroxy-2-((2-(methylamino)ethyl)amino)ethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-((S)-2-((2-aminoethyl)amino)-1-hydroxyethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-((S)-2-iminoimidazolidin-4-yl)-1,3,4-oxadiazol-2-yl)-6-oxo-5,7-diazaspiro [bicyclo[3.2.1]octane-2, 1'-cyclopropan]-7-yl sulfate;

(1R,4S)-4-(5-((R)-2-iminoimidazolidin-4-yl)-1,3,4-oxadiazol-2-yl)-6-oxo-5,7-diazaspiro[bicyclo[3.2.1]octane-2, 1'-cyclopropan]-7-yl sulfate;

2-(((1R,4S)-4-(5-(aminomethyl)-1,3,4-oxadiazol-2-yl)-6-oxo-5,7-diazaspiro[bicycle [3.2.1]octane-2,1'-cyclopropan]-7-yl)oxy)acetate;

2-(((1R,4S)-4-(5-(((tert-butoxycarbonyl)amino)methyl)isoxazol-3-yl)-6-oxo-5,7-diazaspiro[bicyclo[3.2.1]octane-2,1'-cyclopropan]-7-yl)oxy)acetate;

2-(((1R,4S)-4-(5-(aminomethyl)-1,3,4-oxadiazol-2-yl)-6-oxo-5,7-diazaspiro[bicycle [3.2.1]octane-2,1'-cyclopropan]-7-yl)oxy)-2,2-difluoroacetate;

2-(((1R,4S)-4-(5-(((tert-butoxycarbonyl)amino)methyl)isoxazol-3-yl)-6-oxo-5,7-diazaspiro[bicyclo[3.2.1]octane-2,1'-cyclopropan]-7-yl)oxy)-2,2-difluoroacetate;

(1R,4S)-4-(5-((1S,3R)-3-guanidinocyclobutyl)isoxazol-3-yl)-6-oxo-5,7-diazaspiro [bicyclo[3.2.1]octane-2,1'-cyclopropan]-7-yl sulfate;

(1R,4S)-4-(5-(1-hydroxy-2-((2-(methylamino)ethyl)amino)ethyl)isoxazol-3-yl)-6-oxo-5,7-diazaspiro[bicyclo[3.2.1]octane-2,1'-cyclopropan]-7-yl sulfate;

(1R,4S)-4-(5-((S)-1-hydroxy-2-((2-(methylamino)ethyl)amino)ethyl)isoxazol-3-yl)-6-oxo-5,7-diazaspiro[bicyclo[3.2.1]octane-2,1'-cyclopropan]-7-yl sulfate;

(1R,4S)-4-(5-((R)-1-hydroxy-2-((2-(methylamino)ethyl)amino)ethyl)isoxazol-3-yl)-6-oxo-5,7-diazaspiro[bicyclo[3.2.1]octane-2,1'-cyclopropan]-7-yl sulfate;

(1R,4S)-4-(5-(2-((2-aminoethyl)amino)-1-hydroxyethyl)isoxazol-3-yl)-6-oxo-5,7-diazaspiro[bicyclo[3.2.1]octane-2,1'-cyclopropan]-7-yl sulfate;

(1R,4S)-4-(5-((S)-2-((2-aminoethyl)amino)-1-hydroxyethyl)isoxazol-3-yl)-6-oxo-5,7-diazaspiro[bicyclo[3.2.1]octane-2,1'-cyclopropan]-7-yl sulfate;

(1R,4S)-4-(5-((R)-2-((2-aminoethyl)amino)-1-hydroxyethyl)isoxazol3-yl)-6-oxo-5,7-diazaspiro[bicyclo[3.2.1]octane-2,1'-cyclopropan]-7-yl sulfate;

(1R,4S)-4-(5-(2-((2-guanidinoethyl)amino)-1-hydroxyethyl)isoxazol-3-yl)-6-oxo-5,7-diazaspiro[bicyclo[3.2.1]octane-2,1'-cyclopropan]-7-yl sulfate;

(1R,4S)-4-(5-((S)-2-((2-guanidinoethyl)amino)-1-hydroxyethyl)isoxazol-3-yl)-6-oxo-5,7-diazaspiro[bicyclo[3.2.1]octane-2,1'-cyclopropan]-7-yl sulfate;

(1R,4S)-4-(5-((R)-2-((2-guanidinoethyl)amino)-1-hydroxyethyl)isoxazol-3-yl)-6-oxo-5,7-diazaspiro[bicyclo[3.2.1]octane-2,1'-cyclopropan]-7-yl sulfate;

(1R,4S)-4-(5-((1-hydroxy-2-((2-(methylamino)ethyl)amino)ethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-((R)-1-hydroxy-2-((2-(methylamino)ethyl)amino)ethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(2-((2-aminoethyl)amino)-1-hydroxyethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-((R)-2-((2-aminoethyl)amino)-1-hydroxyethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(2-((2-guanidinoethyl)amino)-1-hydroxyethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-((S)-2-((2-guanidinoethyl)amino)-1-hydroxyethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-((R)-2-((2-guanidinoethyl)amino)-1-hydroxyethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(2-(azetidin-3-ylamino)-1-hydroxyethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(1-hydroxy-2-(methylamino)ethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(1-hydroxy-2-(pyrrolidin-3-ylamino)ethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(2-(dimethylamino)-1-hydroxyethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(hydroxy(pyrrolidin-2-yl)methyl)-1,3,4-oxadiazol-2-yl)-6-oxo-5,7-diazaspiro[bicyclo[3.2.1]octane-2,1'-cyclopropan]-7-yl sulfate;

2-hydroxy-N,N,N-trimethyl-2-(5-((1R,4S)-6-oxo-7-(sulfooxy)-5,7-diazaspiro[bicycle [3.2.1]octane-2,1'-cyclopropane]-4-yl)-1,3,4-oxadiazol-2-yl)ethan-1-ammonium;

(1R,4S)-4-(5-(1-hydroxy-2-(piperidin-4-ylamino)ethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(4-hydroxypiperidin-4-yl)isoxazol-3-yl)-6-oxo-5,7-diazaspiro[bicycle [3.2.1]octane-2,1'-cyclopropan]-7-yl sulfate;

(1R,4S)-4-(5-(1-amidinopiperidin-4-yl)isoxazol-3-yl)-6-oxo-5,7-diazaspiro[bicycle [3.2.1]octane-2,1'-cyclopropan]-7-yl sulfate;

(1R,4S)-6-oxo-4-(5-(piperazin-1-yl)isoxazol-3-yl)-5,7-diazaspiro[bicyclo[3.2.1]octane-2,1'-cyclopropan]-7-yl sulfate;

(1R,4S)-6-oxo-4-(5-(2-oxopiperazine-1-yl)isoxazol-3-yl)-5,7-diazaspiro[bicycle[3.2.1] octane-2,1'-cyclopropan]-7-yl sulfate;

(1R,4S)-4-(5-(L-prolyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-((S)-2-((2-(dimethylamino)ethyl)amino)-1-hydroxyethyl)-1,3,4-oxadiazol-2-yl)-6-oxo-5,7-diazaspiro[bicyclo[3.2.1]octane-2,1'-cyclopropan]-7-yl sulfate;

2-(((2S)-2-hydroxy-2-(5-((1R,4S)-6-oxo-7-(sulfooxy)-5,7-diazaspiro[bicycle[3.2.1] octane-2,1'-cyclopropane]-4-yl)-1,3,4-oxadiazol-2-yl)ethyl)amino)-N,N,N-trimethylethan-1-ammonium;

(1R,4S)-6-oxo-4-(5-(2-oxoimidazolidine-4-yl)-1,3,4-oxadiazol-2-yl)-5,7-diazaspiro [bicyclo[3.2.1]octane-2,1'-cyclopropan]-7-yl sulfate;

(1R,4S)-6-oxo-4-(5-(2-oxooxazolidine-5-yl)-1,3,4-oxadiazol-2-yl)-5,7-diazaspiro [bicyclo[3.2.1]octane-2,1'-cyclopropan]-7-yl sulfate;

(1R,4S)-6-oxo-4-(5-(2-oxooxazolidine-4-yl)-1,3,4-oxadiazol-2-yl)-5,7-diazaspiro [bicyclo[3.2.1]octane-2,1'-cyclopropan]-7-yl sulfate;

(1R,4S)-4-(5-(2-imino-1-((methylamino)methyl)imidazolidin-4-yl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(1-((dimethylamino)methyl)-2-iminoimidazolidin-4-yl)-1,3,4-oxadiazol-2-yl)-6-oxo-5,7-diazaspiro[bicyclo[3.2.1]octane-2,1'-cyclopropan]-7-yl sulfate;

1-(2-imino-4-(5-((1R,4S)-6-oxo-7-(sulfooxy)-5,7-diazaspiro[bicyclo[3.2.1]octane-2,1'-cyclopropane]-4-yl)-1,3,4-oxadiazol-2-yl)imidazolidin-1-yl)-N,N,N-trimethylmethylammonium;

(1R,4S)-4-(5-(2-imino-1-((methylamino)methyl)-5-oxoimidazolidin-4-yl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(5-hydroxy-2-imino-1-((methylamino)methyl)imidazolidin-4-yl)-1,3,4-oxadiazol-2-yl)-6-oxo-5,7-diazaspiro[bicyclo[3.2.1]octane-2,1'-cyclopropane]-7-yl sulfate;

(1R,4S)-4-(5-(3-((methylamino)methyl)-2-oxooxazolidine-4-yl)-1,3,4-oxadiazol-2-yl)-6-oxo-5,7-diazaspiro[bicyclo[3.2.1]octane-2,1'-cyclopropane]-7-yl sulfate;

(1R,4S)-4-(5-(1-(aminomethyl)-2-iminoimidazolidin-4-yl)-1,3,4-oxadiazol-2-yl)-6-oxo-5,7-diazaspiro[bicyclo[3.2.1]octane-2,1'-cyclopropane]-7-yl sulfate;

(1R,4S)-4-(5-(5-amino-2-iminoimidazolidin-4-yl)-1,3,4-oxadiazol-2-yl)-6-oxo-5,7-diazaspiro[bicyclo[3.2.1]octane-2,1'-cyclopropane]-7-yl sulfate;

(1R,4S)-4-(5-(2-imino-5-(methylamino)imidazolidin-4-yl)-1,3,4-oxadiazol-2-yl)-6-oxo-5,7-diazaspiro[bicyclo [3.2.1]octane-2,1'-cyclopropane]-7-yl sulfate;

(1R,4S)-4-(5-(5-(dimethylamino)-2-iminoimidazolidin-4-yl)-1,3,4-oxadiazol-2-yl)-6-oxo-5,7-diazaspiro[bicyclo[3.2.1]octane-2,1'-cyclopropane]-7-yl sulfate;

(1R,4S)-4-(5-((R)-2-amino-1-hydroxyethyl)-1,3,4-oxadiazol-2-yl)-6-oxo-5,7-diazaspiro [bicyclo[3.2.1]octane-2,1'-cyclopropane]-7-yl sulfate;

(1R,4S)-4-(5-((S)-2-amino-1-hydroxyethyl)-1,3,4-oxadiazol-2-yl)-6-oxo-5,7-diazaspiro [bicyclo[3.2.1]octane-2,1'-cyclopropane]-7-yl sulfate;

(1R,4S)-4-(5-((S)-1-hydroxy-2-(methylamino)ethyl)-1,3,4-oxadiazol-2-yl)-6-oxo-5,7-diazaspiro[bicyclo[3.2.1]octane-2,1'-cyclopropane]-7-yl sulfate;

(1R,4S)-4-(5-((S)-2-(dimethylamino)-1-hydroxyethyl)-1,3,4-oxadiazol-2-yl)-6-oxo-5,7-diazaspiro[bicyclo[3.2.1]octane-2,1'-cyclopropane]-7-yl sulfate;

2-(((1R,4S)-4-(5-(aminomethyl)-1,3,4-oxadiazol-2-yl)-6-oxo-5,7-diazaspiro[bicycle [3.2.1]octane-2,1'-cyclopropan]-7-yl)oxy)acetate;

2-(((1R,4S)-4-(5-(((tert-butoxycarbonyl)amino)methyl)isoxazol-3-yl)-6-oxo-5,7-diazaspiro[bicyclo[3.2.1]octane-2,1'-cyclopropan]-7-yl)oxy)acetate;

2-(((1R,4S)-4-(5-(aminomethyl)-1,3,4-oxadiazol-2-yl)-6-oxo-5,7-diazaspiro[bicycle [3.2.1]octane-2,1'-cyclopropan]-7-yl)oxy)-2,2-difluoroacetate;

2-(((1R,4S)-4-(5-(((tert-butoxycarbonyl)amino)methyl)isoxazol-3-yl)-6-oxo-5,7-diazaspiro[bicyclo[3.2.1]octane-2,1'-cyclopropan]-7-yl)oxy)-2,2-difluoroacetate.

In another aspect, the present invention provides a preparation method for the compound as shown in formula (I):

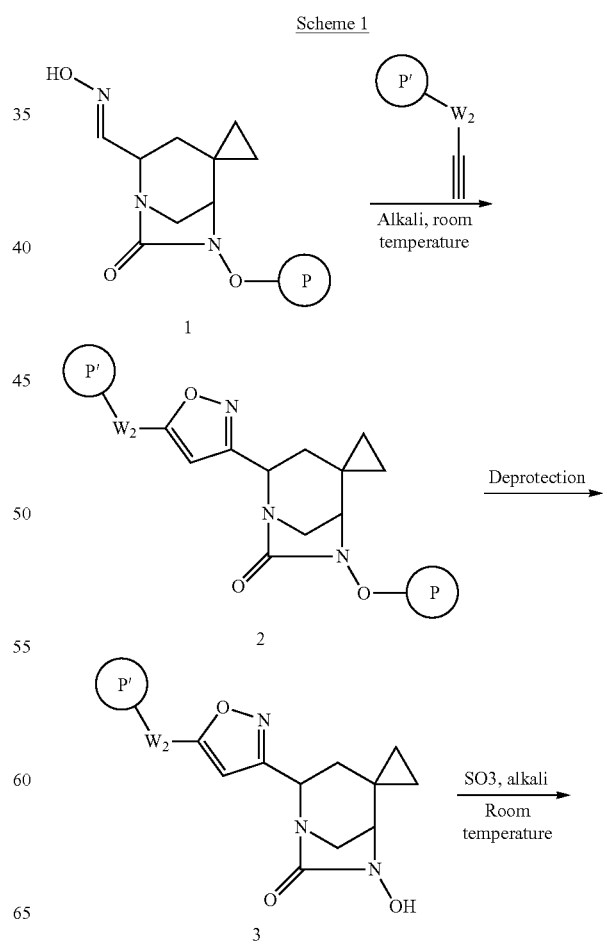

-continued

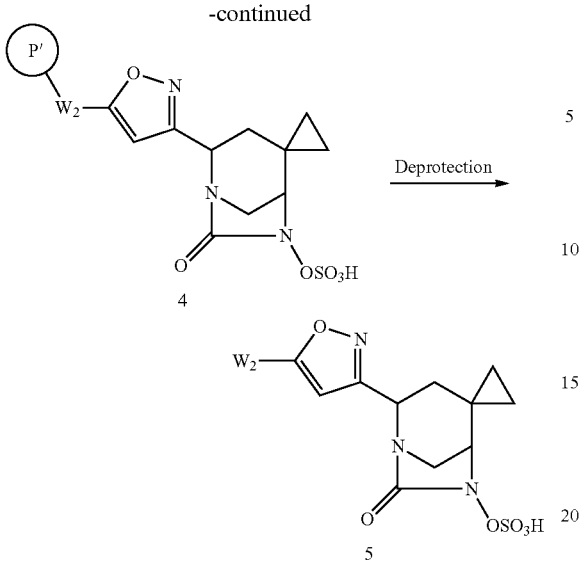

step 1: the intermediate 1 and an alkyne are subjected to cyclization under an alkaline condition to give the intermediate 2;
step 2: the protecting group P in the intermediate 2 is selectively removed to give the intermediate 3;
step 3: the intermediate 3 reacts with SO₃ under an alkaline condition to give the intermediate 4;
step 4: the protecting group P' in the intermediate 4 is removed to give the product 5.

In this case, P is a hydroxy protecting group commonly used in the art. P is a hydroxy or amino protecting group commonly used in the art. B is as defined in formula (I). Hydroxyl or amino protecting groups include, but are not limited to, benzyl, silane protecting groups, ester protecting groups, alkyl ether protecting groups, Boc, Fmoc, Cbz, and the like. See, e.g., Greene, T. W., and Wuts, P. G. M., *Greene's Protective Groups in Organic Synthesis*, 4th edition, John Wiley and Sons.

In step 1, the alkali used in the reaction may be an inorganic alkali or an organic alkali. The inorganic alkali may be selected from hydroxides (e.g., sodium hydroxide, potassium hydroxide, barium hydroxide, lithium hydroxide, calcium hydroxide, and magnesium hydroxide) of alkali metals or alkaline earth metals, carbonates or bicarbonates (e.g., potassium carbonate, sodium carbonate, lithium carbonate, calcium carbonate, magnesium carbonate, and sodium bicarbonate) of alkali metals or alkaline earth metals, alkoxides (e.g., sodium methoxide, sodium ethoxide, sodium tert-butoxide, potassium tert-butoxide, etc.) of alkali metals or alkaline earth metals, amides (e.g., sodium amide, sodium bis(trimethylsilyl)
amide) of alkali metals or alkaline earth metals, and ammonium hydroxide solution. The organic alkali may be selected from organic amines commonly used in the art, such as triethylamine, trimethylamine, pyridine, piperidine, 4-dimethylaminopyridine, morpholine, N-methylmorpholine, N,N,N',N'-tetramethylethylenediamine, DBU, DBN, DABCO, etc.

In step 2 and step 4, deprotection is a routine experimental procedure in the art. See, e.g., Greene, T. W. and Wuts, P. G. M., *Greene's Protective Groups in Organic Synthesis*, 4th edition, John Wiley and Sons.

In step 3, the alkali used in the reaction is as defined in step 1.

Scheme 2

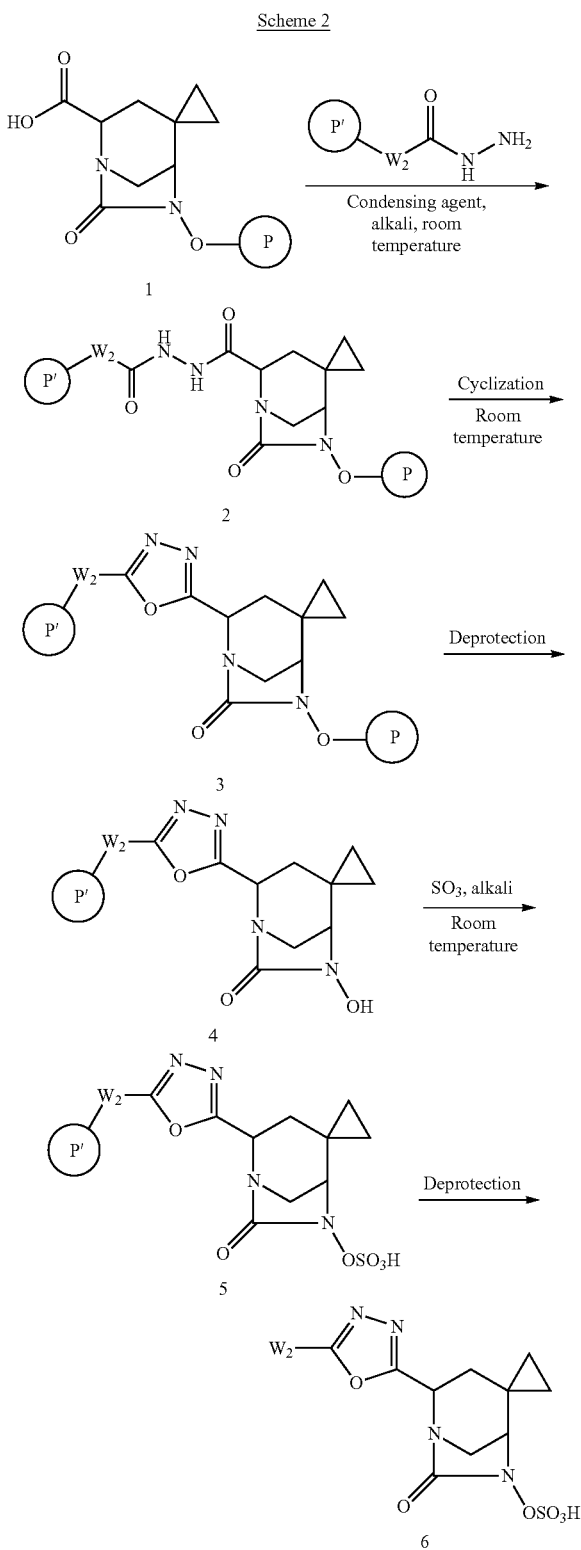

In this case, P is a hydroxy protecting group commonly used in the art. P' is a hydroxy or amino protecting group commonly used in the art. B is as defined in formula (I).

Hydroxyl or amino protecting groups include, but are not limited to, benzyl, silane protecting groups, ester protecting groups, alkyl ether protecting groups, Boc, Fmoc, Cbz, and the like. See, e.g., Greene, T. W., and Wuts, P. G. M., *Greene's Protective Groups in Organic Synthesis,* 4th edition, John Wiley and Sons.

Step 1: the intermediate 1 and hydrazide are subjected to condensation under an alkaline condition to give the intermediate 2, wherein the alkali used in the reaction may be an inorganic alkali or an organic alkali, as defined in step 1 of scheme 1; the condensing agent may be one commonly used in the art for condensation between carboxylic acid and amine, such as carbodiimide-based condensing agents (combinations of CDI, DCC, DIC, EDCI and DMAP, HOBt, HOAt, HOSu, NHPI, NHNI, PFPOH, etc.), onium salt-based condensing agents (HATU, HBTU, HCTU, HAPyU, HBPyU, TBTU, TSTU, TNTU, etc.), organic phosphine-based condensing agents (BOP, PyBOP, PyAOP, DPP-Cl, DPPA, and DECP), and other condensing agents (triphenylphosphine-polyhalomethane, triphenylphosphine-hexachloroacetone, and triphenylphosphine-NBS); and the reaction temperature may be in the range of 0-100° C., preferably in the range of 0-70° C., more preferably in the range of 0-50° C., and most preferably at room temperature.

step 2: the intermediate 2 are subjected to cyclization to give the intermediate 3, wherein the cyclization is carried out in the presence of a condensing agent, and the condensing agent is preferably Burgess reagent; and the reaction temperature may be in the range of 0-100° C., preferably in the range of 0-70° C., more preferably in the range of 0-50° C., and most preferably at room temperature.

step 3: the protecting group P in the intermediate 3 is selectively removed to give the intermediate 4;

step 4: the intermediate 4 reacts with $SO_3$ under an alkaline condition to give the intermediate 5;

step 5: the protecting group P' in the intermediate 5 is removed to give the product 6;

In step 3 and step 5, deprotection is a routine experimental procedure in the art. See, e.g., Greene, T. W. and Wuts, P. G. M., *Greene's Protective Groups in Organic Synthesis,* 4th edition, John Wiley and Sons.

In step 4, the alkali used in the reaction is as defined in step 1 of scheme 1.

In another aspect, the present invention also provides a pharmaceutical composition using the compound as shown in formula (I) or the pharmaceutically acceptable salt thereof as an active ingredient. The composition comprises the compound of the present invention or the pharmaceutically acceptable salt thereof and a pharmaceutically acceptable carrier. The pharmaceutically acceptable carrier may be a solid or a liquid. The solid carrier may be one or more substances used as excipients, diluents, sweeteners, solubilizers, lubricants, binders, tablet disintegrating agents, stabilizers, preservatives, or encapsulating materials. The liquid carrier may be a solvent or a liquid dispersion medium. Suitable solid carriers include, but are not limited to, for example, cellulose, glucose, lactose, mannitol, magnesium stearate, magnesium carbonate, sodium carbonate, sodium saccharin, sucrose, dextrin, talc, starch, pectin, gelatin, tragacanth, acacia, sodium alginate, methylparaben, methylcellulose, sodium carboxymethylcellulose, low-melting-point wax, cocoa butter, and the like. Suitable liquid carriers include, but are not limited to, water, ethanol, polyols (e.g., glycerol, propylene glycol, liquid polyethylene glycols, and the like), vegetable oils (e.g., peanut oil, cottonseed oil, safflower oil, sesame oil, olive oil, corn oil, and soybean oil), glycerides, agar, pyrogen-free water, isotonic saline, Ringer's solutions, and mixtures thereof.

The method for preparing the pharmaceutical composition of the present invention is generally known in the art. Generally known methods for preparing the pharmaceutical composition of the present invention include conventional mixing, granulating, tableting, coating, dissolving or lyophilizing processes.

The therapeutically effective amount of the compound or the pharmaceutical composition comprising the same described herein may be readily determined by routine experimentations. The most effective and convenient route of administration may be determined by routine experimentations.

The pharmaceutical composition of the present invention may be administered to a patient or subject in need of treatment by any suitable route of administration, including oral administration, parenteral administration (including subcutaneous, intramuscular, intravenous, and intradermal administration), nasal spray administration, topical administration, rectal administration, intranasal administration, buccal administration, vaginal administration or administration via an implantable reservoir. In some embodiments, the pharmaceutical composition disclosed herein may be intravenously and/or intraperitoneally administered.

The term "parenteral" as used herein includes subcutaneous, intravenous, intramuscular, intraocular, intravitreal, intraarticular, intrasynovial, intrasternal, intrathecal, intrahepatic, intraperitoneal, intralesional and intracranial injection or infusion techniques. Preferably, these pharmaceutical compositions are administered orally, subcutaneously, intraperitoneally or intravenously.

The orally administered compositions in the present invention include solid dosage forms such as pills, tablets, caplets, capsules (including immediate release, timed release and sustained release formulations), granules and powder; and liquid dosage forms such as solutions, syrups, elixirs, emulsions and suspensions. Sterile solutions or ocular drug delivery devices are intended for ocular administration. Sterile solutions, emulsions and suspensions are intended for parenteral administration.

The pharmaceutical composition of the present invention may additionally comprise one or more β-lactam antibiotics. The β-lactam antibiotics disclosed herein can include penicillins, cephalosporins, monobactams, carbapenems, and penemase inhibitors. Specifically, the β-lactam antibiotics can include penicillin, oxacillin, cloxacillin, dicloxacillin, flucloxacillin, ampicillin, pivampicillin, amoxicillin, carbenicillin, furbenicillin, sulbenicillin, ticarcillin, piperacillin, mecillinam, cephalothin, cephaloridine, cefazolin, cefradine, cefuroxime, cefaclor, cefotaxime, ceftriaxone, ceftazidime, cefoperazone, cefoxitin, imipenem, aztreonam, and the like.

The compound of the present invention or the ester, stereoisomer or pharmaceutically acceptable salt thereof, and the pharmaceutical composition comprising the compound of the present invention or the ester, stereoisomer or pharmaceutically acceptable salt thereof, can be used for treating and/or preventing diseases caused by bacterial infection. Therefore, the compound as shown in the formula (I) disclosed herein or the ester, stereoisomer or pharmaceutically acceptable salt thereof may be used in preparing drugs for treating diseases caused by bacterial infection. In addition, the present invention also relates to a method for inhibiting bacteria or treating and/or preventing diseases caused by bacterial infection, which comprises administering a therapeutically and/or prophylactically effective amount of the compound as shown in formula (I) disclosed herein or the ester, stereoisomer, or pharmaceutically acceptable salt thereof to a patient or subject in need.

In one embodiment, bacteria in diseases caused by bacterial interference are selected from gram-positive bacteria and gram-negative bacteria. The gram-positive bacteria are selected from one or more of *Staphylococcus aureus, Staphylococcus epidermidis, Streptococcus agalactiae, Streptococcus pneumoniae, Streptococcus pyogenes, Enterococcus* spp. and *Clostridium difficile*. The gram-negative bacteria are selected from one or more of *Citrobacter* spp., *Citrobacter freundii, Enterobacter cloacae, Klebsiella pneumoniae, Escherichia coli, Proteus vulgaris, Salmonella* spp., *Serratia marcescens, Shigella* spp., *Pseudomonas aeruginosa, Moraxella mucositis, Neisseria gonorrhoeae, Neisseria meningitidis, Acinetobacter* spp., *Burkholderia* spp., *Campylobacter* spp., *Helicobacter pylori, Vibrio cholerae, Klebsiella pneumoniae, Haemophilus influenzae, Mycobacterium avium* complex, *Mycobacterium abscessus, Mycobacterium kansasii, Mycobacterium ulcerosa, Chlamydophila pneumoniae, Chlamydia trachomatis*, β-hemolytic *Streptococcus, Acinetobacter baumannii, Pseudomonas pyocyaneum, Bacteroides fragilis, Bacillus cereus*, and *Stenotrophomonas maltophilia*. The bacteria in the diseases caused by bacterial interference are preferably selected from gram-negative bacteria.

In one embodiment, diseases caused by the bacteria are selected from one or more of respiratory tract infections (upper respiratory tract infections, lower respiratory tract infections, tracheitis, bronchitis, pneumonia, tuberculosis, and pharyngitis), urinary tract infections (complex urinary tract infections, complicated urinary tract infections, non-complicated urinary tract infections, cystitis, and pyelonephritis), central nervous system infections (encephalitis, meningitis, and brain abscess), ear infections (otitis externa, and otitis media), *pleuropneumoniae* and bronchial infections, intra-abdominal infections, cardiovascular infections (blood infections such as septicemia or bacteremia, endocarditis, myocarditis, and pericarditis), skin or soft tissue infections, bone and joint infections (arthritis, and osteomyelitis), genital infections (genital ulcer, vaginitis, and cervicitis), eye infections (conjunctivitis, keratitis, and endophthalmitis), pharyngeal infections (pharyngitis), and oral infections (gingivitis).

When required, the compounds or pharmaceutical compositions of the present invention can be provided in a package or with a dispensing device containing one or more unit dosage forms. For example, the package can comprise a metal or a plastic foil, or a glass and a rubber stopper (e.g. in a vial). The package or dispensing device can be accompanied by instructions for use of drugs.

The dosage depends on various factors including the age, weight and condition of a patient and the route of administration. The exact dosage to be administered is left to the discretion of the attending physician. The actual dosage levels and time frame of active ingredients of the pharmaceutical composition of the present invention may be varied so as to obtain an amount of the active ingredient that, for a particular patient, composition, and route of administration, may achieve the desired therapeutic response without posing toxicity to the patient. Typically, the medicament or pharmaceutical composition of the present invention is administered at a dose sufficient to reduce or eliminate symptoms associated with bacterial infection.

The preferred dose of the medicament is the maximum dose that a patient can tolerate and that does not produce serious or unacceptable side effects. Exemplary dose ranges include 0.01-250 mg/day, 0.01-100 mg/day, 1-100 mg/day, 10-100 mg/day, 1-10 mg/day, and 0.01-10 mg/day. The preferred dose of the medicament is the maximum dose that a patient can tolerate and that does not produce serious or unacceptable side effects. In examples, the medicament is administered at a dose of about 0.01-100 mg/kg bw/day, 0.1-10 mg/kg/day, or 1.0-10 mg/kg bw/day.

In one embodiment, a therapeutically effective dose results in a serum concentration of a medicament of from about 0.1 ng/mL to about 50-100 mg/mL. Typically, these pharmaceutical compositions should be administered at a dose of about 0.001-2000 mg/kg bw/day. For example, the range of the dose for systemic administration to a human patient may be 1-10 mg/kg, 20-80 mg/kg, 5-50 mg/kg, 75-150 mg/kg, 100-500 mg/kg, 250-750 mg/kg, 500-1000 mg/kg, 1-10 mg/kg, 5-50 mg/kg, 25-75 mg/kg, 50-100 mg/kg, 100-250 mg/kg, 50-100 mg/kg, 250-500 mg/kg, 500-750 mg/kg, 750-1000 mg/kg, 1000-1500 mg/kg, 10 1500-2000 mg/kg, 5 mg/kg, 20 mg/kg, 50 mg/kg, 100 mg/kg, 500 mg/kg, 1000 mg/kg, 1500 mg/kg, or 2000 mg/kg. Pharmaceutical unit dosage forms are prepared with providing about 1-5000 mg (e.g., about 100-2500 mg) of the compound or combination of essential ingredients per unit dosage form. Preferred unit dose formulations are those containing a daily dose or unit, a daily sub-dose, or an appropriate fraction thereof, as discussed herein, of a given ingredient.

The present invention is further illustrated by the following specific examples, which are not intended to limit the present invention. Many modifications and variations may be made by those skilled in the art in light of the above teachings without departing from the spirit and scope of the present invention.

EXAMPLES

Preparation of Intermediates

Preparation of Benzyl (5S)-8-[(benzyloxy)amino]-6-azaspiro[2.5]octane-5-carboxylate Step 1:

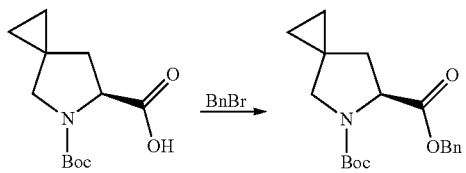

To a 3-neck round-bottom flask was added potassium carbonate (552 g, 3.99 mol, 1.93 eq.) and a solution of (6S)-5-[(tert-butoxy)carbonyl]-5-azaspiro[2.4]heptane-6-carboxylic acid (500 g, 2.07 mol, 1.00 eq.) in N,N-dimethylformamide (1.5 L). Benzyl bromide (354 g, 2.07 mol, 1.00 eq.) was then added dropwise with stirring at the same time. The resulting solution was stirred at room temperature for 2 h. The reaction was then quenched with water (1 L), followed by extraction with EA (1 L×3). The organic phase was dried and concentrated to give 750 g (109%) of crude (6S)-5-azaspiro[2.4]heptane-5,6-dicarboxylic acid 6-benzyl 5-tert-butyl diester in the form of a yellow oil.

Step 2:

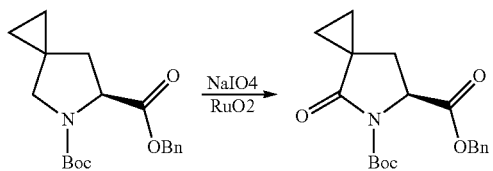

To a 20-L round-bottom flask was added a solution of NaIO$_4$ (1.2 kg, 5.63 mol, 2.70 eq.) in water (4 L) and EA (4.5 L), and RuO$_2$ (50 g). The mixture was stirred, and a solution of (6S)-5-azaspiro[2.4]heptane-5,6-dicarboxylic acid 6-benzyl 5-tert-butyl diester (750 g, 2.26 mol, 1.00 eq.) in ethyl acetate (1 L) was added dropwise. The resulting solution was stirred at room temperature for 4 h. The reaction mixture was filtered through celite. The solution was separated. The aqueous phase was extracted with ethyl acetate (3 L×3), and the organic phases were combined and dried over anhydrous sodium sulfate and concentrated under vacuum. The crude yellow oil was crystallized from hexane to give 560 g (72%) of (6S)-4-oxo-5-azaspiro[2.4]heptane-5,6-dicarboxylic acid 6-benzyl 5-tert-butyl diester in the form of an off-white solid. $^1$H NMR (300 MHz, chloroform-d) δ 0.79 (dtdd, J=12.9, 9.6, 6.7, 3.6 Hz, 2H), 1.22 (qt, J=6.6, 2.8 Hz, 1H), 1.31 (ddt, J=8.3, 5.3, 3.1 Hz, 1H), 1.47 (s, 9H), 1.92 (dd, J=13.3, 3.2 Hz, 1H), 2.55 (dd, J=13.3, 10.0 Hz, 1H), 4.74 (dd, J=10.0, 3.2 Hz, 1H), 5.24 (d, J=2.1 Hz, 2H), 7.38 (d, J=2.2 Hz, 5H).

Step 3:

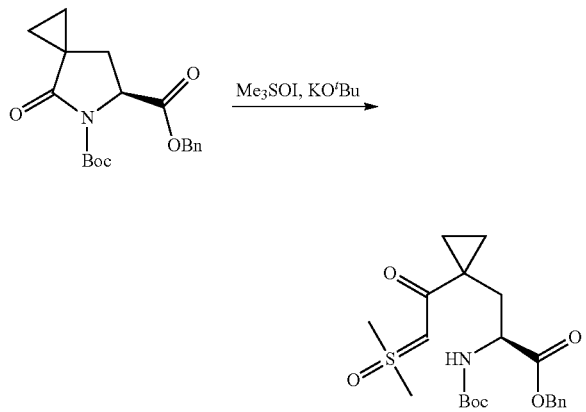

To a 5-L round-bottom flask was added a solution of trimethylsulfoxonium iodide (415 g, 1.89 mol, 1.16 eq.) in N,N-dimethylformamide (2.5 L), and t-BuOK (192 g, 1.71 mol, 1.06 eq.) was added in portions. The mixture was stirred at room temperature for 2 h. A solution of (6S)-4-oxo-5-azaspiro[2.4]heptane-5,6-dicarboxylic acid 6-benzyl 5-tert-butyl diester (560 g, 1.62 mol, 1.00 eq.) in DMF (500 mL) was then added dropwise. The resulting solution was stirred at room temperature for 2 h. The reaction was quenched with NH$_4$Cl (aq) (2 L) and EA (2 L×3) was added for extraction. The solvent was concentrated and the crude product (500 g, crude) was used in the next step without further purification.

Step 4:

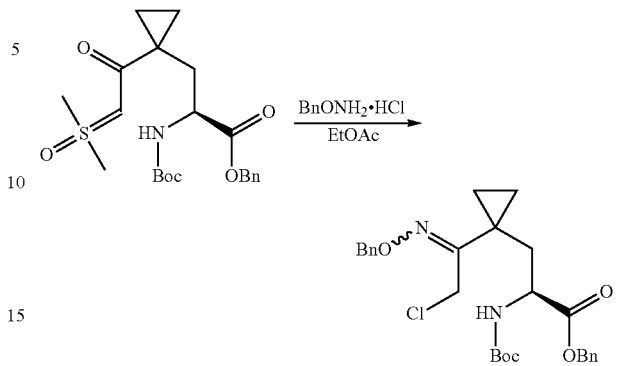

To a 10-L round-bottom flask was added benzyl (2S)-2-[[(tert-butoxy)carbonyl]amino]-3-[1-[2-(dimethylsulfi-nylidene)acetyl]cyclopropyl]propanoate (500 g, crude (from step 3), 1.14 mol, 1.00 eq.) and a solution of O-benzylhydroxylamine hydrochloride (260 g, 1.63 mol, 1.00 eq. (for step 3)) in ethyl acetate (4 L). The resulting solution was stirred at 70° C. overnight. The mixture was filtered and the filtrate was concentrated. The crude product was purified by a silica gel column (TLC:PE:EA=5:1) to give 240 g (30% over two steps) of benzyl (2S)-3-(1-[1-[(benzyloxy)imino]-2-chloroethyl]cyclopropyl)-2-[[(tert-butoxy) carbonyl]amino]propanoate in the form of a colorless oil.

Step 5:

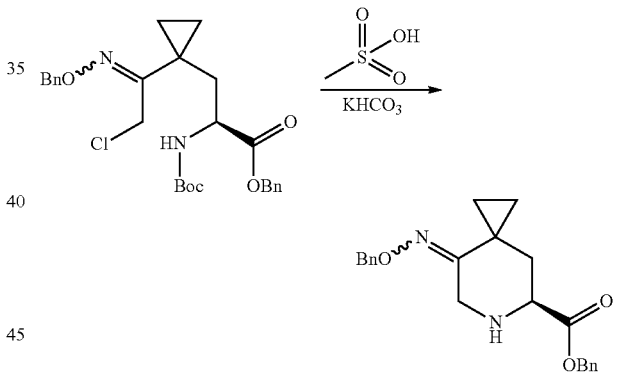

To a 10-L round bottom flask was added a solution of benzyl (2S)-3-(1-[1-[(benzyloxy) imino]-2-chloroethyl]cyclopropyl)-2-[[(tert-butoxy)carbonyl]amino]propanoate (240 g, 479.03 mmol, 1.00 eq.) in ethyl acetate (2.5 L), followed by methanesulfonic acid (137 g, 1.43 mol, 3.00 eq.). The mixture was stirred at 50° C. for 2 h, and then cooled to room temperature. An aqueous solution (2 L) of KHCO$_3$ (240 g, 5.00 eq.) was added dropwise. The resulting solution was stirred in an oil bath at 50° C. for 3 h. The organic phases were separated and the aqueous phase was extracted with EA (1 L×2). The solvent was removed to give 180 g (103%) of crude benzyl (5S)-8-[(benzyloxy)imino]-6-azaspiro[2.5]octane-5-carboxylate in the form of a yellow oil, which was used in the next step without further purification. $^1$H NMR (300 MHz, chloroform-d) δ 7.36 (d, J=11.5 Hz, 9H), 5.20 (s, 2H), 5.02 (s, 2H), 4.34 (d, J=16.0 Hz, 1H), 3.83 (d, J=9.6, 3.7 Hz, 1H), 3.45 (d, J=15.9 Hz, 1H), 2.29 (s, 2H), 2.06 (dd, J=13.2, 9.9 Hz, 1H), 1.73 (dd, J=13.4, 3.7 Hz, 1H), 1.42-1.26 (m, 1H), 0.79 (s, 1H), 0.71-0.58 (m, 1H), 0.56-0.41 (m, 1H).

Step 6:

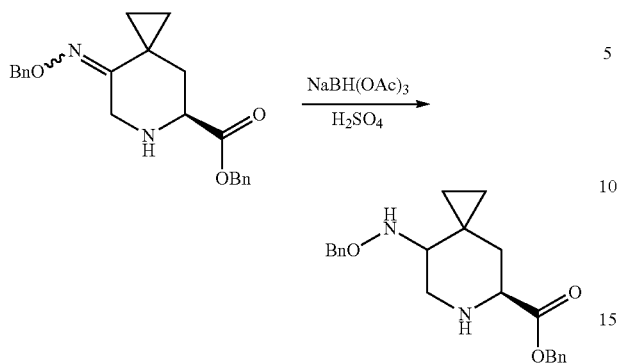

To a 5-L round-bottom flask was added a solution of benzyl (5S)-8-[(benzyloxy)imino]-6-azaspiro[2.5]octane-5-carboxylate (180 g, 493.91 mmol, 1.00 eq.) in ethyl acetate (3 L), followed by sulfuric acid (100 mL, 4.00 eq.) at −20° C. Sodium triacetoxyborohydride (311 g, 1.46 mol, 3.00 eq.) was added at this temperature. The resulting solution was stirred at −20° C. for 5 h. When the reaction was completed, the mixture was alkalified with concentrated $NH_3 \cdot H_2O$, and water (1 L) was added. Then, the mixture was extracted with EA (1 L×3). The organic phase was dried and concentrated. The crude product was purified by a silica gel column (TLC:PE:EA=1:1, Rf=0.35) to give 109 g (62% over two steps) of benzyl (5S)-8-[(benzyloxy)amino]-6-azaspiro[2.5]octane-5-carboxylate in the form of a dark red oil.

Step 7:

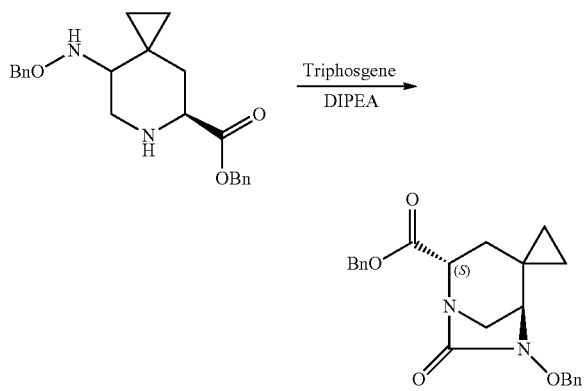

To a 5-L round-bottom flask was added benzyl (5S)-8-[(benzyloxy)amino]-6-azaspiro [2.5]octane-5-carboxylate (107 g, 291.99 mmol, 1.00 eq.) and a solution of DIPEA (75 g, 2.00 eq.) in dichloromethane (3 L), followed by triphosgene (34.5 g, 0.40 eq.) at room temperature. The resulting solution was stirred at room temperature overnight. $H_3PO_4$ (aq) (4 eq.) was added. The reaction mixture was stirred at room temperature for 4 h. The organic phases were separated and concentrated. The crude product was purified by a silica gel column to give 40 g (35%) of the desired product in the form of a yellow oil. $^1$H NMR (400 MHz, chloroform-d) δ −0.06-0.11 (m, 1H), 0.30-0.45 (m, 2H), 0.46-0.59 (m, 1H), 1.48-1.63 (m, 1H), 2.36 (d, J=3.2 Hz, 1H), 2.51 (dd, J=15.2, 8.0 Hz, 1H), 2.98-3.16 (m, 2H), 4.23 (d, J=7.9 Hz, 1H), 4.88 (d, J=11.5 Hz, 1H), 5.03 (d, J=11.5 Hz, 1H), 5.23 (q, J=12.1 Hz, 2H), 7.31-7.48 (m, 10H).

Preparation of (E)-6-(benzyloxy)-7-oxo-1,6-diazaspiro[bicyclo[3.2.1]octane-4,1'-cyclopropane]-2-carbaldehyde Oxime

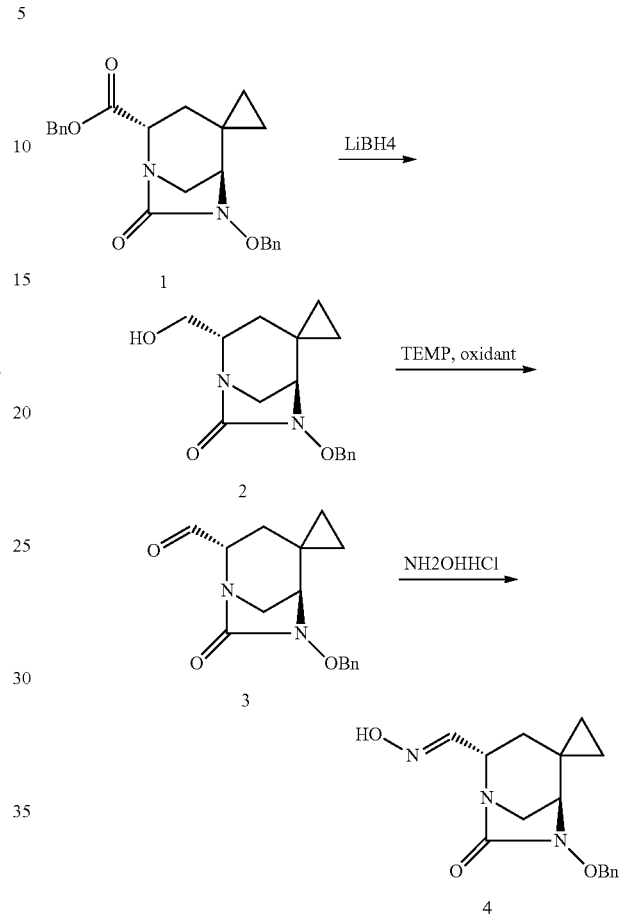

Step 1: Synthesis of Compound 2

To a solution of Compound 1 (10 g, 25.5 mmol) in MeOH (100 mL) at 0° C. was added a solution of $LiBH_4$ (19.1 mL, 4 M, 76.5 mmol) in THF. The solution was stirred at room temperature for 4 h until the reaction was complete. The reaction was quenched with $Na_2HPO_4$ (10% aq) and EA was added for extraction. The organic phase was dried and the solvent was removed to give a crude product. The crude product was purified by a silica gel column (PE:EA=2:1-EA:MeOH=9.5:0.5) to give the desired product (2.5 g, 34%) in the form of a colorless oil. m/z (ES$^+$), [M+H]$^+$=289; ACID, HPLC RT=0.719 min.

Step 2: Synthesis of Compound 3

To a solution of Compound 2 (2.5 g, 8.7 mmol) in DCM (50 mL) at 0° C. was added TEMPO (15 mg). The resulting solution was stirred at 0° C. and 1,3,5-trichloro-1,3,5-triazine-2,4,6-trione (2.1 g, 8.7 mmol) was added in portions, the mixture was stirred at 0° C. for 1 h and then filtered through celite. The filtrate was concentrated to give a crude product, which was used directly in the next step, m/z (ES$^+$), [M+H]$^+$=287; ACID, HPLC RT=0.764 min.

Step 3: Synthesis of Compound 4

A solution of Compound 3 from step 2 and $NH_2OH \cdot HCl$ (786 mg) were dissolved in MeOH (50 mL), and pyridine (2.7 g, 34.8 mmol) was added. The reaction mixture was stirred at room temperature for 2 h. The solvent was removed under reduced pressure. The crude residue was purified by a silica gel column (PE:EA=2:1) to give the desired product (1.2 g, 46% over two steps) in the form of a colorless oil. m/z (ES+), [M+H]+=302; ACID, HPLC RT=0.706 min.

Example 1: Preparation of Compound A

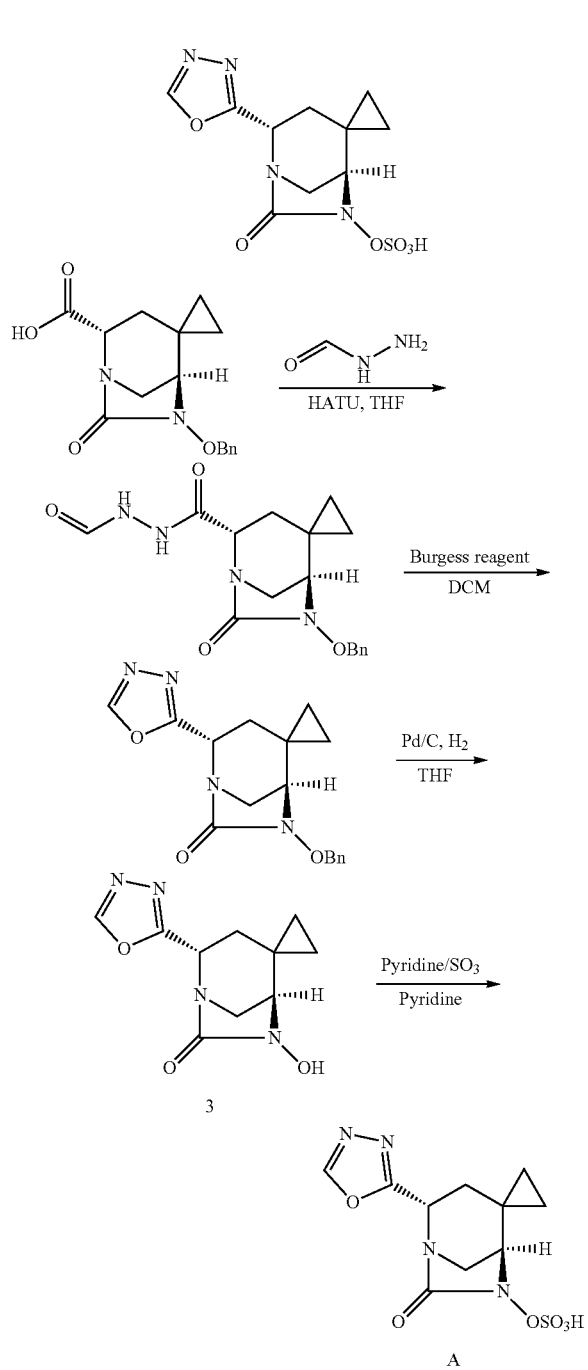

Steps 1-4: Following Steps 2-5 in Synthesis of Compound D

ESI-MS (EI+, m/z): 317, 0.628 min. $^1$H NMR (400 MHz, D$_2$O) δ 0.30-0.44 (m, 2H), 0.48 (tt, J=9.8, 5.6 Hz, 2H), 0.68 (ddt, J=14.9, 10.6, 5.2 Hz, 3H), 1.79 (d, J=16.0 Hz, 2H), 2.56 (dd, J=16.0, 7.7 Hz, 2H), 3.09 (d, J=12.2 Hz, 2H), 3.27 (dd, J=12.2, 3.7 Hz, 2H), 3.43 (d, J=3.7 Hz, 2H), 4.92 (d, J=7.7 Hz, 2H), 8.90 (s, 1H).

Example 2: Synthesis of Compound B

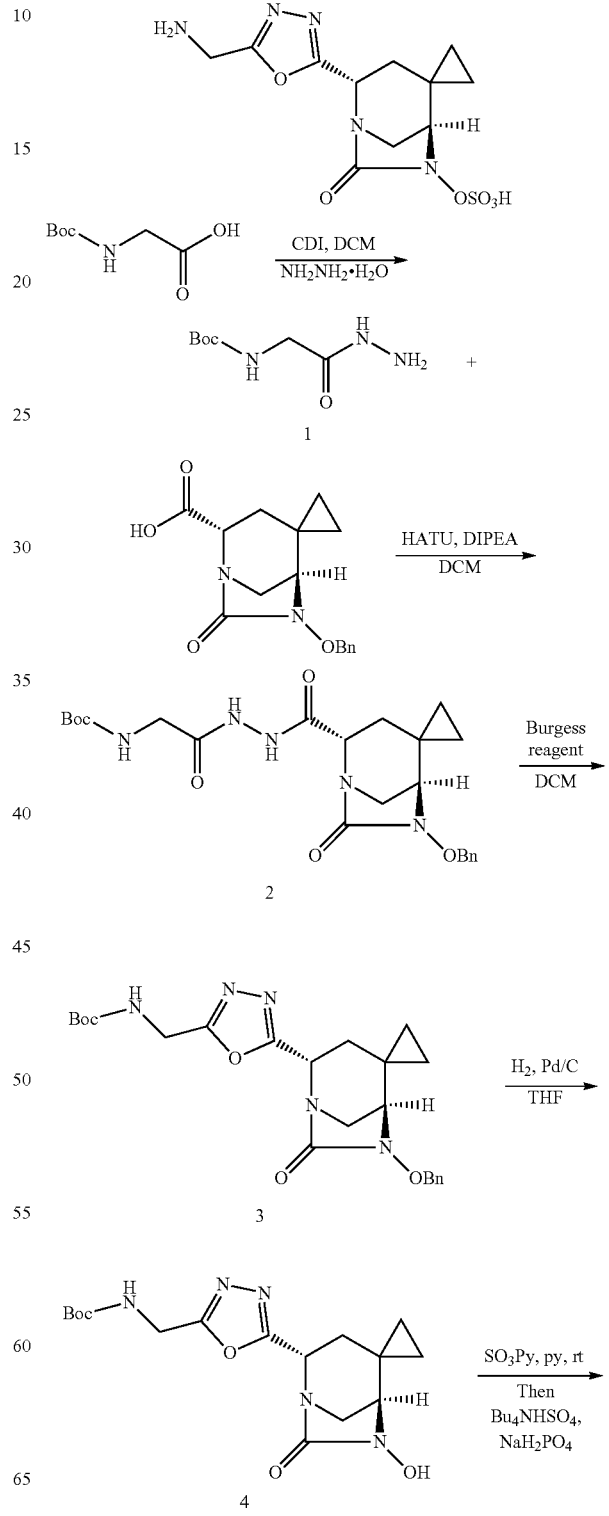

27

-continued

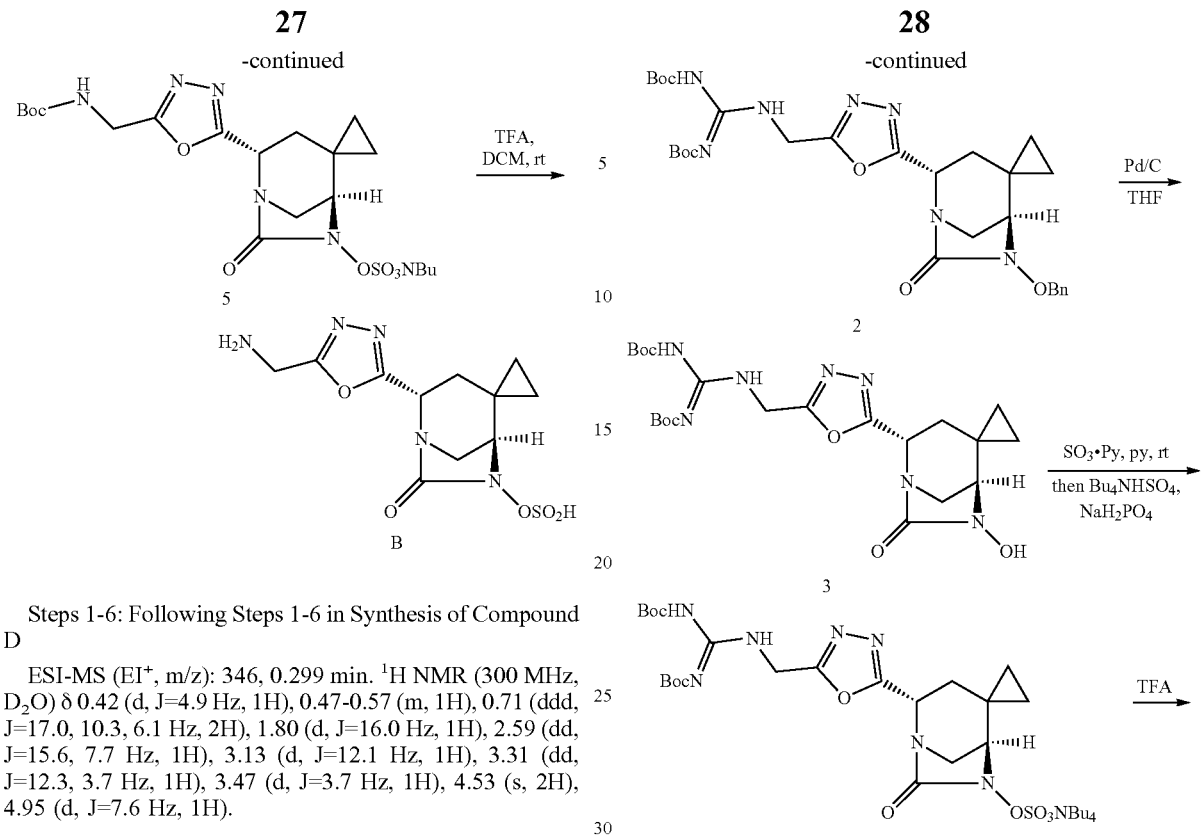

Steps 1-6: Following Steps 1-6 in Synthesis of Compound D

ESI-MS (EI⁺, m/z): 346, 0.299 min. $^1$H NMR (300 MHz, D$_2$O) δ 0.42 (d, J=4.9 Hz, 1H), 0.47-0.57 (m, 1H), 0.71 (ddd, J=17.0, 10.3, 6.1 Hz, 2H), 1.80 (d, J=16.0 Hz, 1H), 2.59 (dd, J=15.6, 7.7 Hz, 1H), 3.13 (d, J=12.1 Hz, 1H), 3.31 (dd, J=12.3, 3.7 Hz, 1H), 3.47 (d, J=3.7 Hz, 1H), 4.53 (s, 2H), 4.95 (d, J=7.6 Hz, 1H).

Example 3: Preparation of Compound C

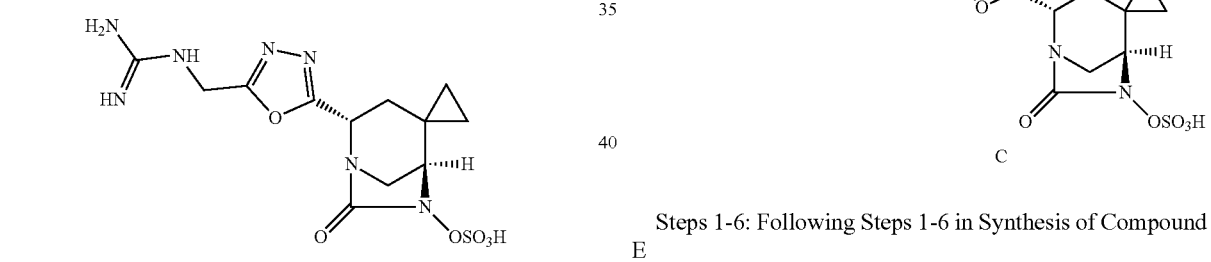

28

-continued

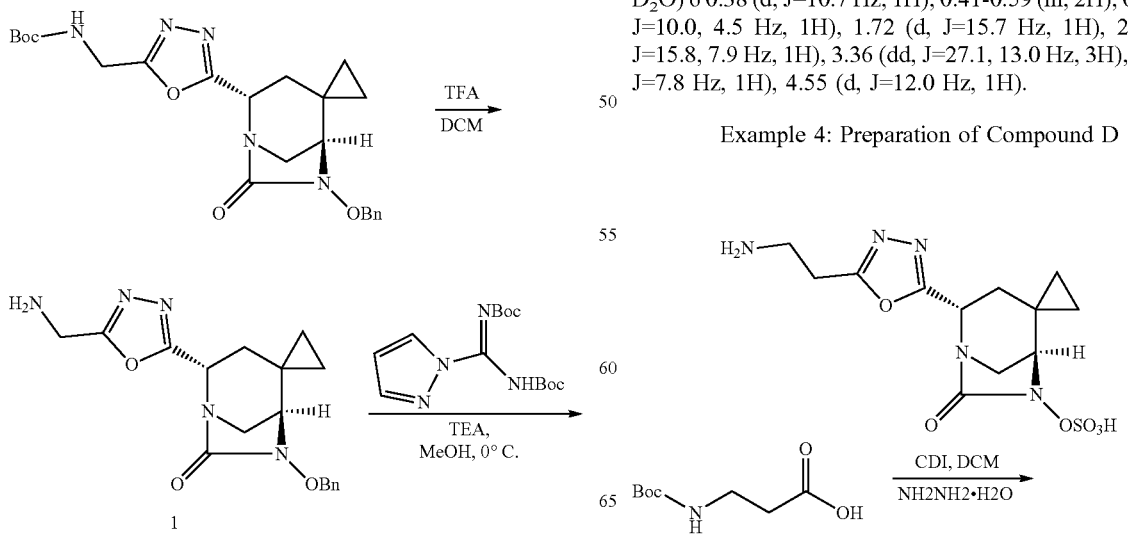

Steps 1-6: Following Steps 1-6 in Synthesis of Compound E

ESI-MS (EI⁺, m/z): 388, 0.173 min. $^1$H NMR (300 MHz, D$_2$O) δ 0.38 (d, J=10.7 Hz, 1H), 0.41-0.59 (m, 2H), 0.70 (dd, J=10.0, 4.5 Hz, 1H), 1.72 (d, J=15.7 Hz, 1H), 2.25 (dd, J=15.8, 7.9 Hz, 1H), 3.36 (dd, J=27.1, 13.0 Hz, 3H), 4.28 (d, J=7.8 Hz, 1H), 4.55 (d, J=12.0 Hz, 1H).

Example 4: Preparation of Compound D

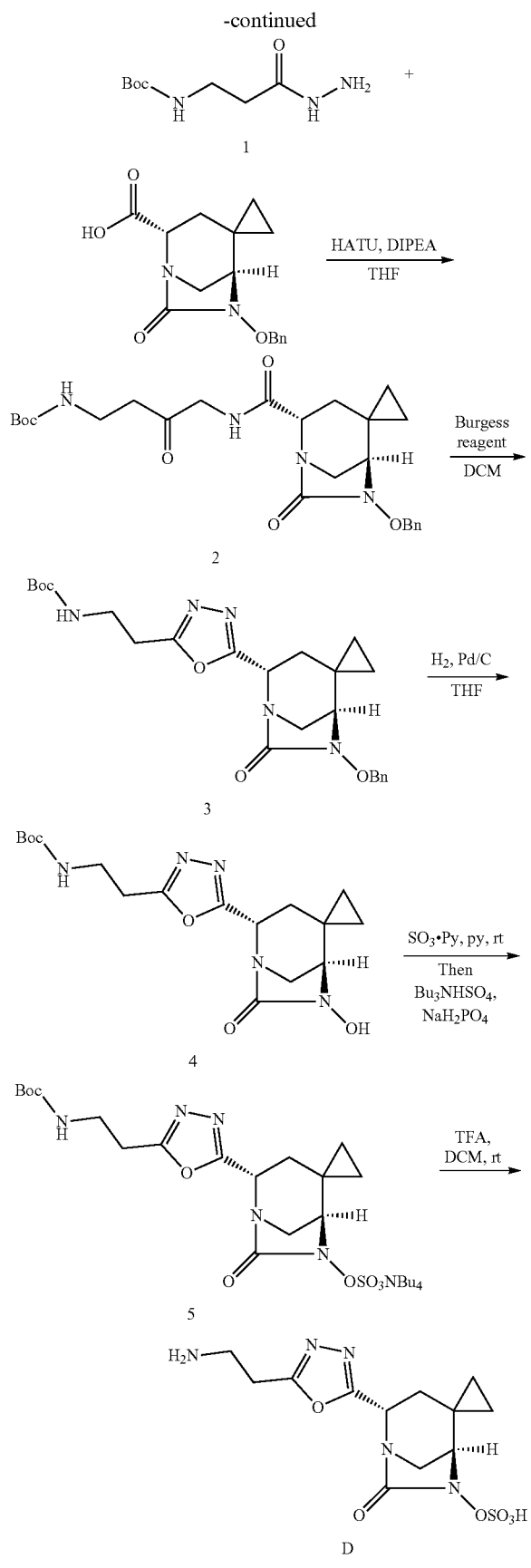

Step 1: Synthesis of Compound 1

To a 50-mL sealed tube was added a solution of 3-(tert-butoxycarbonylamino)propanoic acid (1.89 g, 9.99 mmol, 1.00 eq.) in DCM (20 mL), followed by CDI (1.94 g, 11.98 mmol, 1.20 eq.). The resulting solution was stirred for 1 h at room temperature. Then $NH_2NH_2.H_2O$ (1 mL, 10.00 eq.) was added for reaction of an additional 30 min at room temperature. The resulting mixture was concentrated under vacuum. The crude product was purified by Flash-Prep-HPLC with the following conditions: Column, C18 silica gel; mobile phase, $ACN:H_2O=5\%$ increasing to $ACN:H_2O=30\%$ within 20 min; Detector, UV 254 nm. This resulted in 2 g (99%) of tert-butyl 3-hydrazinyl-3-oxopropylcarbamate in the form of a white solid.

Step 2: Synthesis of Compound 2

To a 20-mL sealed tube were added a solution of Compound 1 (240 mg, 0.79 mmol, 1.00 eq.) in THF (10 mL), tert-butyl 3-hydrazinyl-3-oxopropylcarbamate (400 mg, 1.97 mmol, 2.00 eq.), HATU (760 mg, 2.00 mmol, 2.00 eq.), and DIEA (516 mg, 3.99 mmol, 3.00 eq.). The resulting solution was stirred for 120 min at room temperature. The solids were filtered out. The residue was purified by TLC with ethyl acetate/petroleum ether (1:1). This resulted in 240 mg (62%) of Compound 2 in the form of a white solid. ESI-MS (EI$^+$, m/z): 488, 0.790 min. $^1$H NMR (300 MHz, Methanol-d$_4$) δ 0.22 (dt, J=9.4, 4.6 Hz, 1H), 0.35-0.47 (m, 1H), 0.57 (ddt, J=18.5, 10.1, 5.5 Hz, 2H), 1.45 (s, 9H), 1.77 (d, J=15.0 Hz, 1H), 2.46 (t, J=6.7 Hz, 2H), 3.37 (d, J=4.0 Hz, 4H), 4.89-5.11 (m, 3H), 7.21-7.61 (m, 5H).

Step 3: Synthesis of Compound 3

To a 20-mL sealed tube were added a solution of Compound 2 (240 mg, 0.49 mmol, 1.00 eq.) in DCM (5 mL), and DIEA (130 mg, 1.01 mmol, 2.00 eq.). Burgess reagent (238 mg, 85.00 mmol, 2.00 eq.) was added last. The resulting solution was stirred for 20 h at room temperature. The residue was purified by TLC with ethyl acetate/petroleum ether (1:1). This resulted in 150 mg (65%) of Compound 3 in the form of a white solid. $^1$H NMR (300 MHz, Methanol-d$_4$) δ 0.30 (dd, J=9.7, 5.1 Hz, 1H), 0.40-0.55 (m, 1H), 0.65 (dt, J=10.9, 5.4 Hz, 1H), 0.76 (dt, J=9.1, 5.2 Hz, 1H), 1.40 (s, 8H), 1.77 (d, J=15.4 Hz, 1H), 2.61 (dd, J=14.9, 7.3 Hz, 1H), 2.95-3.20 (m, 4H), 3.42-3.55 (m, 2H), 4.91-5.11 (m, 3H), 7.27-7.62 (m, 5H).

Step 4: Synthesis of Compound 4

To a 50-mL round-bottom flask was added a solution of Compound 3 (150 mg, 0.32 mmol, 1.00 eq.) in THF (15 mL), followed by Pd/C (150 mg, 1.00 eq.). The resulting solution was stirred for 120 min at room temperature under $H_2$. The solids were filtered out. The resulting mixture was concentrated under vacuum. This resulted in 150 mg (124%) of Compound 4 in the form of a white solid. ESI-MS (EI$^+$, m/z): 380, 0.615 min.

Step 5: Synthesis of Compound 5

To a 10-mL sealed tube was added a solution of Compound 4 (150 mg, 0.40 mmol, 1.00 eq.) in DMF (5 mL), followed by SO3.Py (300 mg, 1.90 mmol, 2.00 eq.). The resulting solution was stirred for 20 h at room temperature. 10 mL of $NaH_2PO_4$ was added. Then $NBu_4HSO_4$ (100 mg) was added. The resulting solution was extracted with ethyl acetate (20 mL×2), and the organic phases were combined, dried over anhydrous sodium sulfate and concentrated under vacuum. This resulted in 100 mg (55%) of Compound 5 in the form of a white solid. ESI-MS (EI$^+$, m/z): 460, 0.725 min.

Step 6: Synthesis of Compound D

To a 20-mL sealed tube was added a solution of Compound 5 (100 mg, 0.22 mmol, 1.00 eq.) in DCM (6 mL), followed by TFA (2 mL, 3.00 eq.). The resulting solution was stirred for 120 min at 0° C. in an ice bath and the resulting mixture was concentrated under vacuum. The crude product was purified by Prep-HPLC with the following conditions: Column: XBridge Prep OBD C18 Column 19*250 mm, 5 um; Mobile Phase A: Water (0.1% FA), Mobile Phase B: ACN; Flow rate: 20 mL/min; Gradient: 2% B to 20% B in 7 min; 220, 254 nm; Rt: 6.38 min. This resulted in 2.5 mg (3%) of Compound D. ESI-MS (EI+, m/z): 360, 0.207 min. ¹H NMR (300 MHz, D₂O) δ 0.35-0.46 (m, 1H), 0.51 (td, J=7.2, 3.7 Hz, 1H), 0.71 (tt, J=10.4, 6.0 Hz, 2H), 1.79 (d, J=16.1 Hz, 1H), 2.57 (dd, J=15.7, 8.2 Hz, 1H), 3.15 (d, J=12.1 Hz, 1H), 3.24-3.40 (m, 3H), 3.41-3.54 (m, 3H), 4.91 (d, J=7.6 Hz, 1H).

Example 5: Synthesis of Compound E

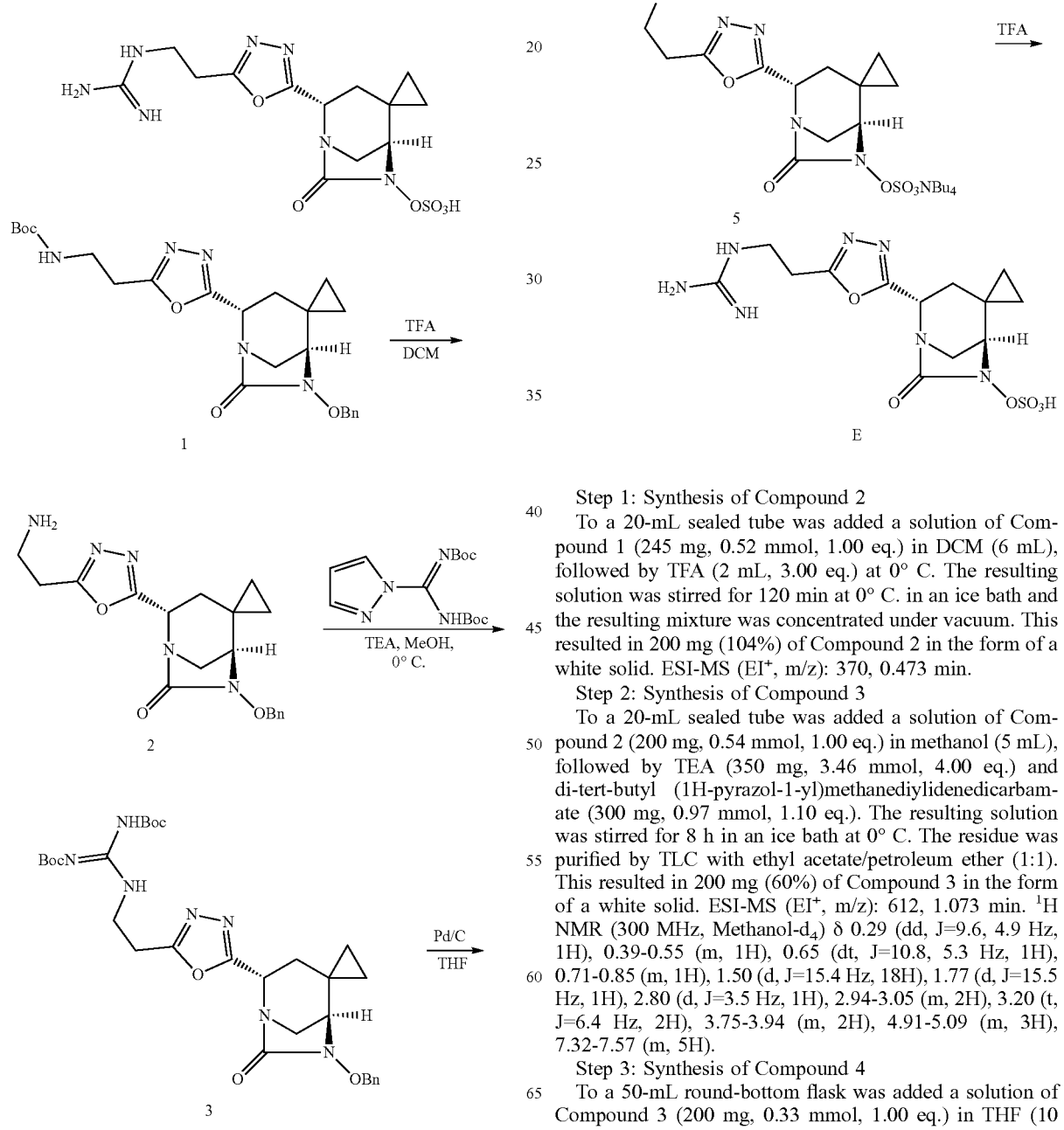

Step 1: Synthesis of Compound 2

To a 20-mL sealed tube was added a solution of Compound 1 (245 mg, 0.52 mmol, 1.00 eq.) in DCM (6 mL), followed by TFA (2 mL, 3.00 eq.) at 0° C. The resulting solution was stirred for 120 min at 0° C. in an ice bath and the resulting mixture was concentrated under vacuum. This resulted in 200 mg (104%) of Compound 2 in the form of a white solid. ESI-MS (EI+, m/z): 370, 0.473 min.

Step 2: Synthesis of Compound 3

To a 20-mL sealed tube was added a solution of Compound 2 (200 mg, 0.54 mmol, 1.00 eq.) in methanol (5 mL), followed by TEA (350 mg, 3.46 mmol, 4.00 eq.) and di-tert-butyl (1H-pyrazol-1-yl)methanediylidenedicarbamate (300 mg, 0.97 mmol, 1.10 eq.). The resulting solution was stirred for 8 h in an ice bath at 0° C. The residue was purified by TLC with ethyl acetate/petroleum ether (1:1). This resulted in 200 mg (60%) of Compound 3 in the form of a white solid. ESI-MS (EI+, m/z): 612, 1.073 min. ¹H NMR (300 MHz, Methanol-d₄) δ 0.29 (dd, J=9.6, 4.9 Hz, 1H), 0.39-0.55 (m, 1H), 0.65 (dt, J=10.8, 5.3 Hz, 1H), 0.71-0.85 (m, 1H), 1.50 (d, J=15.4 Hz, 18H), 1.77 (d, J=15.5 Hz, 1H), 2.80 (d, J=3.5 Hz, 1H), 2.94-3.05 (m, 2H), 3.20 (t, J=6.4 Hz, 2H), 3.75-3.94 (m, 2H), 4.91-5.09 (m, 3H), 7.32-7.57 (m, 5H).

Step 3: Synthesis of Compound 4

To a 50-mL round-bottom flask was added a solution of Compound 3 (200 mg, 0.33 mmol, 1.00 eq.) in THF (10 mL), followed by Pd/C (200 mg, 2.00 eq.). The resulting solution was stirred for 120 min at room temperature under H₂ (1 atm). The solids were filtered out. The resulting mixture was concentrated under vacuum. This resulted in 200 mg (117%) of Compound 4 in the form of a white solid. ESI-MS (EI⁺, m/z): 522, 0.865 min.

Step 4: Synthesis of Compound 5

To a 20-mL sealed tube was added a solution of Compound 4 (200 mg, 0.38 mmol, 1.00 eq.) in DMF (5 mL), followed by SO3.Py (361 mg, 7.00 eq.). The resulting solution was stirred for 20 h at room temperature, and the resulting mixture was concentrated under vacuum. The reaction was then quenched with 10 mL of NaH₂PO₄. Then NBu₄HSO₄ (100 mg) was added to the reaction mixture. The resulting solution was extracted with ethyl acetate (20 mL×2), and the organic phases were combined, dried over anhydrous sodium sulfate and concentrated under vacuum. This resulted in 100 mg (43%) of Compound 5 in the form of a white solid. ESI-MS (EI⁺, m/z): 602, 1.023 min.

Step 5: Synthesis of Compound E

To a 20-mL sealed tube was added a solution of Compound 5 (100 mg, 0.17 mmol, 1.00 eq.) in DCM (6 mL), followed by TFA (2 mL, 3.00 eq.) at 0° C. The resulting solution was stirred for 120 min in an ice bath at 0° C., and the resulting mixture was concentrated under vacuum. The crude product was purified by Prep-HPLC with the following conditions: Column: XBridge Prep OBD C18 Column 19*250 mm, 5 um; Mobile Phase A: Water (0.1% FA), Mobile Phase B: ACN; Flow rate: 20 mL/min; Gradient: 12% B to 23% B in 7 min; 220, 254 nm; Rt: 6.2 min. This resulted in 8 mg (12%) of Compound E. ESI-MS (EI⁺, m/z): 402, 0.418 min. ¹H NMR (300 MHz, D₂O) δ 0.34-0.47 (m, 1H), 0.47-0.58 (m, 1H), 0.70 (ddt, J=14.7, 10.4, 5.9 Hz, 2H), 1.77 (d, J=16.1 Hz, 1H), 2.57 (dd, J=16.5, 7.8 Hz, 1H), 3.21 (t, J=6.4 Hz, 2H), 3.25-3.37 (m, 1H), 3.46 (d, J=3.8 Hz, 1H), 3.64 (t, J=6.4 Hz, 2H), 4.90 (d, J=7.7 Hz, 1H).

Example 6: Preparation of Compound F

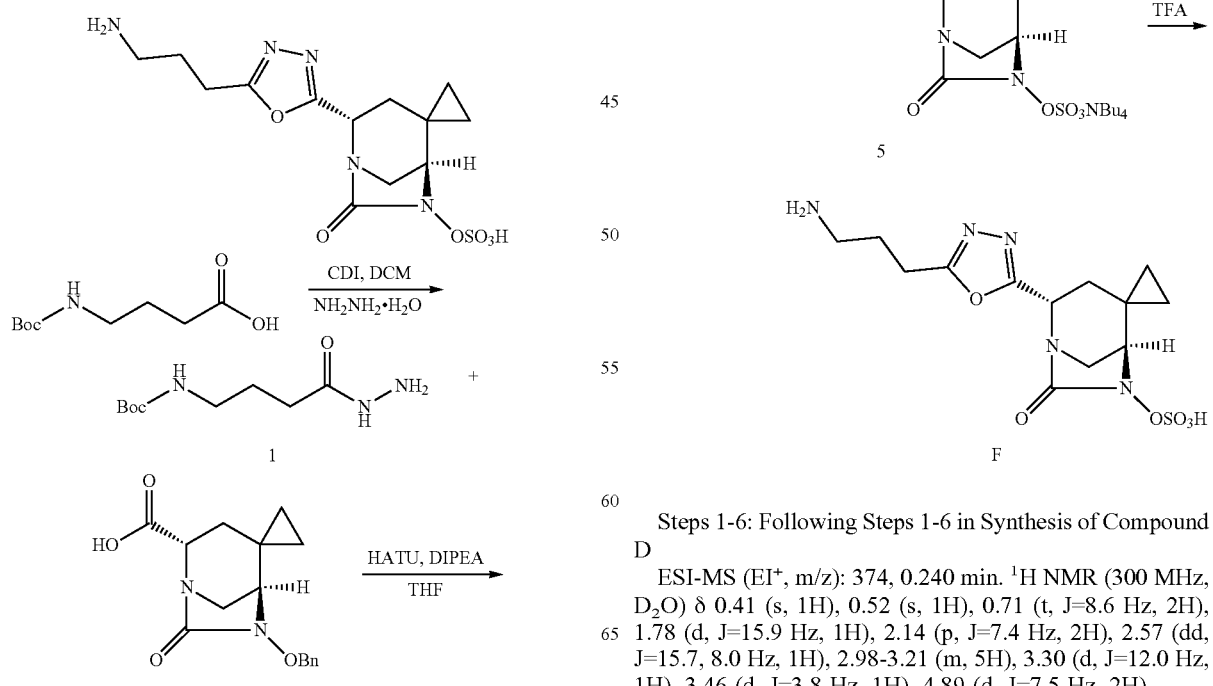

Steps 1-6: Following Steps 1-6 in Synthesis of Compound D

ESI-MS (EI⁺, m/z): 374, 0.240 min. ¹H NMR (300 MHz, D₂O) δ 0.41 (s, 1H), 0.52 (s, 1H), 0.71 (t, J=8.6 Hz, 2H), 1.78 (d, J=15.9 Hz, 1H), 2.14 (p, J=7.4 Hz, 2H), 2.57 (dd, J=15.7, 8.0 Hz, 1H), 2.98-3.21 (m, 5H), 3.30 (d, J=12.0 Hz, 1H), 3.46 (d, J=3.8 Hz, 1H), 4.89 (d, J=7.5 Hz, 2H).

Example 7: Preparation of Compound G
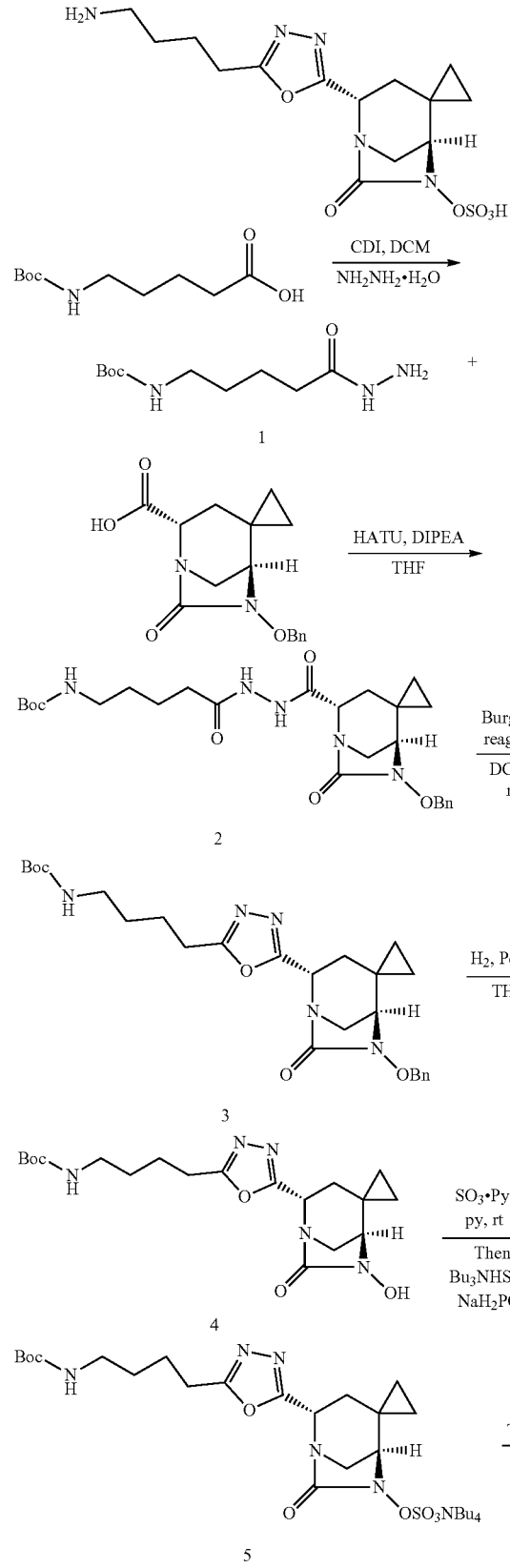
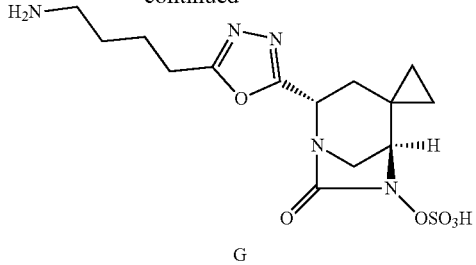
G
Steps 1-6: Following Steps 1-6 in Synthesis of Compound D
ESI-MS (EI⁺, m/z): 388, 0.273 min. ¹H NMR (300 MHz, D₂O) δ 0.42 (d, J=4.9 Hz, 1H), 0.47-0.58 (m, 1H), 0.70 (ddt, J=14.8, 10.4, 5.1 Hz, 2H), 1.73 (q, J=9.2, 7.9 Hz, 2H), 1.83 (dd, J=14.9, 7.9 Hz, 2H), 2.56 (dd, J=15.7, 8.0 Hz, 1H), 2.98 (dt, J=10.3, 7.4 Hz, 3H), 3.10 (d, J=12.1 Hz, 1H), 3.30 (dd, J=12.2, 3.7 Hz, 1H), 3.46 (d, J=3.7 Hz, 1H), 4.89 (d, J=7.8 Hz, 2H).
Example 8: Preparation of Compound H
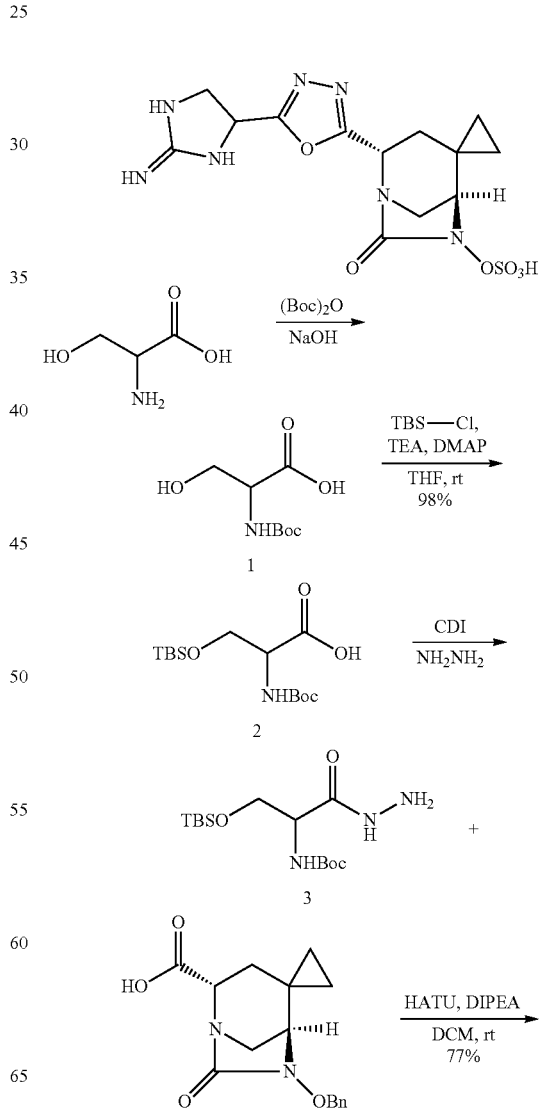

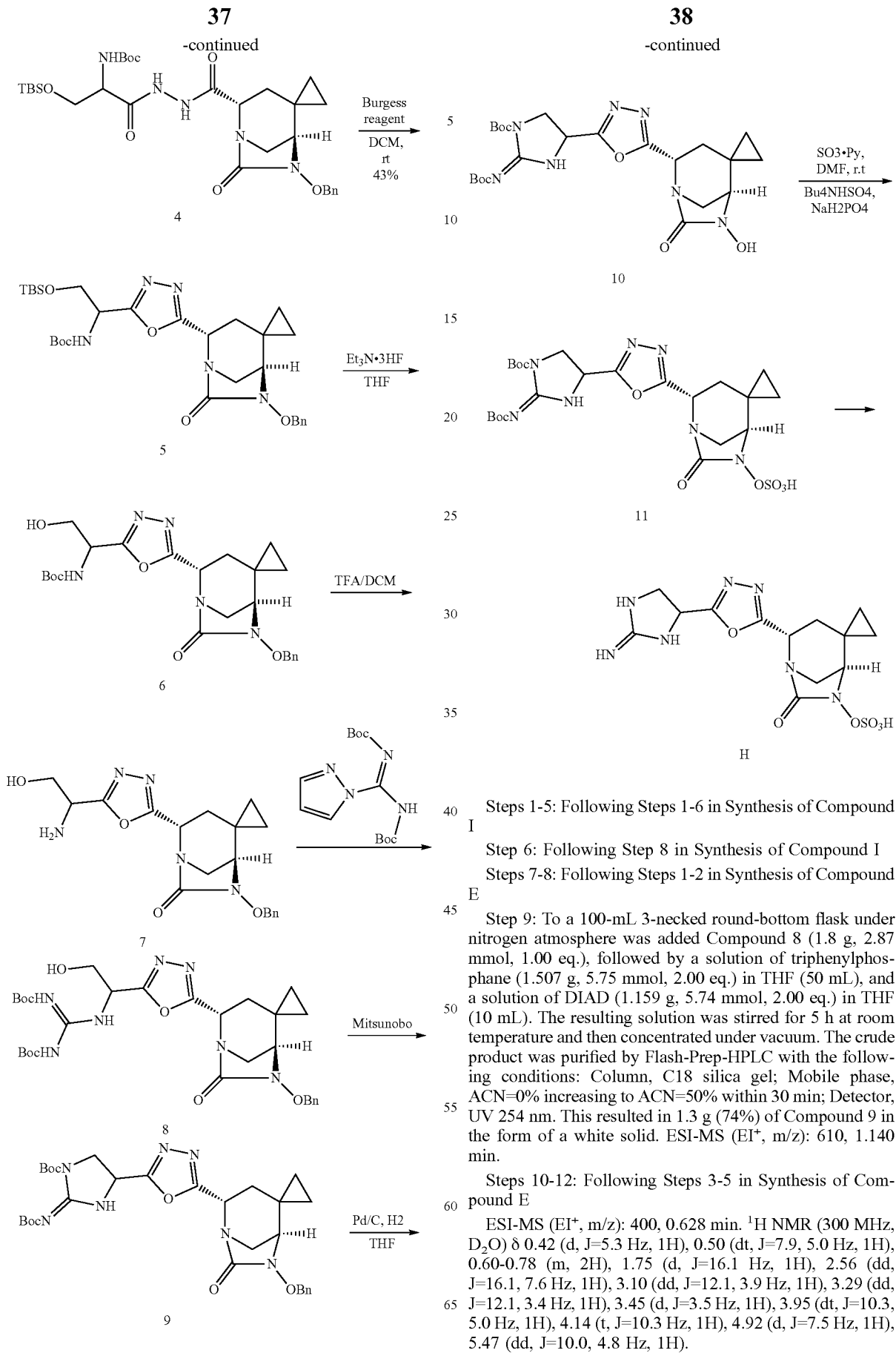

Steps 1-5: Following Steps 1-6 in Synthesis of Compound I

Step 6: Following Step 8 in Synthesis of Compound I

Steps 7-8: Following Steps 1-2 in Synthesis of Compound E

Step 9: To a 100-mL 3-necked round-bottom flask under nitrogen atmosphere was added Compound 8 (1.8 g, 2.87 mmol, 1.00 eq.), followed by a solution of triphenylphosphane (1.507 g, 5.75 mmol, 2.00 eq.) in THF (50 mL), and a solution of DIAD (1.159 g, 5.74 mmol, 2.00 eq.) in THF (10 mL). The resulting solution was stirred for 5 h at room temperature and then concentrated under vacuum. The crude product was purified by Flash-Prep-HPLC with the following conditions: Column, C18 silica gel; Mobile phase, ACN=0% increasing to ACN=50% within 30 min; Detector, UV 254 nm. This resulted in 1.3 g (74%) of Compound 9 in the form of a white solid. ESI-MS (EI$^+$, m/z): 610, 1.140 min.

Steps 10-12: Following Steps 3-5 in Synthesis of Compound E

ESI-MS (EI$^+$, m/z): 400, 0.628 min. $^1$H NMR (300 MHz, D$_2$O) δ 0.42 (d, J=5.3 Hz, 1H), 0.50 (dt, J=7.9, 5.0 Hz, 1H), 0.60-0.78 (m, 2H), 1.75 (d, J=16.1 Hz, 1H), 2.56 (dd, J=16.1, 7.6 Hz, 1H), 3.10 (dd, J=12.1, 3.9 Hz, 1H), 3.29 (dd, J=12.1, 3.4 Hz, 1H), 3.45 (d, J=3.5 Hz, 1H), 3.95 (dt, J=10.3, 5.0 Hz, 1H), 4.14 (t, J=10.3 Hz, 1H), 4.92 (d, J=7.5 Hz, 1H), 5.47 (dd, J=10.0, 4.8 Hz, 1H).

Example 9: Preparation of Compound I

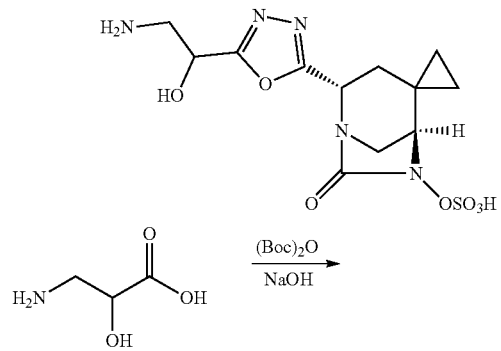

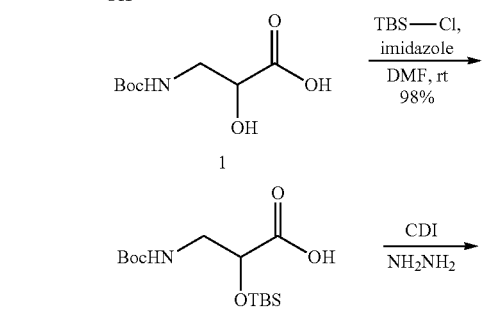

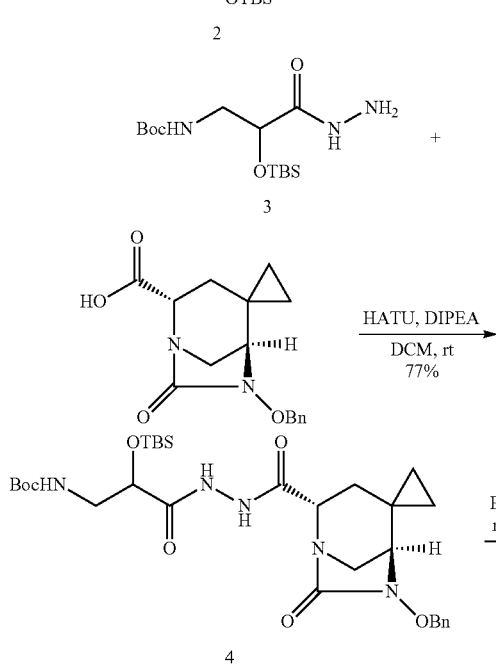

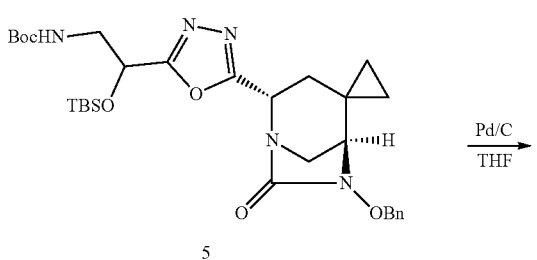

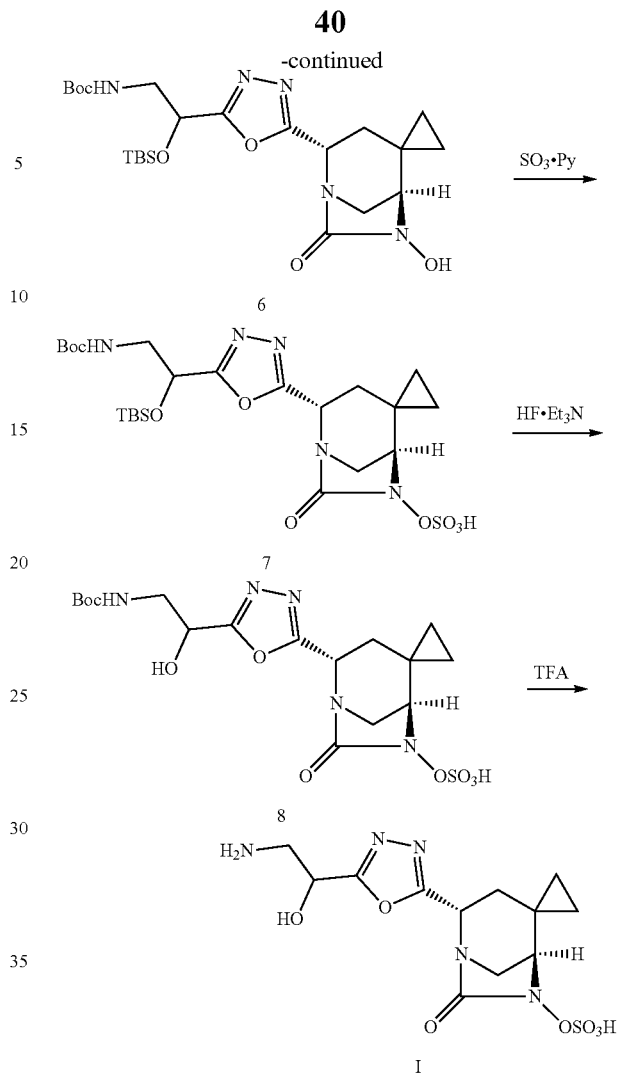

Step 1: Synthesis of Compound 1

To a 500-mL round-bottom flask was added a solution of 3-amino-2-hydroxypropanoic acid (5 g, 47.58 mmol, 1.00 eq.) in dioxane (200 mL), followed by a solution of NaOH (4 g, 100.01 mmol, 2.10 eq.) in water (100 mL). The resulting solution was stirred for 5 min at room temperature and then (Boc)$_2$O (12 g, 54.98 mmol, 1.14 eq.) was added. Then the resulting solution was stirred for 5 h at room temperature. The resulting mixture was washed with EA (200 mL×2). The pH of aqueous phase was adjusted to 1 with HCl (1 mol/L). The resulting solution was extracted with ethyl acetate (200 mL×3), and the organic phases were combined, dried over anhydrous sodium sulfate and concentrated under vacuum. This resulted in 8.6 g (88%) of 3-(tert-butoxycarbonylamino)-2-hydroxypropanoic acid in the form of a colorless oil. ESI-MS (EI$^+$, m/z+Na): 228, 0.793 min.

Step 2: Synthesis of Compound 2

To a 300-mL round-bottom flask were added a solution of 3-(tert-butoxycarbonylamino)-2-hydroxypropanoic acid (8.6 g, 41.91 mmol, 1.00 eq.) in THF (150 mL), TEA (0 mg, 3.00 eq.), and TBS-Cl (8.5 g, 56.40 mmol, 1.40 eq.). The resulting solution was stirred for 20 h at room temperature, and the pH was adjusted to 1 with HCl (1 mol/L). The resulting solution was extracted with ethyl acetate (300 mL×2), and the organic phases were combined, dried over anhydrous sodium sulfate and concentrated under vacuum. This resulted in 14 g (105%) of 3-(tert-butoxycarbonylamino)-2-(tert-butyldimethylsilyloxy)propanoic acid in the form of a white solid. ESI-MS (EI$^+$, m/z+Na): 342, 1.324 min.

Step 3: Synthesis of Compound 3

To a 100-mL round-bottom flask were added a solution of 3-(tert-butoxycarbonylamino)-2-(tert-butyldimethylsilyloxy)propanoic acid (7 g, 21.91 mmol, 1.00 eq.) in DCM (50 mL), and CDI (5.34 g, 32.96 mmol, 1.50 eq.). The resulting solution was stirred for 120 min at room temperature, and then hydrazine (11 g, 220.00 mmol, 10.00 eq.) was added. Then the resulting solution was stirred for 60 min at room temperature, and the resulting mixture was concentrated under vacuum. The crude product was purified by Flash-Prep-HPLC with the following conditions: Column, C18 silica gel; Mobile phase, ACN increasing to ACN=50% within 30 min; Detector, UV 254 nm. This resulted in 2.86 g (39%) of tert-butyl 2-tert-butyldimethylsilyloxy)-3-hydrazinyl-3-oxopropylcarbamate in the form of a white solid. ESI-MS (EI$^+$, m/z): 334, 1.081 min.

Step 4: Synthesis of Compound 4

To a 20-mL sealed tube were added Compound 3 (364 mg, 1.20 mmol, 1.00 eq.), tert-butyl 2-(tert-butyldimethylsilyloxy)-3-hydrazinyl-3-oxopropylcarbamate (442 mg, 1.33 mmol, 1.10 eq.), HATU (912 mg, 2.40 mmol, 2.00 eq.), and a solution of DIPEA (645 mg, 5.00 mmol, 4.00 eq.) in THF (10 mL). The resulting solution was stirred for 2 h at room temperature. The solids were filtered out. The residue was purified by TLC with ethyl acetate/petroleum ether (1/1). This resulted in 730 mg (98%) of Compound 4 in the form of a white solid. ESI-MS (EI$^+$, m/z+): 618, 1.361 min.

Step 5: Synthesis of Compound 5

To a 20-mL sealed tube was added a solution of Compound 4 (730 mg, 1.18 mmol, 1.00 eq.) in DCM (10 mL), followed by DIEA (915 mg, 3.00 eq.) and Burgess reagent (1126 mg, 3.00 eq.). The resulting solution was stirred for 20 h at room temperature. The residue was purified by TLC with ethyl acetate/petroleum ether (1/1). This resulted in 450 mg (63%) of Compound 5 in the form of a white solid. ESI-MS (EI$^+$, m/z+): 600, 1.441 min.

Step 6: Synthesis of Compound 6

To a 50-mL round-bottom flask was added a solution of Compound 5 (900 mg, 1.50 mmol, 1.00 eq.) in THF (20 mL), followed by Pd/C (100 mg, 0.10 eq.). The resulting solution was stirred for 2 h at room temperature under H$_2$. The solids were filtered out. The resulting mixture was concentrated under vacuum. This resulted in 700 mg (92%) of Compound 6 in the form of a white solid. ESI-MS (EI$^+$, m/z+): 510, 1.246 min.

Step 7: Synthesis of Compound 7

To a 20-mL sealed tube was added a solution of Compound 6 (700 mg, 1.37 mmol, 1.00 eq.) in DMF (5 mL), followed by SO3.Py (1.1 g, 6.96 mmol, 5.00 eq.). The resulting solution was stirred for 20 h at room temperature. The crude product was purified by Flash-Prep-HPLC with the following conditions: Column, C18 silica gel; Mobile phase, ACN increasing to ACN=50% within 30 min; Detector, UV 254 nm. This resulted in 500 mg (62%) of Compound 7 in the form of a light yellow solid. ESI-MS (EI$^+$, m/z+Na): 590, 1.336 min.

Step 8: Synthesis of Compound 8

To a 50-mL round-bottom flask was added a solution of Compound 7 (500 mg, 0.85 mmol, 1.00 eq.) in THF (10 mL), followed by 3HF.Et$_3$N (4 mL, 10.00 eq.). The resulting solution was stirred for 20 h at room temperature. The crude product was purified by Flash-Prep-HPLC with the following conditions: Column, C18 silica gel; Mobile phase, CAN increasing to ACN=50% within 30 min; Detector, UV 254 nm. This resulted in 300 mg (74%) of Compound 8 in the form of a white solid. ESI-MS (EI$^+$, m/z+): 476, 0.861 min.

Step 9: Synthesis of Compound I

To a 50-mL round-bottom flask was added a solution of Compound 8 (300 mg, 0.63 mmol, 1.00 eq.) in DCM (10 mL), followed by TFA (3 mL, 10.00 eq.). The resulting solution was stirred for 120 min at 0° C., and the resulting mixture was concentrated under vacuum. The crude product was purified by Prep-HPLC with the following conditions: Column: XBridge Prep OBD C18 Column 19*250 mm, 5 um; Mobile Phase A: Water (0.1% FA), Mobile Phase B: ACN; Flow rate: 20 mL/min; Gradient: 2% B to 18% B in 7 min; 254, 220 nm; Rt: 6.25 min. This resulted in 100 mg (42%) of Compound I. ESI-MS (EI$^+$, m/z+): 376, 0.123 min. $^1$H NMR (300 MHz, D$_2$O) δ 0.27-0.42 (m, 1H), 0.48 (tt, J=9.2, 5.3 Hz, 1H), 0.67 (ddt, J=14.7, 10.4, 5.1 Hz, 2H), 1.77 (d, J=16.0 Hz, 1H), 2.55 (dd, J=15.9, 7.7 Hz, 1H), 3.11 (d, J=12.1 Hz, 1H), 3.28 (dd, J=12.1, 3.7 Hz, 1H), 3.38-3.49 (m, 2H), 3.54 (dd, J=13.4, 3.9 Hz, 1H), 4.91 (d, J=7.6 Hz, 1H), 5.28 (dd, J=8.4, 3.9 Hz, 1H).

Example 10: Preparation of Compound J

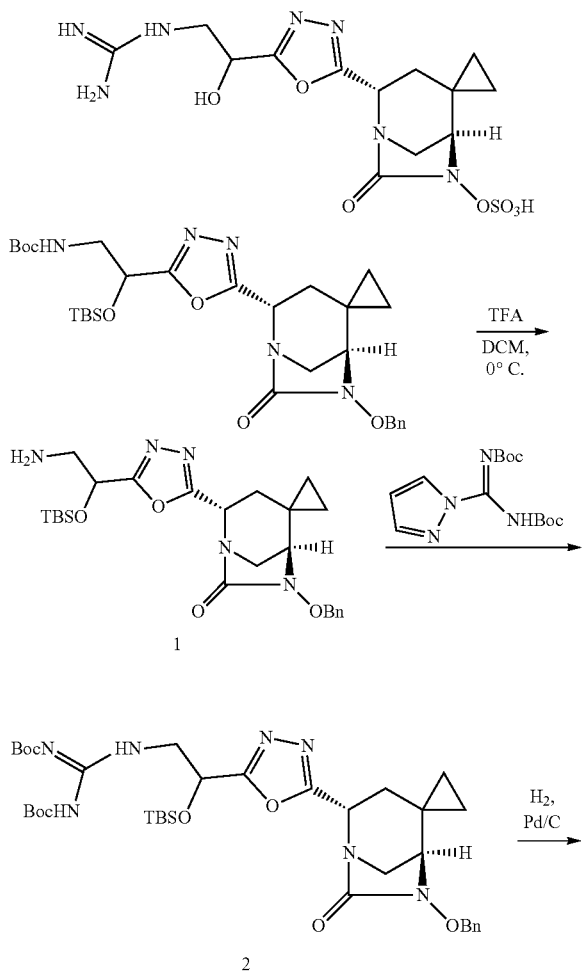

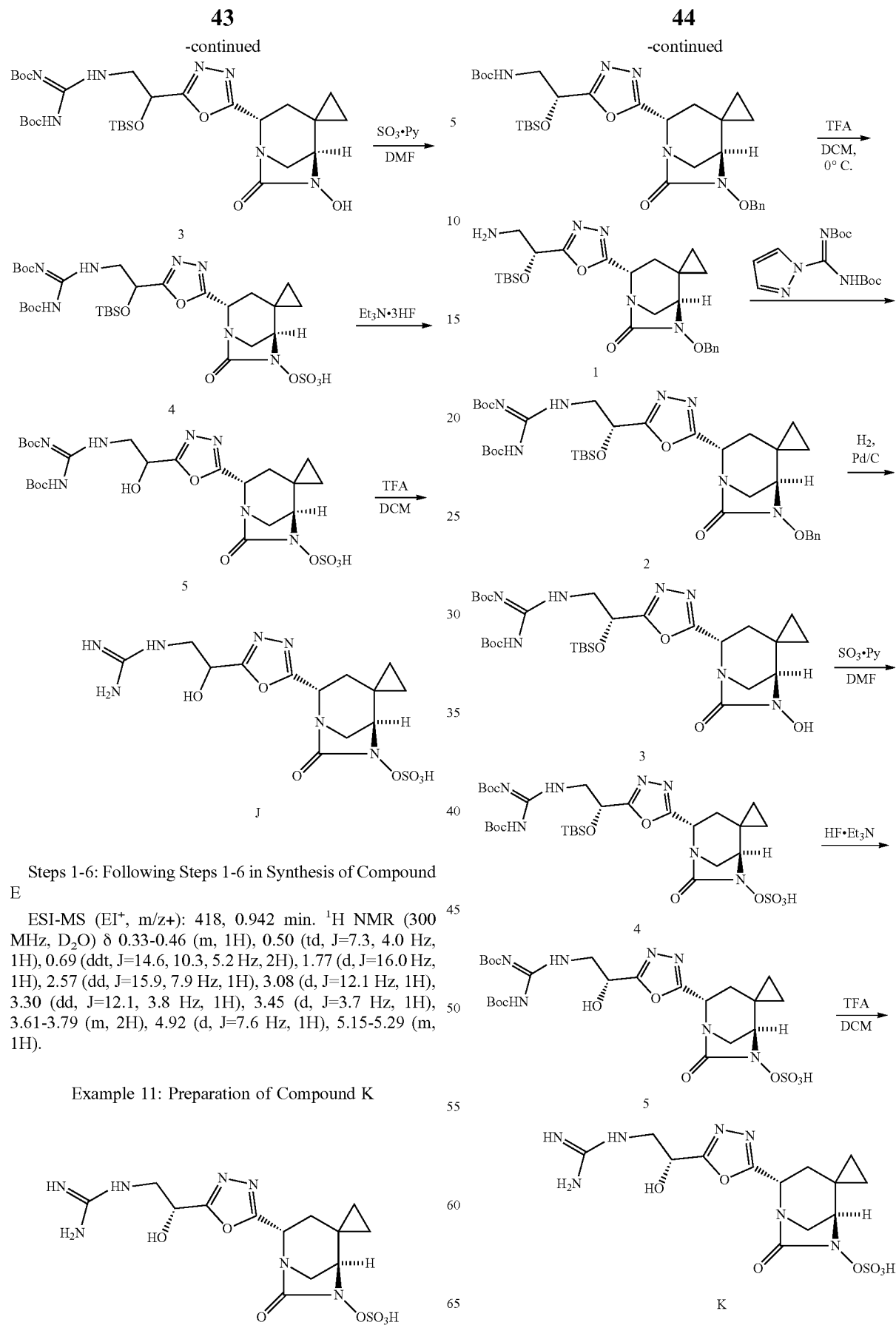
Steps 1-6: Following Steps 1-6 in Synthesis of Compound E
ESI-MS (EI+, m/z+): 418, 0.942 min. $^1$H NMR (300 MHz, D$_2$O) δ 0.33-0.46 (m, 1H), 0.50 (td, J=7.3, 4.0 Hz, 1H), 0.69 (ddt, J=14.6, 10.3, 5.2 Hz, 2H), 1.77 (d, J=16.0 Hz, 1H), 2.57 (dd, J=15.9, 7.9 Hz, 1H), 3.08 (d, J=12.1 Hz, 1H), 3.30 (dd, J=12.1, 3.8 Hz, 1H), 3.45 (d, J=3.7 Hz, 1H), 3.61-3.79 (m, 2H), 4.92 (d, J=7.6 Hz, 1H), 5.15-5.29 (m, 1H).
Example 11: Preparation of Compound K Steps 1-6: Following Steps 1-6 in Synthesis of Compound E ESI-MS (EI+, m/z+): 418, 0.716 min. $^1$H NMR (300 MHz, D$_2$O) δ 0.41 (d, J=5.1 Hz, 1H), 0.45-0.58 (m, 1H), 0.69 (ddt, J=14.7, 10.3, 5.2 Hz, 1H), 1.78 (d, J=16.0 Hz, 1H), 2.58 (dd, J=16.1, 7.8 Hz, 1H), 3.08 (d, J=12.1 Hz, 1H), 3.30 (dd, J=12.0, 3.7 Hz, 1H), 3.46 (d, J=3.6 Hz, 1H), 3.63-3.81 (m, 2H), 4.92 (d, J=7.5 Hz, 1H), 5.17-5.25 (m, 1H).

Example 12: Preparation of Compound L

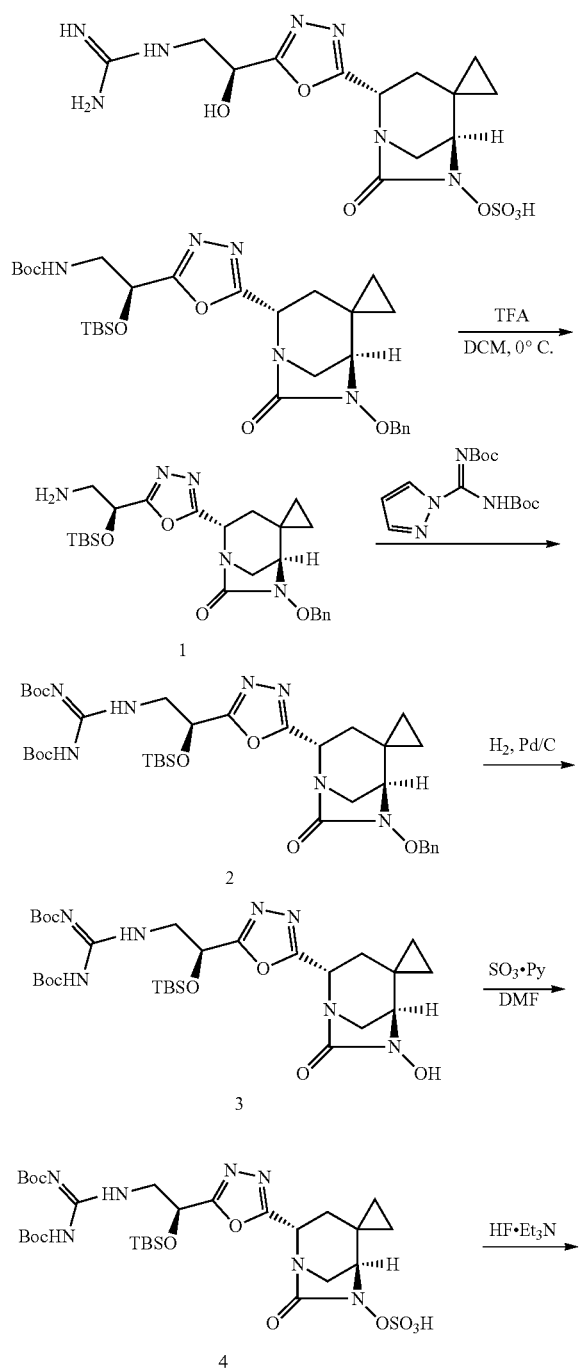

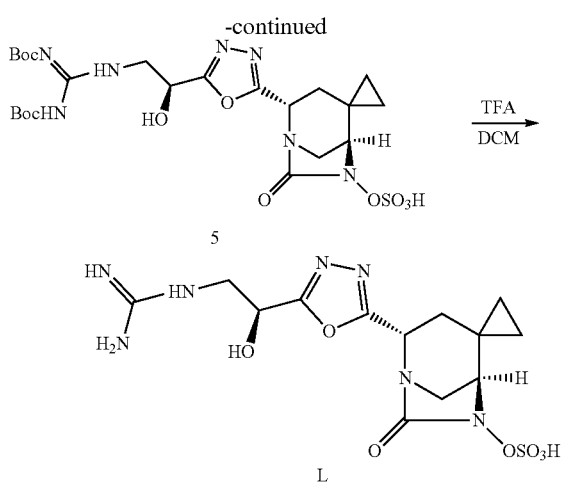

Steps 1-6: Following Steps 1-6 in Synthesis of Compound E

ESI-MS (EI+, m/z+): 418, 0.702 min. $^1$H NMR (300 MHz, D$_2$O) δ 0.32-0.45 (m, 1H), 0.45-0.57 (m, 1H), 0.70 (ddt, J=15.1, 10.4, 5.2 Hz, 2H), 1.78 (d, J=16.0 Hz, 1H), 2.58 (dd, J=15.8, 7.7 Hz, 1H), 3.09 (d, J=12.1 Hz, 1H), 3.31 (dd, J=12.3, 4.2 Hz, 1H), 3.46 (d, J=3.7 Hz, 1H), 3.64-3.78 (m, 2H), 4.93 (d, J=7.6 Hz, 1H), 5.20 (t, J=5.2 Hz, 1H).

Example 13: Preparation of Compound M

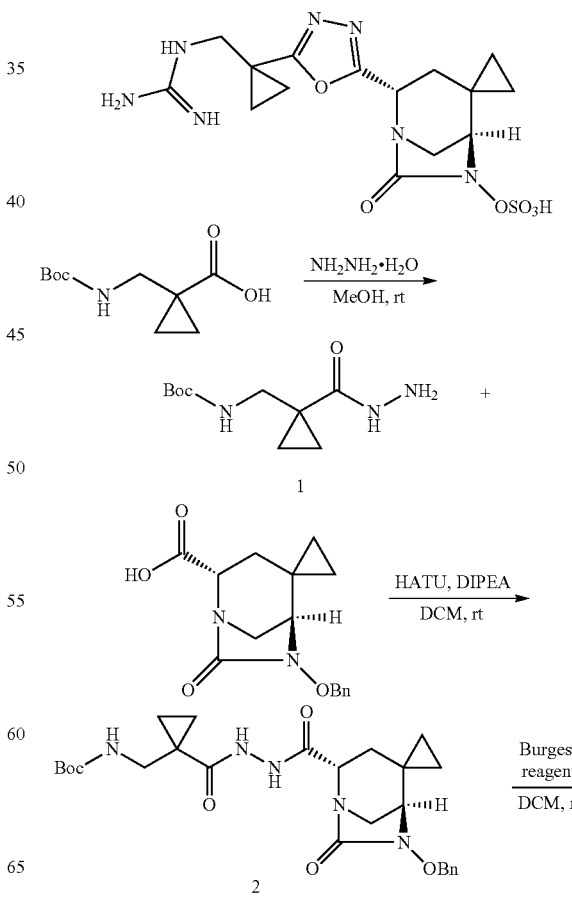

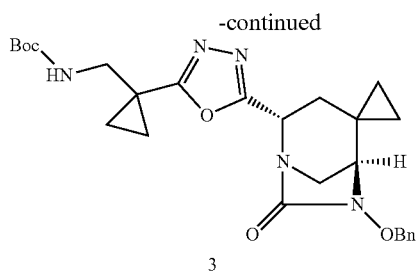
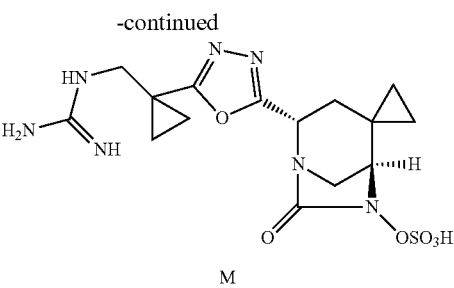
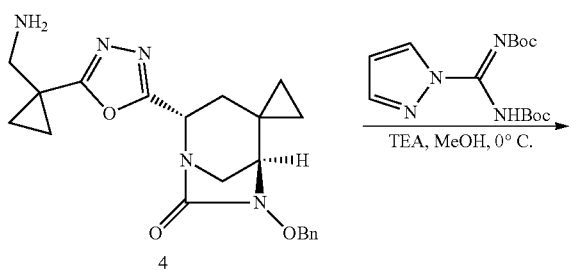
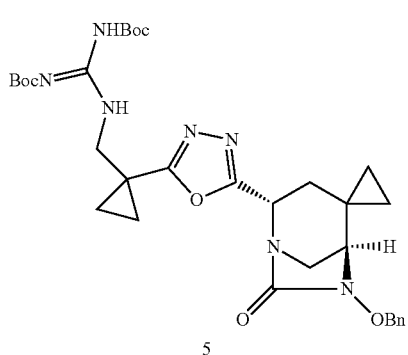
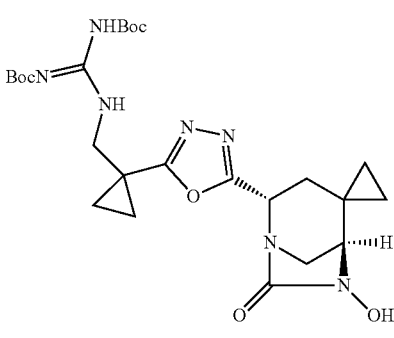
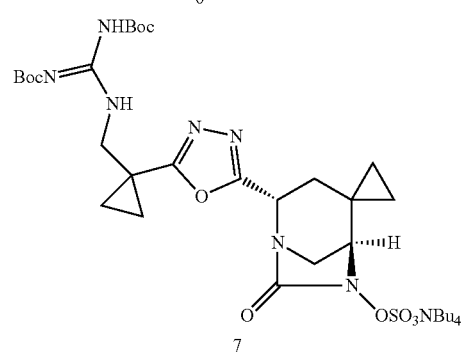
Steps 1-3: Following Steps 1-3 in Synthesis of Compound D
Steps 4-8: Following Steps 1-5 in Synthesis of Compound E
ESI-MS (EI+, m/z+): 428, 0.323 min. $^1$H NMR (400 MHz, D$_2$O) δ 0.37 (dd, J=9.5, 4.9 Hz, 1H), 0.41-0.52 (m, 1H), 0.60 (dt, J=10.5, 5.1 Hz, 1H), 0.68 (dt, J=9.6, 5.1 Hz, 1H), 1.15-1.25 (m, 2H), 1.30-1.43 (m, 2H), 1.68 (d, J=16.1 Hz, 1H), 2.50 (dd, J=16.0, 7.8 Hz, 1H), 3.04 (d, J=12.1 Hz, 1H), 3.23 (dd, J=12.2, 3.5 Hz, 1H), 3.40 (d, J=3.7 Hz, 1H), 3.55 (s, 2H), 4.80 (d, J=7.6 Hz, 1H).
Example 14: Preparation of Compound N
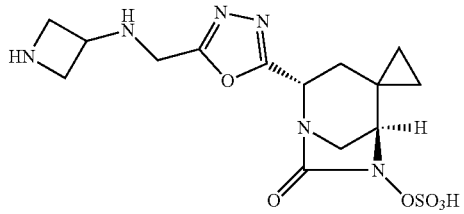
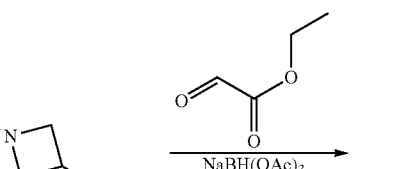
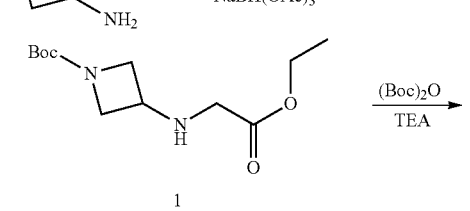
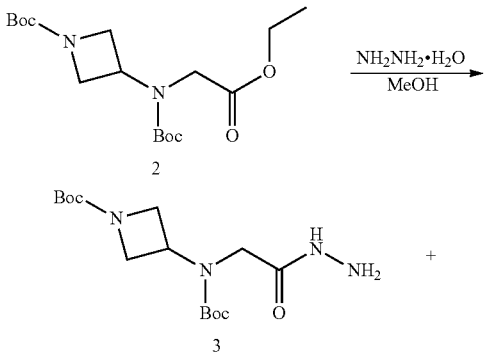

-continued
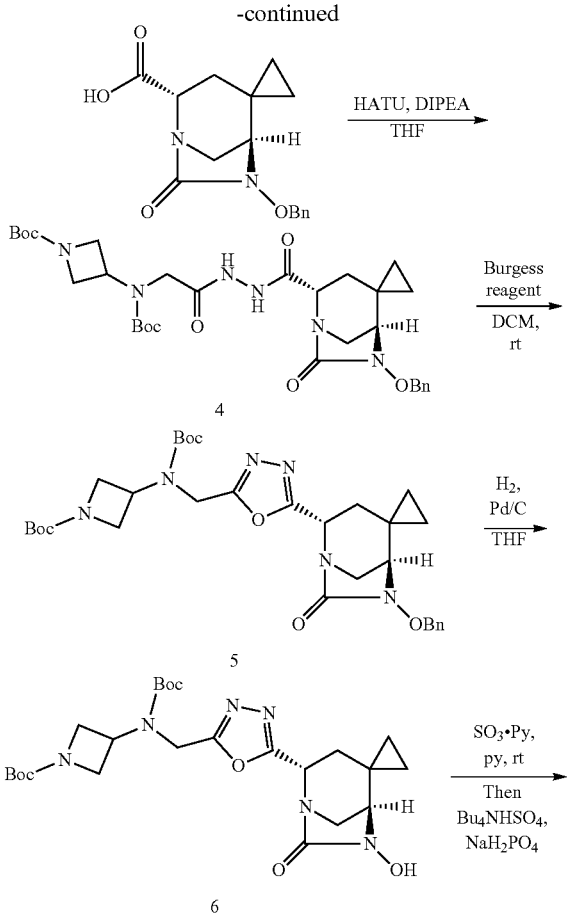
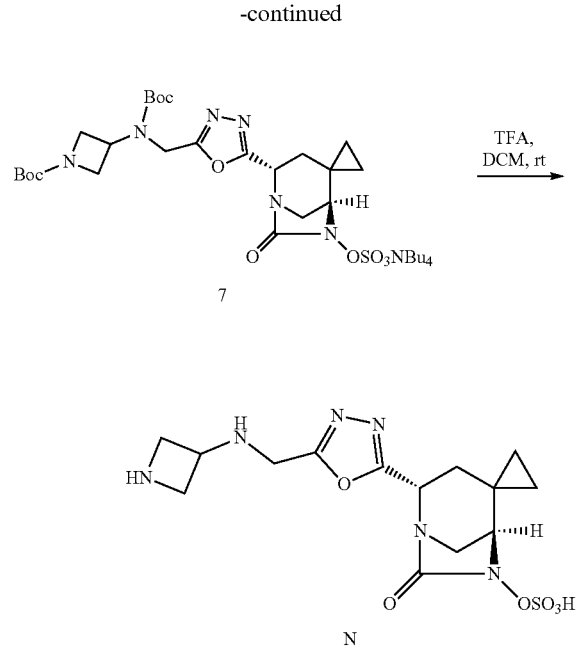
Steps 3-8: Following Steps 1-6 in Synthesis of Compound D
ESI-MS (EI⁺, m/z+): 401, 0.223 min. $^{1}$H NMR (300 MHz, D$_2$O) δ 0.42 (d, J=4.9 Hz, 1H), 0.45-0.58 (m, 1H), 0.62-0.78 (m, 2H), 1.78 (d, J=15.9 Hz, 1H), 2.57 (dd, J=16.0, 7.9 Hz, 1H), 3.10 (d, J=12.1 Hz, 1H), 3.21-3.37 (m, 1H), 3.46 (d, J=3.7 Hz, 1H), 3.81-4.01 (m, 2H), 4.07 (s, 2H), 4.10-4.29 (m, 2H), 4.92 (d, J=7.6 Hz, 1H).
Example 15: Preparation of Compound O
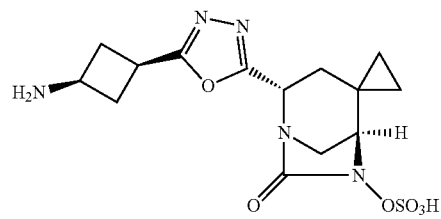
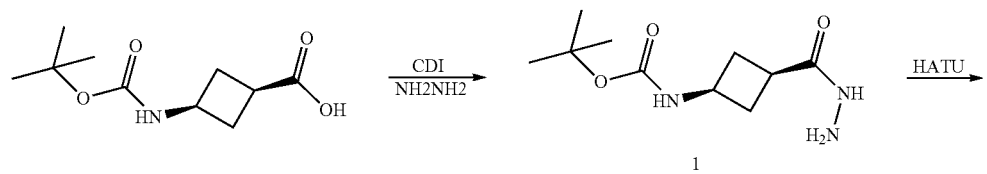
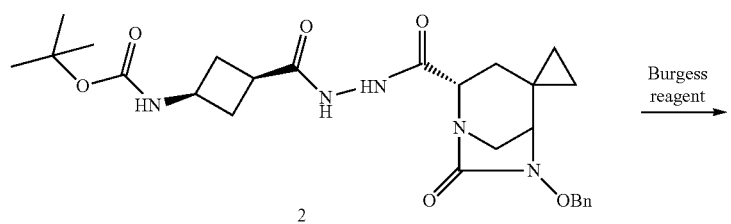

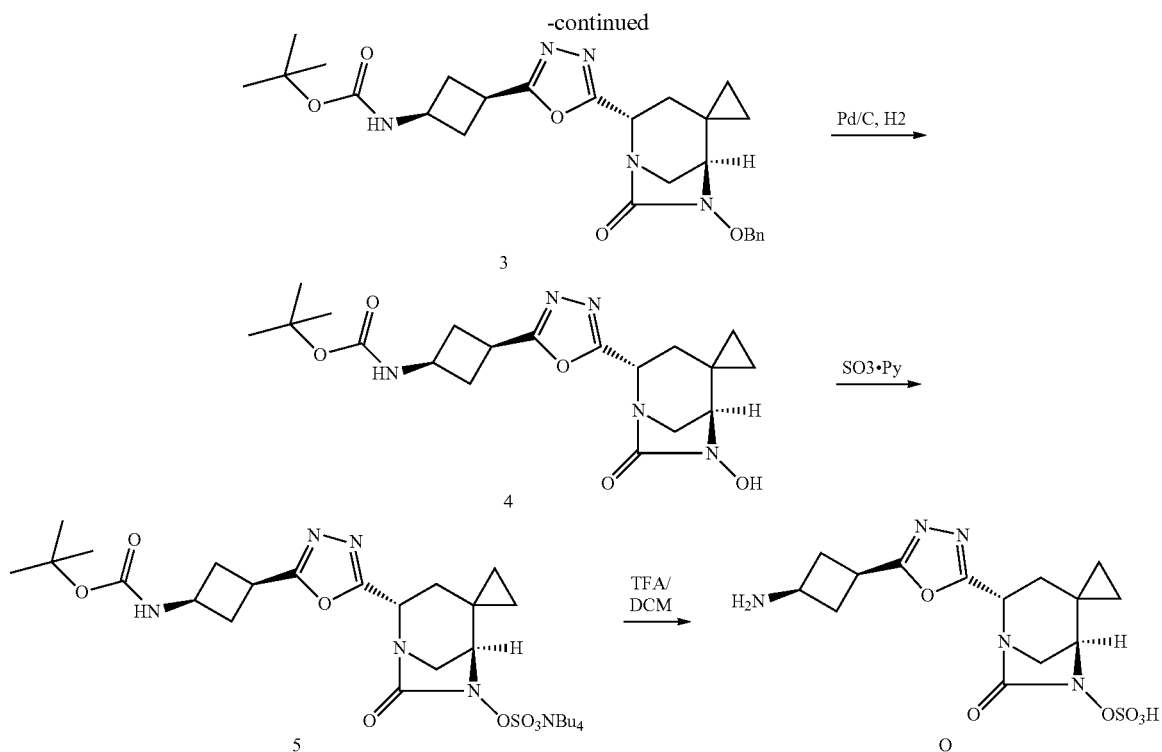
Steps 1-6: Following Steps 1-6 in Synthesis of Compound D
ESI-MS (EI+, m/z+): 386, 0.642 min. ¹H NMR (300 MHz, D₂O) δ 0.30-0.45 (m, 1H), 0.48 (td, J=7.5, 6.8, 3.6 Hz, 1H), 0.68 (ddt, J=17.5, 10.3, 6.0 Hz, 2H), 1.76 (d, J=16.0 Hz, 1H), 2.54 (dd, J=15.6, 7.7 Hz, 3H), 2.72-2.91 (m, 2H), 3.09 (d, J=12.1 Hz, 1H), 3.27 (dd, J=12.2, 3.6 Hz, 1H), 3.44 (d, J=3.6 Hz, 1H), 3.67 (ddd, J=18.0, 9.8, 8.2 Hz, 1H), 3.91 (p, J=8.7 Hz, 1H), 4.87 (d, J=7.6 Hz, 1H).
Example 16: Preparation of Compound P
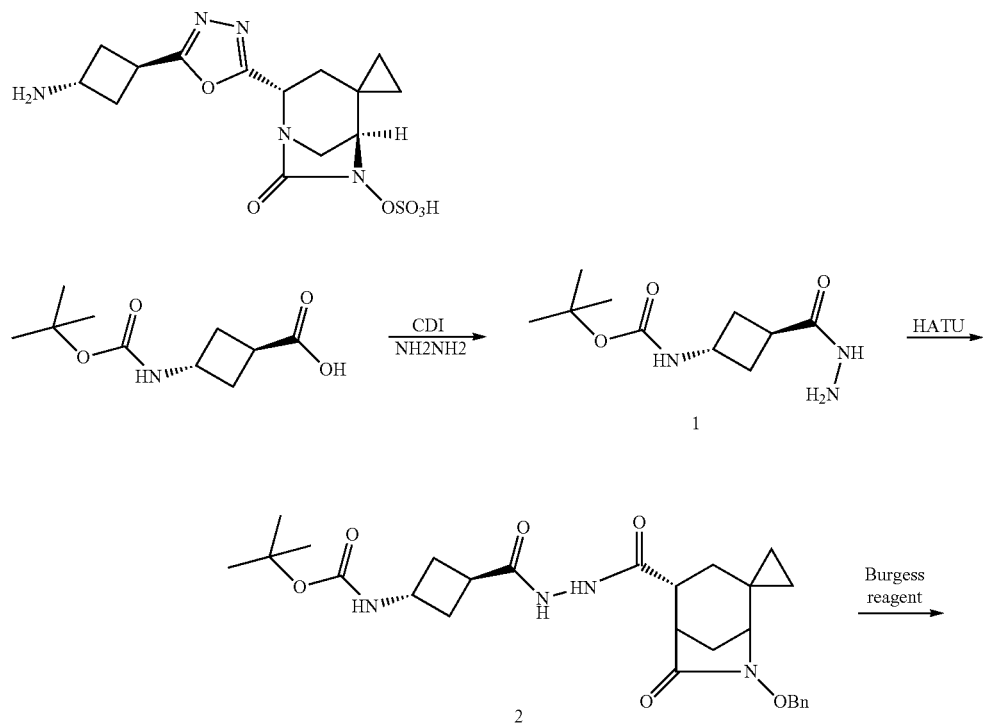

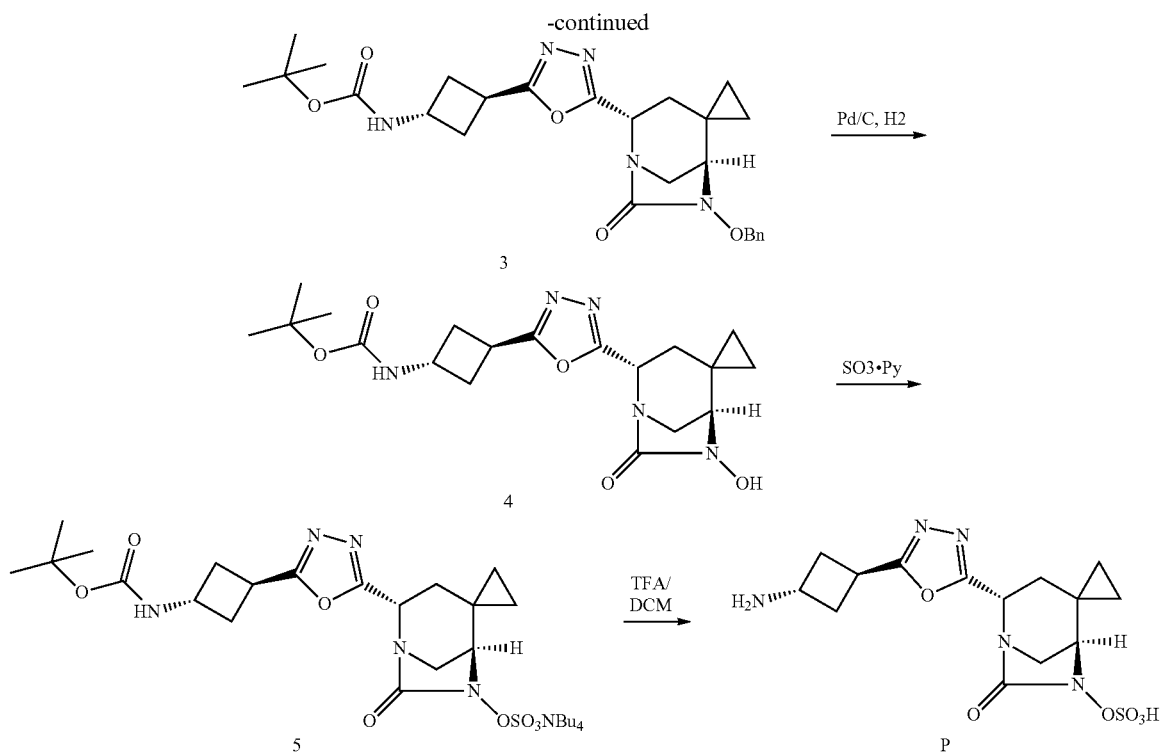
Steps 1-6: Following Steps 1-6 in Synthesis of Compound D
ESI-MS (EI⁺, m/z+): 386, 2.005 min. ¹H NMR (300 MHz, D$_2$O) δ 0.33-0.45 (m, 1H), 0.45-0.55 (m, 1H), 0.68 (ddt, J=14.5, 10.3, 5.1 Hz, 2H), 1.76 (d, J=16.0 Hz, 1H), 2.55 (dd, J=16.3, 8.0 Hz, 1H), 2.72 (dd, J=10.5, 6.4 Hz, 4H), 3.10 (d, J=12.1 Hz, 1H), 3.28 (dd, J=12.2, 3.9 Hz, 1H), 3.44 (d, J=3.7 Hz, 1H), 3.84-3.99 (m, 1H), 3.99-4.18 (m, 1H), 4.88 (d, J=7.6 Hz, 1H).
Example 17: Preparation of Compound Q
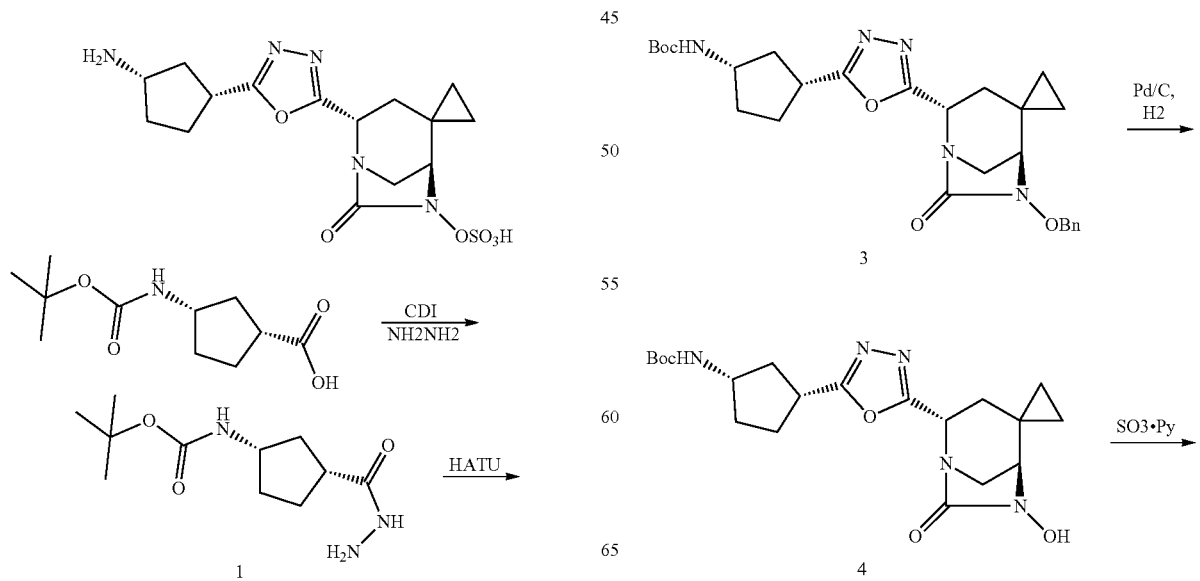

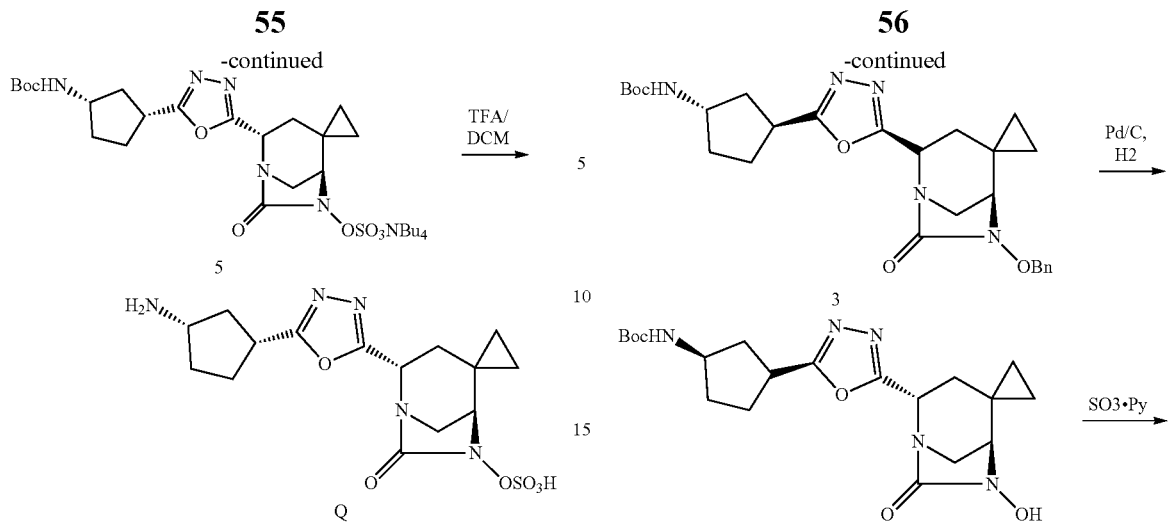

Steps 1-6: Following Steps 1-6 in Synthesis of Compound D

ESI-MS (EI+, m/z+): 400, 682 min. ¹H NMR (300 MHz, D₂O) δ 0.40 (t, J=12 Hz, 1H), 0.49 (tt, J=8.7, 5.2 Hz, 1H), 0.69 (ddt, J=14.8, 10.2, 5.0 Hz, 2H), 1.71-1.90 (m, 2H), 1.90-2.14 (m, 2H), 2.14-2.30 (m, 2H), 2.50-2.62 (m, 1H), 2.67 (dd, J=13.5, 7.7 Hz, 1H), 3.10 (d, J=12.1 Hz, 1H), 3.28 (dd, J=12.1, 3.7 Hz, 1H), 3.45 (d, J=3.6 Hz, 1H), 3.55 (p, J=8.1 Hz, 1H), 3.80 (p, J=7.7 Hz, 1H), 4.87 (d, J=7.6 Hz, 1H).

Example 18: Preparation of Compound R

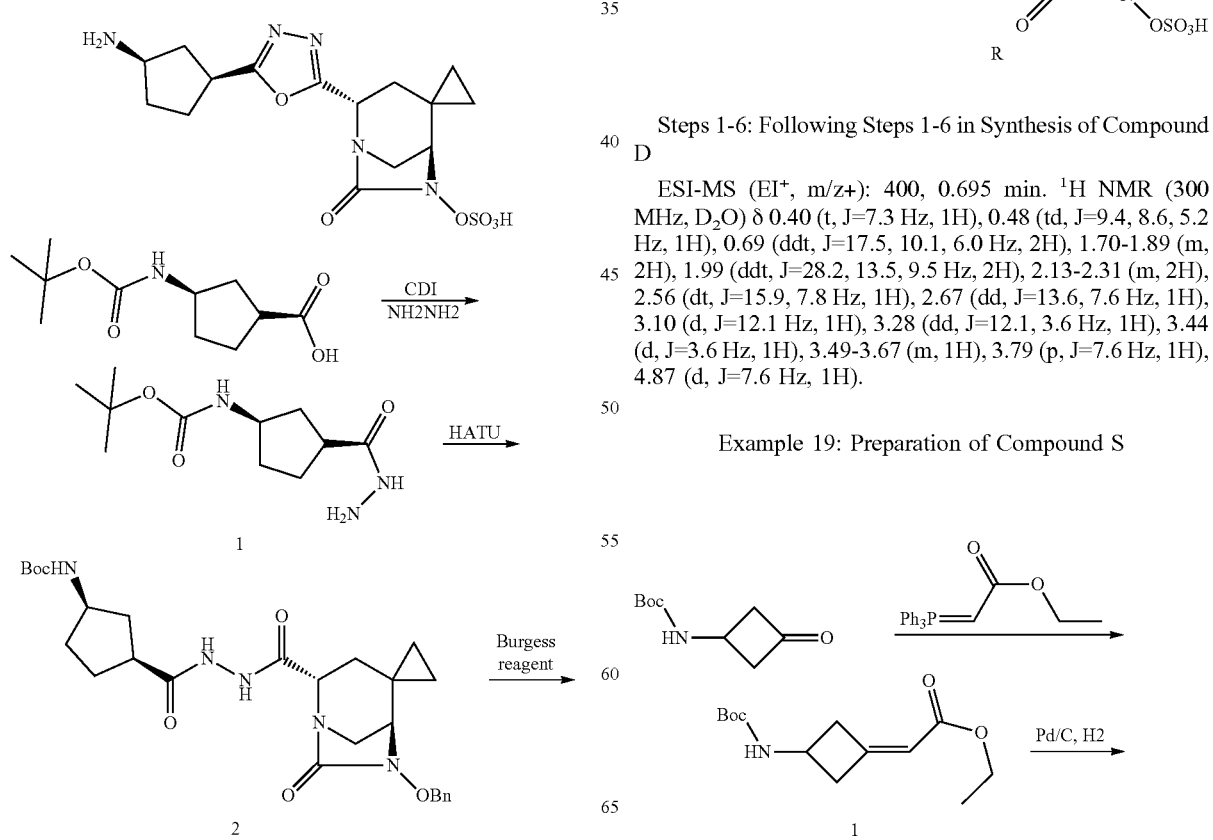

Steps 1-6: Following Steps 1-6 in Synthesis of Compound D

ESI-MS (EI+, m/z+): 400, 0.695 min. ¹H NMR (300 MHz, D₂O) δ 0.40 (t, J=7.3 Hz, 1H), 0.48 (td, J=9.4, 8.6, 5.2 Hz, 1H), 0.69 (ddt, J=17.5, 10.1, 6.0 Hz, 2H), 1.70-1.89 (m, 2H), 1.99 (ddt, J=28.2, 13.5, 9.5 Hz, 2H), 2.13-2.31 (m, 2H), 2.56 (dt, J=15.9, 7.8 Hz, 1H), 2.67 (dd, J=13.6, 7.6 Hz, 1H), 3.10 (d, J=12.1 Hz, 1H), 3.28 (dd, J=12.1, 3.6 Hz, 1H), 3.44 (d, J=3.6 Hz, 1H), 3.49-3.67 (m, 1H), 3.79 (p, J=7.6 Hz, 1H), 4.87 (d, J=7.6 Hz, 1H).

Example 19: Preparation of Compound S

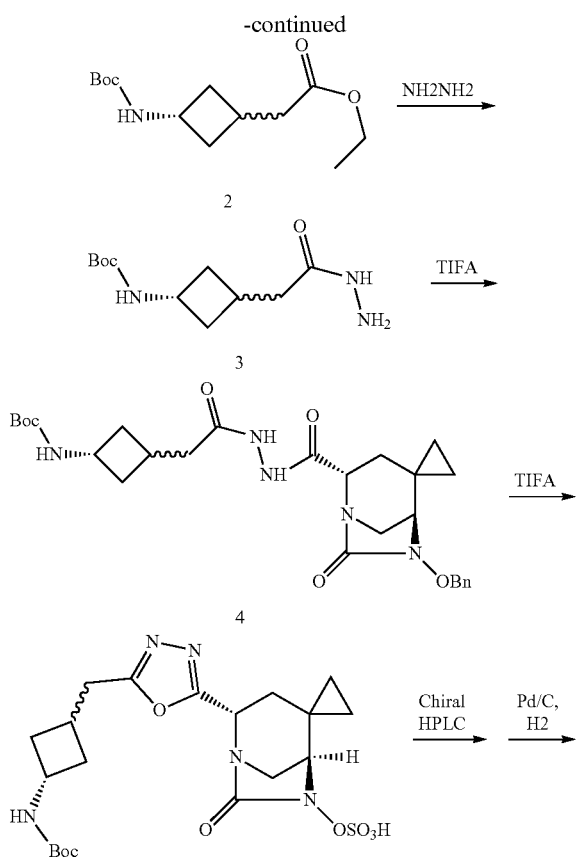

Step 1: Synthesis of Compound 1

To a 250-mL round-bottom flask was added a solution of tert-butyl 3-oxocyclobutylcarbamate (7.4 g, 39.95 mmol, 1.00 eq.) in toluene (80 mL), followed by ethyl (triphenylphosphoranylidene)acetate (15.31 g, 43.95 mmol, 1.10 eq.). The resulting solution was stirred for 120 min in an oil bath at 100° C. The reaction mixture was concentrated under vacuum. The crude product was purified by Flash-Prep-HPLC with the following conditions: Column, silica gel; Mobile phase, EA/PE=10% increasing to EA/PE=60% within 30 min; Detector, UV 254 nm. This resulted in 6.2 g (61%) of ethyl 2-(3-(tert-butoxycarbonylamino)cyclobutylidene)acetate in the form of a colorless oil. ESI-MS (EI+, m/z 2n+1): 511, 0.906 min.

Step 2: Synthesis of Compound 2

To a 250-mL round-bottom flask was added a solution of ethyl 2-(3-(tert-butoxycarbonylamino)cyclobutylidene)acetate (6.2 g, 24.28 mmol, 1.00 eq.) in methanol (100 mL), followed by palladium carbon (1.8 g, 0.10 eq.). The resulting solution was stirred for 100 min at room temperature under $H_2$ (1 atm). The solids were filtered out. The resulting mixture was concentrated under vacuum. This resulted in 6.2 g (99%) of ethyl 2-(3-[[(tert-butoxy)carbonyl]amino]cyclobutyl)acetate in the form of a white solid. ESI-MS (EI+, m/z+Na): 280, 1.172 min.

Steps 3-8: Following Steps 1-6 in Synthesis of Compound D

ESI-MS (EI+, m/z+): 400, 0.668 min. $^1$H NMR (300 MHz, $D_2O$) δ 0.30-0.42 (m, 1H), 0.42-0.53 (m, 1H), 0.66 (ddt, J=14.7, 10.2, 5.0 Hz, 2H), 1.73 (d, J=16.0 Hz, 1H), 1.82-2.01 (m, 2H), 2.55 (dq, J=15.3, 8.2 Hz, 4H), 2.93-3.14 (m, 3H), 3.26 (dd, J=12.0, 3.6 Hz, 1H), 3.42 (d, J=3.5 Hz, 1H), 3.68 (p, J=8.5 Hz, 1H), 4.85 (d, J=7.5 Hz, 1H).

Example 20: Preparation of Compound T

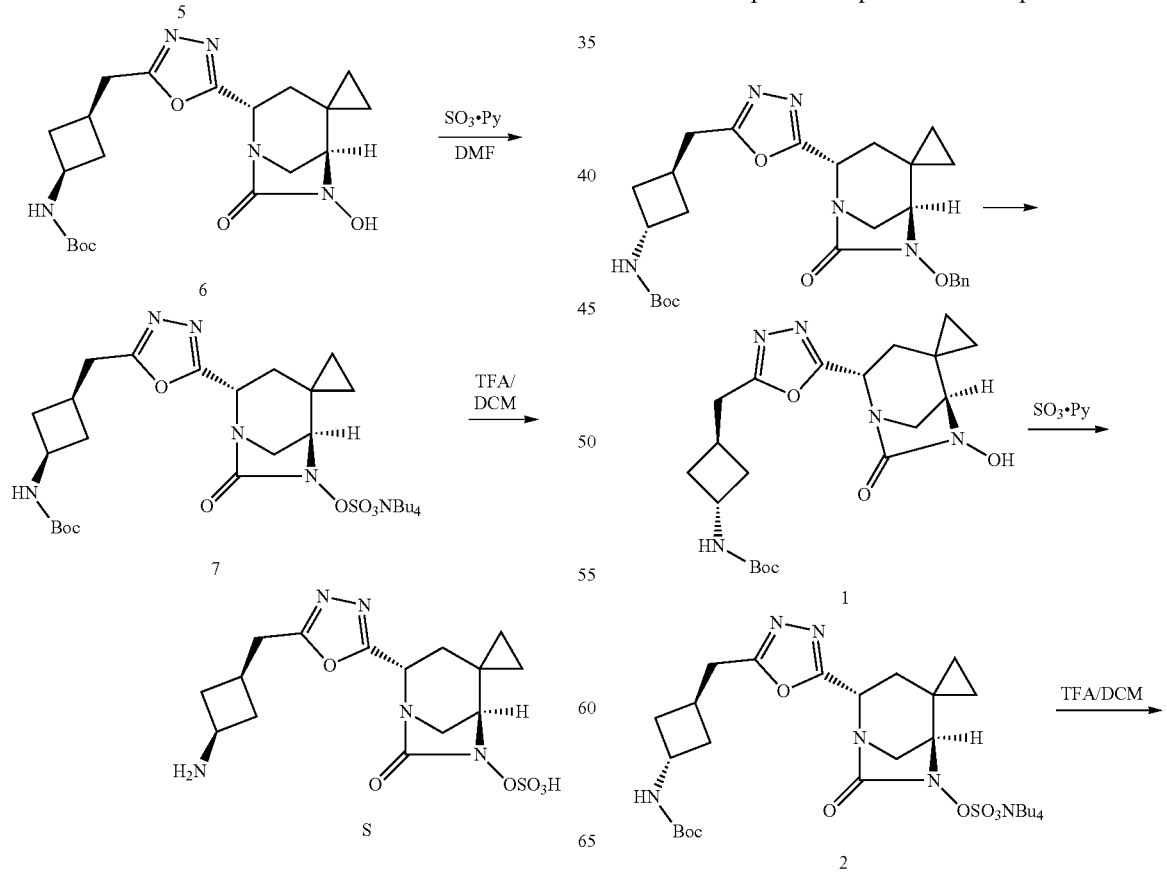

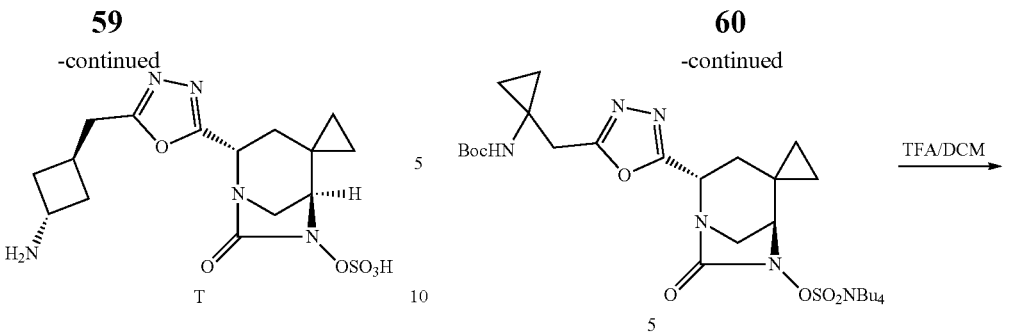

Steps 1-3: Following Steps 4-6 in Synthesis of Compound D

ESI-MS (EI+, m/z+): 400, 0.654 min. ¹H NMR (300 MHz, D₂O) δ 0.39 (d, J=4.8 Hz, 1H), 0.42-0.53 (m, 1H), 0.67 (ddt, J=19.5, 9.8, 5.5 Hz, 2H), 1.73 (d, J=16.0 Hz, 1H), 2.12-2.28 (m, 2H), 2.28-2.40 (m, 2H), 2.53 (dd, J=15.9, 7.7 Hz, 1H), 2.87 (s, 1H), 3.05-3.17 (m, 2H), 3.26 (dd, J=12.1, 3.3 Hz, 1H), 3.42 (d, J=3.4 Hz, 1H), 3.88 (p, J=7.2 Hz, 1H), 4.85 (d, J=7.6 Hz, 1H).

Example 21: Preparation of Compound U

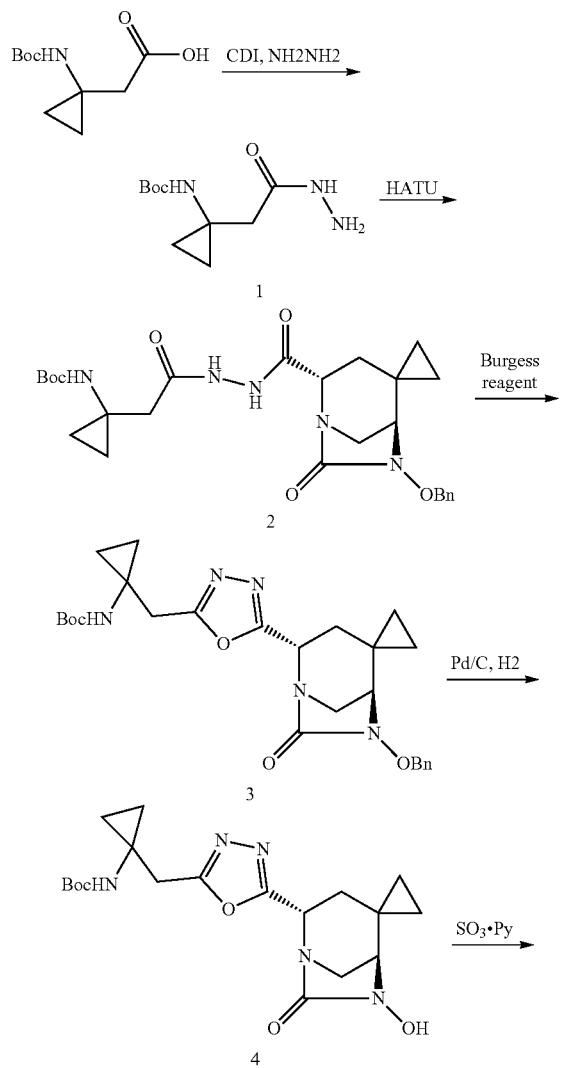

Steps 1-6: Following Steps 1-6 in Synthesis of Compound D

ESI-MS (EI+, m/z+): 386, 0.654 min. ¹H NMR (300 MHz, D₂O) δ 0.39 (t, J=7.3 Hz, 1H), 0.43-0.53 (m, 1H), 0.68 (ddt, J=17.7, 10.1, 5.9 Hz, 2H), 0.96-1.17 (m, 4H), 1.76 (d, J=16.0 Hz, 1H), 2.55 (dd, J=16.0, 7.9 Hz, 1H), 3.10-3.27 (m, 2H), 3.32 (s, 2H), 3.43 (d, J=3.5 Hz, 1H), 4.89 (d, J=7.6 Hz, 1H).

Example 22: Preparation of Compound V

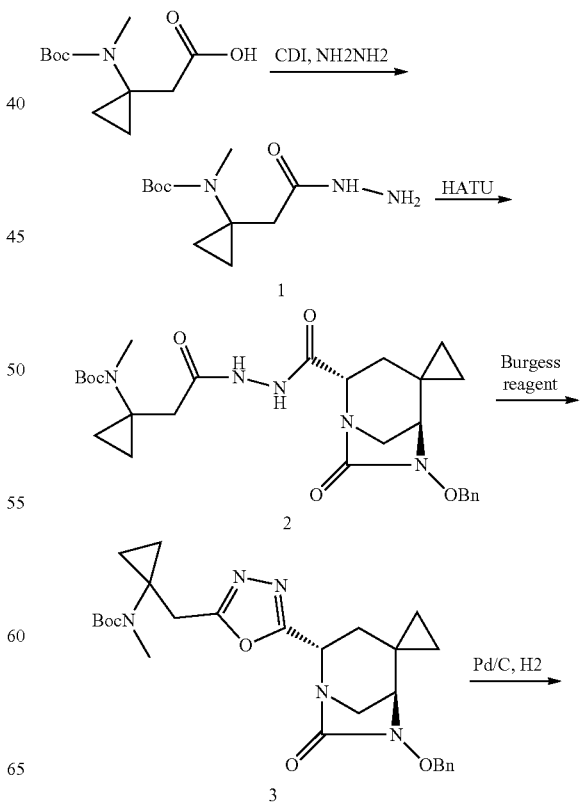

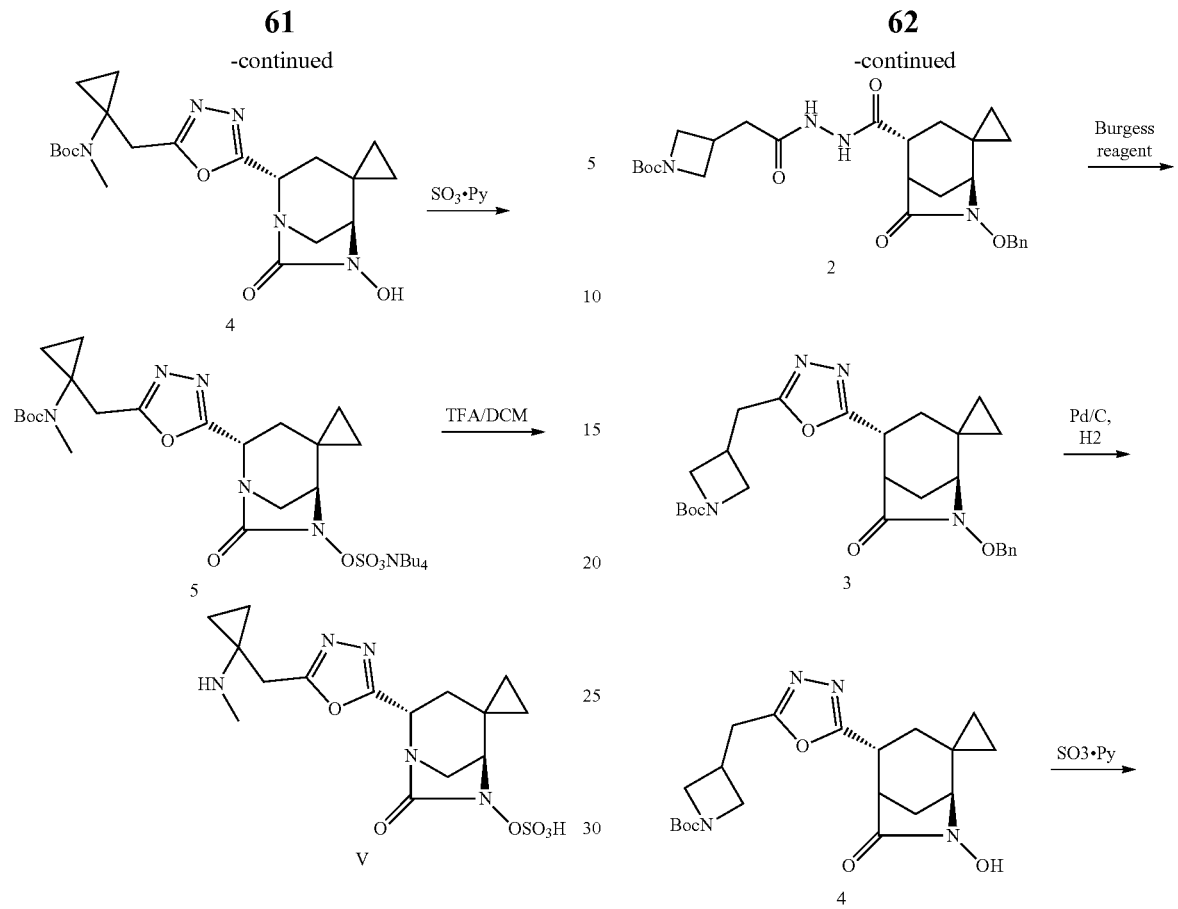
Steps 1-6: Following Steps 1-6 in Synthesis of Compound D
ESI-MS (EI+, m/z+): 400, 0.668 min. ¹H NMR (300 MHz, D₂O) δ 0.30-0.43 (m, 1H), 0.43-0.55 (m, 1H), 0.58-0.75 (m, 2H), 1.07 (h, J=3.8 Hz, 2H), 1.10-1.24 (m, 2H), 1.75 (d, J=16.0 Hz, 1H), 2.55 (dd, J=16.0, 7.8 Hz, 1H), 2.71 (s, 3H), 3.14 (d, J=12.1 Hz, 1H), 3.28 (dd, J=12.3, 3.6 Hz, 1H), 3.40 (s, 2H), 3.43 (d, J=3.7 Hz, 1H), 4.89 (d, J=7.6 Hz, 1H).
Example 23: Preparation of Compound W
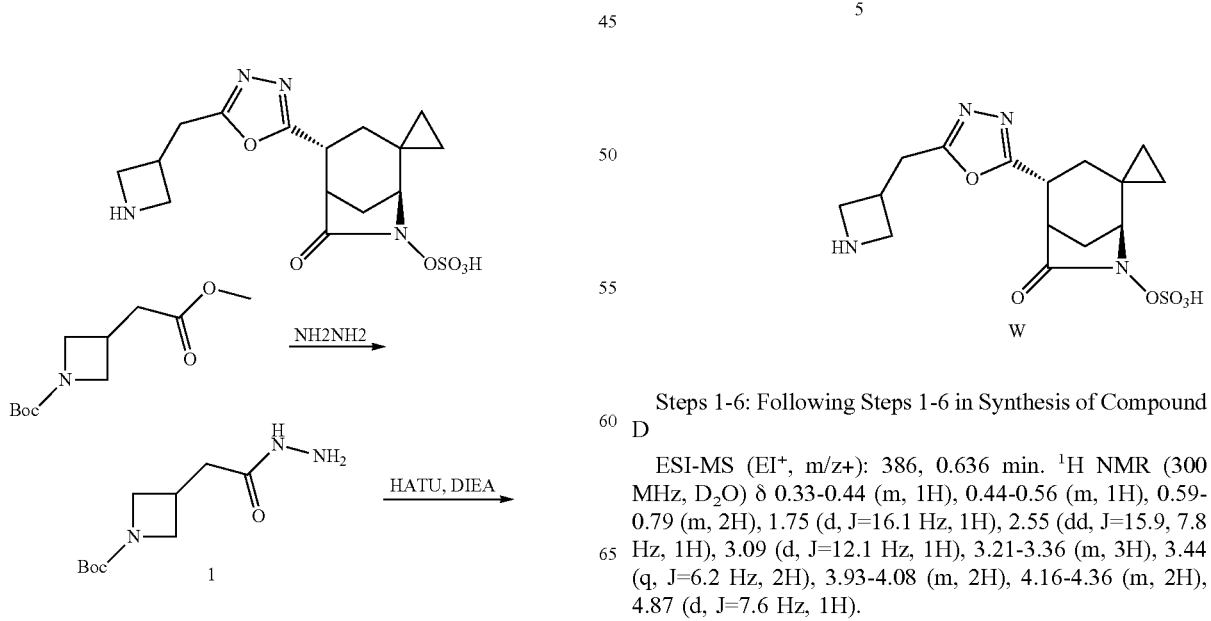
Steps 1-6: Following Steps 1-6 in Synthesis of Compound D
ESI-MS (EI+, m/z+): 386, 0.636 min. ¹H NMR (300 MHz, D₂O) δ 0.33-0.44 (m, 1H), 0.44-0.56 (m, 1H), 0.59-0.79 (m, 2H), 1.75 (d, J=16.1 Hz, 1H), 2.55 (dd, J=15.9, 7.8 Hz, 1H), 3.09 (d, J=12.1 Hz, 1H), 3.21-3.36 (m, 3H), 3.44 (q, J=6.2 Hz, 2H), 3.93-4.08 (m, 2H), 4.16-4.36 (m, 2H), 4.87 (d, J=7.6 Hz, 1H).

Example 24: Preparation of Compound X
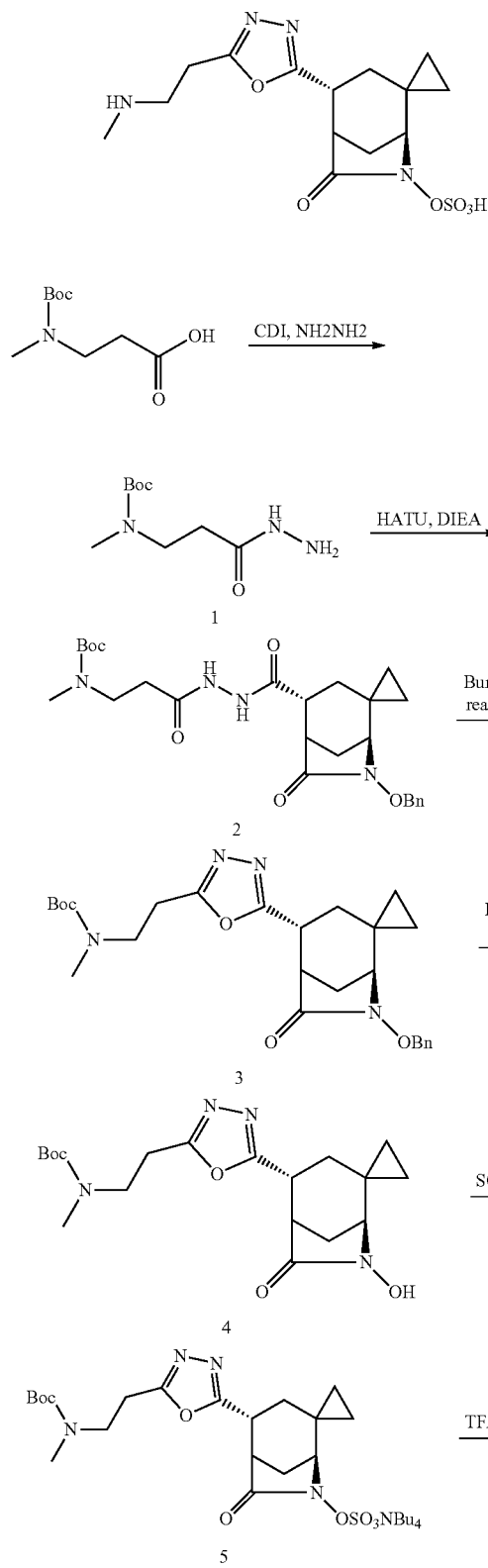
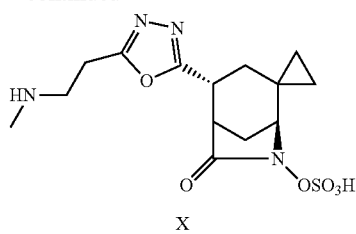
Steps 1-6: Following Steps 1-6 in Synthesis of Compound D
ESI-MS (EI$^+$, m/z+): 374, 0.615 min. $^1$H NMR (300 MHz, D$_2$O) δ 0.33-0.45 (m, 1H), 0.49 (td, J=7.3, 3.6 Hz, 1H), 0.68 (ddt, J=14.6, 10.3, 5.1 Hz, 2H), 1.76 (d, J=16.0 Hz, 1H), 2.55 (dd, J=15.9, 7.7 Hz, 1H), 2.73 (s, 3H), 3.13 (d, J=12.1 Hz, 1H), 3.27 (dd, J=12.1, 3.8 Hz, 1H), 3.32-3.41 (m, 2H), 3.41-3.54 (m, 3H), 4.88 (d, J=7.6 Hz, 1H).
Example 25: Preparation of Compound Y
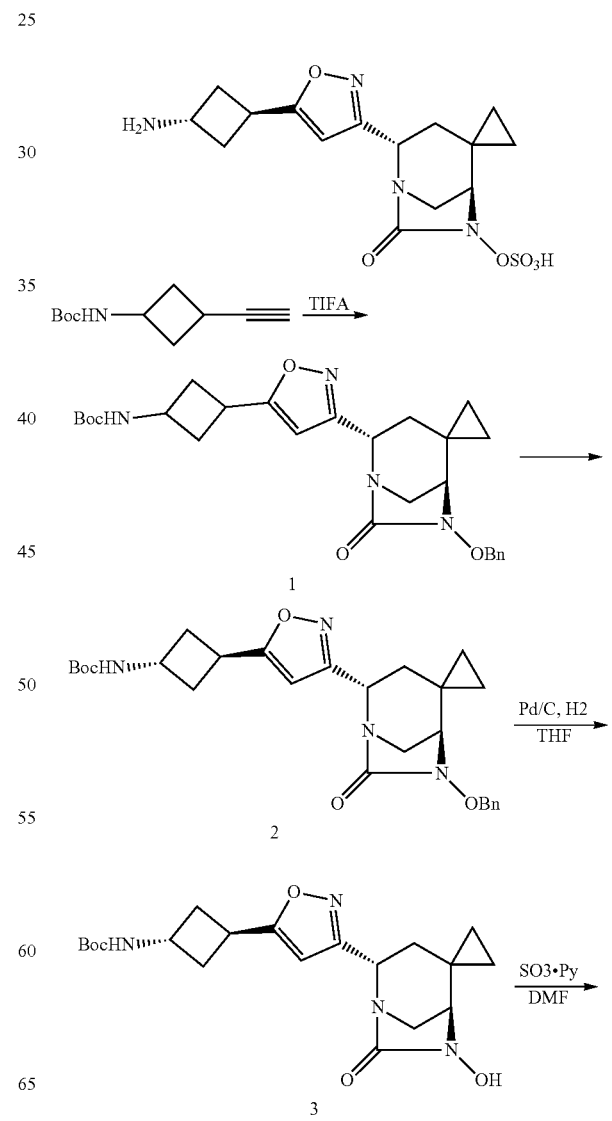

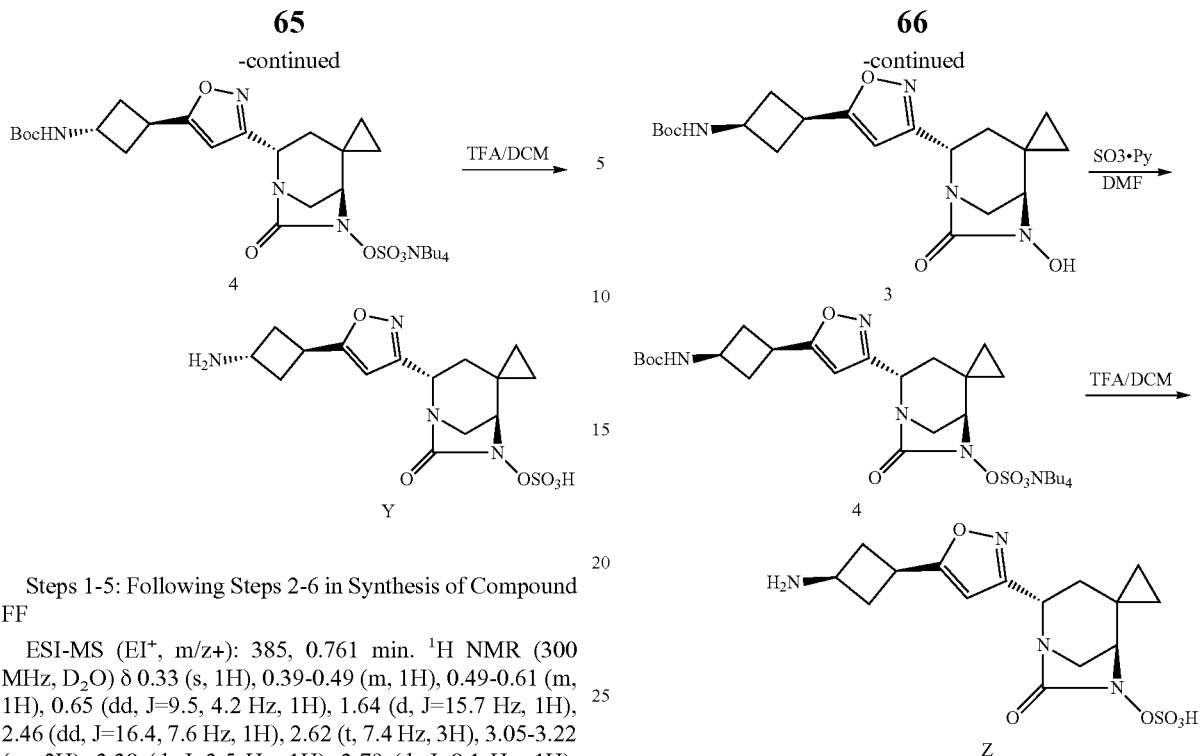

Steps 1-5: Following Steps 2-6 in Synthesis of Compound FF

ESI-MS (EI+, m/z+): 385, 0.761 min. $^1$H NMR (300 MHz, D$_2$O) δ 0.33 (s, 1H), 0.39-0.49 (m, 1H), 0.49-0.61 (m, 1H), 0.65 (dd, J=9.5, 4.2 Hz, 1H), 1.64 (d, J=15.7 Hz, 1H), 2.46 (dd, J=16.4, 7.6 Hz, 1H), 2.62 (t, 7.4 Hz, 3H), 3.05-3.22 (m, 2H), 3.38 (d, J=3.5 Hz, 1H), 3.79 (d, J=8.1 Hz, 1H), 3.91-4.11 (m, 1H), 4.73 (s, 1H), 6.35 (d, J=7.7 Hz, 1H), 8.35 (s, 0H).

Example 26: Preparation of Compound Z

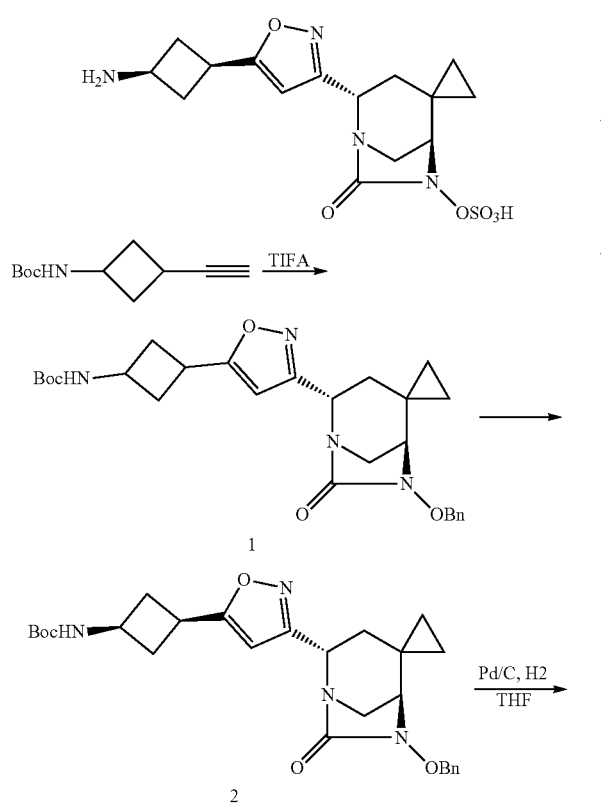

Steps 1-5: Following Steps 2-6 in Synthesis of Compound FF

ESI-MS (EI+, m/z+): 385, 0.774 min. $^1$H NMR (300 MHz, D$_2$O) δ 0.32 (dt, J=9.3, 4.7 Hz, 1H), 0.37-0.48 (m, 1H), 0.56 (dt, J=10.2, 5.0 Hz, 1H), 0.66 (dt, J=9.6, 5.0 Hz, 1H), 1.63 (d, J=15.8 Hz, 1H), 2.29-2.52 (m, 3H), 2.64-2.84 (m, 2H), 3.03-3.29 (m, 2H), 3.37 (d, J=3.4 Hz, 1H), 3.53 (ddd, J=18.0, 9.9, 8.1 Hz, 1H), 3.73-3.96 (m, 1H), 4.72 (s, 1H), 6.32 (s, 1H).

Example 27: Preparation of Compound AA

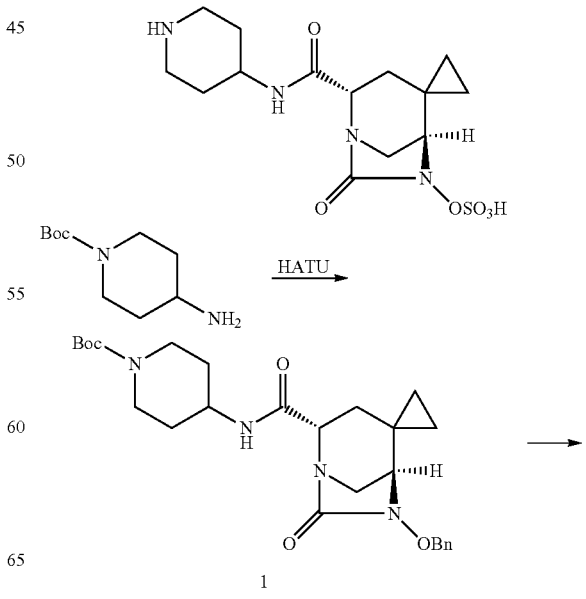

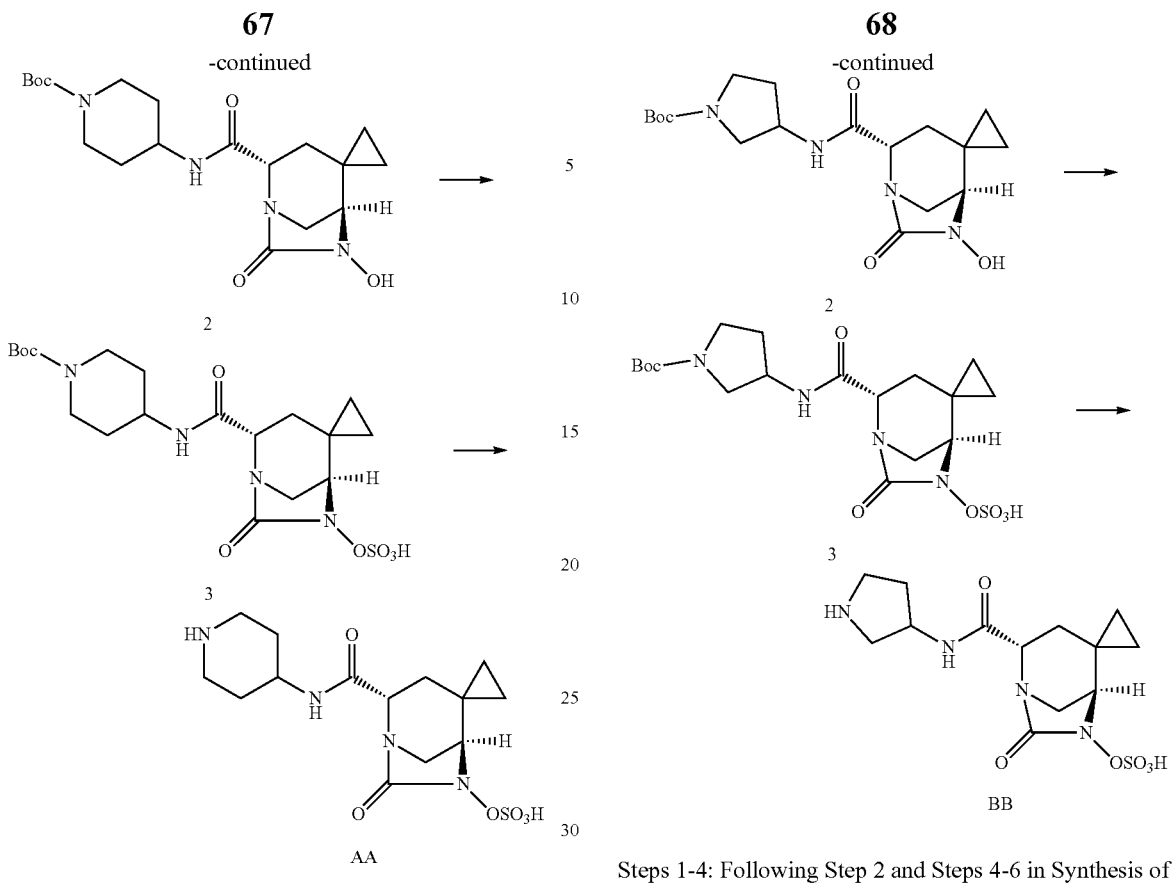

Steps 1-4: Following Step 2 and Steps 4-6 in Synthesis of Compound D

ESI-MS (EI⁺, m/z+): 375, 0.716 min. ¹H NMR (400 MHz, D₂O) δ 0.29 (dt, J=8.1, 4.2 Hz, 1H), 0.41 (dtd, J=18.5, 9.0, 4.5 Hz, 2H), 0.63 (dt, J=10.2, 4.7 Hz, 1H), 1.59-1.77 (m, 3H), 1.98-2.10 (m, 2H), 2.14 (dd, J=15.6, 7.9 Hz, 1H), 2.97-3.11 (m, 3H), 3.27 (dd, 11.9, 3.7 Hz, 1H), 3.31-3.45 (m, 3H), 3.95 (t, J=11.0, 4.0 Hz, 1H), 4.05 (d, J=7.8 Hz, 1H).

Example 28: Preparation of Compound BB

Steps 1-4: Following Step 2 and Steps 4-6 in Synthesis of Compound D

ESI-MS (EI⁺, m/z+): 361, 0.662 min. ¹H NMR (400 MHz, D₂O) δ 0.31 (dd, J=9.8, 4.6 Hz, 1H), 0.42 (dtd, J=18.5, 9.0, 4.5 Hz, 2H), 0.64 (dt, J=10.2, 4.6 Hz, 1H), 1.66 (d, J=15.6 Hz, 1H), 2.02 (tt, J=16.0, 8.5 Hz, 1H), 2.14 (dd, J=15.6, 7.9 Hz, 1H), 2.31 (dp, J=13.3, 6.7, 6.0 Hz, 1H), 3.08 (dd, J=11.8, 8.8 Hz, 1H), 3.17-3.32 (m, 2H), 3.34 (dd, J=11.1, 3.6 Hz, 2H), 3.43 (dt, J=12.1, 7.5 Hz, 1H), 3.52 (dt, J=12.5, 8.2 Hz, 1H), 4.06 (d, J=7.8 Hz, 1H), 4.48 (dq, J=12.1, 6.8, 6.1 Hz, 1H).

Example 29: Preparation of Compound CC

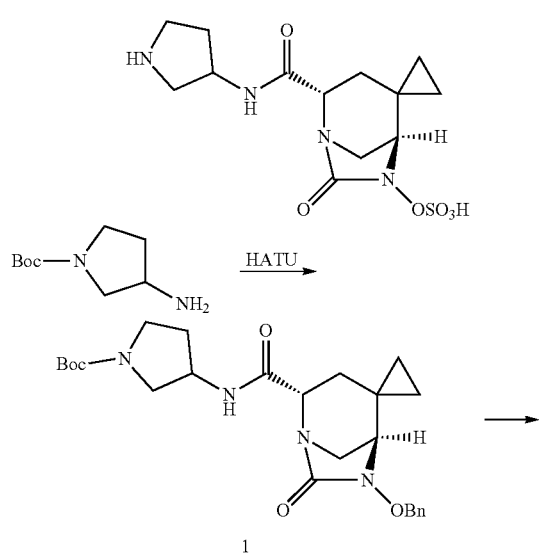

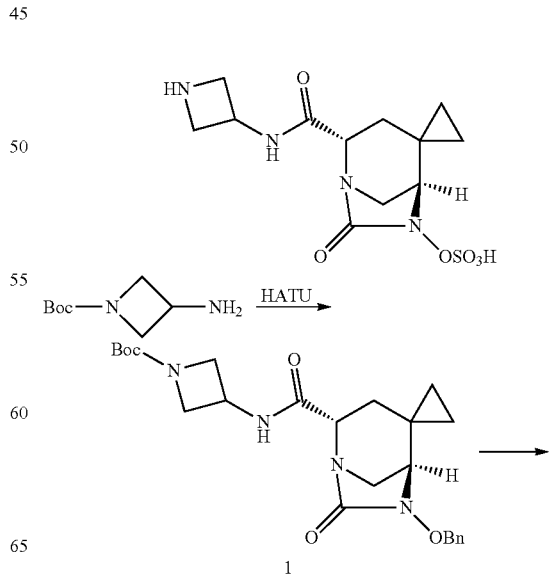

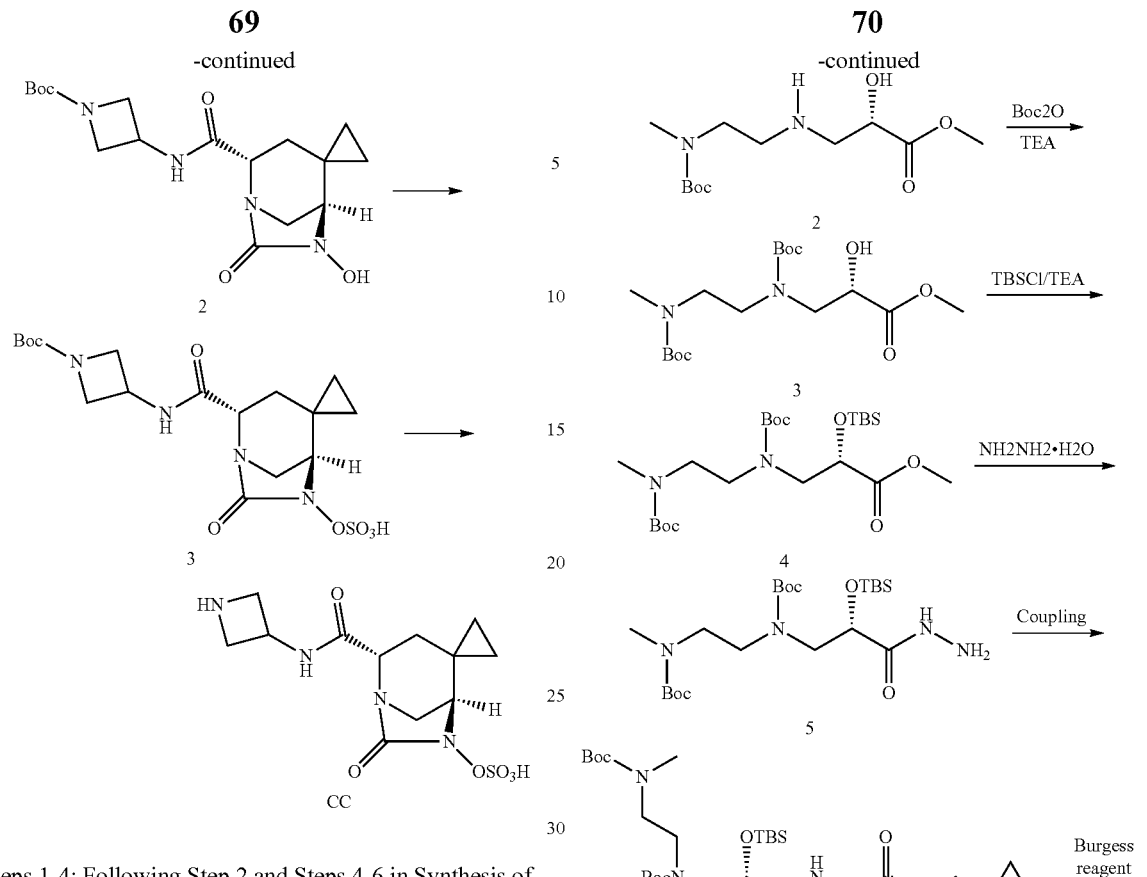
Steps 1-4: Following Step 2 and Steps 4-6 in Synthesis of Compound D
ESI-MS (EI+, m/z+): 347, 0.572 min. ¹H NMR (400 MHz, D₂O) δ 0.29 (dd, J=9.8, 4.2 Hz, 1H), 0.41 (tp, J=9.1, 4.3 Hz, 2H), 0.60-0.70 (m, 1H), 1.65 (d, J=15.6 Hz, 1H), 2.15 (dd, J=15.7, 7.9 Hz, 1H), 3.07 (d, J=11.9 Hz, 1H), 3.29 (dd, J=11.9, 3.7 Hz, 1H), 3.35 (d, J=3.8 Hz, 1H), 4.07 (d, J=7.9 Hz, 1H), 4.11-4.22 (m, 2H), 4.28 (dd, J=11.3, 8.8 Hz, 2H), 4.75 (d, 7=7.9 Hz, 1H).
Example 30: Preparation of Compound DD
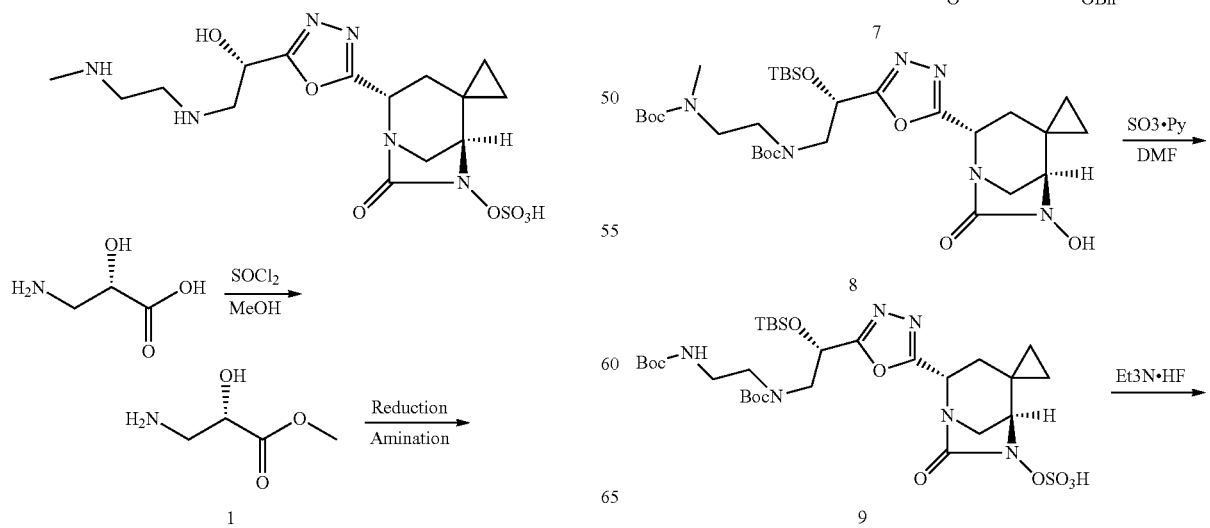

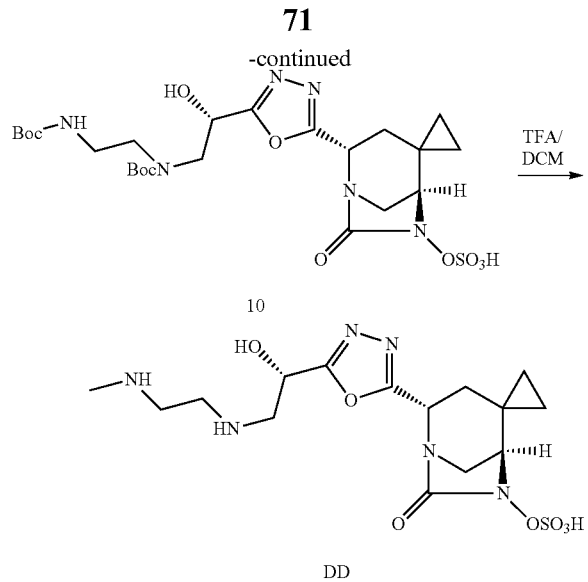

DD

Step 1: Synthesis of Compound 1

To a 500-mL round-bottom flask was added (S)-3-amino-2-hydroxypropanoic acid (20 g, 190.31 mmol, 1.00 eq.) in MeOH (250 mL). SOCl$_2$ (56 g, 470.71 mmol, 2.50 eq.) was added in the mixture at 0° C. The resulting solution was stirred for 15 h in an oil bath at 65° C. The resulting mixture was concentrated under vacuum. This resulted in 22 g (97%) of (S)-methyl 3-amino-2-hydroxypropanoate in the form of a colorless oil. ESI-MS (EI$^+$, m/z+): 120, 0.156 min.

Step 2: Synthesis of Compound 2

To a 100-mL round-bottom flask were added tert-butyl N-methyl-N-(2-oxoethyl) carbamate (5.2 g, 30.02 mmol, 1.00 eq.), a solution of (S)-methyl 3-amino-2-hydroxypropanoate (4.3 g, 36.10 mmol, 1.20 eq.) in MeOH (30 mL), and sodium triacetoxyborohydride (12.72 g, 60.02 mmol, 2.00 eq.). The resulting solution was stirred for 2 h at room temperature. The resulting mixture was concentrated under vacuum. The crude product was purified by Flash-Prep-HPLC with the following conditions: Column, C18 silica gel; Mobile phase, ACN=10% increasing to ACN=50% within 60 min; Detector, UV 254 nm. This resulted in 3 g (36%) of (S)-methyl 3-(2-(tert-butoxycarbonyl(methyl) amino) ethylamino)-2-hydroxypropanoate in the form of a colorless oil. (EI$^+$, m/z+): 277, 0.381 min.

Step 3: Synthesis of Compound 3

To a 100-mL round-bottom flask were added (S)-methyl 3-(2-(tert-butoxycarbonyl (methyl)amino)ethylamino)-2-hydroxypropanoate (5 g, 18.09 mmol, 1.00 eq.), (Boc)$_2$O (4.8 g, 21.99 mmol, 1.20 eq.), and a solution of TEA (2.7 g, 26.68 mmol, 1.50 eq.) in DCM (20 mL). The resulting solution was stirred for 15 h at room temperature. The resulting mixture was concentrated under vacuum. The crude product was purified by Flash-Prep-HPLC with the following conditions: Column, C18 silica gel; Mobile phase, ACN=10% increasing to ACN=60% within 50 min; Detector, UV 254 nm. This resulted in 2.5 g (37%) of (S)-methyl 3-(tert-butoxycarbonyl(2-(tert-butoxycarbonyl(methyl) amino)ethyl)amino)-2-hydroxypropanoate in the form of a colorless oil. (EI$^+$, m/z+): 377, 0.879 min.

Step 4: Synthesis of Compound 4

To a 100-mL round-bottom flask were added (S)-methyl 3-(tert-butoxycarbonyl(2-(tert-butoxycarbonyl(methyl) amino)ethyl)amino)-2-hydroxypropanoate (2.5 g, 6.64 mmol, 1.00 eq.), TEA (1 g, 9.88 mmol, 1.50 eq.), DMAP (100 mg, 0.10 eq.), and a solution of TBS-Cl (1.2 g, 7.96 mmol, 1.20 eq.) in DCM (30 mL). The resulting solution was stirred for 15 h at room temperature. The resulting mixture was concentrated under vacuum. The crude product was purified by Flash-Prep-HPLC with the following conditions: Column, C18 silica gel; Mobile phase, ACN=10% increasing to ACN=60% within 50 min; Detector, UV 254 nm. This resulted in 850 mg (26%) of Compound 4 in the form of a white solid. (EI$^+$, m/z+): 513, 1.611 min.

Steps 5-9: Following Steps 1-5 in Synthesis of Compound D

Steps 10-11: Following Steps 8-9 in Synthesis of Compound I (EI$^+$, m/z+): 433, 0.548 min. $^1$H NMR (300 MHz, D$_2$O) δ 0.39 (d, J=5.1 Hz, 1H), 0.46 (d, J=14.0 Hz, 1H), 0.54-0.76 (m, 2H), 1.76 (d, J=16.0 Hz, 1H), 2.54 (dd, J=15.9, 7.8 Hz, 1H), 2.72 (s, 3H), 3.10 (d, J=12.1 Hz, 1H), 3.28 (d, J=12.3 Hz, 1H), 3.46 (dt, J=18.5, 11.3 Hz, 4H), 3.59 (d, J=8.1 Hz, 2H), 4.90 (d, J=7.4 Hz, 1H), 5.24-5.42 (m, 1H).

Example 31: Preparation of Compound EE

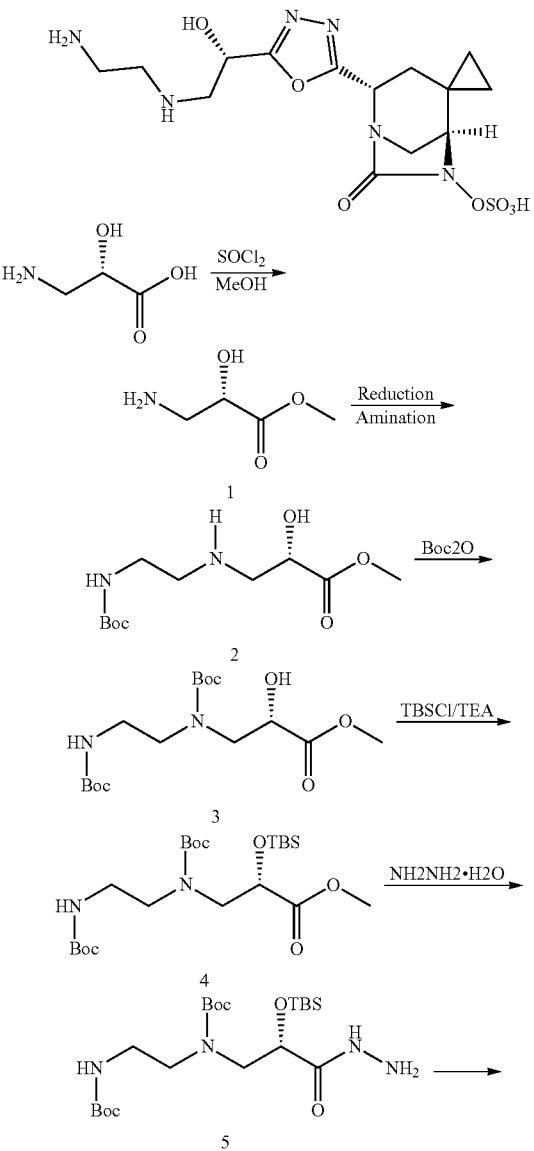

-continued
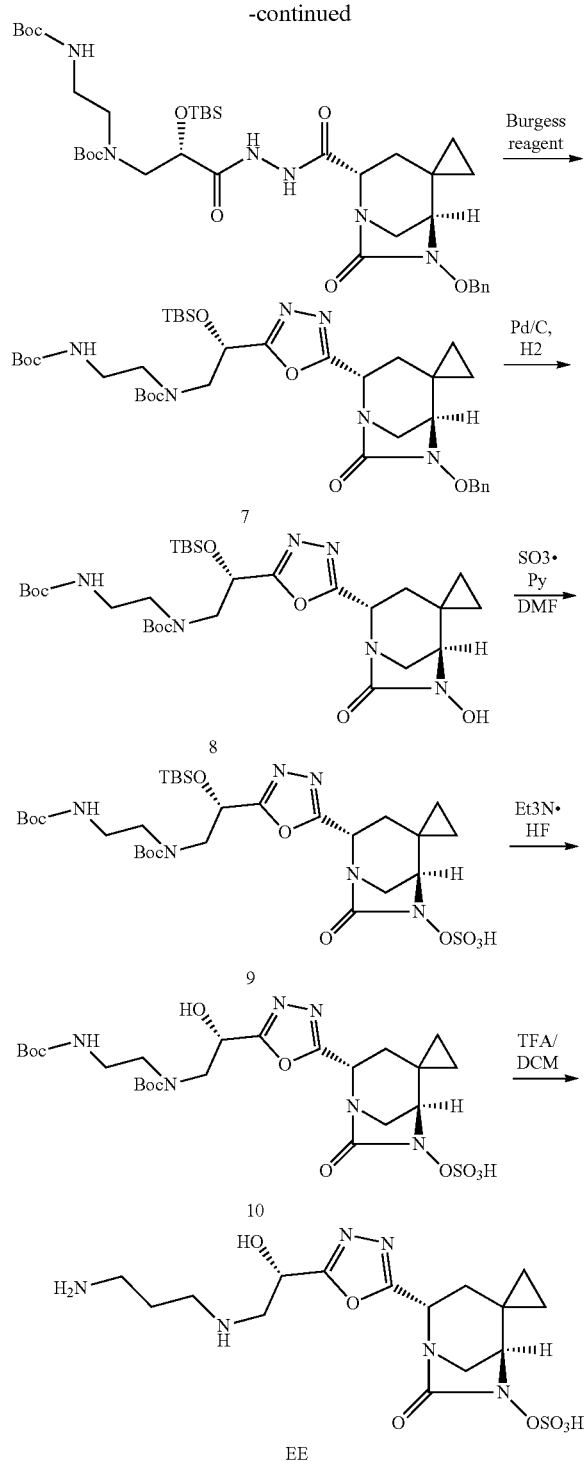
Steps 1-4: Following Steps 1-4 in Synthesis of Compound DD
Steps 5-9: Following Steps 1-5 in Synthesis of Compound D
Steps 10-11: Following Steps 8-9 in Synthesis of Compound I
(EI+, m/z+): 419, 0.534 min. $^1$H NMR (300 MHz, D$_2$O) δ 0.31-0.44 (m, 1H), 0.44-0.54 (m, 1H), 0.68 (ddt, J=18.1, 10.3, 5.9 Hz, 2H), 1.77 (d, J=16.0 Hz, 1H), 2.55 (dd, J=16.1, 7.8 Hz, 1H), 3.10 (d, J=12.1 Hz, 1H), 3.28 (dd, J=12.1, 3.7 Hz, 1H), 3.35 (dd, J=10.3, 4.2 Hz, 2H), 3.45 (dd, J=7.8, 5.0 Hz, 3H), 3.52-3.69 (m, 2H), 4.90 (d, J=7.6 Hz, 1H), 5.34 (dd, J=8.0, 4.3 Hz, 1H).
Example 32: Preparation of Compound FF
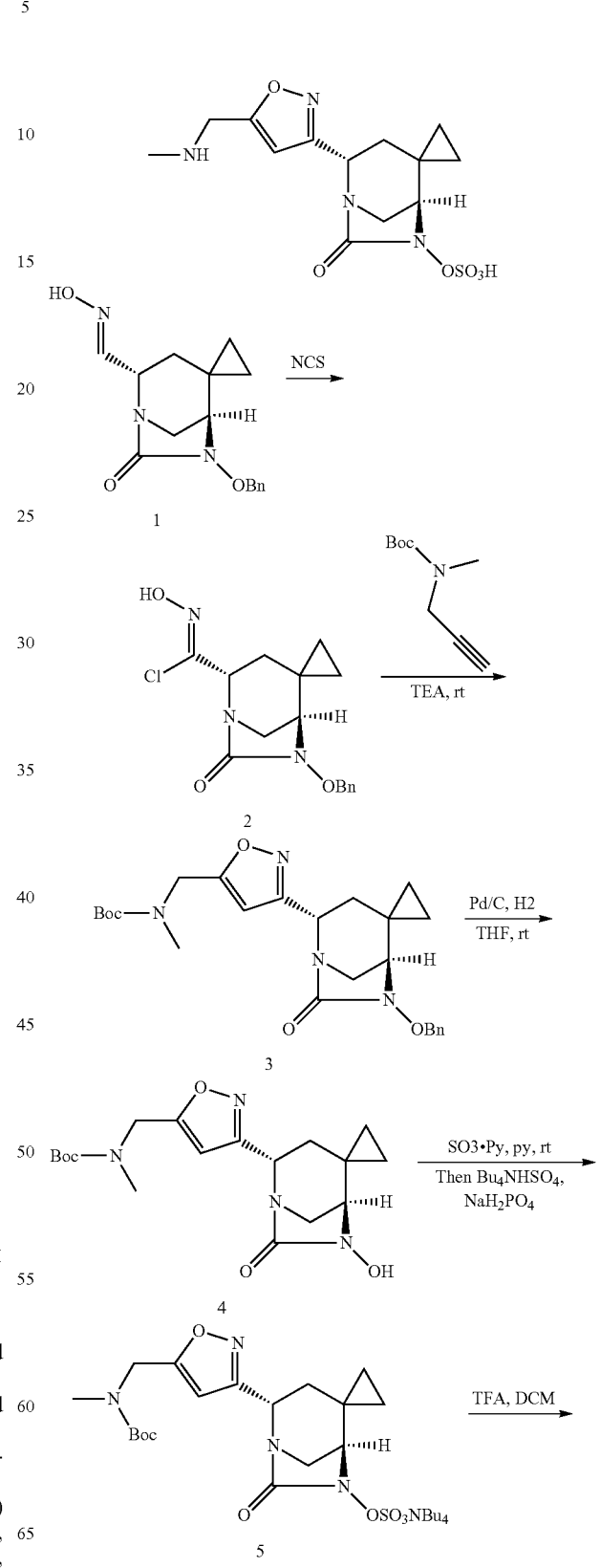

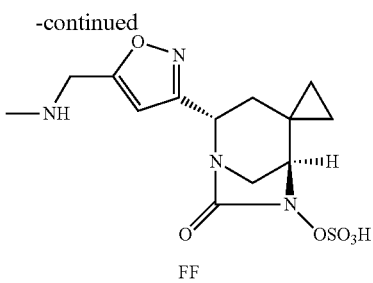

FF

Step 1: Synthesis of Compound 2

Chloropyrrolidine-2,5-dione (0.146 g, 1.10 mmol) was added to (E)-7-(benzyloxy)-6-oxo-5,7-diazaspiro[bicyclo[3.2.1]octane-2,1'-cyclopropane]-4-carbaldehyde oxime (0.3 g, 1.00 mmol) in DCM (8 mL), and then pyridine (1 drop) was added thereto. The resulting mixture was stirred at room temperature for 16 h. The solvent was removed under reduced pressure to give (1R,4S,Z)-7-(benzyloxy)-N-hydroxy-6-oxo-5,7-diazaspiro[bicyclo[3.2.1] octane-2,1'-cyclopropane]-4-carbimidoyl chloride (0.330 g, 99%) in the form of a brown gum. The product was used in the next step directly without further purification. m/z (ES+), [M+H]+=336; ACID, HPLC tR=1.092 min.

Step 2: Synthesis of Compound 3

Tert-butyl methyl(prop-2-yn-1-yl)carbamate (0.200 g, 1.18 mmol) was added to (1R,4S,Z)-7-(benzyloxy)-N-hydroxy-6-oxo-5,7-diazaspiro[bicyclo[3.2.1]octane-2,1'-cyclopropane]-4-carbimidoyl chloride (0.33 g, 0.98 mmol) in DCM (8 mL), followed by the addition of TEA (0.137 mL, 0.98 mmol). The resulting mixture was stirred at room temperature for 16 h. The solvent was removed under reduced pressure. The crude product was purified by flash C18-flash chromatography with gradient elution (0 to 65% MeCN in water). Pure fractions were evaporated to dryness to give tert-butyl ((3-((1R,4S)-7-(benzyloxy)-6-oxo-5,7-diazaspiro[bicyclo[3.2.1]octane-2,1'-cyclopropan]-4-yl)isoxazol-5-yl)methyl)(methyl)carbamate (0.160 g, 34.7%) in the form of a white solid, m/z (ES+), [M+H]+=469; ACID, HPLC tR=1.305 min. $^1$H NMR (300 MHz, Chloroform-d) δ 1.48 (s, 10H), 2.22 (t, J=2.5 Hz, 1H), 2.93 (s, 3H), 4.05 (s, 2H).

Step 3: Synthesis of Compound 4

A solution of tert-butyl ((3-((1R,4S)-7-(benzyloxy)-6-oxo-5,7-diazaspiro[bicycle[3.2.1] octane-2,1'-cyclopropan]-4-yl)isoxazol-5-yl)methyl)(methyl)carbamate (0.16 g, 0.34 mmol) and Pd—C (0.036 g, 0.34 mmol) in THF (10 mL) was stirred under an atmosphere of hydrogen at room temperature for 8 h. The solids were filtered out. The solvent was removed under reduced pressure to give tert-butyl ((3-((1R,4S)-7-hydroxy-6-oxo-5,7-diazaspiro[bicycle[3.2.1]octane-2,1'-cyclopropan]-4-yl)isoxazol-5-yl)methyl)(methyl)carbamate (0.110 g, 85%) in the form of a solid, m/z (ES+), [M+H]+=379; ACID, HPLC tR=1.047 min.

Step 4: Synthesis of Compound 5

Pyridine compound with sulfur trioxide (0.278 g, 1.74 mmol) was added to a solution of tert-butyl ((3-((1R,4S)-7-hydroxy-6-oxo-5,7-diazaspiro[bicyclo[3.2.1]octane-2,1'-cyclopropan]-4-yl)isoxazol-5-yl)methyl)(methyl)carbamate (0.11 g, 0.29 mmol) in DMF (2 mL). The resulting mixture was stirred at 50° C. for 4 h. The solvent was removed under reduced pressure. The residue was redissolved in NaH$_2$PO$_4$ (1.5 M, 10 mL) and then Bn$_4$NHSO$_4$ (200 mg) was added and stirred for 20 min. The reaction mixture was extracted with ethyl acetate, and the organic phase was evaporated to give tetrabutylammonium (1R,4S)-4-(5-(((methylamino)methyl)isoxazol-3-yl)-6-oxo-5,7-diazaspiro[bicyclo[3.2.1]octane-2,1'-cyclopropan]-7-yl sulfate (0.100 g, 57.4%). m/z (ES+), [M+H]+=459; ACID, HPLC tR=1.038 min.

Step 5: Synthesis of Compound FF

TFA (0.5 ml, 6.49 mmol) was added to a solution of tetrabutylammonium (1R,4S)-4-(5-((methylamino)methyl)isoxazol-3-yl)-6-oxo-5,7-diazaspiro[bicyclo[3.2.1]octane-2,1'-cyclopropan]-7-yl sulfate (0.1 g, 0.17 mmol) in DCM (2 mL) at 0° C. The resulting mixture was stirred at 0° C. for 8 h. The solvent was removed under reduced pressure and the residue was diluted with ether. The precipitate was collected via centrifugation (3 times), and the solid was purified by Prep-HPLC (Column: Xselect CSH OBD Column 30*150 mm 5 um n; Mobile Phase A: Water (0.1% FA), Mobile Phase B: ACN; Flow rate: 60 mL/min; Gradient: 2% B to 15% B in 7 min; 254; 220 nm; Rt: 5.93 min). Fractions containing the desired compound were evaporated to dryness to give (1R,4S)-4-(5-((methylamino)methyl)isoxazol-3-yl)-6-oxo-5,7-diazaspiro[bicyclo[3.2.1]octane-2,1'-cyclohexane]-7-yl hydrogen sulfate (10.00 mg, 16.74%). m/z (ES+), [M+H]+=359; ACID, HPLC tR=0.682 min. $^1$H NMR (400 MHz, D$_2$O) δ 0.33 (d, J=9.7 Hz, 1H), 0.41 (dd, J=9.0, 5.1 Hz, 1H), 0.50-0.58 (m, 1H), 0.64 (dd, J=9.6, 5.0 Hz, 1H), 1.66 (d, J=16.0 Hz, 1H), 2.46 (dd, J=16.2, 7.4 Hz, 1H), 2.69 (s, 3H), 3.07 (d, J=12.0 Hz, 1H), 3.14-3.25 (m, 1H), 3.37 (d, J=3.7 Hz, 1H), 4.39 (s, 2H), 4.74 (d, J=7.7 Hz, 1H), 6.68 (s, 1H).

Example 33: Preparation of Compound GG

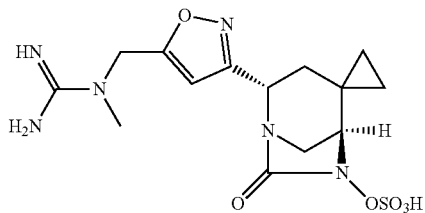

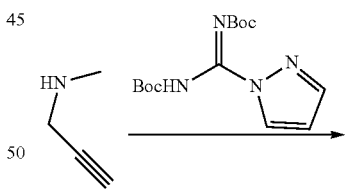

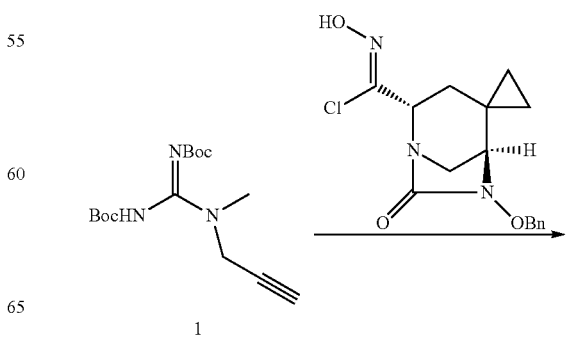

1

-continued

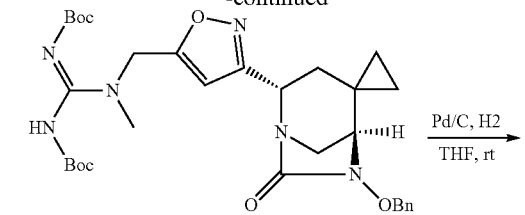

2

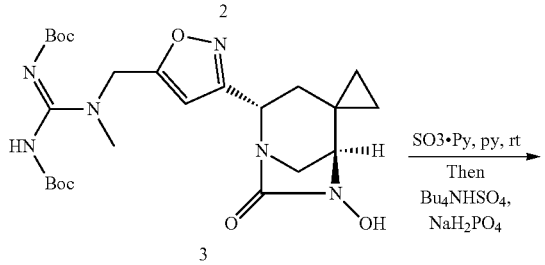

3

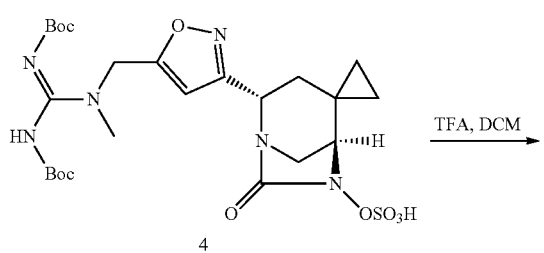

4

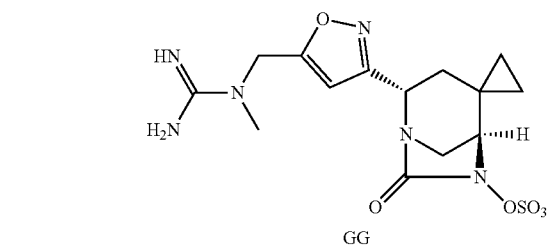

GG

Step 1: Synthesis of Compound 1

Tert-butyl (E)-(((tert-butoxycarbonyl)imino)(1H-pyrazol-1-yl)methyl)carbamate (1.976 g, 6.37 mmol) was added to a solution of N-methylprop-2-yn-1-amine (0.4 g, 5.79 mmol) and TEA (2.420 mL, 17.36 mmol) in MeOH (10 mL). The resulting mixture was stirred at 0° C. for 16 h. The solvent was removed under reduced pressure. The crude product was purified by flash silica chromatography with gradient elution (1 to 10% EtOAc in petroleum ether). Pure fractions were evaporated to dryness to give Product 1 (0.500 g, 27.7%) in the form of a white solid, m/z (ES$^+$), [M+H]$^+$=312; ACID, HPLC tR=0.954 min.

Steps 2-5: Following Steps 3-6 in Synthesis of Compound FF

Compound GG:

m/z (ES$^+$), [M+H]$^+$=401; ACID, HPLC tR=1.114 min. $^1$H NMR (400 MHz, D$_2$O) δ 0.32 (s, 1H), 0.43 (s, 1H), 0.54 (s, 1H), 0.61-0.71 (m, 0H), 1.65 (d, J=15.6 Hz, 0H), 2.46 (dd, J=15.9, 7.7 Hz, 0H), 3.03 (s, 1H), 3.08 (d, J=12.0 Hz, 1H), 3.19 (d, J=11.8 Hz, 0H), 3.37 (d, J=3.6 Hz, 0H), 4.69 (s, 2H), 4.73 (s, 1H), 6.51 (s, 0H).

Example 34: Preparation of Compound HH

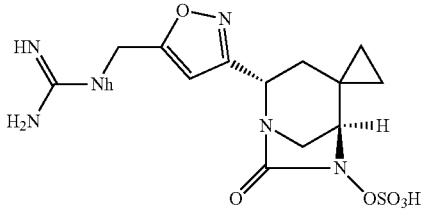

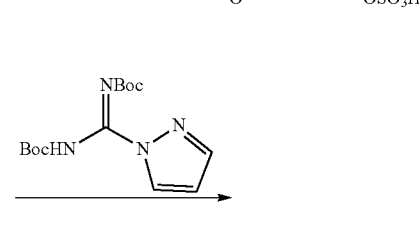

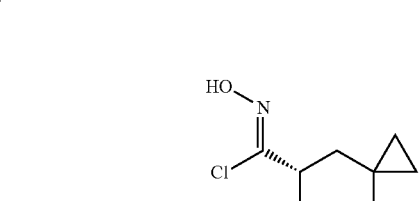

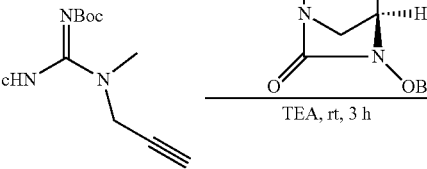

1

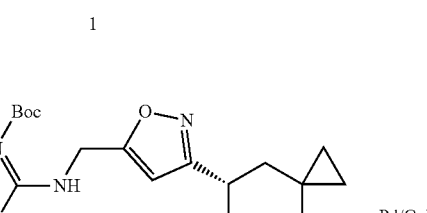

2

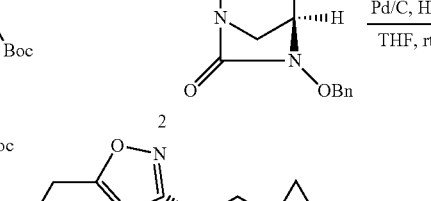

3

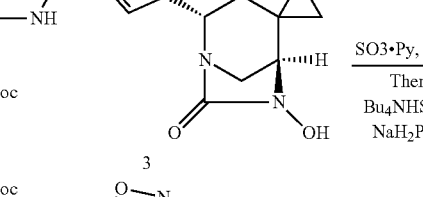

4

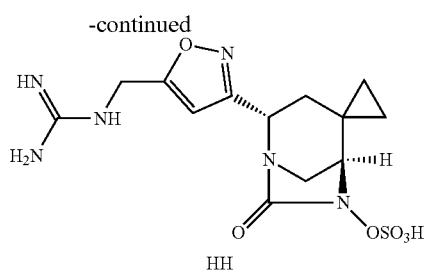

Steps 1-5: Following Steps 1-5 in Synthesis of Compound GG m/z (ES⁺), [M+H]⁺=298; ACID, HPLC RT=1.274 min. ¹H NMR (400 MHz, Chloroform-d) δ 1.52 (d, J=1.0 Hz, 18H), 2.29 (t, J=2.6 Hz, 1H), 4.26 (dd, J=4.9, 2.6 Hz, 2H), 8.49 (s, 1H), 11.47 (s, 1H).

Compound HH:

m/z (ES⁺), [M+H]⁺=387; ACID, HPLC tR=0.724 min. ¹H NMR (400 MHz, Chloroform-d) δ 1.52 (d, J=1.0 Hz, 18H), 2.29 (t, J=2.6 Hz, 1H), 4.26 (dd, J=4.9, 2.6 Hz, 2H), 8.49 (s, 1H), 11.47 (s, 1H).

Example 35: Preparation of Compound II

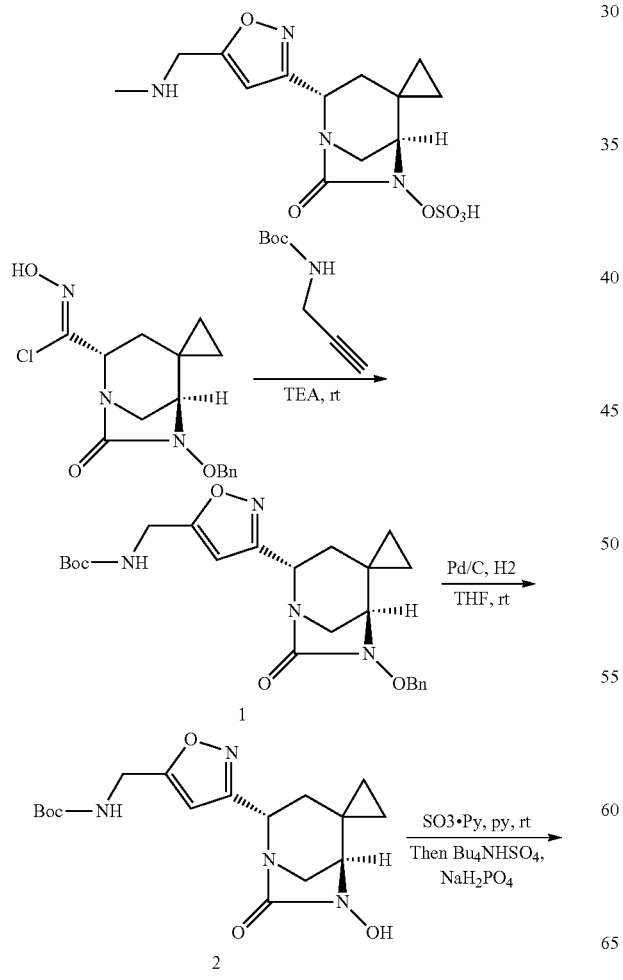

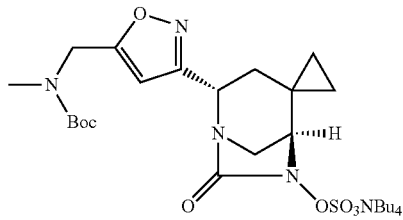

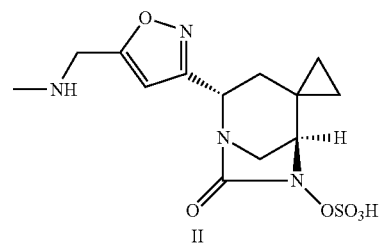

Steps 1-4: Following Steps 3-6 in Synthesis of Compound FF

Compound II:

m/z (ES⁺), [M+H]⁺=345; ACID, HPLC tR=0.646 min. ¹H NMR (400 MHz, D₂O) δ 0.31 (s, 1H), 0.43 (s, 1H), 0.55 (d, J=5.7 Hz, 1H), 0.60-0.71 (m, 1H), 1.65 (d, J=16.0 Hz, 1H), 2.45 (dd, J=15.8, 7.2 Hz, 1H), 3.08 (d, J=11.9 Hz, 1H), 3.18 (d, J=11.5 Hz, 1H), 3.36 (d, J=3.6 Hz, 1H), 4.32 (s, 2H), 4.74 (s, 1H), 6.60 (s, 1H), 8.33 (s, 0H).

Example 36: Preparation of Compound JJ

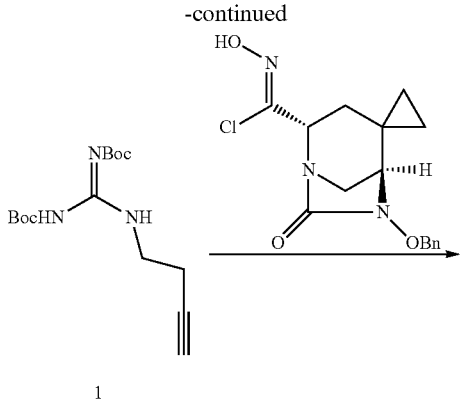

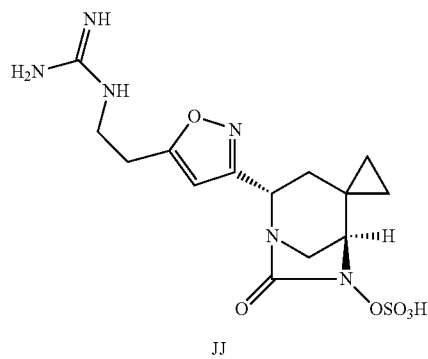

Step 1: Following Step 1 in Synthesis of Compound GG m/z (ES+), [M+H]+=312; ACID, HPLC tR=1.178 min. $^1$H NMR (400 MHz, Chloroform-d) δ 1.52 (d, J=1.7 Hz, 18H), 2.07 (t, J=2.6 Hz, 1H), 2.49 (td, J=6.6, 2.6 Hz, 2H), 3.63 (q, J=6.5 Hz, 2H), 8.64 (s, 1H), 11.51 (s, 1H).

Steps 2-5: Following Steps 3-6 in Synthesis of Compound FF

Compound JJ:

m/z (ES+), [M+H]+=401; ACID, HPLC tR=0.808 min. $^1$H NMR (400 MHz, D$_2$O) δ 0.32 (dt, J=9.9, 5.0 Hz, 1H), 0.43 (dt, J=9.1, 5.3 Hz, 1H), 0.55 (dt, J=10.3, 5.1 Hz, 1H), 0.66 (dt, J=10.0, 5.2 Hz, 1H), 1.63 (d, J=15.8 Hz, 1H), 2.46 (dd, J=15.9, 7.4 Hz, 1H), 3.05 (dd, J=13.4, 7.0 Hz, 3H), 3.19 (dd, J=12.0, 3.6 Hz, 1H), 3.37 (d, J=3.7 Hz, 1H), 3.51 (t, J=6.4 Hz, 2H), 4.73 (s, 1H), 6.34 (s, 1H).

Example 37: Preparation of Compound KK

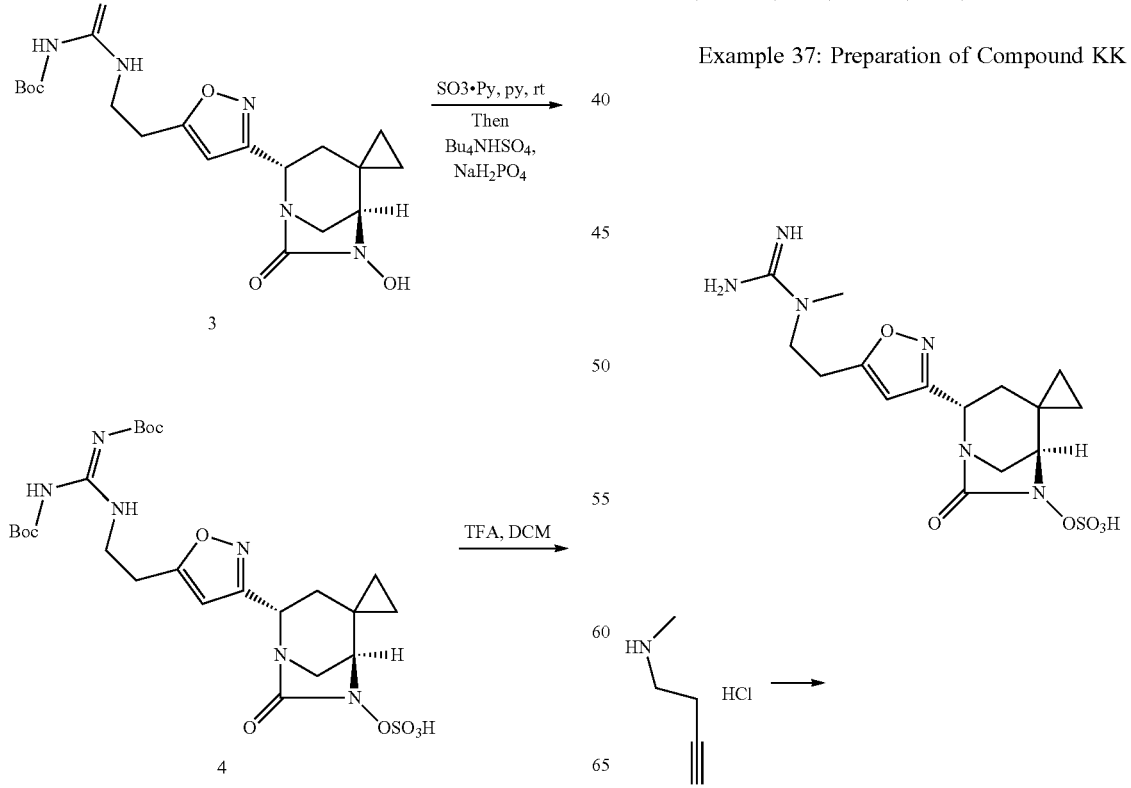

-continued
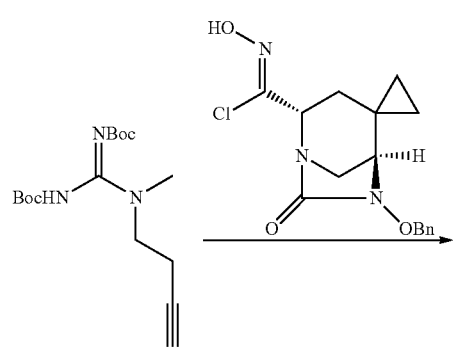
1
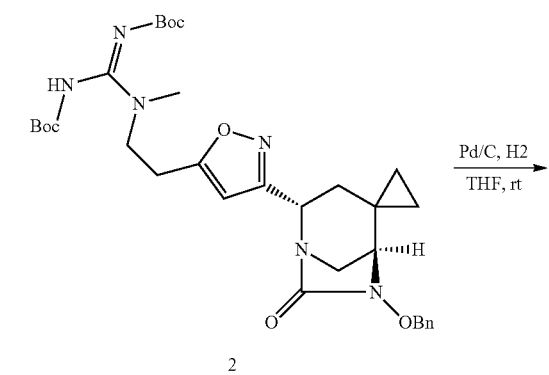
2
Pd/C, H2
THF, rt
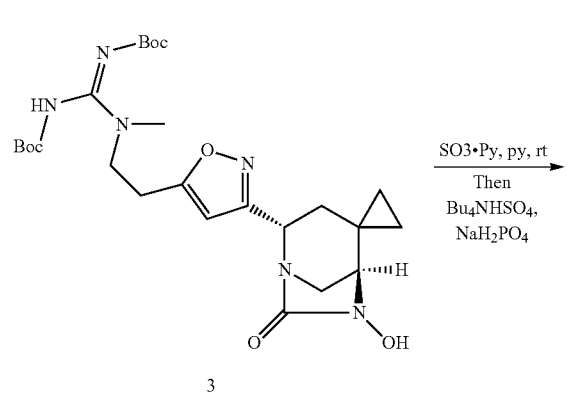
3
SO3·Py, py, rt
Then
Bu4NHSO4,
NaH2PO4
TFA, DCM
4
-continued
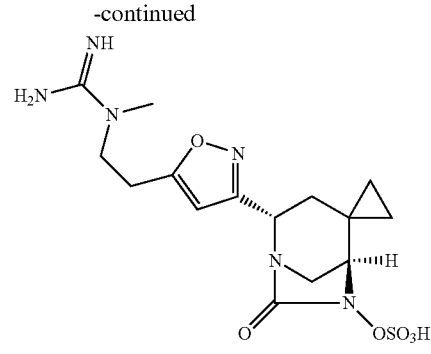
KK
Steps 1-5: Following Steps 1-5 in Synthesis of Compound GG
Compound KK:
m/z (ES$^+$), [M+H]$^+$=415; ACID, HPLC tR=1.283 min. $^1$H NMR (400 MHz, D$_2$O) δ 0.32 (dt, J=9.9, 5.0 Hz, 1H), 0.43 (dt, J=9.1, 5.3 Hz, 1H), 0.55 (dt, J=10.3, 5.1 Hz, 1H), 0.66 (dt, J=10.0, 5.2 Hz, 1H), 1.63 (d, J=15.8 Hz, 1H), 2.46 (dd, J=15.9, 7.4 Hz, 1H), 3.05 (dd, J=13.4, 7.0 Hz, 3H), 3.19 (dd, J=12.0, 3.6 Hz, 1H), 3.37 (d, J=3.7 Hz, 1H), 3.51 (t, J=6.4 Hz, 2H), 4.73 (s, 1H), 6.34 (s, 1H).
Example 38: Preparation of Compound LL
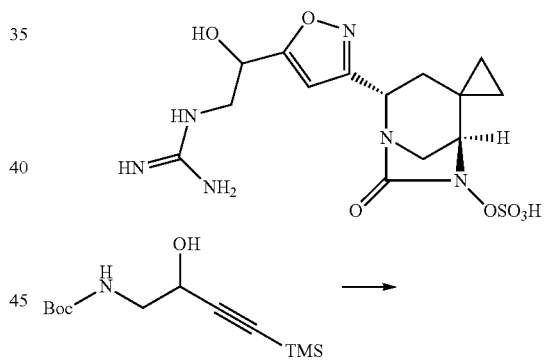
1
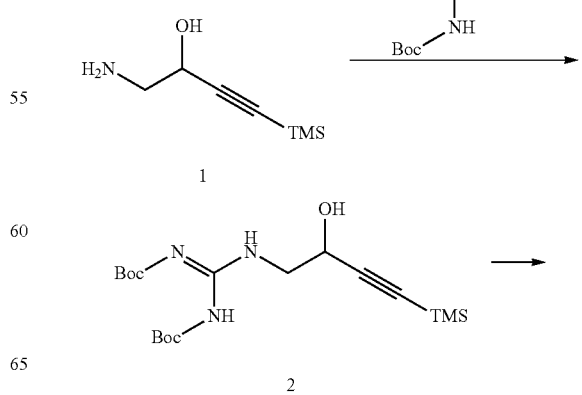
2

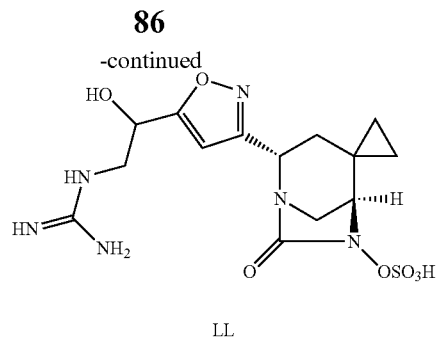

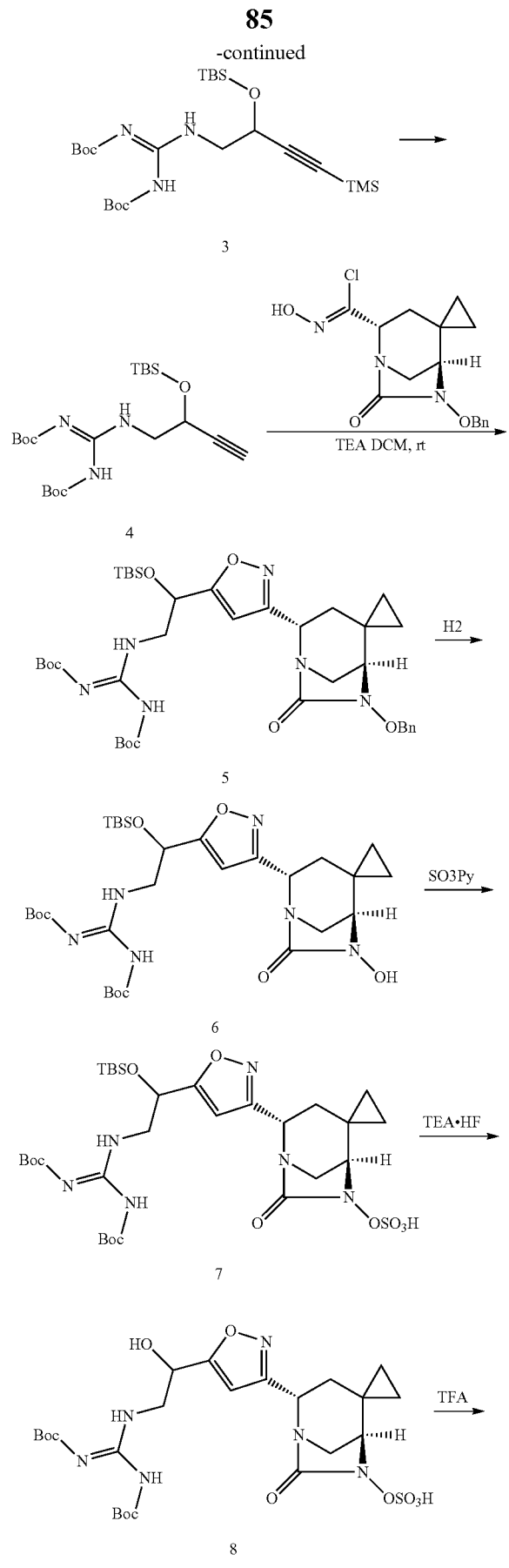

Step 1: Following Step 1 in Synthesis of Compound UU
Step 2: Following Step 1 in Synthesis of Compound GG
m/z (ES⁺), [M+H]⁺=400; ACID, HPLC tR=1.276 min. ¹H NMR (400 MHz, Chloroform-d) δ 0.20 (s, 9H), 1.48 (s, 10H), 3.20-3.36 (m, 1H), 3.49 (s, 1H), 4.46 (dd, J=7.0, 3.8 Hz, 1H), 4.98 (s, 1H).

Step 3: Synthesis of Compound 3

TBS-Cl (0.415 g, 2.75 mmol) was added to a solution of Compound 2 (1 g, 2.50 mmol) and TEA (0.698 mL, 5.01 mmol) in DCM (20 mL). The resulting mixture was stirred at room temperature for 4 h. The solvent was removed under reduced pressure. The crude product was purified by flash silica chromatography with gradient elution (1 to 10% EtOAc in petroleum ether). Pure fractions were evaporated to dryness to give Compound 3 (1.100 g, 86%) in the form of a gum. m/z (ES⁺), [M+H]⁺=514; ACID, HPLC tR=1.532 min.

Step 4: Synthesis of Compound 4

K₂CO₃ (0.403 g, 2.92 mmol) was added to a solution of Compound 3 (0.75 g, 1.46 mmol) in MeOH (20 mL). The resulting mixture was stirred at room temperature for 4 h. The solvent was removed under reduced pressure. The crude product was purified by flash silica chromatography with gradient elution (0 to 10% EtOAc in petroleum ether). Pure fractions were evaporated to dryness to give Compound 4 (0.6 g) in the form of a gum. ¹H NMR (300 MHz, Chloroform-d) δ 0.13 (dd, 2=9.9, 6.9 Hz, 6H), 0.91 (s, 9H), 1.49 (d, J=5.2 Hz, 16H), 2.39-2.49 (m, 1H), 4.50 (ddd, J=7.9, 4.2, 2.0 Hz, 1H).

Steps 5-7: Following Steps 3-5 in Synthesis of Compound FF

Step 8: Synthesis of Compound 8

TEA HF (0.068 g, 0.56 mmol) was added to a solution of (1R,4S)-4-(5-((E)-8-((tert-butoxycarbonyl)amino)-2,2,3,3,12,12-hexamethyl-10-oxo-4,11-dioxa-7,9-diaza-3-silatridec-8-en-5-yl)isoxazol-3-yl)-6-oxo-5,7-diazaspiro[bicyclo[3.2.1]octane-2,1'-cyclopropan]-7-yl hydrogen sulfate (0.102 g, 0.14 mmol) in THF (2.000 mL). The resulting mixture was stirred at room temperature for 14 h. The solvent was removed under reduced pressure to give (1R,4S)-4-(5-(2-((E)-2,3-bis(tert-butoxycarbonyl)guanidino)-1-hydroxyethyl)isoxazol-3-yl)-6-oxo-5,7-diazaspiro[bicyclo[3.2.1]octane-2,1'-cyclopropan]-7-yl hydrogen sulfate (0.080 g, 93%) in the form of a gum. m/z (ES⁺), [M+H]⁺=617; ACID, HPLC tR=1.044 min.

Step 9: Following Step 6 in Synthesis of Compound LL
m/z (ES+), [M+H]+=417; ACID, HPLC tR=0.716 min. ¹H NMR (400 MHz, D₂O) δ 0.30 (s, 1H), 0.41 (dt, J=9.1, 5.3 Hz, 1H), 0.49-0.58 (m, 1H), 0.63 (dd, J=10.0, 4.9 Hz, 1H), 1.63 (d, J=15.9 Hz, 1H), 2.45 (dd, J=15.3, 7.3 Hz, 1H), 3.04 (dd, J=12.0, 5.3 Hz, 1H), 3.18 (d, J=11.8 Hz, 1H), 3.35 (d, J=3.7 Hz, 1H), 3.57 (d, J=5.1 Hz, 1H), 5.04 (t, J=5.2 Hz, 1H), 6.48 (s, 1H).

Example 39: Preparation of Compound MM

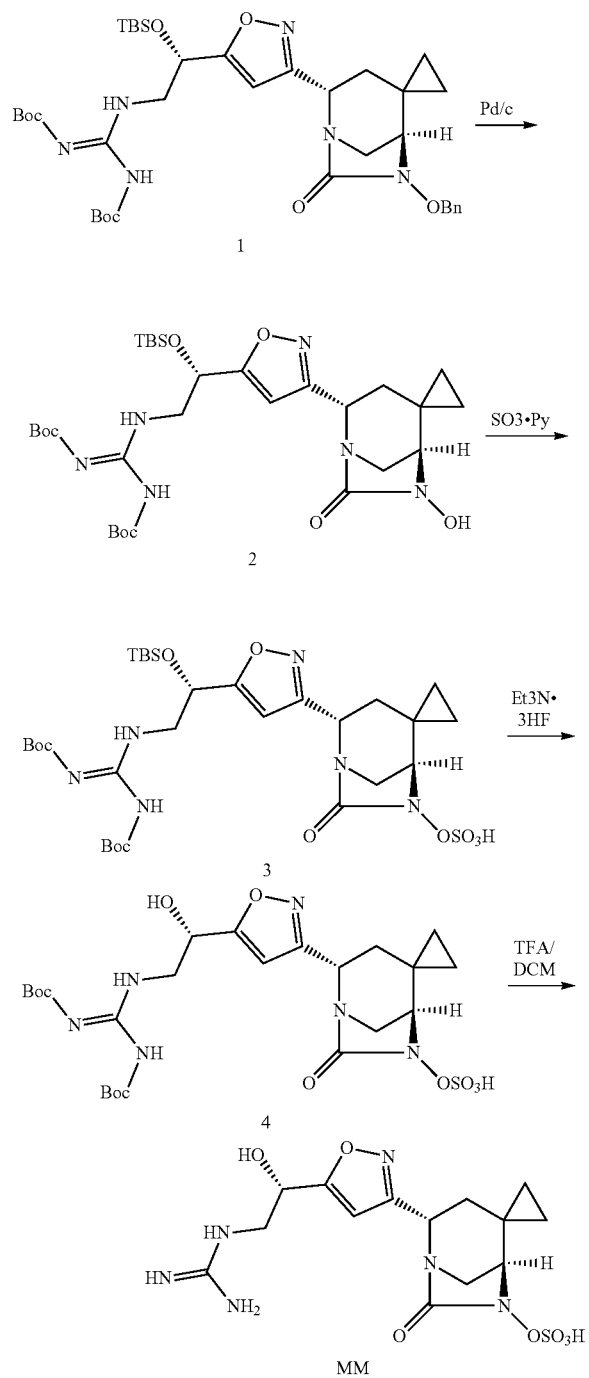

Example 40: Preparation of Compound NN

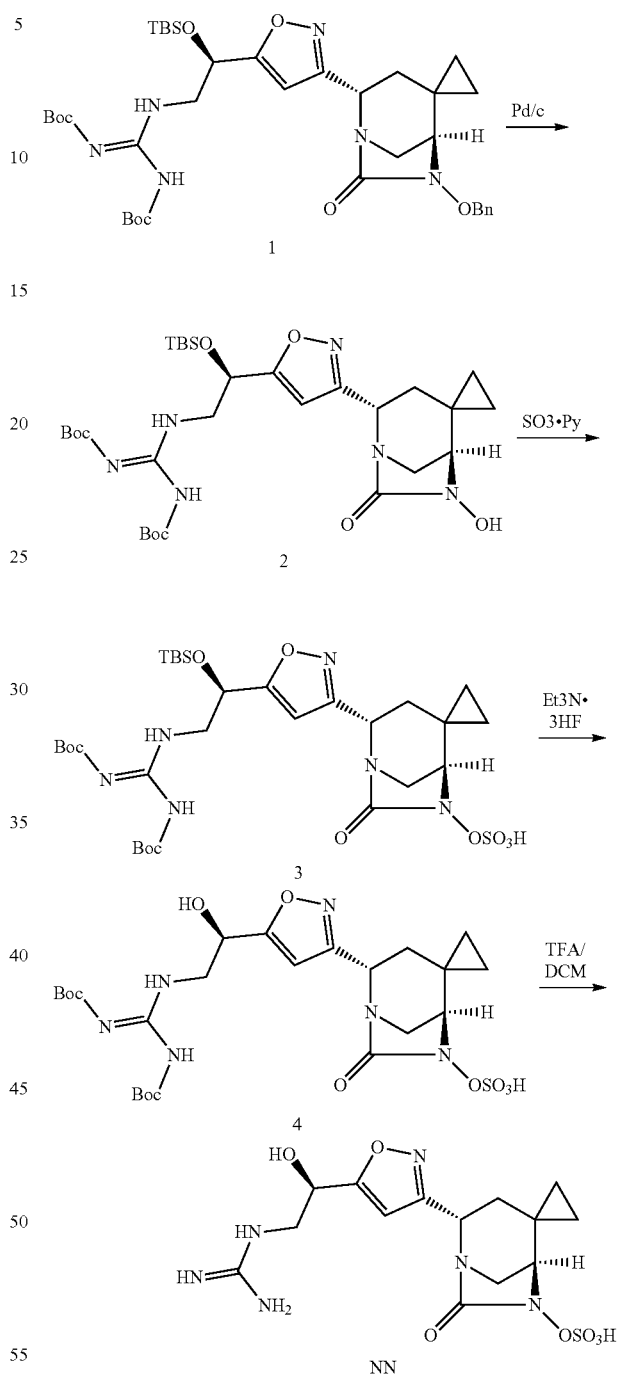

Steps 1-4: Following Steps 6-9 in Synthesis of Compound I

Compound MM:

ESI-MS (EI+, m/z+): 417, 0.721 min. $^1$H NMR (300 MHz, D$_2$O) δ 0.33 (dd, J=9.6, 4.5 Hz, 1H), 0.43 (dt, J=8.6, 5.1 Hz, 1H), 0.56 (dt, J=10.2, 5.0 Hz, 1H), 0.66 (dt, J=9.8, 5.0 Hz, 1H), 1.65 (d, J=15.7 Hz, 1H), 2.46 (dd, J=16.1, 7.9 Hz, 1H), 3.05 (d, J=12.0 Hz, 1H), 3.20 (dd, J=11.9, 3.6 Hz, 1H), 3.37 (d, J=3.7 Hz, 1H), 3.59 (d, J=5.2 Hz, 2H), 4.74 (d, J=7.4 Hz, 1H), 5.06 (t, J=5.1 Hz, 1H), 6.50 (s, 1H).

Steps 1-4: Following Steps 6-9 in Synthesis of Compound I

ESI-MS (EI+, m/z+): 417, 0.721 min. $^1$H NMR (300 MHz, D$_2$O) δ 0.33 (dd, J=9.6, 4.6 Hz, 1H), 0.43 (dt, J=8.6, 5.1 Hz, 1H), 0.56 (dt, J=10.0, 5.0 Hz, 1H), 0.65 (dd, J=9.6, 4.4 Hz, 1H), 1.65 (d, J=15.8 Hz, 1H), 2.47 (dd, J=16.2, 7.3 Hz, 1H), 3.06 (d, J=12.0 Hz, 1H), 3.19 (dd, J=12.0, 3.6 Hz, 1H), 3.37 (d, J=3.6 Hz, 1H), 3.59 (dd, J=5.3, 1.7 Hz, 2H), 4.75 (s, 1H), 5.06 (t, J=5.2 Hz, 1H), 6.50 (s, 1H).

Example 41: Preparation of Compound OO
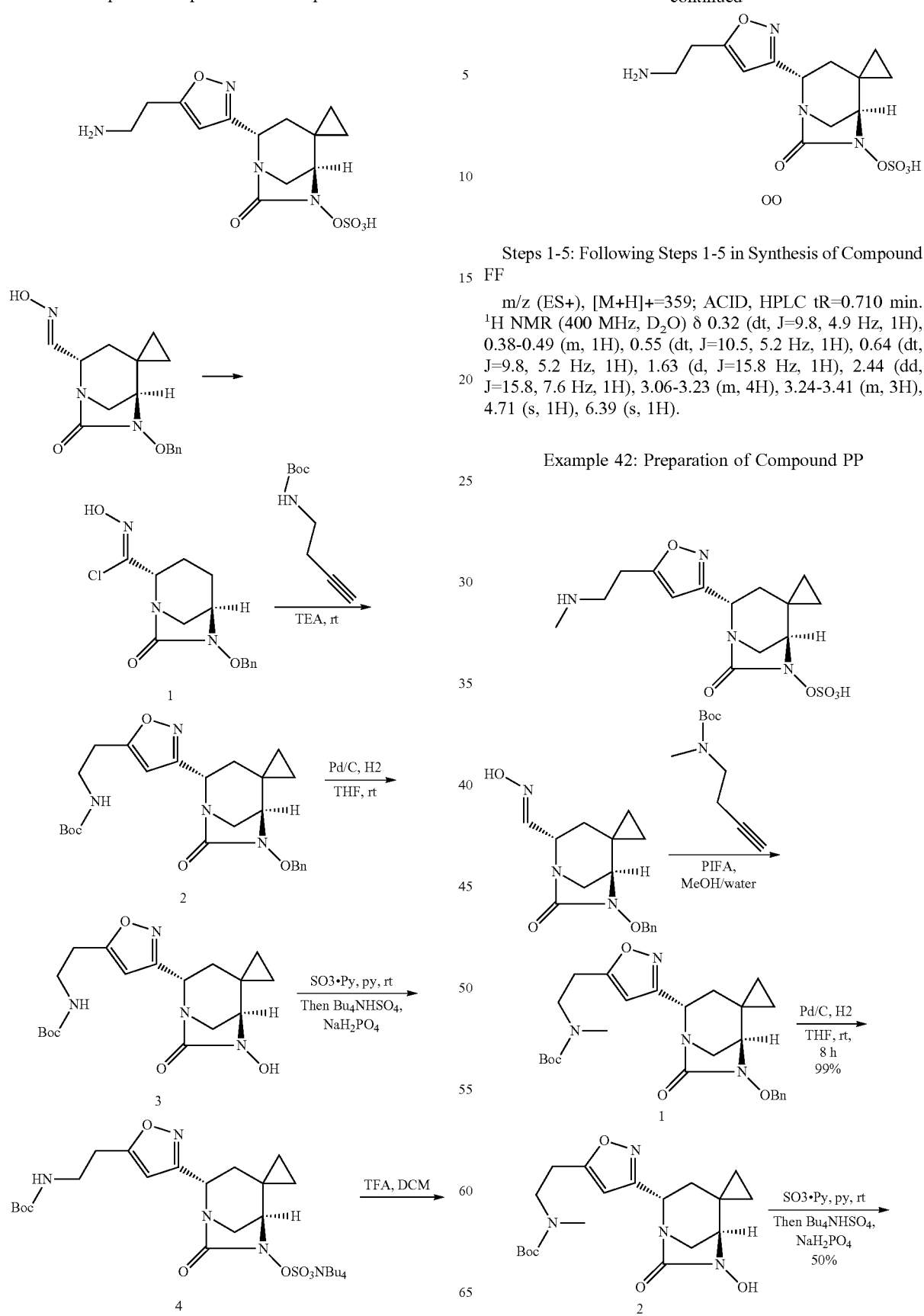
Steps 1-5: Following Steps 1-5 in Synthesis of Compound FF
m/z (ES+), [M+H]+=359; ACID, HPLC tR=0.710 min. $^1$H NMR (400 MHz, D$_2$O) δ 0.32 (dt, J=9.8, 4.9 Hz, 1H), 0.38-0.49 (m, 1H), 0.55 (dt, J=10.5, 5.2 Hz, 1H), 0.64 (dt, J=9.8, 5.2 Hz, 1H), 1.63 (d, J=15.8 Hz, 1H), 2.44 (dd, J=15.8, 7.6 Hz, 1H), 3.06-3.23 (m, 4H), 3.24-3.41 (m, 3H), 4.71 (s, 1H), 6.39 (s, 1H).
Example 42: Preparation of Compound PP

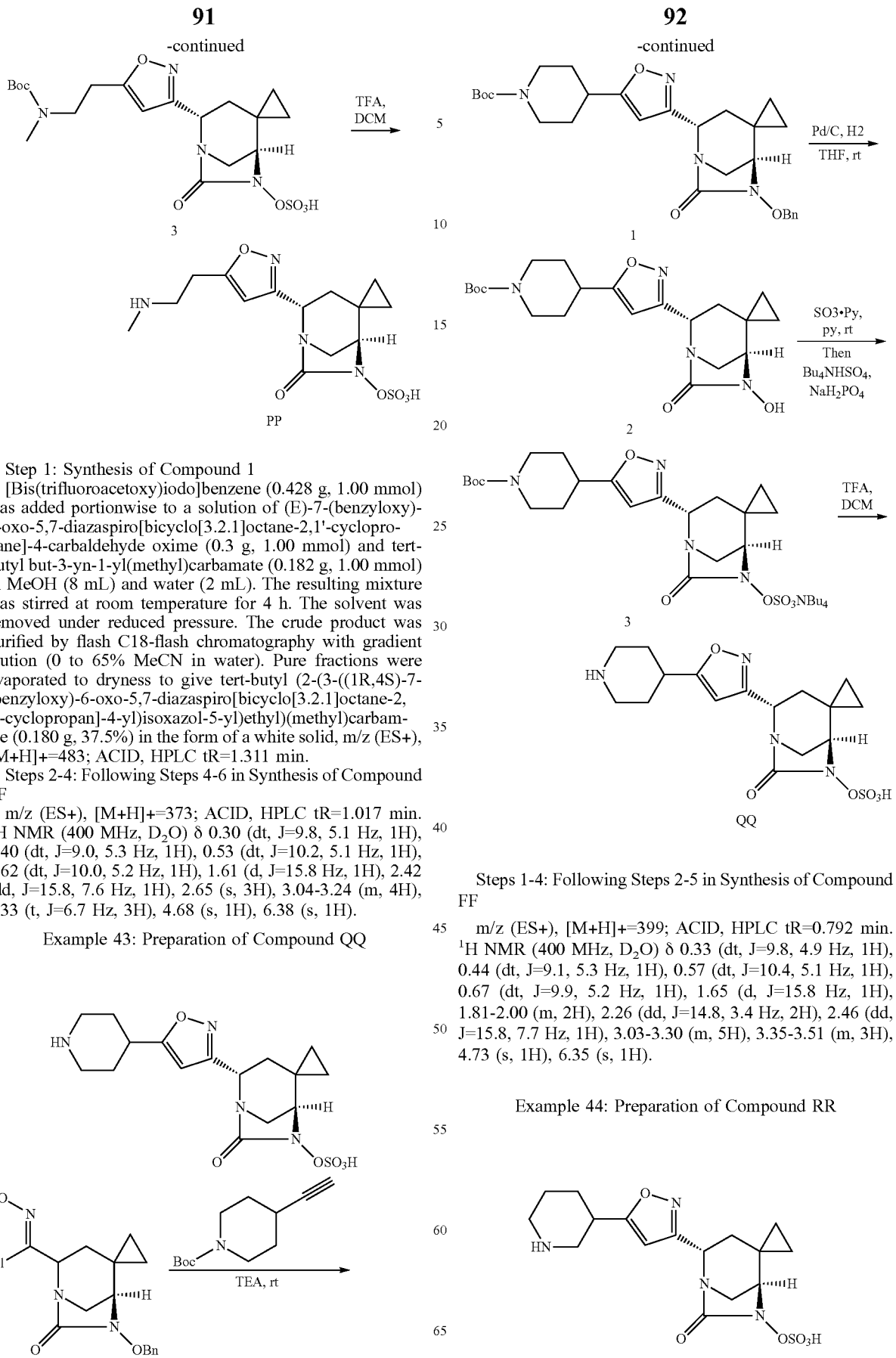

Step 1: Synthesis of Compound 1

[Bis(trifluoroacetoxy)iodo]benzene (0.428 g, 1.00 mmol) was added portionwise to a solution of (E)-7-(benzyloxy)-6-oxo-5,7-diazaspiro[bicyclo[3.2.1]octane-2,1'-cyclopropane]-4-carbaldehyde oxime (0.3 g, 1.00 mmol) and tert-butyl but-3-yn-1-yl(methyl)carbamate (0.182 g, 1.00 mmol) in MeOH (8 mL) and water (2 mL). The resulting mixture was stirred at room temperature for 4 h. The solvent was removed under reduced pressure. The crude product was purified by flash C18-flash chromatography with gradient elution (0 to 65% MeCN in water). Pure fractions were evaporated to dryness to give tert-butyl (2-(3-((1R,4S)-7-(benzyloxy)-6-oxo-5,7-diazaspiro[bicyclo[3.2.1]octane-2,1'-cyclopropan]-4-yl)isoxazol-5-yl)ethyl)(methyl)carbamate (0.180 g, 37.5%) in the form of a white solid, m/z (ES+), [M+H]+=483; ACID, HPLC tR=1.311 min.

Steps 2-4: Following Steps 4-6 in Synthesis of Compound FF m/z (ES+), [M+H]+=373; ACID, HPLC tR=1.017 min. $^1$H NMR (400 MHz, D$_2$O) δ 0.30 (dt, J=9.8, 5.1 Hz, 1H), 0.40 (dt, J=9.0, 5.3 Hz, 1H), 0.53 (dt, J=10.2, 5.1 Hz, 1H), 0.62 (dt, J=10.0, 5.2 Hz, 1H), 1.61 (d, J=15.8 Hz, 1H), 2.42 (dd, J=15.8, 7.6 Hz, 1H), 2.65 (s, 3H), 3.04-3.24 (m, 4H), 3.33 (t, J=6.7 Hz, 3H), 4.68 (s, 1H), 6.38 (s, 1H).

Example 43: Preparation of Compound QQ

Steps 1-4: Following Steps 2-5 in Synthesis of Compound FF m/z (ES+), [M+H]+=399; ACID, HPLC tR=0.792 min. $^1$H NMR (400 MHz, D$_2$O) δ 0.33 (dt, J=9.8, 4.9 Hz, 1H), 0.44 (dt, J=9.1, 5.3 Hz, 1H), 0.57 (dt, J=10.4, 5.1 Hz, 1H), 0.67 (dt, J=9.9, 5.2 Hz, 1H), 1.65 (d, J=15.8 Hz, 1H), 1.81-2.00 (m, 2H), 2.26 (dd, J=14.8, 3.4 Hz, 2H), 2.46 (dd, J=15.8, 7.7 Hz, 1H), 3.03-3.30 (m, 5H), 3.35-3.51 (m, 3H), 4.73 (s, 1H), 6.35 (s, 1H).

Example 44: Preparation of Compound RR

93
-continued
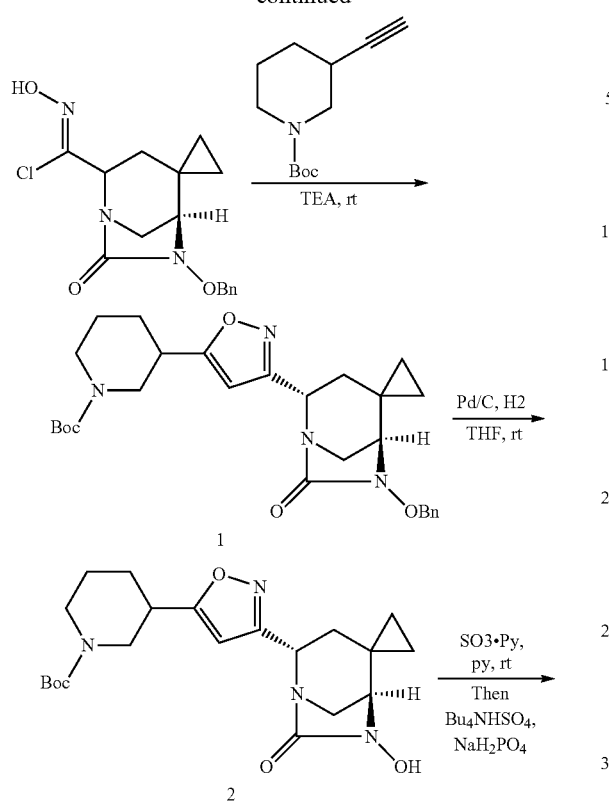
Steps 1-4: Following Steps 2-5 in Synthesis of Compound FF
m/z (ES+), [M+H]+=399; ACID, HPLC tR=0.806 min. $^1$H NMR (400 MHz, D$_2$O) δ 0.31 (dd, J=9.5, 4.9 Hz, 1H), 0.41 (dt, J=9.1, 5.4 Hz, 1H), 0.54 (dt, J=10.3, 5.0 Hz, 1H), 0.64 (dt, J=9.8, 5.2 Hz, 1H), 1.63 (d, J=15.8 Hz, 1H), 1.68-1.83 (m, 2H), 1.94 (s, 1H), 2.16 (s, 1H), 2.43 (dd, J=15.9, 7.5 Hz, 1H), 2.91-3.05 (m, 1H), 3.05-3.22 (m, 3H), 3.26-3.42 (m, 3H), 3.59 (d, J=12.5 Hz, 1H), 6.37 (s, 1H).
94
Example 45: Preparation of Compound SS
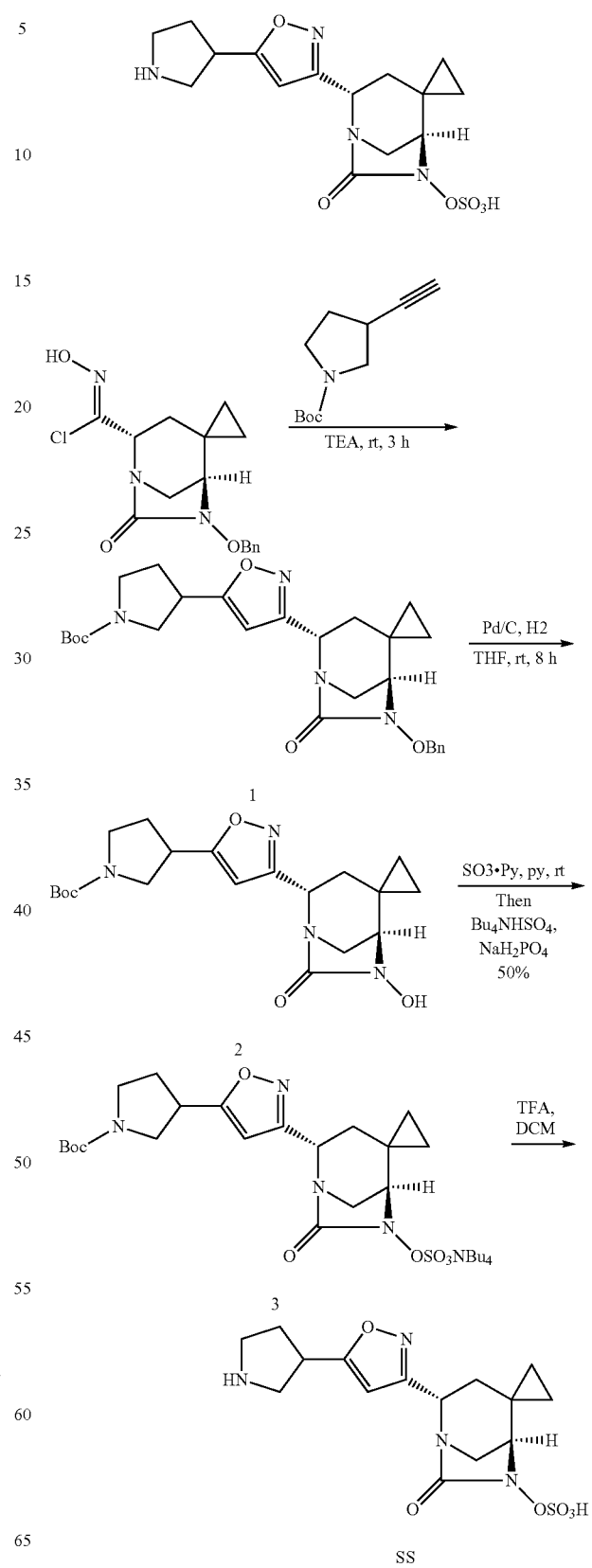

Steps 1-4: Following Steps 2-5 in Synthesis of Compound FF m/z (ES+), [M+H]+=385; ACID, HPLC tR=0.764 min. $^1$H NMR (400 MHz, D$_2$O) δ 0.31 (dt, J=10.0, 5.1 Hz, 1H), 0.41 (dt, J=9.0, 5.3 Hz, 1H), 0.54 (dt, J=10.3, 5.1 Hz, 1H), 0.64 (dt, J=9.8, 5.2 Hz, 1H), 1.63 (d, J=15.8 Hz, 1H), 2.11-2.26 (m, 1H), 2.43 (dd, J=13.7, 7.3 Hz, 2H), 3.05-3.20 (m, 2H), 3.29-3.52 (m, 4H), 3.68 (dd, J=12.1, 8.2 Hz, 1H), 3.83 (p, J=7.6 Hz, 1H), 6.41 (s, 1H).

Example 46: Preparation of Compound TT

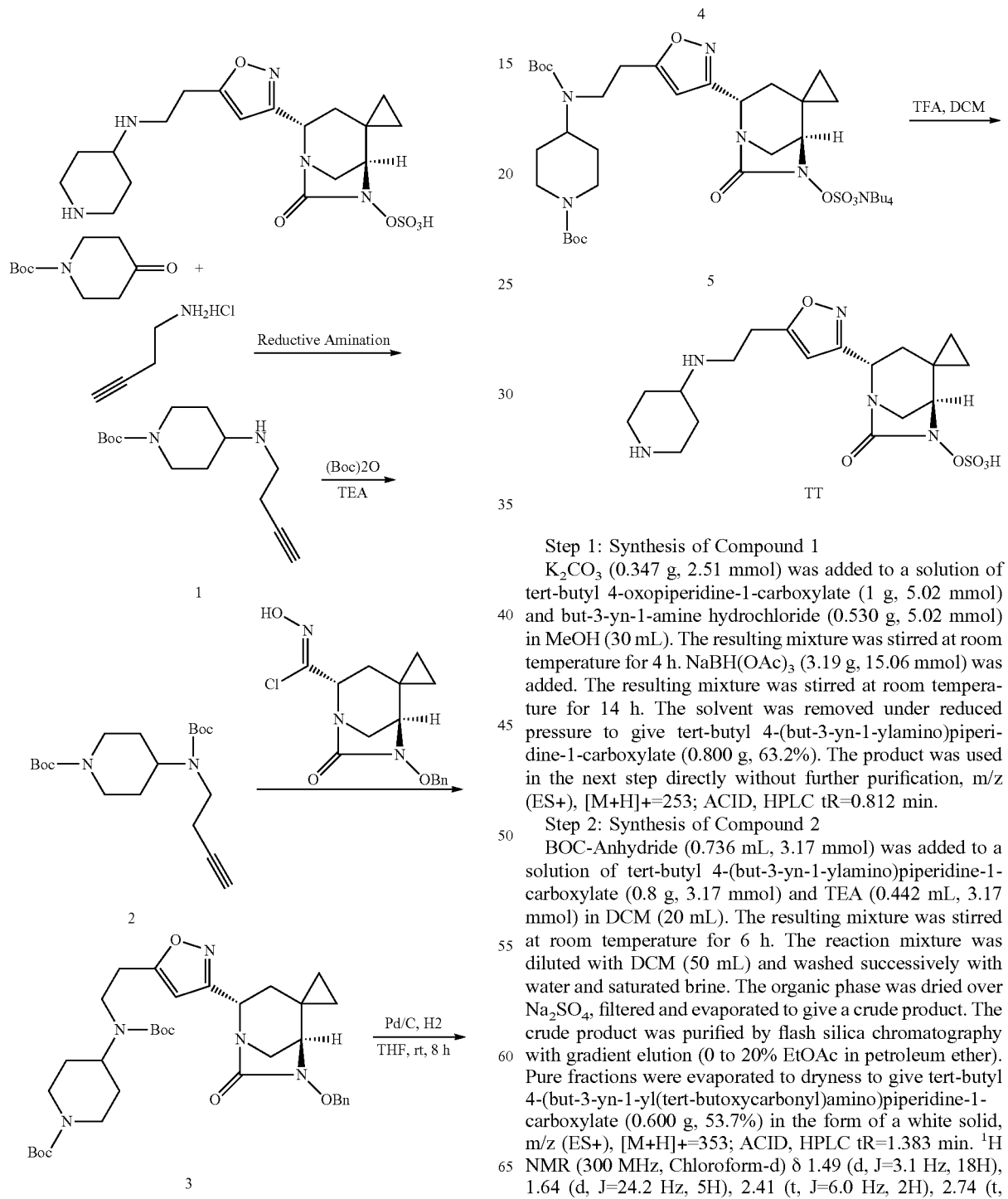

Step 1: Synthesis of Compound 1

K$_2$CO$_3$ (0.347 g, 2.51 mmol) was added to a solution of tert-butyl 4-oxopiperidine-1-carboxylate (1 g, 5.02 mmol) and but-3-yn-1-amine hydrochloride (0.530 g, 5.02 mmol) in MeOH (30 mL). The resulting mixture was stirred at room temperature for 4 h. NaBH(OAc)$_3$ (3.19 g, 15.06 mmol) was added. The resulting mixture was stirred at room temperature for 14 h. The solvent was removed under reduced pressure to give tert-butyl 4-(but-3-yn-1-ylamino)piperidine-1-carboxylate (0.800 g, 63.2%). The product was used in the next step directly without further purification, m/z (ES+), [M+H]+=253; ACID, HPLC tR=0.812 min.

Step 2: Synthesis of Compound 2

BOC-Anhydride (0.736 mL, 3.17 mmol) was added to a solution of tert-butyl 4-(but-3-yn-1-ylamino)piperidine-1-carboxylate (0.8 g, 3.17 mmol) and TEA (0.442 mL, 3.17 mmol) in DCM (20 mL). The resulting mixture was stirred at room temperature for 6 h. The reaction mixture was diluted with DCM (50 mL) and washed successively with water and saturated brine. The organic phase was dried over Na$_2$SO$_4$, filtered and evaporated to give a crude product. The crude product was purified by flash silica chromatography with gradient elution (0 to 20% EtOAc in petroleum ether). Pure fractions were evaporated to dryness to give tert-butyl 4-(but-3-yn-1-yl(tert-butoxycarbonyl)amino)piperidine-1-carboxylate (0.600 g, 53.7%) in the form of a white solid, m/z (ES+), [M+H]+=353; ACID, HPLC tR=1.383 min. $^1$H NMR (300 MHz, Chloroform-d) δ 1.49 (d, J=3.1 Hz, 18H), 1.64 (d, J=24.2 Hz, 5H), 2.41 (t, J=6.0 Hz, 2H), 2.74 (t, J=12.5 Hz, 2H), 3.27 (s, 2H), 4.21 (d, J=12.8 Hz, 2H).

Steps 3-6: Following Steps 2-5 in Synthesis of Compound FF m/z (ES+), [M+H]+=442; ACID, HPLC tR=0.672 min. $^1$H NMR (400 MHz, D$_2$O) δ 0.36 (dt, J=10.2, 5.2 Hz, 1H), 0.41-0.54 (m, 1H), 0.59 (dt, J=10.4, 5.2 Hz, 1H), 0.69 (dt, J=9.8, 5.2 Hz, 1H), 1.67 (d, J=15.8 Hz, 1H), 1.83 (qd, J=13.1, 3.6 Hz, 2H), 2.35 (d, J=14.0 Hz, 2H), 2.49 (dd, J=16.2, 7.4 Hz, 2H), 3.06 (td, J=13.4, 2.8 Hz, 2H), 3.16 (t, J=12.2 Hz, 1H), 3.20-3.30 (m, 2H), 3.41 (d, J=3.5 Hz, 1H), 3.49 (q, J=7.9, 7.2 Hz, 2H), 3.52-3.63 (m, 2H), 4.74 (d, J=7.3 Hz, 2H), 6.44 (s, 1H).

Example 47: Preparation of Compound UU

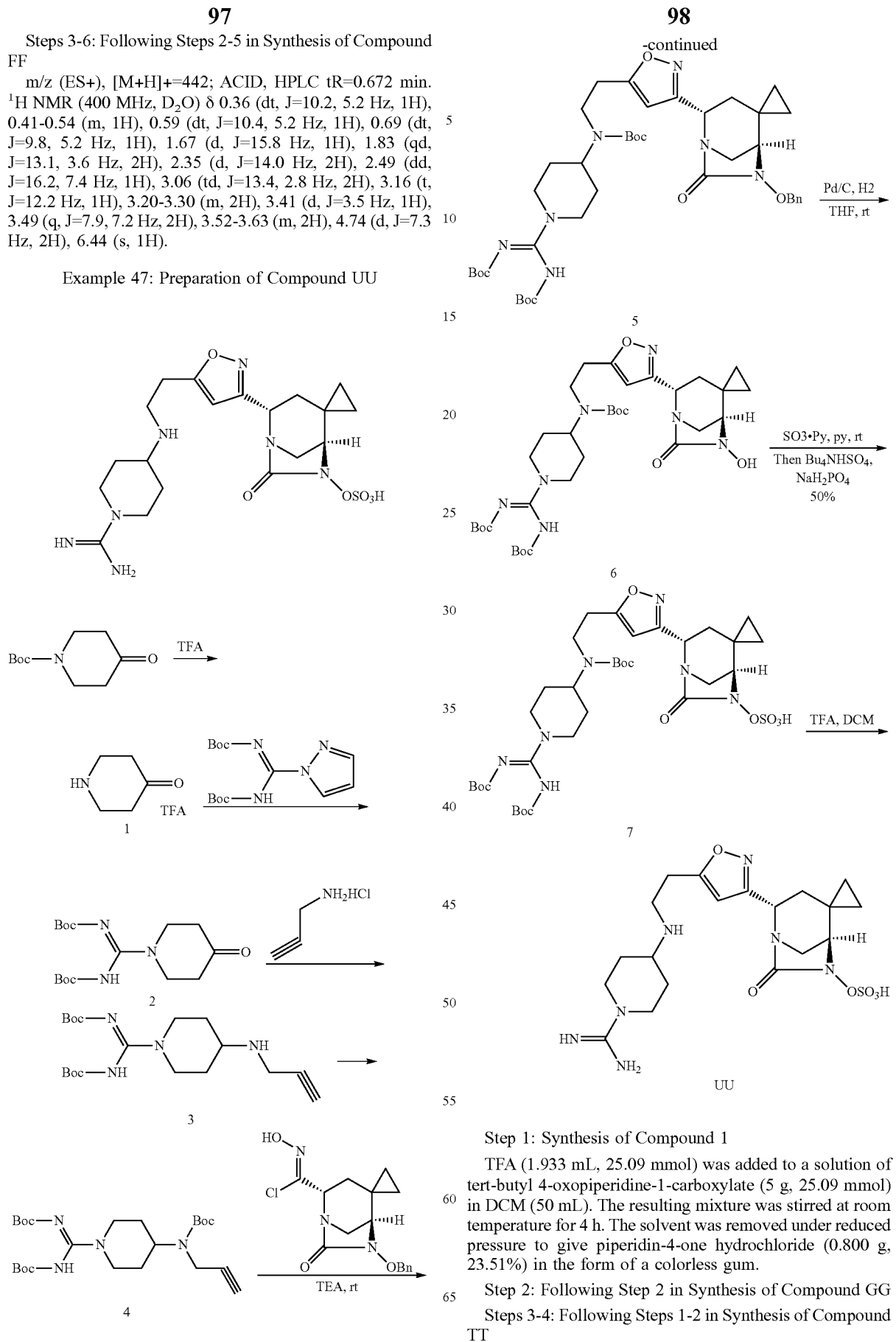

Step 1: Synthesis of Compound 1

TFA (1.933 mL, 25.09 mmol) was added to a solution of tert-butyl 4-oxopiperidine-1-carboxylate (5 g, 25.09 mmol) in DCM (50 mL). The resulting mixture was stirred at room temperature for 4 h. The solvent was removed under reduced pressure to give piperidin-4-one hydrochloride (0.800 g, 23.51%) in the form of a colorless gum.

Step 2: Following Step 2 in Synthesis of Compound GG

Steps 3-4: Following Steps 1-2 in Synthesis of Compound TT

¹H NMR (400 MHz, Chloroform-d) δ 1.49 (d, J=7.8 Hz, 29H), 1.75 (s, 3H), 2.01 (d, J=6.0 Hz, 1H), 2.06 (s, 2H), 2.40 (s, 2H), 3.01 (d, J=38.2 Hz, 2H), 3.24 (s, 4H), 4.21 (s, 2H).

Steps 5-8: Following Steps 2-5 in Synthesis of Compound FF

Compound UU:

m/z (ES+), [M+H]+=484; ACID, HPLC tR=0.948 min. ¹H NMR (400 MHz, D₂O) δ 0.33 (dd, J=9.6, 4.8 Hz, 1H), 0.43 (dt, J=8.9, 5.3 Hz, 1H), 0.56 (dt, J=10.4, 5.1 Hz, 1H), 0.66 (dt, J=9.7, 5.2 Hz, 1H), 1.54-1.72 (m, 3H), 2.15 (d, J=12.4 Hz, 2H), 2.46 (dd, J=15.8, 7.5 Hz, 1H), 2.98-3.29 (m, 6H), 3.36-3.53 (m, 4H), 3.89 (d, J=14.3 Hz, 2H), 6.40 (s, 1H), 8.35 (s, 1H).

Example 48: Preparation of Compound VV

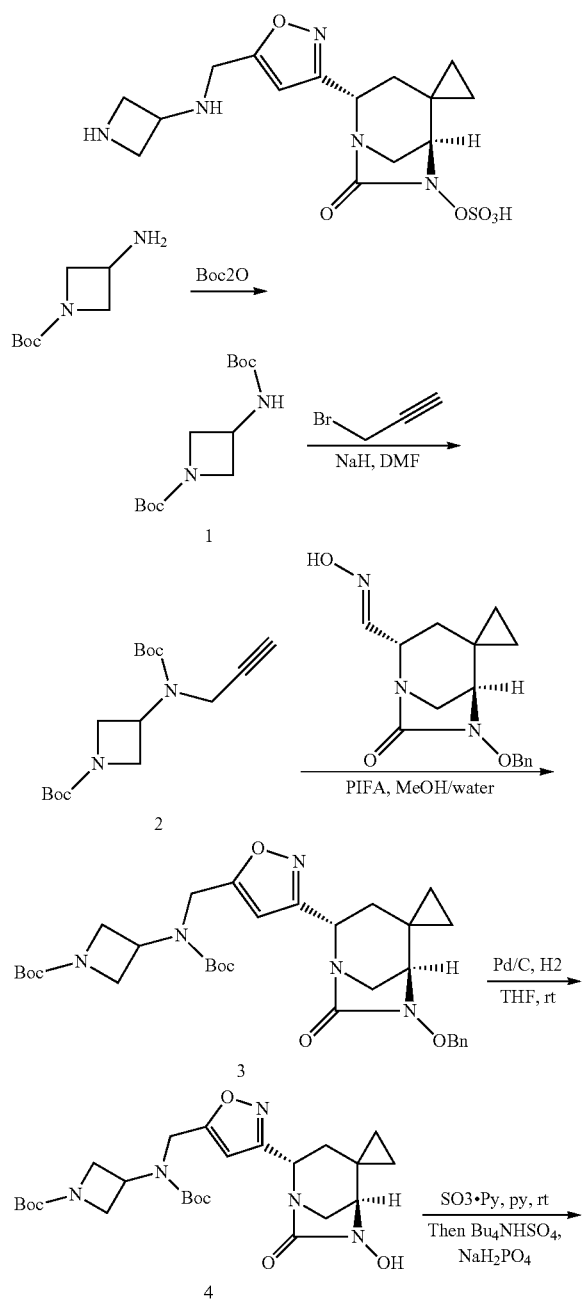

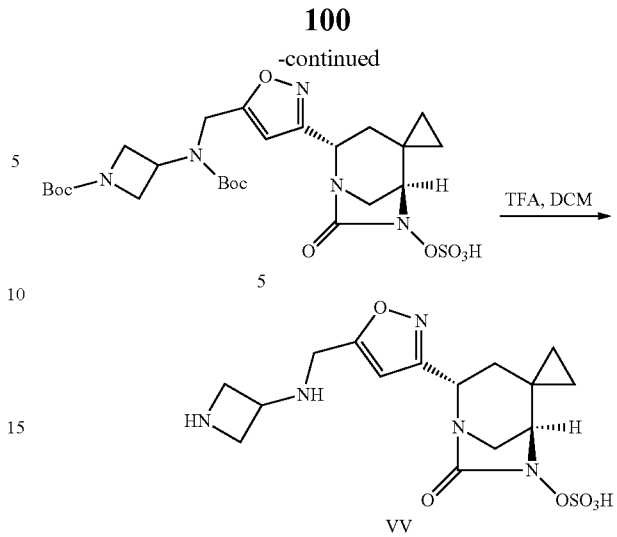

Step 1: Following Step 2 in Synthesis of Compound TT

Step 2:

NaH (1.469 g, 36.72 mmol) was added to a solution of tert-butyl 3-((tert-butoxycarbonyl)amino)azetidine-1-carboxylate (5 g, 18.36 mmol) in DMF (50 mL). The resulting mixture was stirred at room temperature for 1 h. 3-bromopro-1-yne (2.402 g, 20.19 mmol) was added. The resulting mixture was stirred at room temperature for 3 h. The reaction was quenched with water (100 mL), and EtOAc was added for extraction. The organic phase was dried over Na₂SO₄, filtered and evaporated to give a white solid. The crude product was purified by flash silica chromatography with gradient elution (0 to 20% EtOAc in petroleum ether). Pure fractions were evaporated to dryness to give tert-butyl 3-((tert-butoxycarbonyl)(prop-2-yn-1-yl)amino)azetidine-1-carboxylate (0.800 g, 14.04%) in the form of a white solid, m/z (ES+), [M+H]+=311; ACID, HPLC tR=1.265 min. ¹H NMR (400 MHz, Chloroform-d) δ 1.46 (s, 9H), 1.50 (s, 8H), 2.23 (t, J=2.4 Hz, 1H), 4.05-4.18 (m, 6H), 4.42-4.81 (m, 1H).

Steps 3-6: Following Steps 1-4 in Synthesis of Compound PP

Compound VV:

m/z (ES+), [M+H]+=400; ACID, HPLC tR=0.729 min. ¹H NMR (400 MHz, D₂O) δ 0.31 (dt, J=10.1, 5.1 Hz, 1H), 0.41 (dt, J=9.1, 5.3 Hz, 1H), 0.53 (dt, J=10.3, 5.1 Hz, 1H), 0.63 (dt, J=9.8, 5.2 Hz, 1H), 1.61 (d, J=15.8 Hz, 1H), 2.44 (dd, J=15.7, 7.7 Hz, 1H), 3.05 (d, J=12.0 Hz, 1H), 3.16 (dd, J=12.0, 3.7 Hz, 1H), 3.35 (d, J=3.6 Hz, 1H), 3.79 (ddd, J=10.8, 7.3, 3.1 Hz, 2H), 3.85-3.95 (m, 3H), 4.06 (dd, J=11.2, 7.6 Hz, 2H), 6.40 (s, 1H).

Example 49: Preparation of Compound WW

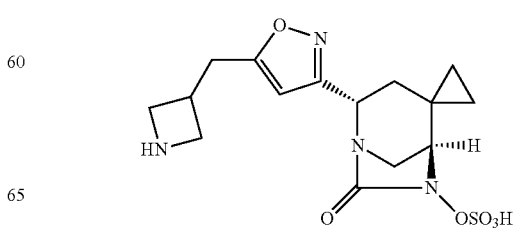

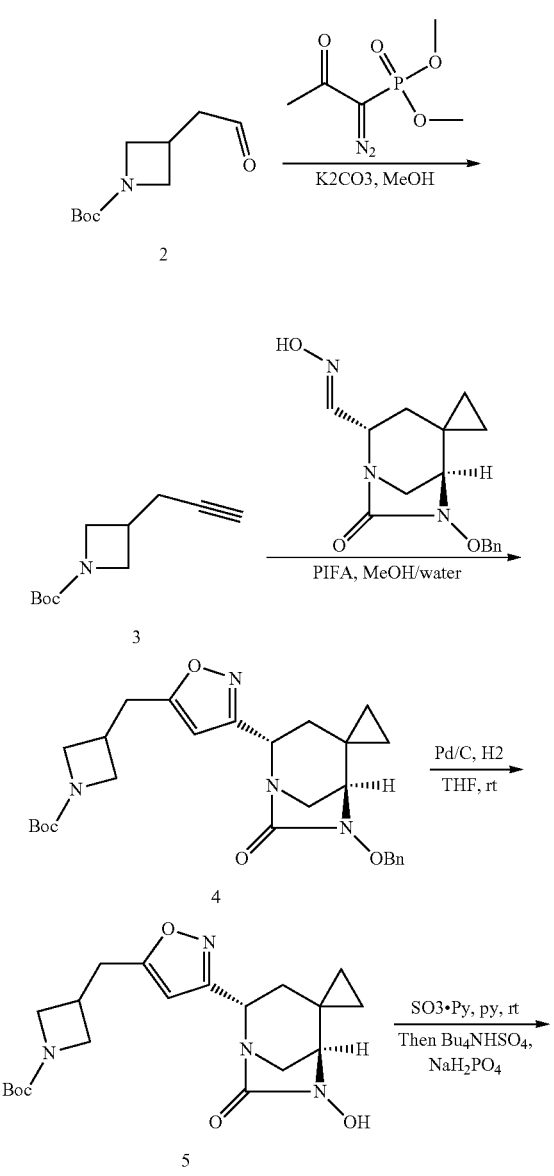

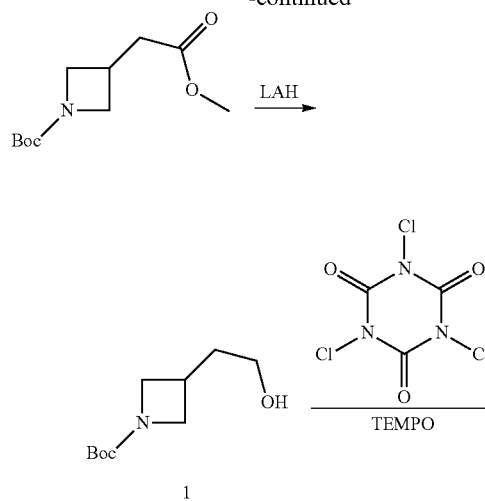

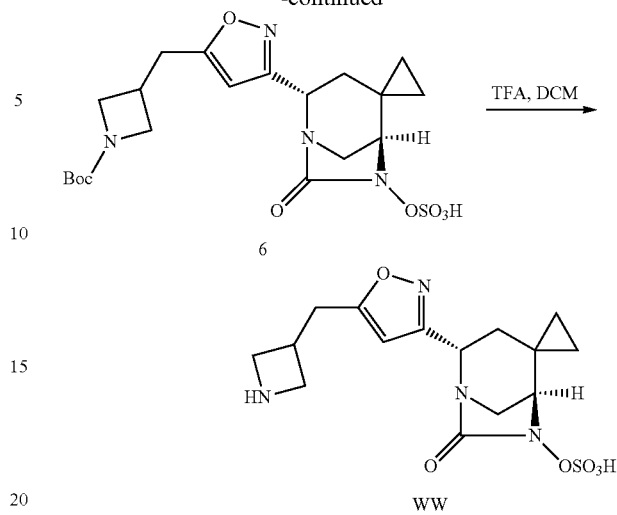

Step 1: Synthesis of Compound 1

LAH (0.828 g, 21.81 mmol) was added portionwise to a solution of tert-butyl 3-(2-methoxy-2-oxoethyl)azetidine-1-carboxylate (5 g, 21.81 mmol) in THF (100 mL) at 0° C. The reaction mixture was stirred at room temperature for 2 h. The reaction was quenched with water (50 mL), and EtOAc was added for extraction. The organic phase was dried over $Na_2SO_4$, filtered and evaporated to give a colorless gum. The crude product was purified by flash silica chromatography with gradient elution (0 to 50% EtOAc in petroleum ether). Pure fractions were evaporated to dryness to give tert-butyl 3-(2-hydroxyethyl)azetidine-1-carboxylate (3.50 g, 80%) in the form of a white solid, m/z (ES+), [M+H-tBu]+=146; ACID, HPLC tR=1.079 min.

Step 2: Synthesis of Compound 2

TEMPO (0.272 g, 1.74 mmol) was added to a solution of tert-butyl 3-(2-hydroxyethyl) azetidine-1-carboxylate (3.5 g, 17.39 mmol) and 1,3,5-triazinane-2,4,6-trione (2.469 g, 19.13 mmol) in DCM (80 mL) at 0° C. The resulting mixture was stirred at room temperature for 2 h. The reaction mixture was filtered through celite. The solvent was removed under reduced pressure to give tert-butyl 3-(2-oxoethyl)azetidine-1-carboxylate (3.40 g, 98%) in the form of a pale yellow gum. $^1$H NMR (400 MHz, Chloroform-d) δ 1.44 (s, 9H), 2.84 (d, J=7.4 Hz, 2H), 2.90-3.00 (m, 1H), 3.58 (dd, J=8.8, 5.4 Hz, 2H), 4.14 (t, J=8.5 Hz, 2H), 9.78 (s, 1H).

Step 3: Synthesis of Compound 3

$K_2CO_3$ (4.16 g, 30.11 mmol) was added to a solution of tert-butyl 3-(2-oxoethyl) azetidine-1-carboxylate (3 g, 15.06 mmol) in MeOH (3 mL) at 0° C. The resulting mixture was stirred at 0° C. for 10 min. A solution of dimethyl (1-diazo-2-oxopropyl)phosphonate (2.89 g, 15.06 mmol) in MeOH (3 mL) was added dropwise to the above mixture. The resulting mixture was stirred at room temperature for 16 h. The reaction mixture was poured into water (50 mL) and extracted with EtOAc. The organic phase was dried over $Na_2SO_4$, filtered and evaporated to give a gum. The crude product was purified by flash silica chromatography with gradient elution (0 to 15% EtOAc in petroleum ether). Pure fractions were evaporated to dryness to give tert-butyl 3-(prop-2-yn-1-yl)azetidine-1-carboxylate (1.900 g, 64.6%) in the form of a white solid.

Steps 4-7: Following Steps 1-4 in Synthesis of Compound PP

Compound WW:

m/z (ES+), [M+H]+=385; ACID, HPLC tR=0.670 min. $^1$H NMR (400 MHz, D$_2$O) δ 0.30 (dt, J=9.8, 5.0 Hz, 1H), 0.40 (dt, J=8.9, 5.3 Hz, 1H), 0.53 (dt, J=10.4, 5.1 Hz, 1H), 0.63 (dt, J=9.9, 5.2 Hz, 1H), 1.60 (d, J=15.8 Hz, 1H), 2.42 (dd, J=15.9, 7.4 Hz, 1H), 3.03-3.19 (m, 4H), 3.22-3.42 (m, 2H), 3.90 (dd, J=10.1, 7.9 Hz, 2H), 4.05-4.20 (m, 2H), 4.68 (d, J=7.7 Hz, 1H), 6.26 (s, 1H).

Example 50: Preparation of Compound XX

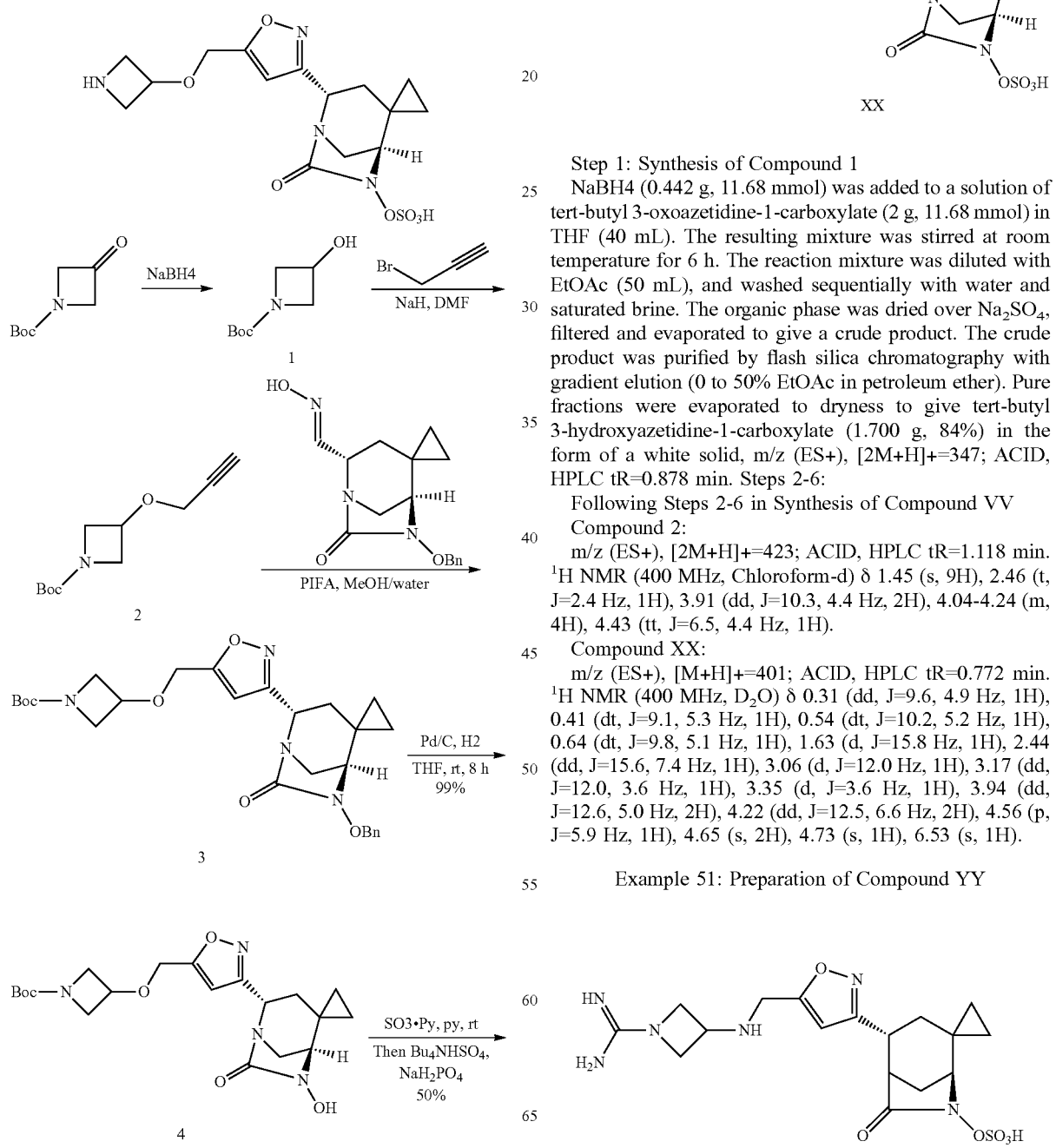

Step 1: Synthesis of Compound 1

NaBH4 (0.442 g, 11.68 mmol) was added to a solution of tert-butyl 3-oxoazetidine-1-carboxylate (2 g, 11.68 mmol) in THF (40 mL). The resulting mixture was stirred at room temperature for 6 h. The reaction mixture was diluted with EtOAc (50 mL), and washed sequentially with water and saturated brine. The organic phase was dried over Na$_2$SO$_4$, filtered and evaporated to give a crude product. The crude product was purified by flash silica chromatography with gradient elution (0 to 50% EtOAc in petroleum ether). Pure fractions were evaporated to dryness to give tert-butyl 3-hydroxyazetidine-1-carboxylate (1.700 g, 84%) in the form of a white solid, m/z (ES+), [2M+H]+=347; ACID, HPLC tR=0.878 min. Steps 2-6:

Following Steps 2-6 in Synthesis of Compound VV

Compound 2:

m/z (ES+), [2M+H]+=423; ACID, HPLC tR=1.118 min. $^1$H NMR (400 MHz, Chloroform-d) δ 1.45 (s, 9H), 2.46 (t, J=2.4 Hz, 1H), 3.91 (dd, J=10.3, 4.4 Hz, 2H), 4.04-4.24 (m, 4H), 4.43 (tt, J=6.5, 4.4 Hz, 1H).

Compound XX:

m/z (ES+), [M+H]+=401; ACID, HPLC tR=0.772 min. $^1$H NMR (400 MHz, D$_2$O) δ 0.31 (dd, J=9.6, 4.9 Hz, 1H), 0.41 (dt, J=9.1, 5.3 Hz, 1H), 0.54 (dt, J=10.2, 5.2 Hz, 1H), 0.64 (dt, J=9.8, 5.1 Hz, 1H), 1.63 (d, J=15.8 Hz, 1H), 2.44 (dd, J=15.6, 7.4 Hz, 1H), 3.06 (d, J=12.0 Hz, 1H), 3.17 (dd, J=12.0, 3.6 Hz, 1H), 3.35 (d, J=3.6 Hz, 1H), 3.94 (dd, J=12.6, 5.0 Hz, 2H), 4.22 (dd, J=12.5, 6.6 Hz, 2H), 4.56 (p, J=5.9 Hz, 1H), 4.65 (s, 2H), 4.73 (s, 1H), 6.53 (s, 1H).

Example 51: Preparation of Compound YY

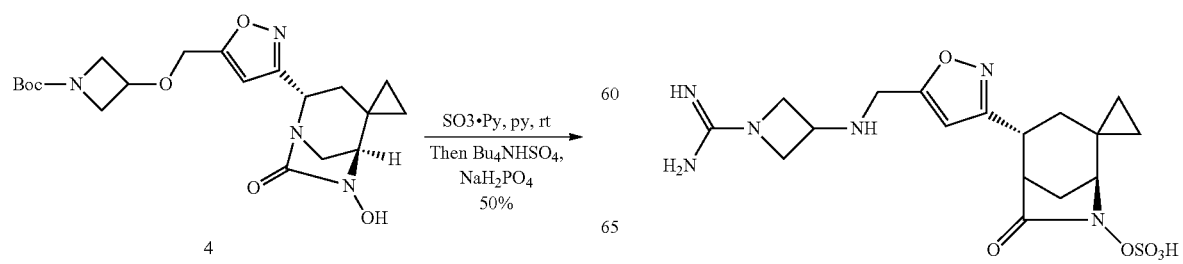

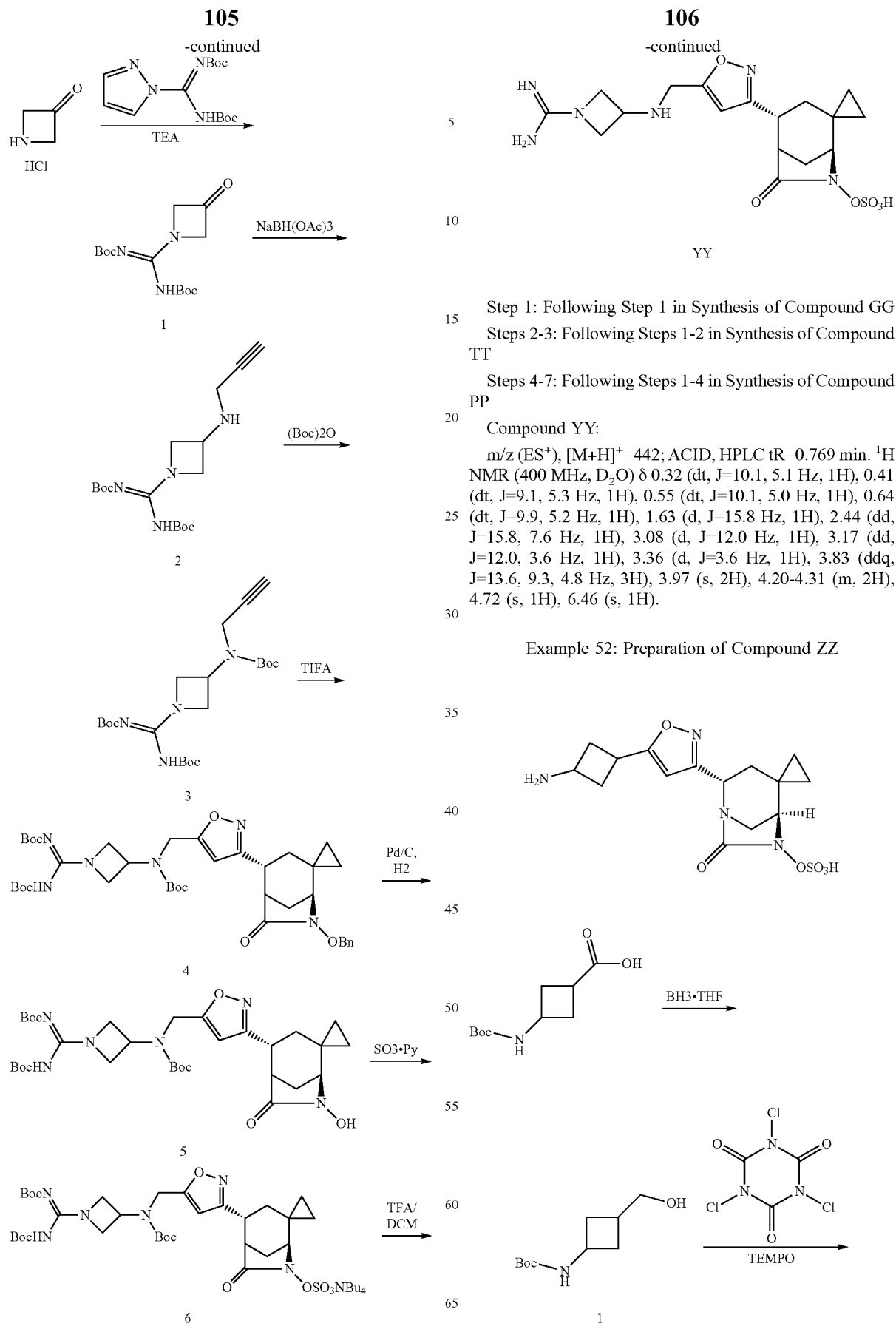
Step 1: Following Step 1 in Synthesis of Compound GG
Steps 2-3: Following Steps 1-2 in Synthesis of Compound TT
Steps 4-7: Following Steps 1-4 in Synthesis of Compound PP
Compound YY:
m/z (ES$^+$), [M+H]$^+$=442; ACID, HPLC tR=0.769 min. $^1$H NMR (400 MHz, D$_2$O) δ 0.32 (dt, J=10.1, 5.1 Hz, 1H), 0.41 (dt, J=9.1, 5.3 Hz, 1H), 0.55 (dt, J=10.1, 5.0 Hz, 1H), 0.64 (dt, J=9.9, 5.2 Hz, 1H), 1.63 (d, J=15.8 Hz, 1H), 2.44 (dd, J=15.8, 7.6 Hz, 1H), 3.08 (d, J=12.0 Hz, 1H), 3.17 (dd, J=12.0, 3.6 Hz, 1H), 3.36 (d, J=3.6 Hz, 1H), 3.83 (ddq, J=13.6, 9.3, 4.8 Hz, 3H), 3.97 (s, 2H), 4.20-4.31 (m, 2H), 4.72 (s, 1H), 6.46 (s, 1H).
Example 52: Preparation of Compound ZZ

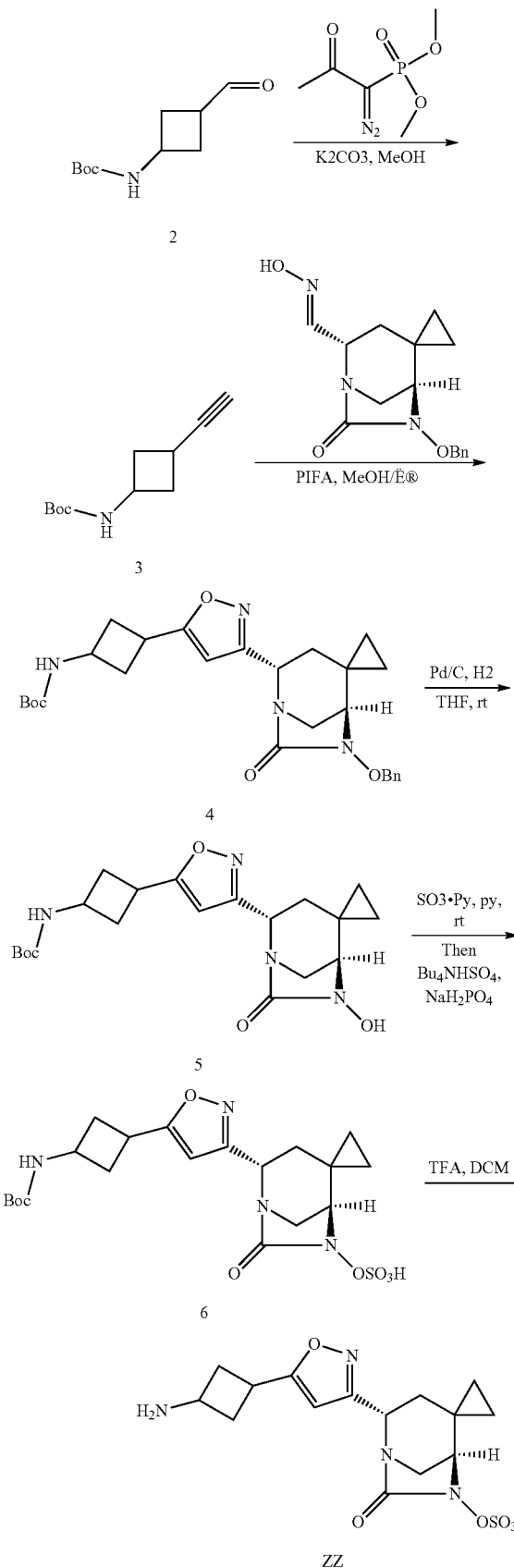

Step 1:

BH₃.THF (62.7 mL, 62.72 mmol) was added dropwise to a solution (40 mL) of 3-((tert-butoxycarbonyl)amino)cyclobutane-1-carboxylic acid (9 g, 41.81 mmol) in THF. The resulting mixture was stirred at room temperature for 4 h. The reaction was quenched with water (50 mL), and extracted with EtOAc. The organic phase was dried over Na₂SO₄, filtered and evaporated to give a gum. The crude product was purified by flash silica chromatography with gradient elution (0 to 5% MeOH in DCM). Pure fractions were evaporated to dryness to give tert-butyl(3-(hydroxymethyl)cyclobutyl)carbamate (7.10 g, 84%) in the form of a gum. $^1$H NMR (400 MHz, chloroform-d) δ 1.39 (s, 9H), 1.53-1.68 (m, 1H), 1.89-2.02 (m, 1H), 2.12 (dd, J=14.1, 6.8 Hz, 2H), 2.36 (d, J=7.7 Hz, 1H), 3.04 (s, 1H), 3.50 (d, J=5.6 Hz, 1H), 3.60 (d, J=7.2 Hz, 1H), 3.86-4.06 (m, 1H), 4.06-4.22 (m, 0H), 5.00 (s, 1H).

Steps 2-7: Following Steps 2-7 in Synthesis of Compound WW

Compound 2:

$^1$H NMR (400 MHz, chloroform-d) δ 1.36-1.55 (m, 9H), 2.02-2.15 (m, 2H), 2.18 (d, J=9.5 Hz, 1H), 2.56 (q, J=9.1, 8.3 Hz, 1H), 2.64-2.78 (m, 1H), 2.92 (p, J=7.8 Hz, 1H), 3.05 (s, 0H), 4.04-4.32 (m, 1H), 4.73 (s, 1H), 9.71 (d, J=2.1 Hz, 1H), 9.85 (d, J=1.9 Hz, 0H).

Compound 3:

$^1$H NMR (400 MHz, chloroform-d) δ 1.45 (d, J=2.5 Hz, 9H), 1.97 (qd, J=9.4, 2.4 Hz, 1H), 2.11-2.28 (m, 2H), 2.43-2.51 (m, 1H), 2.57-2.78 (m, 2H), 2.94 (d, J=3.7 Hz, 0H), 4.04 (d, J=7.5 Hz, 0H), 4.43 (s, 0H), 4.75 (s, 1H).

Compound ZZ:

Isomer 1: m/z (ES⁺), [M+H]⁺=385; ACID, HPLC tR=0.665 min. Isomer 2: m/z (ES⁺), [M+H]⁺=385; ACID, HPLC tR=0.692 min. $^1$H NMR (400 MHz, D₂O) δ 0.23-0.36 (m, 1H), 0.41 (dt, J=9.9, 5.3 Hz, 1H), 0.49-0.59 (m, 1H), 0.63 (dt, J=9.9, 5.2 Hz, 1H), 1.61 (dd, J=15.8, 4.2 Hz, 1H), 2.28-2.50 (m, 2H), 2.60 (t, J=8.2 Hz, 2H), 2.66-2.79 (m, 1H), 3.04-3.22 (m, 2H), 3.35 (s, 1H), 3.51 (p, J=9.8 Hz, 1H), 3.69-3.89 (m, 1H), 4.01 (p, J=7.2 Hz, 1H), 6.32 (d, J=17.8 Hz, 1H).

Example 53: Preparation of Compound AAA

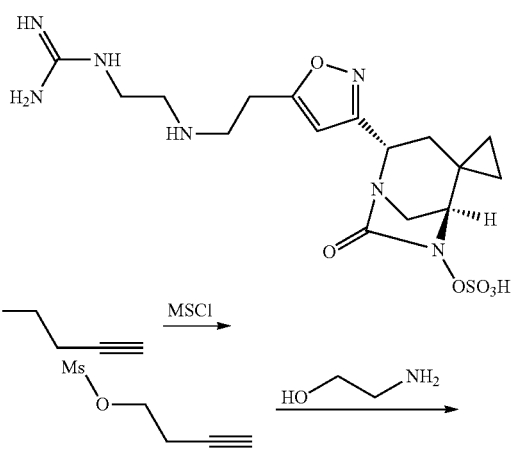

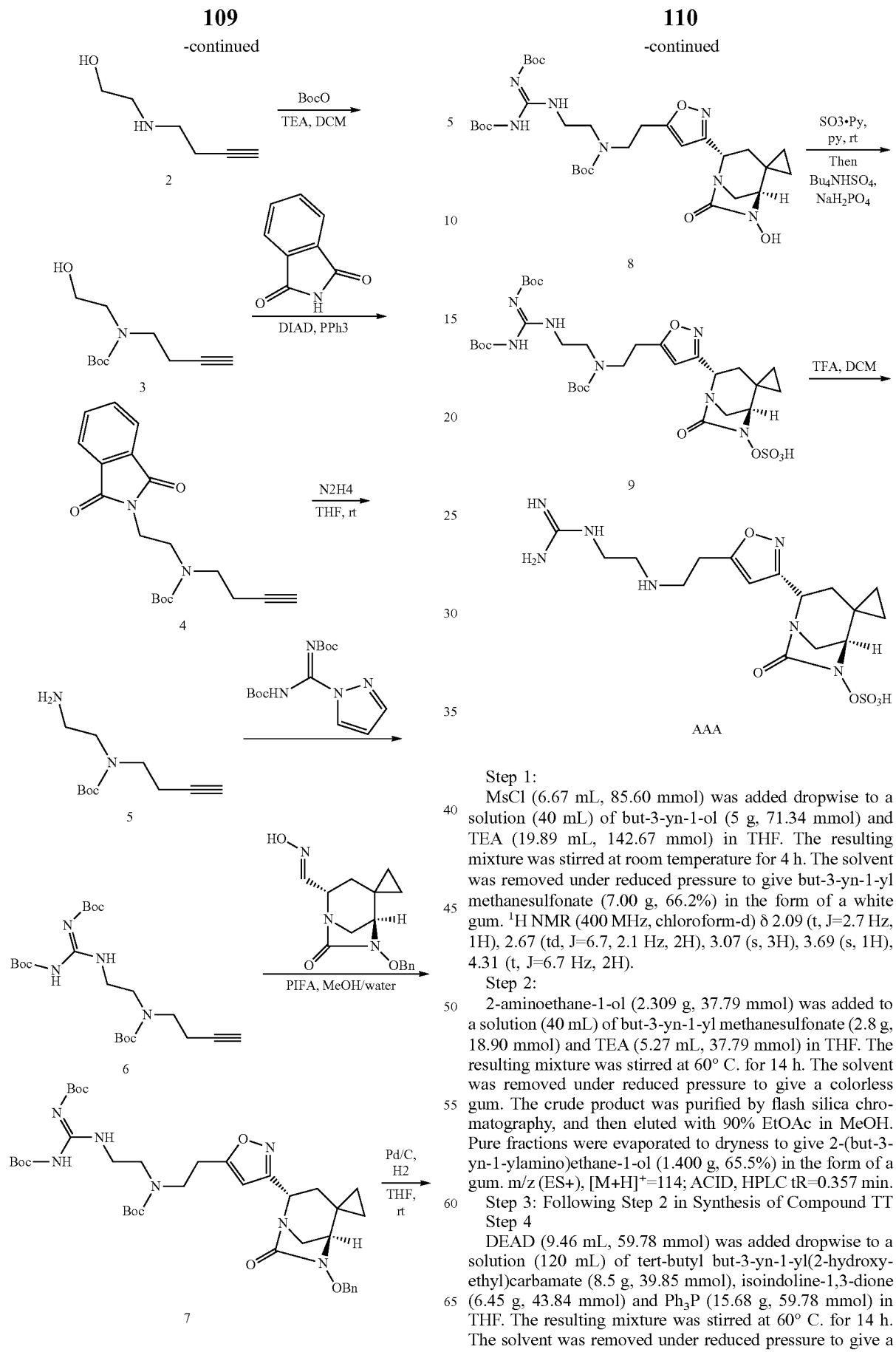

Step 1:
MsCl (6.67 mL, 85.60 mmol) was added dropwise to a solution (40 mL) of but-3-yn-1-ol (5 g, 71.34 mmol) and TEA (19.89 mL, 142.67 mmol) in THF. The resulting mixture was stirred at room temperature for 4 h. The solvent was removed under reduced pressure to give but-3-yn-1-yl methanesulfonate (7.00 g, 66.2%) in the form of a white gum. $^1$H NMR (400 MHz, chloroform-d) δ 2.09 (t, J=2.7 Hz, 1H), 2.67 (td, J=6.7, 2.1 Hz, 2H), 3.07 (s, 3H), 3.69 (s, 1H), 4.31 (t, J=6.7 Hz, 2H).

Step 2:
2-aminoethane-1-ol (2.309 g, 37.79 mmol) was added to a solution (40 mL) of but-3-yn-1-yl methanesulfonate (2.8 g, 18.90 mmol) and TEA (5.27 mL, 37.79 mmol) in THF. The resulting mixture was stirred at 60° C. for 14 h. The solvent was removed under reduced pressure to give a colorless gum. The crude product was purified by flash silica chromatography, and then eluted with 90% EtOAc in MeOH. Pure fractions were evaporated to dryness to give 2-(but-3-yn-1-ylamino)ethane-1-ol (1.400 g, 65.5%) in the form of a gum. m/z (ES+), [M+H]$^+$=114; ACID, HPLC tR=0.357 min.

Step 3: Following Step 2 in Synthesis of Compound TT

Step 4
DEAD (9.46 mL, 59.78 mmol) was added dropwise to a solution (120 mL) of tert-butyl but-3-yn-1-yl(2-hydroxyethyl)carbamate (8.5 g, 39.85 mmol), isoindoline-1,3-dione (6.45 g, 43.84 mmol) and Ph$_3$P (15.68 g, 59.78 mmol) in THF. The resulting mixture was stirred at 60° C. for 14 h. The solvent was removed under reduced pressure to give a colorless gum. The crude product was purified by flash silica chromatography with gradient elution (0 to 15% EtOAc in petroleum ether). Pure fractions were evaporated to dryness to give tert-butyl but-3-yn-1-yl(2-(1,3-dioxoisoindolin-2-yl)ethyl)carbamate (10.50 g, 77%) in the form of a white gum. $^1$H NMR (400 MHz, chloroform-d) δ 1.26 (d, J=4.6 Hz, 9H), 1.96 (s, 1H), 2.44 (ddq, J=18.8, 6.8, 4.7, 3.5 Hz, 2H), 3.38 (dt, J=21.2, 6.9 Hz, 2H), 3.57 (t, J=5.9 Hz, 2H), 3.85 (q, J=6.1, 5.6 Hz, 2H), 4.98 (tp, J=12.5, 6.3 Hz, 2H), 7.64-7.80 (m, 3H), 7.84 (ddt, J=10.8, 5.4, 3.1 Hz, 2H).

Step 5

Hydrazine (3.74 g, 116.82 mmol) was added to a solution (50 mL) of tert-butyl but-3-yn-1-yl(2-(1,3-dioxoisoindolin-2-yl)ethyl)carbamate (4 g, 11.68 mmol) in THF. The resulting mixture was stirred at room temperature for 14 h. The solvent was removed under reduced pressure to give tert-butyl(2-aminoethyl)(but-3-yn-1-yl)carbamate (2.100 g, 85%). m/z (ES+), [M+H]+=213; ACID, HPLC tR=0.812 min.

Step 6 Following Step 1 in Synthesis of Compound GG $^1$H NMR (400 MHz, DMSO-d$_6$) δ 1.33-1.43 (m, 18H), 1.47 (s, 9H), 2.39 (td, J=7.3, 2.5 Hz, 2H), 2.81 (s, 1H), 3.29 (t, J=7.2 Hz, 2H), 3.34-3.46 (m, 4H), 8.38 (s, 1H), 11.51 (d, J=31.8 Hz, 1H).

Steps 7-10: Following Steps 1-4 in Synthesis of Compound PP

Compound AAA:

m/z (ES$^+$), [M+H]$^+$=444; ACID, HPLC tR=0.898 min. $^1$H NMR (300 MHz, D$_2$O) δ 0.34 (dt, J=9.6, 4.7 Hz, 1H), 0.44 (dt, J=8.6, 5.1 Hz, 1H), 0.58 (dt, J=10.1, 4.9 Hz, 1H), 0.68 (dt, J=9.7, 4.9 Hz, 1H), 1.66 (d, J=15.8 Hz, 1H), 2.47 (dd, J=15.8, 7.5 Hz, 1H), 3.14-3.29 (m, 6H), 3.38 (t, J=4.9 Hz, 3H), 3.51 (t, J=6.0 Hz, 2H), 4.74 (s, 1H), 6.42 (s, 1H), 8.37 (s, 1H).

Example 54: Synthesis of Compound BBB

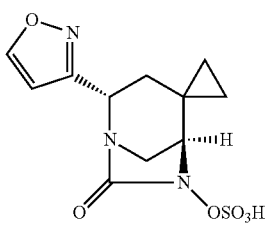

Step 1: Synthesis of Compound 2

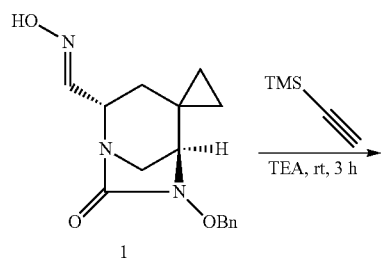

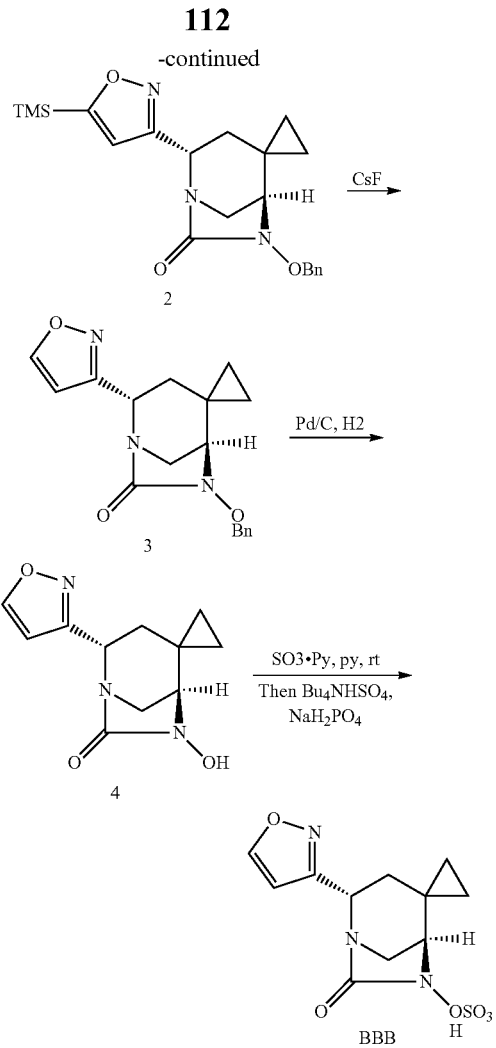

To a 50-mL sealed tube was added a solution (20 mL) of Compound 1 (300 mg, 1 mmol, 1.00 eq.) and ethynyltrimethylsilane (150 mg, 1.5 mmol, 1.5 eq.) in MeOH:H$_2$O=5:1. The resulting solution was stirred at 0° C., and PIFA (645 mg, 1.5 mmol, 1.5 eq.) was added in two batches. The reaction mixture was stirred at room temperature for 2 h. The crude residue was purified by Prep-TLC (PE:EA=2:1) to give a desired product (160 mg, 40.5%) in the form of a colorless oil. ESI-MS (EI$^+$, m/z): 398, 1.115 min.

Step 2: Synthesis of Compound 3

To a 50-mL sealed tube was added a solution (10 mL) of Compound 2 (160 mg, 1 mmol, 1.00 eq.) and CsF (181 mg, 1.2 mmol, 3 eq.) in MeOH. The solution was stirred at room temperature overnight. The reaction mixture was filtered and the filtrate was concentrated. The crude product was purified by Prep-TLC to give a desired product (100 mg, 76.9%) in the form of a colorless oil. ESI-MS (EI$^+$, m/z): 326, 0.954 min.

Step 3: Synthesis of Compound 4

To a 50-mL round-bottom flask was added a solution (15 mL) of Compound 3 (100 mg, 0.3 mmol, 1.00 eq.) in THF, followed by Pd/C (10 mg, catalytic group). The resulting solution was stirred at room temperature for 120 min in the presence of H$_2$ (1 atm). The mixture was filtered and the solids were discarded. The resulting mixture was concentrated under vacuum. This resulted in 100 mg of Compound 4 (crude) in the form of a colorless oil. ESI-MS (EI$^+$, m/z): 236, 0.855 min.

Step 4: Synthesis of Compound BBB

To a 50-mL sealed tube was added a solution (5 mL) of Compound 4 (100 mg, 0.3 mmol, 1.00 eq.) in DMF, followed by SO₃.Py (270 mg, 1.7 mmol, 4.00 eq.). The resulting solution was stirred for 20 h at room temperature. Purification was directly conducted by Prep-HPLC (phase A: water (10 mmol/L NH₄HCO₃); phase B: ACN) to give an ammonium salt (10.9 mg). ESI-MS (EI⁺, m/z): 316, 0.95 min. ¹H NMR (400 MHz, D₂O) δ 0.37 (dd, J=9.6, 4.7 Hz, 1H), 0.42-0.56 (m, 1H), 0.61 (dt, J=10.5, 5.2 Hz, 1H), 0.69 (dt, J=9.6, 5.2 Hz, 1H), 1.71 (d, J=15.9 Hz, 1H), 2.52 (dd, J=15.9, 7.8 Hz, 2H), 3.09-3.25 (m, 2H), 3.41 (d, J=3.6 Hz, 2H), 4.80 (d, J=7.6 Hz, 2H), 6.58 (d, J=1.7 Hz, 1H), 8.63 (d, J=1.7 Hz, 1H).

Example 55: Preparation of Compound CCC

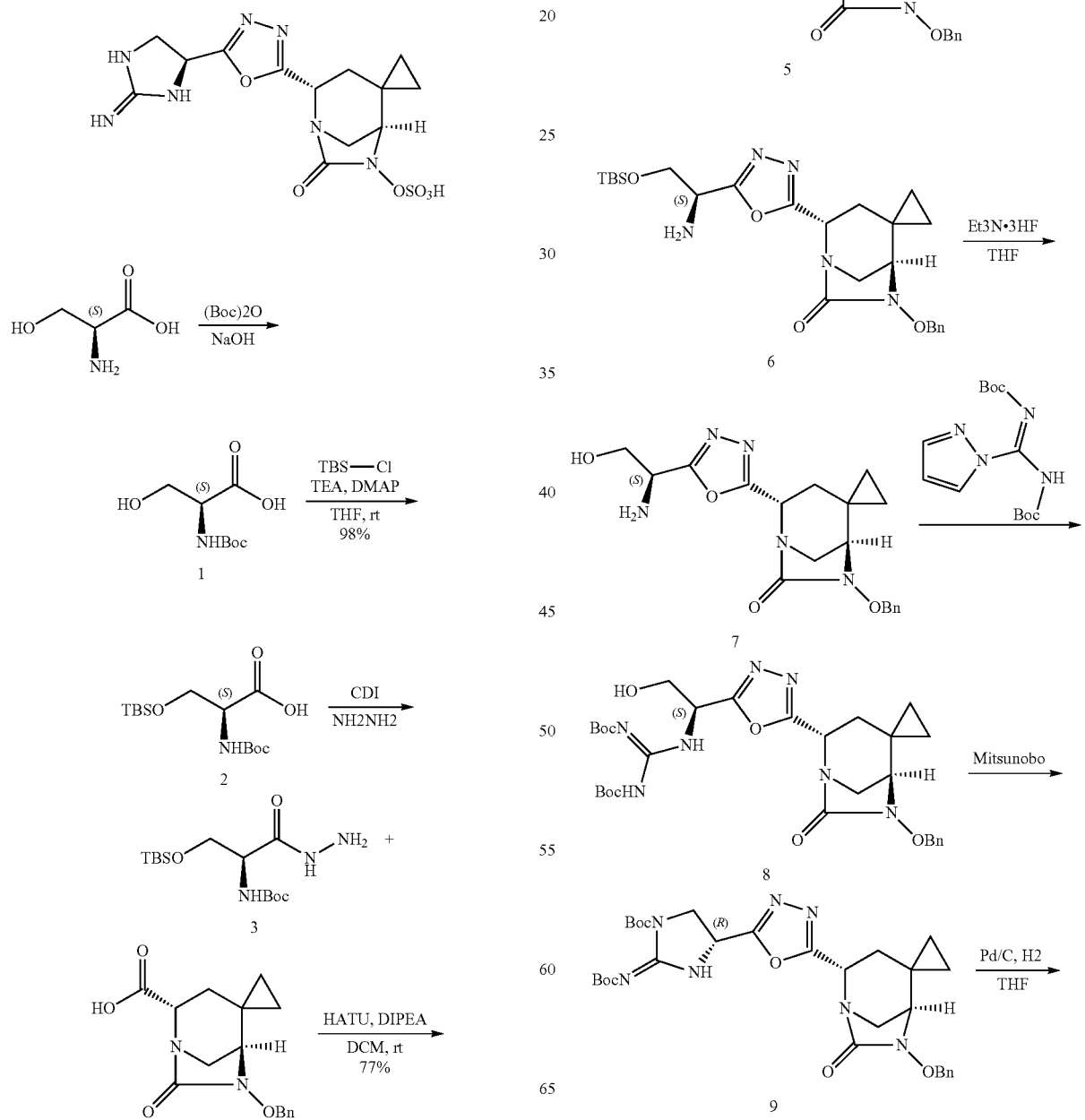

-continued

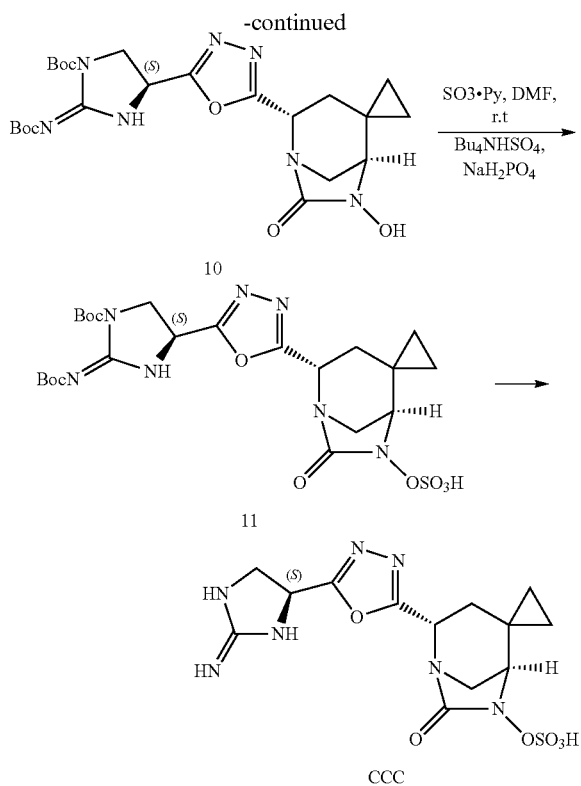

Step 1: Synthesis of Compound 1

To a 500-mL round-bottom flask was added a solution (200 mL) of L-serine (5 g, 47.58 mmol, 1.00 eq.) in dioxane, followed by an aqueous solution (100 mL) of NaOH (4 g, 100.01 mmol, 2.10 eq.). The resulting solution was stirred for 5 min at room temperature. (Boc)$_2$O (12 g, 54.98 mmol, 1.14 eq.) was added. The resulting solution was stirred for an additional 16 h at room temperature. The resulting mixture (2×200 mL) was extracted with EA. The pH of the aqueous phase was adjusted to about 1 with HCl (1 mol/L). The resulting solution was extracted with ethyl acetate (200 mL×3), and the organic phases were combined, dried over anhydrous sodium sulfate and concentrated under vacuum. This resulted in 10.2 g of 2(S)-2-[[(tert-butoxy)carbonyl]amino]-3-hydroxypropionic acid (crude) in the form of a colorless oil. ESI-MS (EI$^+$, m/z+Na): 228, 0.779 min.

Step 2: Synthesis of Compound 2

To a 500-mL round-bottom flask were added a solution (200 mL) of 2(S)-2-[[(tert-butoxy)carbonyl]amino]-3-hydroxypropionic acid (10.2 g, 49.71 mmol, 1.00 eq.) in THF, TEA (10 g, 98.82 mmol, 2.00 eq.), DMAP (6 g, 49.11 mmol, 1.00 eq.), and TBS-Cl (10.5 g, 69.66 mmol, 1.40 eq.). The resulting solution was stirred for 16 h at room temperature. After the reaction was completed, the pH was adjusted to 1 with HCl (1 mol/L). The resulting solution was extracted with ethyl acetate (300 mL×2), and the organic phases were combined, dried over anhydrous sodium sulfate and concentrated under vacuum. This resulted in 16.3 g of 2(S)-2-[[(tert-butoxy)carbonyl]amino]-3-[(tert-butyldimethylsilyl)oxy]propionic acid (crude) in the form of a colorless oil. ESI-MS (EI$^+$, m/z+Na): 320, 0.553 min.

Step 3: Synthesis of Compound 3

To a 200-mL round-bottom flask was added a solution (100 mL) of 2(S)-2-[[(tert-butoxy)carbonyl]amino]-3-[(tert-butyldimethylsilyl)oxy]propanoic acid (16.3 g, 51.02 mmol, 1.00 eq.) in DCM. CDI (12.4 g, 76.54 mmol, 1.50 eq.) was added in batches at room temperature. The resulting solution was stirred for 120 min at room temperature, and then hydrazine (11 g, 220.00 mmol, 10.00 eq.) was added. The resulting solution was stirred for an additional 60 min at room temperature. The resulting mixture was concentrated under vacuum. The crude product was purified by Flash Prep-HPLC under the following conditions: Column: C18 silica gel; Mobile phase: ACN increasing to ACN=50% within 30 min; Detector: UV 254 nm. This resulted in 11 g of tert-butyl N-[(1S)-2-[(tert-butyldimethylsilyl)oxy]-1-(hydrazinocarbonyl)ethyl]carbamate (65%) in the form of a white solid. ESI-MS (EI$^+$, m/z+): 334, 1.168 min. $^1$H NMR (DMSO-d6, 400 MHz): δ (ppm) 0.84 (s, 9H), 1.38 (s, 9H), 3.50-3.81 (m, 2H), 3.96-4.13 (m, 1H), 4.20 (d, J=3.6 Hz, 2H), 6.58 (d, J=8.8 Hz, 1H), 9.10 (s, 1H)

Step 4: Synthesis of Compound 4

To a 200-mL round-bottom flask was added a solution (100 mL) of Compound 3 (3.5 g, 10.49 mmol, 1.00 eq.), (1R,4S)-7-(benzyloxy)-6-oxo-5,7-diazaspiro[bicyclo[3.2.1]octane-2,1'-cyclopropane]-4-carboxylic acid (4.7 g, 15.55 mmol, 1.2 eq.), DIPEA (4.5 g, 34.88 mmol, 3.00 eq.), and HATU (8.74 g, 23.00 mmol, 4.00 eq.) in THF. The resulting solution was stirred for 2 h at room temperature. The mixture was filtered and the solids were discarded. The residue was purified by a silica gel column with ethyl acetate/petroleum ether (1/5 to 1/1). This resulted in 7 g of Compound 4 (100%, purity 95.6%) in the form of a white solid. ESI-MS (EI$^+$, m/z+): 618, 1.404 min.

Step 5: Synthesis of Compound 5

To a 200-mL round-bottom flask was added a solution of Compound 4 (7 g, 11.33 mmol, 1.00 eq.) in DCM (100 mL), followed by DIEA (5.67 g, 43.95 mmol, 3.50 eq.), and Burgess reagent (10.42 g, 43.97 mmol, 3.50 eq.). The resulting solution was stirred for 20 h at room temperature. The residue was purified by a silica gel column with ethyl acetate/petroleum ether (1/5 to 1/1) to give 6 g of Compound 5 (88%) in the form of a white solid. ESI-MS (EI$^+$, m/z+): 600, 1.487 min.

Step 6: Synthesis of Compound 6

To a 100-mL round-bottom flask was added a solution (40 mL) of Compound 5 (6 g, 10 mmol, 1.00 eq.) in DCM, followed by TFA (10 mL, 10.00 eq.). The resulting solution was stirred at 0° C. and at room temperature for 120 min. The resulting mixture was concentrated under vacuum. This resulted in 6 g of Compound 6 in the form of a white solid. ESI-MS (EI$^+$, m/z): 500, 1.538 min.

Step 7: Synthesis of Compound 7

To a 100-mL round-bottom flask was added a solution (60 mL) of Compound 6 (6 g, 10 mmol, 1.00 eq.) in THF, followed by 3HF Et3N (15 mL, 10.00 eq.). The resulting solution was stirred for 2 h at room temperature. The crude product was purified by Flash Prep-HPLC under the following conditions: Column: C18 silica gel; Mobile phase: ACN increasing to ACN=50% within 30 min; Detector: UV 254 nm. This resulted in 6 g of Compound 7 (crude) in the form of a white solid. ESI-MS (EI$^+$, m/z+): 386, 0.878 min.

Step 8: Synthesis of Compound 8

To a 100-mL sealed tube were added a solution (100 mL) of Compound 7 in ACN, TEA (6.3 g, 42.32 mmol, 4.00 eq.), and di-tert-butyl(1H-pyrazol-1-yl)methanediyl idenediaminedicarbamate (5.28 g, 17 mmol, 1.10 eq.). The resulting solution was stirred at 40° C. for 16 h. The residue was purified by a silica gel column with ethyl acetate/petroleum ether (1:10 to 1:1). This resulted in 4.6 g of Compound 8 (73% over three steps) in the form of a white solid. ESI-MS (EI$^+$, m/z): 628, 1.359 min. $^1$H NMR (methanol-d4, 400 MHz): δ (ppm) 0.30 (p, J=5.4 Hz, 1H), 0.48 (dt, J=9.1, 5.5

Hz, 1H), 0.71 (ddt, J=44.0, 9.5, 5.7 Hz, 2H), 1.45 (d, J=2.5 Hz, 9H), 1.58 (s, 9H), 1.76 (d, J=15.4 Hz, 1H), 2.51-2.68 (m, 1H), 3.80-4.20 (m, 2H), 4.77-4.86 (m, 1H), 4.94-5.13 (m, 2H), 5.50 (dt, J=6.7, 3.6 Hz, 1H), 7.29-7.55 (m, 5H)

Step 9: Synthesis of Compound 9

To a 500-mL three-necked round-bottom flask purged and maintained with an inert atmosphere of nitrogen, were added a solution (250 mL) of Compound 8 (4.6 g, 7.33 mmol, 1.00 eq.) and triphenylphosphane (3.15 g, 11 mmol, 1.50 eq.) in THF, and a solution (10 mL) of DIAD (2.5 g, 11 mmol, 1.50 eq.) in THF. The resulting solution was stirred for 5 h at room temperature. The resulting mixture was concentrated under vacuum. The crude product was purified by Flash Prep-HPLC under the following conditions: Column: C18 silica gel; Mobile phase: ACN=0% increasing to ACN=50% within 50 min; Detector: UV 254 nm. This resulted in 3.9 g (74%) of Compound 9 in the form of a white solid. ESI-MS (EI$^+$, m/z): 610, 1.119 min.

Step 10: Synthesis of Compound 10

To a 1000-mL round-bottom flask was added a solution (500 mL) of Compound 9 (3.5 g, 5.74 mmol, 1.00 eq.) in THF, followed by Pd/C (400 mg). The resulting solution was stirred for 5 h at room temperature in the presence of H$_2$ (1 atm). The mixture was filtered and the solids were discarded. The resulting mixture was concentrated under vacuum. This resulted in 2.5 g of crude Compound 10 in the form of a white solid. ESI-MS (EI$^+$, m/z): 520, 0.964 min.

Step 11: Synthesis of Compound 11

To a 250-mL sealed tube was added a solution (50 mL) of Compound 10 (2.5 g, 4.8 mmol, 1.00 eq.) in DMF, followed by SO$_3$.Py (3.03 g, 19.2 mmol, 4.00 eq.). The resulting solution was stirred for 20 h at room temperature. The resulting mixture was concentrated under vacuum. The reaction was then quenched by the addition of 10 mL of NaH$_2$PO$_4$. Then NBu$_4$HSO$_4$ (100 mg) was added to the reaction mixture. The resulting solution was extracted with ethyl acetate (20 mL×2), and the organic phases were combined, dried over anhydrous sodium sulfate and concentrated under vacuum. The residue was purified by Flash Prep-HPLC under the following conditions: Column: C18 silica gel; Mobile phase: ACN=0% increasing to ACN=50% within 40 min; Detector: UV 254 nm. This resulted in 2.0 g of Compound 11 (69.4%). ESI-MS (EI$^+$, m/z): 600, 1.014 min.

Step 12: Synthesis of Compound CCC

When purified by flash chromatography, Compound 11 was unstable and readily stripped of Boc protecting groups in the mobile phase. At the time of concentration, a product stripped of one Boc was obtained. The product stripped of one Boc was stirred in warm water (pH=6-7) to give a product CCC stripped of two Boc protecting groups. The product was purified by Prep-HPLC under the following conditions: Column: Xselect CSH OBD C18 column 19×250 mm, 5 μm; Mobile phase A: water (0.1% FA); Mobile phase B: ACN; Flow rate: 25 mL/min; Gradient: from 4% B to 4% B within 13 min; 220/254 nm; Rt: 11.27, 12.23 min. This resulted in 43.4 mg of Compound CCC. ESI-MS (EI$^+$, m/z): 400, 0.650 min. $^1$H NMR (400 MHz, D$_2$O) δ (ppm) 0.34-0.61 (m, 2H), 0.63-0.92 (m, 1H), 1.82 (d, J=16.0 Hz, 1H), 2.64 (dd, J=16.1, 7.8 Hz, 1H), 3.18 (d, J=12.2 Hz, 1H), 3.36 (dd, J=12.2, 3.8 Hz, 1H), 3.52 (d, J=3.8 Hz, 1H), 4.02 (dd, J=10.5, 4.8 Hz, 1H), 4.21 (t, J=10.3 Hz, 1H), 4.99 (d, J=7.6 Hz, 1H), 5.54 (dd, J=10.0, 4.8 Hz, 1H).

Example 56: Preparation of Compound DDD

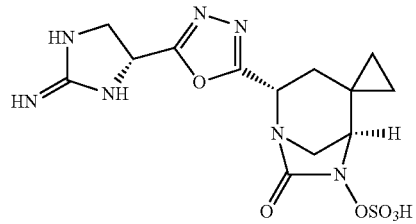

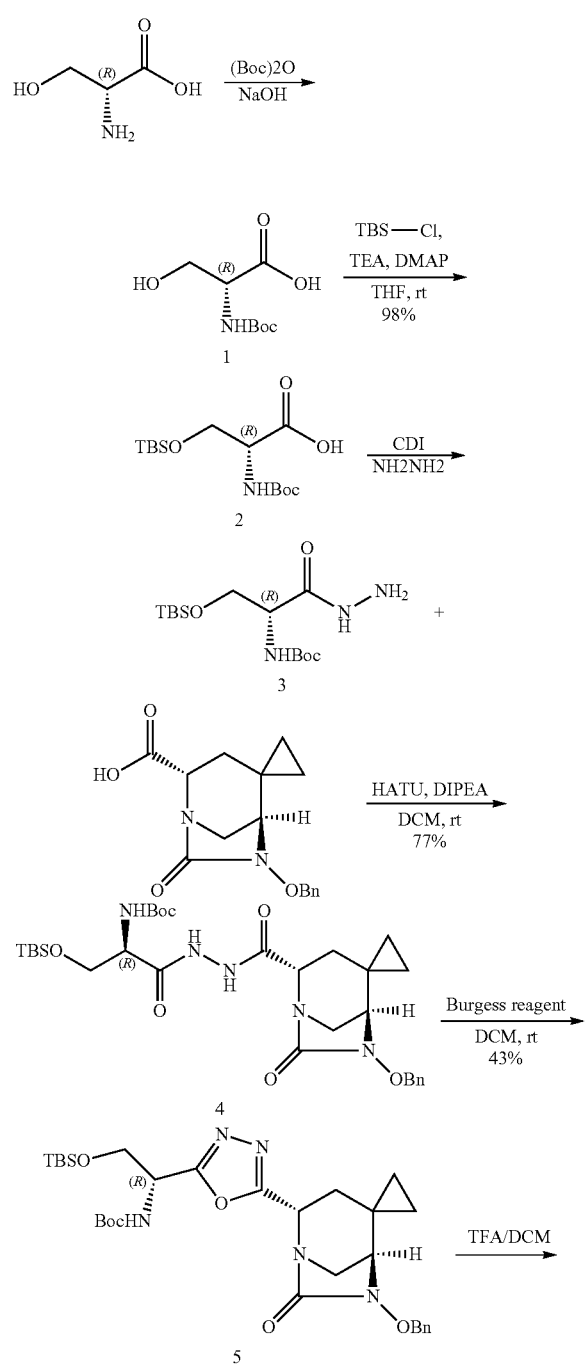

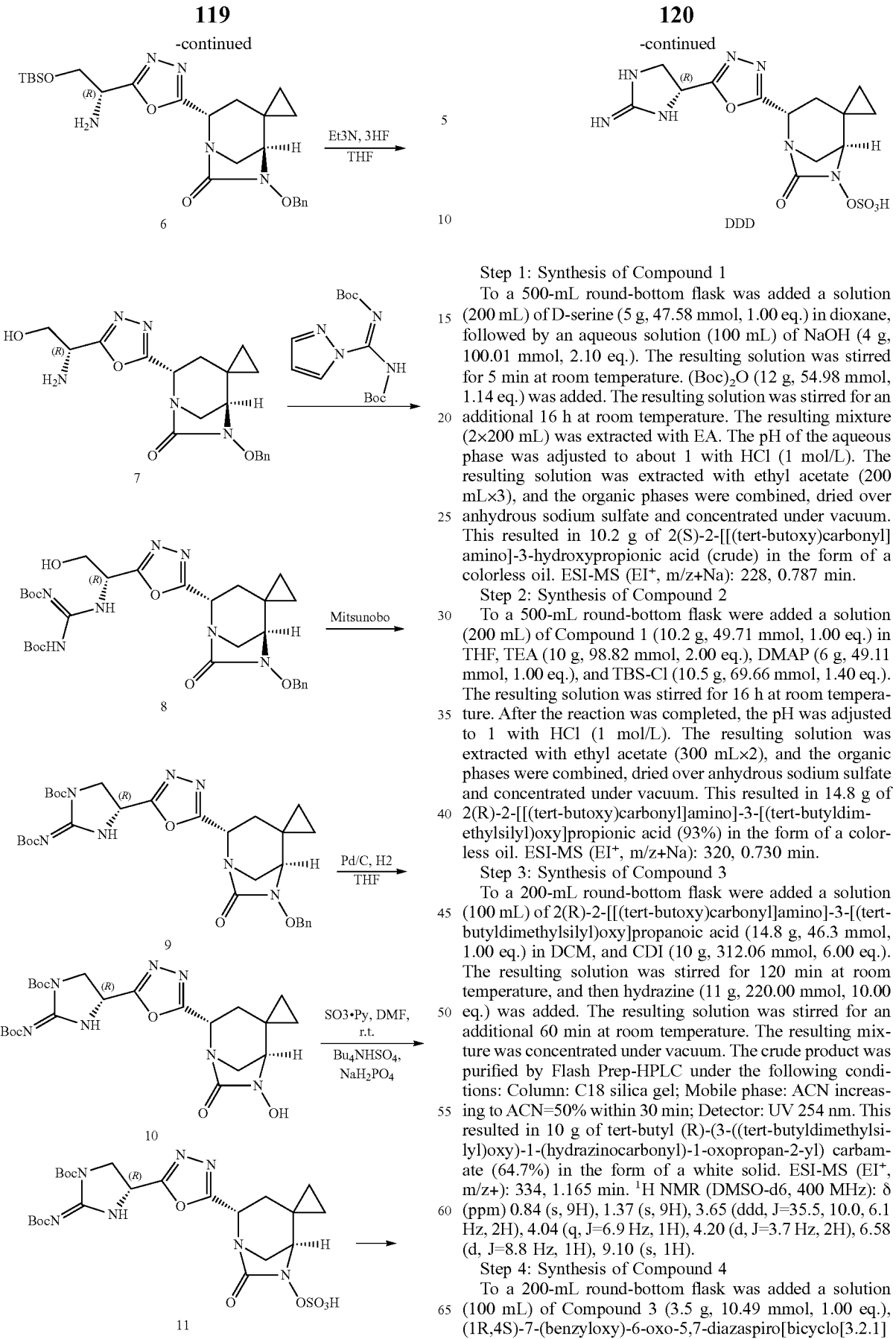

Step 1: Synthesis of Compound 1

To a 500-mL round-bottom flask was added a solution (200 mL) of D-serine (5 g, 47.58 mmol, 1.00 eq.) in dioxane, followed by an aqueous solution (100 mL) of NaOH (4 g, 100.01 mmol, 2.10 eq.). The resulting solution was stirred for 5 min at room temperature. (Boc)$_2$O (12 g, 54.98 mmol, 1.14 eq.) was added. The resulting solution was stirred for an additional 16 h at room temperature. The resulting mixture (2×200 mL) was extracted with EA. The pH of the aqueous phase was adjusted to about 1 with HCl (1 mol/L). The resulting solution was extracted with ethyl acetate (200 mL×3), and the organic phases were combined, dried over anhydrous sodium sulfate and concentrated under vacuum. This resulted in 10.2 g of 2(S)-2-[[(tert-butoxy)carbonyl]amino]-3-hydroxypropionic acid (crude) in the form of a colorless oil. ESI-MS (EI$^+$, m/z+Na): 228, 0.787 min.

Step 2: Synthesis of Compound 2

To a 500-mL round-bottom flask were added a solution (200 mL) of Compound 1 (10.2 g, 49.71 mmol, 1.00 eq.) in THF, TEA (10 g, 98.82 mmol, 2.00 eq.), DMAP (6 g, 49.11 mmol, 1.00 eq.), and TBS-Cl (10.5 g, 69.66 mmol, 1.40 eq.). The resulting solution was stirred for 16 h at room temperature. After the reaction was completed, the pH was adjusted to 1 with HCl (1 mol/L). The resulting solution was extracted with ethyl acetate (300 mL×2), and the organic phases were combined, dried over anhydrous sodium sulfate and concentrated under vacuum. This resulted in 14.8 g of 2(R)-2-[[(tert-butoxy)carbonyl]amino]-3-[(tert-butyldimethylsilyl)oxy]propionic acid (93%) in the form of a colorless oil. ESI-MS (EI$^+$, m/z+Na): 320, 0.730 min.

Step 3: Synthesis of Compound 3

To a 200-mL round-bottom flask were added a solution (100 mL) of 2(R)-2-[[(tert-butoxy)carbonyl]amino]-3-[(tert-butyldimethylsilyl)oxy]propanoic acid (14.8 g, 46.3 mmol, 1.00 eq.) in DCM, and CDI (10 g, 312.06 mmol, 6.00 eq.). The resulting solution was stirred for 120 min at room temperature, and then hydrazine (11 g, 220.00 mmol, 10.00 eq.) was added. The resulting solution was stirred for an additional 60 min at room temperature. The resulting mixture was concentrated under vacuum. The crude product was purified by Flash Prep-HPLC under the following conditions: Column: C18 silica gel; Mobile phase: ACN increasing to ACN=50% within 30 min; Detector: UV 254 nm. This resulted in 10 g of tert-butyl (R)-(3-((tert-butyldimethylsilyl)oxy)-1-(hydrazinocarbonyl)-1-oxopropan-2-yl) carbamate (64.7%) in the form of a white solid. ESI-MS (EI$^+$, m/z+): 334, 1.165 min. $^1$H NMR (DMSO-d6, 400 MHz): δ (ppm) 0.84 (s, 9H), 1.37 (s, 9H), 3.65 (ddd, J=35.5, 10.0, 6.1 Hz, 2H), 4.04 (q, J=6.9 Hz, 1H), 4.20 (d, J=3.7 Hz, 2H), 6.58 (d, J=8.8 Hz, 1H), 9.10 (s, 1H).

Step 4: Synthesis of Compound 4

To a 200-mL round-bottom flask was added a solution (100 mL) of Compound 3 (3.5 g, 10.49 mmol, 1.00 eq.), (1R,4S)-7-(benzyloxy)-6-oxo-5,7-diazaspiro[bicyclo[3.2.1]octane-2,1'-cyclopropane]-4-carboxylic acid (4.7 g, 15.55 mmol, 1.2 eq.), DIPEA (4.5 g, 34.88 mmol, 3.00 eq.), and HATU (8.74 g, 23.00 mmol, 4.00 eq.) in THF. The resulting solution was stirred for 2 h at room temperature. The mixture was filtered and the solids were discarded. The residue was purified by a silica gel column with ethyl acetate/petroleum ether (1/5 to 1/1). This resulted in 7.8 g of Compound 4 (crude) in the form of a white solid. ESI-MS (EI$^+$, m/z+): 618, 1.402 min.

Step 5: Synthesis of Compound 5

To a 200-mL round-bottom flask were added a solution of Compound 4 (7.8 g, 12.6 mmol, 1.00 eq.) in DCM (100 mL), followed by DIEA (5.67 g, 43.95 mmol, 3.50 eq.), and Burgess reagent (10.42 g, 43.97 mmol, 3.50 eq.). The resulting solution was stirred for 20 h at room temperature. The residue was purified by a silica gel column with ethyl acetate/petroleum ether (1/5 to 1/1) to give 6 g of Compound 5 (88% over two steps) in the form of a white solid. ESI-MS (EI$^+$, m/z+Na): 622, 1.477 min. $^1$H NMR (chloroform-d, 400 MHz): δ (ppm)-0.16 (s, 6H), 0.06-0.26 (m, 1H), 0.50 (ddt, J=36.1, 9.3, 5.7 Hz, 2H), 0.79 (d, J=2.0 Hz, 9H), 1.45 (d, J=3.4 Hz, 8H), 2.67 (dd, J=15.3, 7.8 Hz, 1H), 2.79 (s, 2H), 2.81-2.99 (m, 2H), 3.70-4.17 (m, 2H), 4.64-4.94 (m, 2H), 5.05 (d, J=11.5 Hz, 2H), 5.44 (t, J=11.3 Hz, 1H), 7.39 (ddd, J=19.3, 6.1, 2.4 Hz, 5H).

Step 6: Synthesis of Compound 6

To a 100-mL round-bottom flask was added a solution (40 mL) of Compound 5 (6 g, 10 mmol, 1.00 eq.) in DCM, followed by TFA (10 mL, 10.00 eq.). The resulting solution was stirred at 0° C. and at room temperature for 120 min. The resulting mixture was concentrated under vacuum. This resulted in 6 g of Compound 6 (crude), which was directly used in the next step without purification. ESI-MS (EI$^+$, m/z+Na): 500, 1.546 min.

Step 7: Synthesis of Compound 7

To a 100-mL round-bottom flask was added a solution (60 mL) of Compound 6 (6 g, 10 mmol, 1.00 eq.) in THF, followed by 3HF Et3N (15 mL, 10.00 eq.). The resulting solution was stirred for 2 h at room temperature. The crude product was purified by Flash Prep-HPLC under the following conditions: Column: C18 silica gel; Mobile phase: ACN increasing to ACN=50% within 40 min; Detector: UV 254 nm. This resulted in 3.8 g of Compound 7 in the form of a white solid. ESI-MS (EI$^+$, m/z+Na): 386, 0.878 min.

Step 8: Synthesis of Compound 8

To a 100-mL round-bottom flask were added a solution (100 mL) of Compound 7 (3.8 g, 9.8 mmol, 1.00 eq.) in ACN, TEA (6.3 g, 42.32 mmol, 4.30 eq.), and di-tert-butyl (1H-pyrazol-1-yl)methanediyl idenediaminedicarbamate (5.28 g, 17 mmol, 1.70 eq.). The resulting solution was stirred at 40° C. for 16 h. The residue was purified by a silica gel column with ethyl acetate/petroleum ether (1:10 to 1:1). This resulted in 4.6 g of Compound 8 (75.4%) in the form of a white solid. ESI-MS (EI$^+$, m/z+Na): 628, 1.356 min. $^1$H NMR (methanol-d, 400 MHz): δ (ppm) 0.30 (dq, J=10.0, 5.2, 4.2 Hz, 1H), 0.48 (dt, J=9.1, 5.5 Hz, 1H), 0.48-0.85 (m, 3H), 1.46 (d, J=2.5 Hz, 9H), 1.58 (s, 18H), 2.04 (s, 2H), 2.47-2.71 (m, 1H), 2.84 (d, J=6.9 Hz, 2H), 4.01 (dt, J=11.5, 3.5 Hz, 1H), 4.05-4.23 (m, 2H), 4.83 (s, 1H), 4.94-5.12 (m, 2H), 5.50 (dt, J=7.1, 3.6 Hz, 1H), 7.21-7.55 (m, 5H), 7.64 (s, 1H).

Step 9: Synthesis of Compound 9

To a 500-mL three-necked round-bottom flask purged and maintained with an inert atmosphere of nitrogen, were added a solution (250 mL) of Compound 8 (4.6 g, 7.33 mmol, 1.00 eq.) and triphenylphosphane (3.15 g, 11 mmol, 1.50 eq.) in THF, and a solution (10 mL) of DIAD (2.5 g, 11 mmol, 1.50 eq.) in THF. The resulting solution was stirred for 5 h at room temperature. The resulting mixture was concentrated under vacuum. The crude product was purified by Flash Prep-HPLC under the following conditions: Column: C18 silica gel; Mobile phase: ACN=0% increasing to ACN=60% within 30 min; Detector: UV 254 nm. This resulted in 3.9 g (87.6%) of Compound 9 in the form of a white solid. ESI-MS (EI$^+$, m/z+Na): 610, 1.120 min.

Step 10: Synthesis of Compound 10

To a 1000-mL round-bottom flask was added a solution (500 mL) of Compound 9 (3.5 g, 5.74 mmol, 1.00 eq.) in THF, followed by Pd/C (300 mg). The resulting solution was stirred for 5 h at room temperature in the presence of H$_2$ (1 atm). The mixture was filtered and the solids were discarded. The resulting mixture was concentrated under vacuum. This resulted in 2.5 g of Compound 10 (crude) in the form of a yellow solid. ESI-MS (EI$^+$, m/z+Na): 520, 0.967 min.

Step 11: Synthesis of Compound 11

To a 250-mL sealed tube was added a solution (50 mL) of Compound 10 (2.5 g, 4.8 mmol, 1.00 eq.) in DMF, followed by SO3.Py (3.03 g, 19.2 mmol, 4.00 eq.). The resulting solution was stirred for 20 h at room temperature. The resulting mixture was concentrated under vacuum. The reaction was then quenched by the addition of 10 mL of NaH$_2$PO$_4$. Then NBu$_4$HSO$_4$ (100 mg) was added to the reaction mixture. The resulting solution was extracted with ethyl acetate (20 mL×2), and the organic phases were combined, dried over anhydrous sodium sulfate and concentrated under vacuum. The residue was purified by Flash Prep-HPLC under the following conditions: Column: C18 silica gel; Mobile phase: ACN=0% increasing to ACN=80% within 30 min; Detector: UV 254 nm. This resulted in 2.0 g of Compound 11 (69.4%). ESI-MS (EI$^+$, m/z+Na): 600, 1.012 min.

Step 12: Synthesis of Compound DDD

When purified by flash chromatography, Compound 11 was unstable and readily stripped of Boc protecting groups in the mobile phase. At the time of concentration, a product stripped of one Boc was obtained. The product stripped of one Boc was stirred in warm water (pH=6-7) to give a product DDD stripped of two Boc protecting groups. The product was purified by Prep-HPLC under the following conditions: Column: Xselect CSH OBD C18 column 19×250 mm, 5 μm; Mobile phase A: water (0.1% FA); Mobile phase B: ACN; Flow rate: 25 mL/min; Gradient: from 4% B to 4% B within 13 min; 220/254 nm; Rt: 11.27, 12.23 min. This resulted in 105 mg of Compound DDD. ESI-MS (EI$^+$, m/z): 400, 0.650 min. HPLC: 4.360, purity: 97%. $^1$H NMR (D$_2$O, 400 MHz): δ (ppm) 0.34-0.61 (m, 2H), 0.63-0.92 (m, 1H), 1.82 (d, J=16.0 Hz, 1H), 2.64 (dd, J=16.1, 7.8 Hz, 1H), 3.18 (d, J=12.2 Hz, 1H), 3.36 (dd, J=12.2, 3.8 Hz, 1H), 3.52 (d, J=3.8 Hz, 1H), 4.02 (dd, J=10.5, 4.8 Hz, 1H), 4.21 (t, J=10.3 Hz, 1H), 4.99 (d, J=7.6 Hz, 1H), 5.54 (dd, J=10.0, 4.8 Hz, 1H).

Example 57: Preparation of Compound EEE

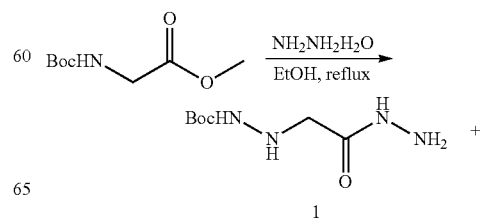

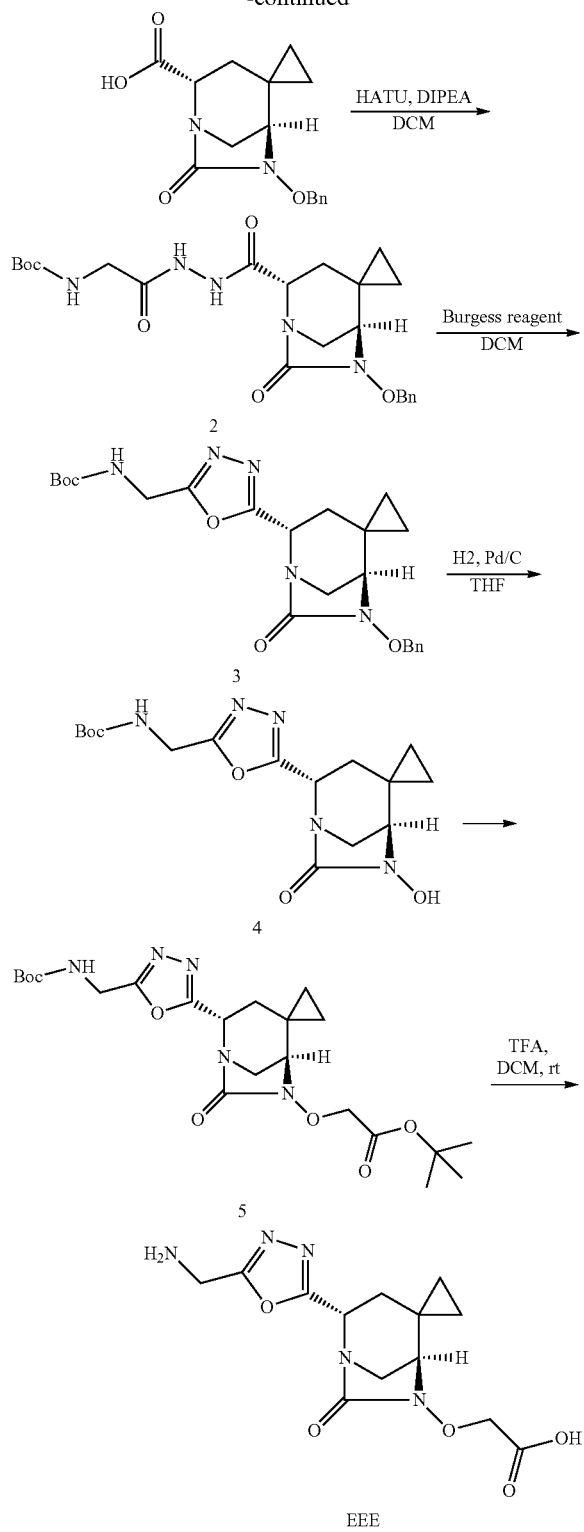

next step directly without further purification, m/z (ES+) [M+Na]+=212, acid, HPLC tR=0.509 min.

Step 2: Synthesis of Compound 2

To a 100-mL round-bottom flask was added a solution (300 mL) of (1R,4S)-7-(benzyloxy)-6-oxo-5,7-diazaspiro[bicyclo[3.2.1]octane-2,1'-cyclopropane]-4-carboxylic acid (2 g, 6.6 mmol, 1.00 eq.), tert-butyl (2-hydrazino-2-oxo-ethyl)carbamate (2.5 g crude, 13.2 mmol, 2.00 eq.), and HATU (5.03 g, 13 mmol, 2.00 eq.) in THF at 0° C. Then DIPEA (2.56 g, 20 mmol, 3.00 eq.) was added. The resulting solution was stirred at 0° C. for 2 h. The mixture was filtered and the solids were discarded. The filtrate was concentrated, and purified by silica gel column chromatography with gradient elution (0-60% MeOH/DCM) to give a crude product (3.3 g, 100%) in the form of a pale yellow solid, m/z (ES+), [M+H]+=474; TFA, HPLC tR=1.131 min.

Step 3: Synthesis of Compound 3

To a 100-mL round-bottom flask was added a solution (50 mL) of Compound 2 (3.3 g, 7 mmol, 1.00 eq.) and DIEA (2.69 g, 21 mmol, 3 eq.) in DCM. Then Burgess reagent (5 g, 21 mmol, 3 eq.) was added. The resulting solution was stirred for 20 h at room temperature. The resulting mixture was concentrated under reduced pressure. The crude product was purified by silica gel column chromatography with gradient elution (0-60% EA/PE) to give Compound 3 (3.5 g, crude) in the form of a pale yellow solid, m/z (ES+), [M+H]+=456; TFA, HPLC tR=1.181 min.

Step 4: Synthesis of Compound 4

To a 250-mL round-bottom flask was added a solution (100 mL) of Compound 3 (3.3 g, 7 mmol) in THF, followed by Pd/C (600 mg). The resulting solution was stirred for 2 h at room temperature in the presence of $H_2$ (1 atm). The mixture was filtered and the solids were discarded. The filtrate was concentrated under reduced pressure to give 2.8 g of crude product in the form of a white solid, which was used directly in the next step, m/z (ES+), [M+Na]+=388; TFA, HPLC tR=0.736 min.

Step 5: Preparation of Compound 5

To a 25-mL round-bottom flask was added a solution (10 mL) of Compound 4 (219 mg, 0.6 mmol) in DCM. Triethylamine (90 mg, 0.9 mmol, 1.5 eq.) and tert-butyl 2-bromoacetate (350 mg, 1.8 mmol, 3 eq.) were added at 0° C. The resulting solution was stirred at 0° C. overnight. The crude product was purified by silica gel column chromatography with gradient elution (0-60% EA/PE) to give Compound 5 (70 mg, 24.3%) in the form of a pale yellow solid, m/z (ES+), [M+H]+=480; TFA, HPLC tR=1.200 min.

Step 6: Synthesis of Compound EEE

To a 25-mL round-bottom flask was added a solution (10 mL) of Compound 5 (70 mg, 0.14 mmol) in DCM. TFA (5 mL) was added at 0° C. The resulting solution was stirred at 0° C. for 2 h. The crude product was purified by Prep-HPLC (XBridge Prep C18 OBD column, 5μ silica, 19 mm in diameter, 150 mm in length) using a progressively smaller polar mixture of water (containing 0.01% FA) and acetonitrile as eluent. The fractions containing the desired compound were evaporated to dryness to give 2-(((1R,4S)-4-(5-(aminomethyl)-1,3,4-oxadiazol-2-yl)-6-oxo-5,7-diazaspiro[bicyclo[3.2.1]octane-2,1'-cyclopropane]-7-yl)oxy)acetic acid (11.9 mg, 25.3%). m/z (ES+), [M+H]+=324; TFA, HPLC tR=0.418 min. $^1$H NMR (300 MHz, DMSO-d6) δ 7.59 (s, 2H), 4.82 (d, J=7.5 Hz, 1H), 4.63 (d, J=16.4 Hz, 1H), 4.31 (d, J=32.3 Hz, 1H), 4.11 (d, J=6.2 Hz, 2H), 3.03 (d, J=10.9 Hz, 1H), 2.85 (d, J=11.7 Hz, 2H), 1.71 (d, J=15.3 Hz, 1H), 1.27 (d, J=6.8 Hz, 1H), 0.81 (d, J=6.2 Hz, 1H), 0.65 (s, 1H), 0.40 (d, J=8.2 Hz, 2H).

Step 1: Synthesis of Compound 1

To a solution (50 mL) of tert-butoxycarbonylglycine methyl ester (9 g, 47.6 mmol, 1 eq.) in ethanol was added a $NH_2NH_2 \cdot H_2O$ solution (15 mL). The reaction mixture was stirred at 70° C. for 2 h. The solvent was evaporated away under reduced pressure. The crude product was used in the

Example 58: Preparation of Compound FFF

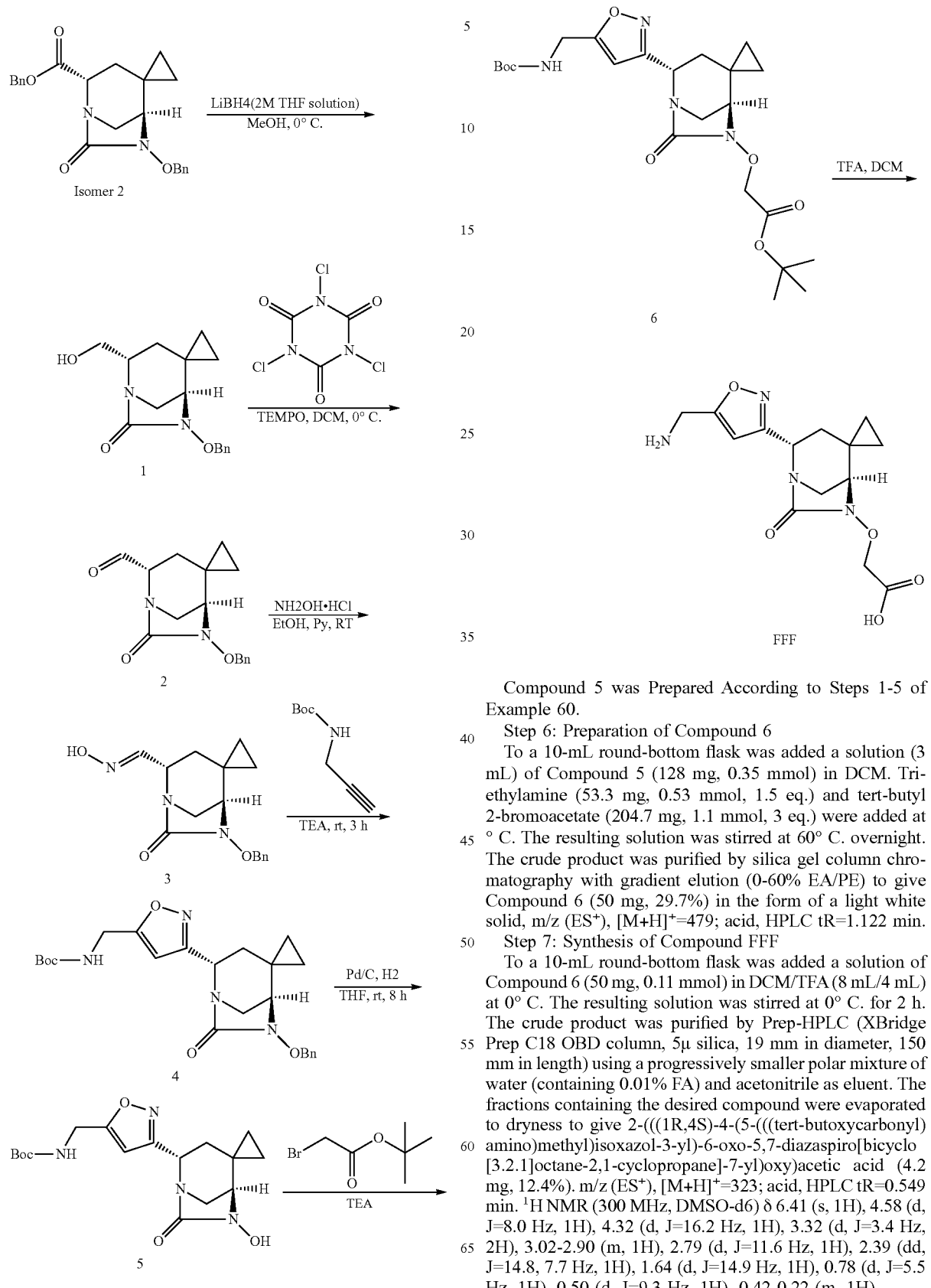

Compound 5 was Prepared According to Steps 1-5 of Example 60.

Step 6: Preparation of Compound 6

To a 10-mL round-bottom flask was added a solution (3 mL) of Compound 5 (128 mg, 0.35 mmol) in DCM. Triethylamine (53.3 mg, 0.53 mmol, 1.5 eq.) and tert-butyl 2-bromoacetate (204.7 mg, 1.1 mmol, 3 eq.) were added at 0° C. The resulting solution was stirred at 60° C. overnight. The crude product was purified by silica gel column chromatography with gradient elution (0-60% EA/PE) to give Compound 6 (50 mg, 29.7%) in the form of a light white solid, m/z (ES$^+$), [M+H]$^+$=479; acid, HPLC tR=1.122 min.

Step 7: Synthesis of Compound FFF

To a 10-mL round-bottom flask was added a solution of Compound 6 (50 mg, 0.11 mmol) in DCM/TFA (8 mL/4 mL) at 0° C. The resulting solution was stirred at 0° C. for 2 h. The crude product was purified by Prep-HPLC (XBridge Prep C18 OBD column, 5μ silica, 19 mm in diameter, 150 mm in length) using a progressively smaller polar mixture of water (containing 0.01% FA) and acetonitrile as eluent. The fractions containing the desired compound were evaporated to dryness to give 2-(((1R,4S)-4-(5-(((tert-butoxycarbonyl)amino)methyl)isoxazol-3-yl)-6-oxo-5,7-diazaspiro[bicyclo[3.2.1]octane-2,1-cyclopropane]-7-yl)oxy)acetic acid (4.2 mg, 12.4%). m/z (ES$^+$), [M+H]$^+$=323; acid, HPLC tR=0.549 min. $^1$H NMR (300 MHz, DMSO-d6) δ 6.41 (s, 1H), 4.58 (d, J=8.0 Hz, 1H), 4.32 (d, J=16.2 Hz, 1H), 3.32 (d, J=3.4 Hz, 2H), 3.02-2.90 (m, 1H), 2.79 (d, J=11.6 Hz, 1H), 2.39 (dd, J=14.8, 7.7 Hz, 1H), 1.64 (d, J=14.9 Hz, 1H), 0.78 (d, J=5.5 Hz, 1H), 0.50 (d, J=9.3 Hz, 1H), 0.42-0.22 (m, 1H).

Example 59: Preparation of Compound GGG

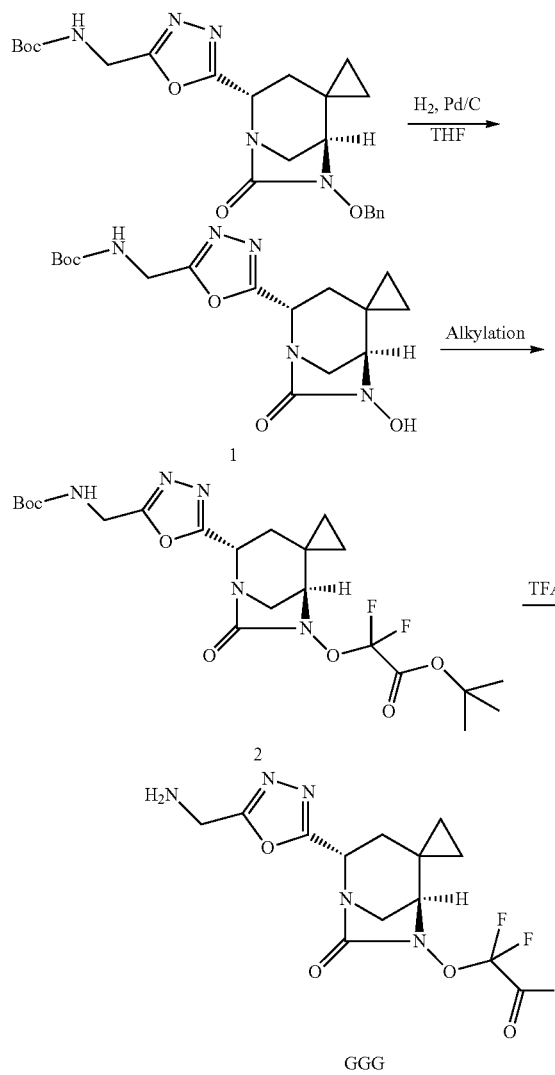

Step 1: Preparation of Compound 1

To a 100-mL round-bottom flask was added a solution of Compound 1 (455 mg, 1 mmol) in THF (20 mL), followed by Pd/C (100 mg). The resulting solution was stirred for 2 h at room temperature in the presence of $H_2$ (1 atm). The mixture was filtered and the solids were discarded. The filtrate was concentrated under reduced pressure to give 2.8 g of crude product in the form of a white solid, which was used directly in the next step, m/z (ES+), [M+Na]+=388; TFA, HPLC tR=0.736 min.

Step 2: Preparation of Compound 2

To a 10-mL round-bottom flask was added a solution of Compound 1 (200 mg, 0.55 mmol) in DMF (100 mL). Potassium carbonate (151 mg, 1.1 mmol, 2 eq.) and ethyl 2-bromo-2,2-difluoroacetate (126 mg, 0.55 mmol, 1 eq.) were added at room temperature. The resulting solution was stirred for 4 h at room temperature. The crude product was purified by silica gel column chromatography with gradient elution (0-60% EA/PE) to give Compound 2 (74 mg, 26.3%) in the form of a light white solid, m/z (ES+), [M+H]+=516; TFA, HPLC=1.273 min.

Step 3: Synthesis of Compound GGG

To a 10-mL round-bottom flask was added a solution of Compound 2 (74 mg, 0.14 mmol) in DCM (10 mL). TFA (5 mL) was added at 0° C. The resulting solution was stirred at 0° C. for 2 h. The crude product was purified by Prep-HPLC (XBridge Prep C18 OBD column, 5μ silica, 19 mm in diameter, 150 mm in length) using a progressively smaller polar mixture of water (containing 0.01% FA) and acetonitrile as eluent. The fractions containing the desired compound were evaporated to dryness to give 2-(((1R,4S)-4-(5-(aminomethyl)-1,3,4-oxadiazol-2-yl)-6-oxo-5,7-diazaspiro[bicyclo[3.2.1]octane-2,1'-cyclopropane]-7-yl) oxy)-2,2-difluoroacetic acid (6.4 mg, 12.4%). m/z (ES+), [M+H]+=360; TFA, HPLC tR=0.660 min. 1H NMR (300 MHz, D2O) δ 4.98 (d, J=7.7 Hz, 2H), 4.42 (d, J=12.1 Hz, 2H), 3.39 (d, J=3.8 Hz, 1H), 3.33-3.18 (m, 1H), 3.15 (d, J=12.2 Hz, 1H), 2.61 (d, J=7.7 Hz, 1H), 1.80 (d, J=16.0 Hz, 1H), 0.84-0.59 (m, 2H), 0.64-0.31 (m, 3H).

Example 60: Preparation of Compound HHH

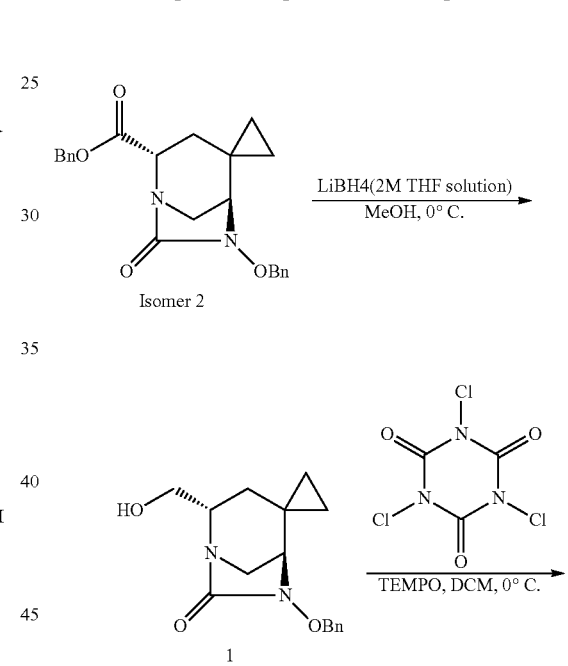

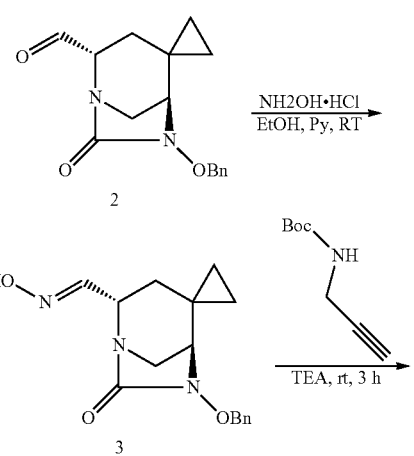

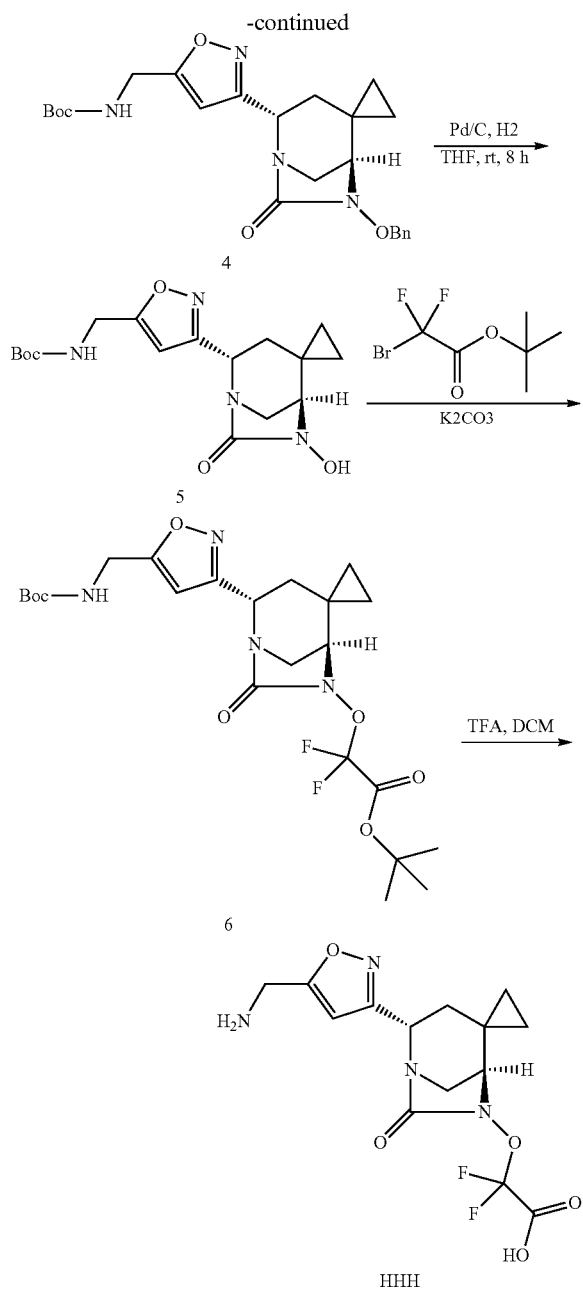

Step 1: Synthesis of Compound 1

LiBH4/THF (1.13 g, 51 mmol, 4 eq.) was added to a solution of benzyl (1R,4S)-7-(benzyloxy)-6-oxo-5,7-diazaspiro[bicyclo[3.2.1]octane-2,1'-cyclopropane]-4-carboxylate (5 g, 12.76 mmol, 1 eq.) in methanol (50 mL) at 0° C. The mixture was stirred at 0° C. for 4-5 h. The reaction was carefully quenched at 0° C. by the addition of saturated NaH2PO4 (50 mL). The mixture was diluted with water (20 mL) and extracted three times with DCM. The combined organic phases were concentrated and purified by silica gel column chromatography (hexane/ethyl acetate from 100:0 to 100:1) to give the desired product, namely Compound 1 (2.6 g, 71%). m/z (ES+), [M+H]+=289; acid, HPLC tR=0.789 min.

Step 2: Synthesis of Compound 2

TEMPO (14.08 mg, 9 mmol, 0.01 eq.) was added in portions to a solution of Compound 1 (2.6 g, 9 mmol, 1 eq.) and 1,3,5-trichloro-1,3,5-triazinane (2.08 g, 9 mmol, 1 eq.) in DCM (25 mL) at 0° C. The mixture was stirred at 0° C. for 2 h and filtered through celite. The filtrate was dried over sodium sulfate and concentrated to give the crude product Compound 2, which was directly used in the next step without further purification, m/z (ES+), [M+H]+=287; acid, HPLC tR=0.931 min.

Step 3: Synthesis of Compound 3

A solution of the crude product Compound 2 (2.6 g, 8.74 mmol, 1 eq.), hydroxylamine hydrochloride (0.69 g, 10.1 mmol, 1.16 eq.) and pyridine (2.76 g, 34.9 mmol, 4 eq.) in ethanol (25 mL) was stirred at room temperature for 2 h. The reaction mixture was then concentrated. The residue was diluted with DCM, washed with water and saturated sodium chloride, dried over Na2SO4, and then concentrated. The residue was purified by silica gel column chromatography (hexane/ethyl acetate from 100:0 to 100:1) to give the desired product, namely Compound 3 (1.48 g, 54%). m/z (ES+), [M+H]+=287; acid, HPLC tR=0.873 min.

Step 4: Synthesis of Compound 4

Phenyl-I3-iodoalkanediyl-bis(2,2,2-trifluoroacetate) (3.6 g, 8.37 mmol, 1.5 eq.) was added in portions to a solution of Compound 3 (1.48 g, 5.58 mmol, 1 eq.) and ten-butyl prop-2-yn-1-yl carbamate (0.86 g, 5.58 mmol, 1 eq.) in methanol (20 mL) and water (4 mL). The resulting mixture was stirred at room temperature for 4 h. The solvent was removed under reduced pressure. The crude product was purified by flash C18-flash chromatography with gradient elution (0 to 65% acetonitrile in water). The pure fractions were evaporated to dryness to give Compound 4 (250 mg, 11%) in the form of a white solid, m/z (ES+), [M+H]+=455; acid, HPLC tR=1.288 min. 1H NMR (300 MHz, chloroform-d) δ 7.48-7.33 (m, 6H), 6.32 (s, 1H), 5.09 (d, J=11.5 Hz, 1H), 4.93 (d, J=11.5 Hz, 2H), 4.69 (d, J=7.4 Hz, 1H), 4.45 (s, 2H), 2.96 (dd, J=11.6, 3.7 Hz, 1H), 2.85 (d, J=11.4 Hz, 1H), 2.61 (dd, J=15.1, 7.5 Hz, 1H), 2.40 (d, J=3.7 Hz, 1H), 1.79 (d, J=15.1 Hz, 1H), 1.48 (s, 9H), 0.72 (dt, J=10.2, 5.4 Hz, 1H), 0.51 (ddd, J=20.9, 9.9, 5.3 Hz, 2H), 0.17-0.03 (m, 1H).

Step 5: Synthesis of Compound 5

To a 100-mL round-bottom flask was added a solution of Compound 4 (128 mg, 2.8 mmol) in THF (6 mL), and then Pd/C (20 mg) was added. The resulting solution was stirred for 2 h at room temperature in the presence of H2 (1 atm). The mixture was filtered and the solids were discarded. The filtrate was concentrated under reduced pressure to give 128 mg of the crude product Compound 5 in the form of a white solid, which was used directly in the next step, m/z (ES+), [M+H]+=365; acid, HPLC tR=0.822 min.

Step 6: Synthesis of Compound 6

To a 10-mL round-bottom flask was added a solution of Compound 5 (150 mg, 0.41 mmol) in DMF (5 mL). Potassium carbonate (113.6 mg, 0.82 mmol, 2 eq.) and tert-butyl 2-bromo-2,2-difluoroacetate (94.5 mg, 0.41 mmol, 1 eq.) were added at 0° C. The resulting solution was stirred at 60° C. overnight. The crude product was purified by silica gel column chromatography with gradient elution (0-60% EA/PE) to give Compound 6 (50 mg, 23.69%) in the form of a light white solid, m/z (ES+), [M+H]+=515; acid, HPLC tR=1.325 min.

Step 7: Synthesis of Compound HHH

To a 10-mL round-bottom flask was added a solution of Compound 6 (50 mg, 0.11 mmol) in DCM/TFA (8 mL/4 mL) at 0° C. The resulting solution was stirred at 0° C. for 2 h. The crude product was purified by Prep-HPLC (XBridge Prep C18 OBD column, 5μ silica, 19 mm in diameter, 150 mm in length) using a progressively smaller polar mixture of water (containing 0.01% FA) and acetonitrile as eluent. The fractions containing the desired compound were evaporated to dryness to give 2-(((1R,4S)-4-(5-(((tert-butoxycarbonyl)amino)methyl)isoxazol-3-yl)-6-oxo-5,7-diazaspiro[bicyclo[3.2.1]octane-2,1'-cyclopropane]-7-yl)oxy)-2,2-difluoroacetic acid (1.5 mg, 4.3%). m/z (ES+), [M+H]+=359; acid, HPLC tR=0.868 min. 1H NMR (400 MHz, chloroform-d) δ 8.23-7.58 (m, 2H), 6.61 (s, 1H), 4.85-4.62 (d, J=18.8 Hz, 1H), 4.31-4.21 (s, 2H), 3.29-3.21 (m, 1H), 3.15-3.05 (m, 1H), 2.88-2.78 (m, 1H), 2.51-2.42 (m, 1H), 1.72-1.60 (d, J=6.6 Hz, 1H), 0.70-0.61 (m, 1H), 0.53-0.45 (m, 1H), 0.43-0.39 (m, 1H), 0.38-0.30 (m, 1H).

Example 61: Synthesis of Compound III

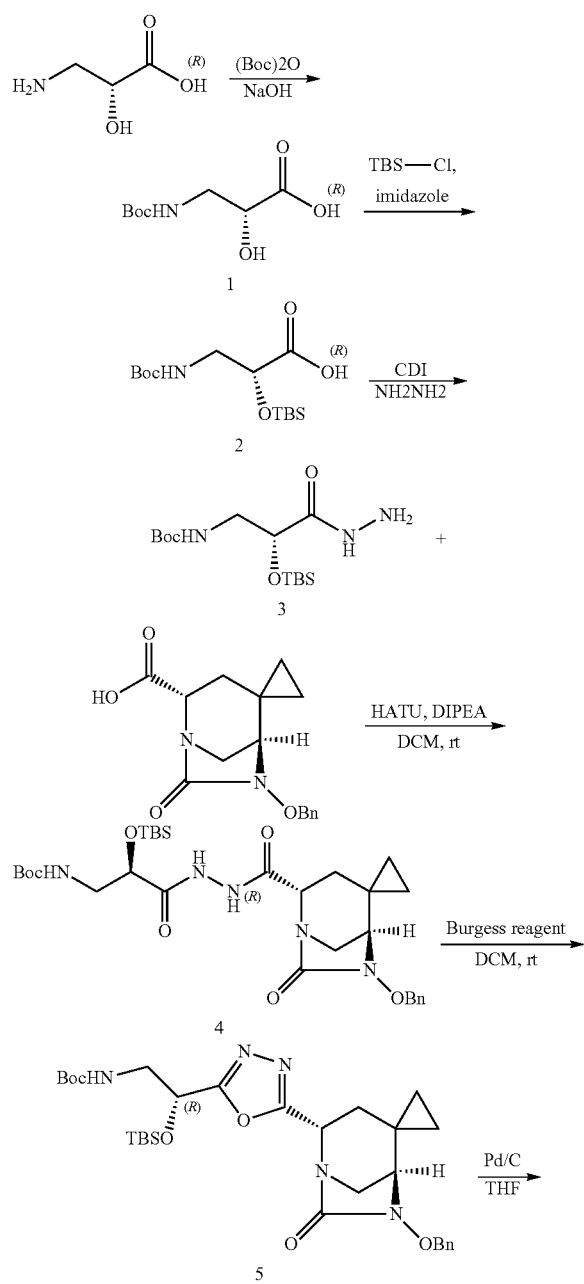

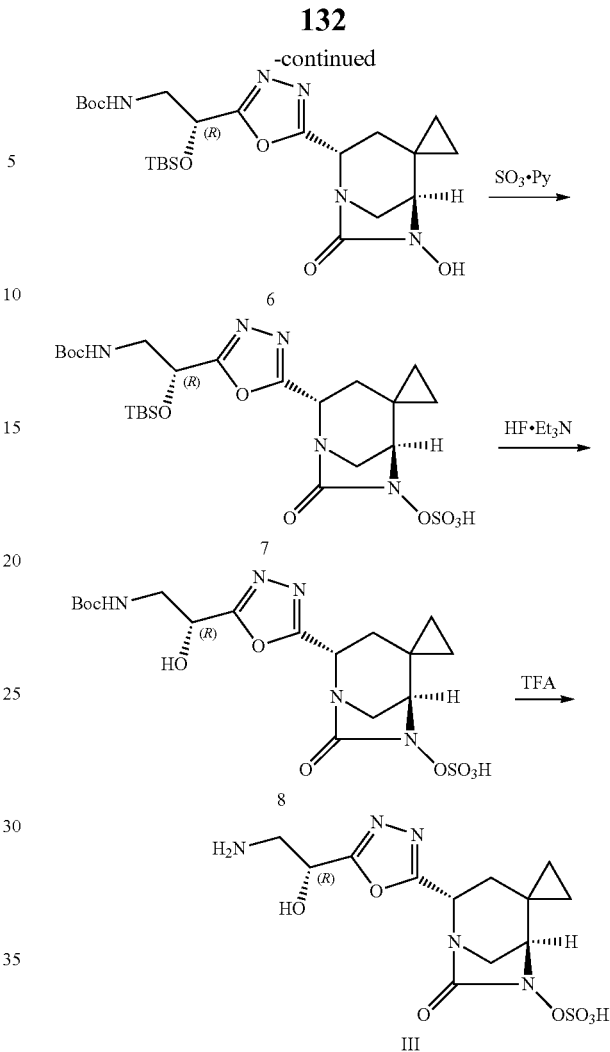

Step 1: Synthesis of Compound 1

To a 500-mL round-bottom flask was added a solution of (R)-3-amino-2-hydroxypropanoic acid (3 g, 28.57 mmol, 1.00 eq.) in dioxane (60 mL), and the solution was cooled in an ice bath. In the meantime, a solution of sodium hydroxide (2.4 g, 60 mmol, 2.10 eq.) in water (60 mL) was added. The resulting solution was stirred at 0° C. for 5 min. A solution of di-tert-butyl dicarbonate ((Boc)₂O) (7.1 g, 32.57 mmol, 1.14 eq.) in dioxane (20 mL) was then added dropwise at 0° C. The resulting solution was stirred at room temperature overnight. The resulting mixture was washed with ethyl acetate (200 mL×2). The pH of aqueous phase was adjusted to about 2 with HCl (1 mol/L). The resulting solution was extracted with ethyl acetate (200 mL×2). The organic phases were combined, dried over sodium sulfate and concentrated under vacuum to give 5.2 g of crude (R)-3-((tert-butoxycarbonyl)amino)-2-hydroxypropanoic acid in the form of a colorless oil. m/z (ES+), [M+Na]+=228; HPLC tR=0.701 min.

Step 2: Synthesis of Compound 2

To a 250-mL round-bottom flask was added a solution of (R)-3-((tert-butoxycarbonyl) amino)-2-hydroxypropanoic acid (5.2 g, 25.36 mmol, 1.00 eq.) and tert-butyldimethylsilyl chloride (TBSCl) (5.32 g, 35.5 mol, 1.40 eq.) in tetrahydrofuran (80 mL). Then triethylamine (5.12 g, 50.72 mol, 2 eq.) was added dropwise. The resulting solution was stirred for 20 h at room temperature. The pH of the resulting solution was adjusted to about 2 with HCl (1 mol/L). The resulting solution was extracted with ethyl acetate (300 mL×2). The organic phases were combined, dried over sodium sulfate and concentrated under vacuum to give 9 g of crude (R)-3-((tert-butoxycarbonyl)amino)-2-((terr-butyldimethylsilyl)oxy)propanoic acid in the form of a white solid, m/z (ES+), [M+H]⁺=320; HPLC tR=3.01 min.

Step 3: Synthesis of Compound 3

To a 250-mL round-bottom flask was added a solution of (R)-3-((/err-butoxycarbonyl) amino)-2-((tert-butyldimethylsilyl)oxy)propanoic acid (9 g, 28.21 mmol, 1.00 eq.) in dichloromethane (100 mL). N',N-carbonyldiimidazole (CDI) (7 g, 42.32 mmol, 1.50 eq.) was added in portions at 0° C. The resulting solution was stirred for 120 min at room temperature. Hydrazine hydrate (NH₂NH₂.H₂O) (98%) (7 g, 140 mmol, 5 eq.) was then added dropwise at room temperature. The resulting solution was stirred for an additional 60 min at room temperature. The organic phase was separated and concentrated under vacuum. The crude product was purified by column chromatography (petroleum ether/ethyl acetate=1/5-1/1) to give 3.7 g (38.9% over 3 steps) of tert-butyl (R)-(2-((tert-butyldimethylsilyl)oxy)-3-hydrazino-3-oxopropyl)carbamate in the form of a white solid, m/z (ES+), [M+H]⁺=334; HPLC tR=1.093 min.

Step 4: Synthesis of Compound 4

To a 100-mL round-bottom flask was added a solution of (1R,4S)-7-(benzyloxy)-6-oxo-5,7-diazaspiro[bicyclo[3.2.1]octane-2,1'-cyclopropane]-4-carboxylic acid (3 g, 10 mmol, 1.00 eq.), tert-butyl (R)-(2-((tert-butyldimethylsilyl)oxy)-3-hydrazino-3-oxopropyl)carbamate (3.7 g, 11.1 mmol, 1.10 eq.), and 2-(7-oxybenzotriazole)-N,N,N',N'-tetramethyluronium hexafluorophosphate (HAUT) (5.7 g, 15 mmol, 1.5 eq.) in tetrahydrofuran (50 mL) at 0° C. N,N-Diisopropylethylamine (DIPEA) (3.22 g, 25 mmol, 2.5 eq.) was added dropwise at 0° C. The resulting solution was stirred at 0° C. for 2 h. The solid was filtered off and the filtrate was concentrated. The crude product was purified by column chromatography (petroleum ether/ethyl acetate=1/5-1/1) to give 4.5 g of crude product 4 in the form of a yellow solid, m/z (ES⁺), [M+H]⁺=618; HPLC tR=1.351 min. 1H NMR (chloroform-d, 400 MHz): δ (ppm) 0.10 (td, J=8.8, 8.1, 5.2 Hz, 1H), 0.15 (d, J=6.3 Hz, 6H), 0.43 (dt, J=8.9, 6.3 Hz, 1H), 0.54 (td, J=9.2, 4.5 Hz, 2H), 0.93 (s, 9H), 2.26-2.46 (m, 2H), 2.81 (s, 6H), 3.12 (dd, J=11.7, 3.9 Hz, 1H), 3.20-3.45 (m, 2H), 3.59 (dt, J=13.4, 6.5 Hz, 1H), 4.01-4.18 (m, 2H), 4.29 (t, J=4.7 Hz, 1H), 4.85-5.10 (m, 2H), 5.36 (s, 1H), 7.34-7.49 (m, 5H), 8.48 (d, J=86.2 Hz, 2H).

Step 5: Synthesis of Compound 5

To a 100-mL round-bottom flask was added a solution of intermediate 4 (4.5 g, 7.3 mmol, 1.00 eq.) and DIEA (3.8 g, 29 mmol, 4.00 eq.) in dichloromethane (40 mL). Then Burgess reagent (6.9 g, 29 mmol, 4.00 eq.) was added in portions at room temperature. The resulting solution was stirred for 20 h at room temperature. The mixture was concentrated. The residue was purified by column chromatography (petroleum ether/ethyl acetate=1/5-1/1) to give 4.3 g (73% over 2 steps) of product 5 in the form of a white solid, m/z (ES+), [M+Na]⁺=622; HPLC tR=1.400 min. 1H NMR (methanol-d4, 300 MHz): δ (ppm) 0.06 (s, 3H), 0.16 (s, 3H), 0.31 (dt, J=10.1, 5.3 Hz, 1H), 0.43-0.54 (m, 1H), 0.66 (dt, J=10.8, 5.4 Hz, 1H), 0.78 (dt, J=9.5, 5.3 Hz, 1H), 0.90 (s, 9H), 1.40 (s, 8H), 1.75 (d, J=15.4 Hz, 1H), 2.44-2.74 (m, 1H), 2.76-2.89 (m, 2H), 3.03 (d, J=2.4 Hz, 2H), 3.46 (d, J=6.4 Hz, 2H), 4.84 (d, J=7.6 Hz, 1H), 4.93-5.15 (m, 3H), 7.34-7.57 (m, 5H).

Step 6: Synthesis of Compound 6

To a 250-mL round-bottom flask was added a solution of intermediate 5 (4 g, 6.67 mmol, 1.00 eq.) in tetrahydrofuran (100 mL), followed by Pd/C (1 g). The resulting solution was stirred for 2 h at room temperature in the presence of H₂ (1 atm). After the reaction was completed, the solid was filtered off. The resulting filtrate was concentrated under vacuum to give 4 g of crude product 6 in the form of a white solid, m/z (ES+), [M+Na]⁺=532; HPLC tR=1.238 min.

Step 7: Synthesis of Compound 7

To a 50-mL round-bottom flask was added a solution of intermediate 6 (4 g, 6.67 mmol, 1.00 eq.) in DMF (30 mL) at room temperature, followed by SO₃.Py (5.3 g, 33.5 mmol, 5.00 eq.) in portions. The resulting solution was stirred for 20 h at room temperature. The resulting mixture was concentrated under vacuum. To the crude product was added 40 mL of a saturated sodium dihydrogen sulfate solution. Then 3 g of tetrabutylammonium hydrogen sulfate was added. The solution was then extracted with ethyl acetate (100 mL×2). The organic phases were combined, dried over sodium sulfate and concentrated under vacuum to give 5 g of crude product 7 in the form of a pale yellow solid, m/z (ES+), [M−H]⁺=588; HPLC tR=2.311 min. 1H NMR (methanol-d4, 400 MHz): δ (ppm) 0.07 (d, J=2.7 Hz, 3H), 0.16 (s, 3H), 0.37 (dt, J=10.3, 5.5 Hz, 1H), 0.49 (dt, J=9.0, 5.6 Hz, 1H), 0.71-0.89 (m, 3H), 0.91 (s, 9H), 1.03 (d, J=7.4 Hz, 9H), 1.24 (d, J=7.1 Hz, 3H), 1.82 (d, J=15.4 Hz, 1H), 2.59-2.76 (m, 1H), 3.35-3.63 (m, 3H), 4.11 (q, J=7.2 Hz, 2H), 4.95-5.15 (m, 1H).

Step 8: Synthesis of Compound 8

To a 100-mL round-bottom flask was added a solution of intermediate 7 (5 g, 8.5 mmol, 1.00 eq.) in tetrahydrofuran (40 mL). 3HF.Et₃N (5 mL) was added dropwise at room temperature. The resulting solution was stirred for 20 h at room temperature. The reaction mixture was concentrated under vacuum. The crude product was purified by flash column chromatography (under the following conditions: C-18 column; Mobile phase: acetonitrile increasing from 0% to 100% within 30 min; Detector: UV 220 nm) to give 3 g of crude product 8 in the form of a yellow oil. m/z (ES+), [M−H]⁺=474; HPLC tR=1.261 min.

Step 9: Synthesis of Compound III

To a 500-mL round-bottom flask was added a solution of intermediate 8 (3 g, 6.3 mmol, 1.00 eq.) in dichloromethane (50 mL), and trifluoroacetic acid (15 mL, 10.00 eq.) was added dropwise thereto at 0° C. The resulting solution was stirred at 0° C. for 120 min. The resulting mixture was concentrated under vacuum at 0° C. Diethyl ether was added to suspend the product as a solid. The product was collected by centrifugation. The crude product was purified by preparative high-performance liquid chromatography (conditions: Mobile phase A: water (no buffer); Mobile phase B: acetonitrile; Flow rate: 40 mL/min; Gradient: from 0% B to 15% B within 7 min; 254, 220 nm; tR=3.4 min) to give (1R,4S)-4-(5-((R)-2-amino-1-hydroxyethyl)-1,3,4-oxadiazol-2-yl-6-oxo-5,7-diazaspiro[bicyclo[3.2.1]octane-2,1'-cyclopropane]-7-yl sulfuric acid (798.3 mg, 29.7% over 4 steps) in the form of a white solid, m/z (ES+), [M+H]⁺=376; HPLC tR=0.683 min. 1H NMR (D₂O, 400 MHz): δ (ppm) 0.38 (p, J=5.0 Hz, 1H), 0.42-0.55 (m, 1H), 0.58-0.74 (m, 2H), 1.77 (dd, J=16.1, 4.3 Hz, 1H), 2.29-2.66 (m, 1H), 2.96-3.21 (m, 1H), 3.28 (dt, J=12.4, 4.3 Hz, 1H), 3.43 (qd, J=8.3, 7.4, 4.3 Hz, 2H), 3.47-3.66 (m, 1H), 4.91 (dd, J=7.9, 4.2 Hz, 1H), 5.18-5.37 (m, 1H).

Example 62: Synthesis of Compound JJJ

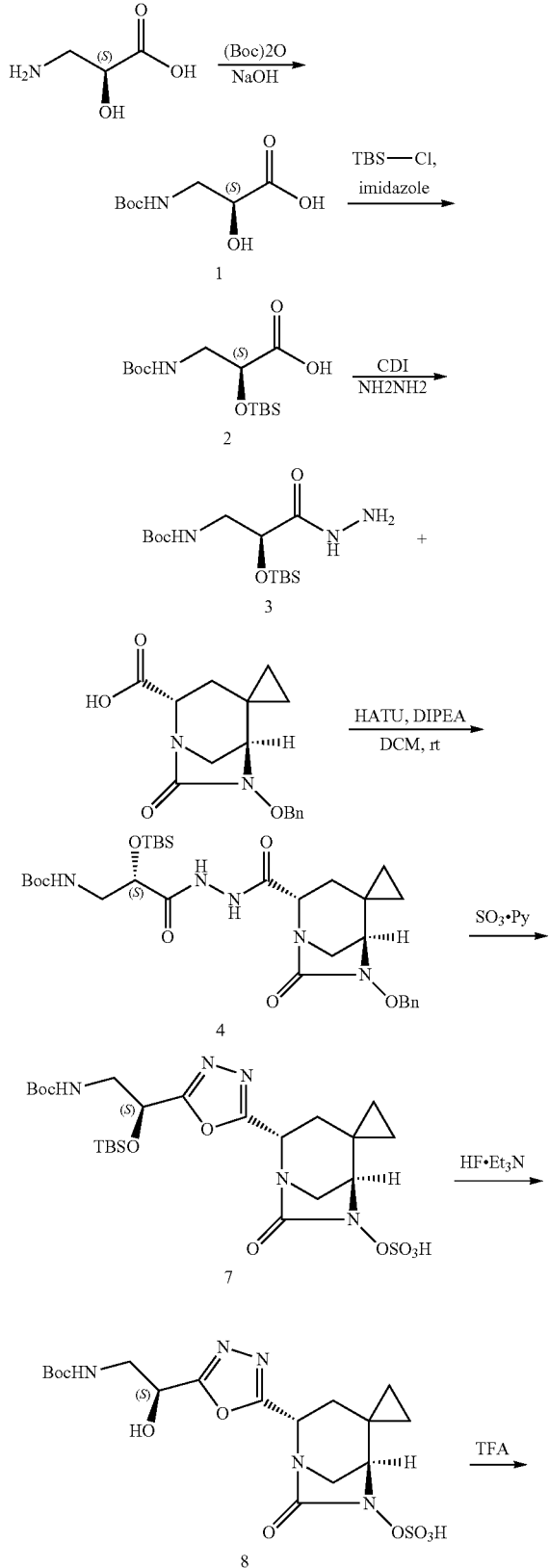

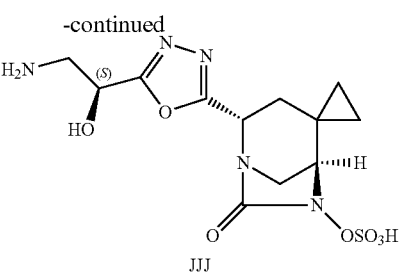

JJJ

Step 1: Synthesis of Compound 1

To a 5-L round-bottom flask was added a solution of (S)-3-amino-2-hydroxypropanoic acid (95 g, 904 mmol, 1.00 eq.) in dioxane (1.9 L), and the solution was cooled in an ice bath. In the meantime, an aqueous solution (1.9 L) of sodium hydroxide (76 g, 1.9 mol, 2.10 eq.) was added. The resulting solution was stirred at 0° C. for 5 min. Then (Boc)$_2$O (225 g, 1.03 mol, 1.14 eq.) was added dropwise at 0° C. The resulting solution was stirred at room temperature overnight. The resulting mixture was washed with ethyl acetate (2 L×2). The pH of the aqueous phase was adjusted to 2 with HCl (1 mol/L). The resulting solution was extracted with ethyl acetate (3 L×2). The organic phases were combined, dried over sodium sulfate and concentrated under vacuum to give 195 g of crude (S)-3-((tert-butoxy carbonyl) amino)-2-hydroxypropanoic acid in the form of a colorless oil. m/z (ES+), [M+Na]$^+$=228; HPLC tR=0.692 min.

Step 2: Synthesis of Compound 2

To a 5-L round-bottom flask was added a solution of (S)-3-((tert-butoxycarbonyl) amino)-2-hydroxypropanoic acid (190 g, 0.926 mol, 1.00 eq.) and TBSCl (190 g, 1.29 mol, 1.40 eq.) in tetrahydrofuran (3 L). Then triethylamine (187 g, 1.85 mol, 2 eq.) was added dropwise. The resulting solution was stirred for 20 h at room temperature. The pH of the resulting solution was adjusted to about 2 with HCl (1 mol/L). The resulting solution was then extracted with ethyl acetate (3 L×2). The organic phases were combined, dried over sodium sulfate and concentrated under vacuum to give 300 g of crude (S)-3-((tert-butoxycarbonyl) amino)-2-((tert-butyldimethylsilyl)oxy)propanoic acid in the form of a white solid, m/z (ES+), [M+Na]$^+$=342; HPLC tR=2.080 min.

Step 3: Synthesis of Compound 3

To a 5-L round-bottom flask was added a solution of (S)-3-((tert-butoxycarbonyl) amino)-2-((tert-butyldimethylsilyl)oxy)propanoic acid (300 g, 940 mmol, 1.00 eq.) in dichloromethane (3 L), and then CDI (228 g, 1.41 mol, 1.50 eq.) was added in portions at 0° C. The resulting solution was stirred at room temperature for 120 min, and then NH$_2$NH$_2$·H$_2$O (98%) (235 g, 4.7 mol, 5 eq.) was added dropwise at room temperature. The resulting solution was stirred for an additional 60 min at room temperature. The organic phase was separated and concentrated under vacuum. The crude product was purified by column chromatography (petroleum ether/ethyl acetate=1/5-1/1) to give 35 g (11.6%) of tert-butyl (S)-(2-((tert-butyldimethylsilyl) oxy)-3-hydrazino-3-oxopropyl)carbamate in the form of a white solid, m/z (ES+), [M+H]$^+$=334; HPLC tR=1.046 min. 1H NMR (DMSO-d$_6$, 300 MHz): δ (ppm) 0.01 (d, J=35.0 Hz, 6H), 0.85 (s, 9H), 1.36 (s, 9H), 2.92-3.20 (m, 2H), 3.96-4.14 (m, 2H), 6.70 (t, J=5.7 Hz, 1H), 8.79 (s, 1H).

Step 4: Synthesis of Compound 4

To a 1-L round-bottom flask was added a solution of (1R,4S)-7-(benzyloxy)-6-oxo-5,7-diazaspiro[bicyclo[3.2.1]octane-2,1'-cyclopropane]-4-carboxylic acid (28.5 g, 94 mmol, 1.00 eq.), tert-butyl (S)-(2-((tert-butyldimethylsilyl)oxy)-3-hydrazinyl-3-oxopropyl)carbamate (35 g, 104 mmol, 1.10 eq.) and HATU (53.3 g, 141 mmol, 1.5 eq.) in dry tetrahydrofuran (300 mL). DIPEA (30 g, 235 mmol, 2.5 eq.) was added dropwise at 0° C. The resulting solution was stirred at 0° C. for 2 h, and then the solid was filtered off. The crude product was purified by column chromatography (petroleum ether/ethyl acetate=1/5-1/1) to give 60 g of crude product 4 in the form of a yellow solid, m/z (ES+), [M+H]$^+$=618; HPLC tR=1.320 min. 1H NMR (chloroform-d, 300 MHz): δ (ppm) 0.04-0.11 (m, 1H), 0.17 (d, 6H), 0.34-0.63 (m, 3H), 0.94 (s, 9H), 1.42 (s, 9H), 2.24-2.38 (m, 2H), 2.79 (s, 10H), 3.12 (dd, J=11.7, 3.5 Hz, 1H), 3.44 (t, J=5.6 Hz, 2H), 4.01-4.18 (m, 2H), 4.30 (t, J=4.9 Hz, 1H), 4.83-5.10 (m, 3H), 5.29 (s, 1H), 7.30-7.45 (m, 5H), 8.41 (dd, J=55.5, 3.8 Hz, 2H).

Step 5: Synthesis of Compound 5

To a 1-L round-bottom flask was added a solution of product 4 (60 g, 97 mmol, 1.00 eq.) and DIEA (52 g, 388 mmol, 4.00 eq.) in dichloromethane (500 mL). Then Burgess reagent (95 g, 388 mmol, 4.00 eq.) was added in portions. The resulting solution was stirred for 20 h at room temperature. The mixture was concentrated. The residue was purified by column chromatography (petroleum ether/ethyl acetate=1/5-1/1) to give 45 g (79% over 2 steps) of product 5 in the form of a yellow solid, m/z (ES+), [M+H]$^+$=600; HPLC tR=1.400 min. 1H NMR (methanol-d4, 300 MHz): δ (ppm) 0.06 (s, 3H), 0.15 (s, 3H), 0.27 (dd, J=9.6, 5.1 Hz, 1H), 0.46 (dt, J=9.3, 5.3 Hz, 1H), 0.58-0.80 (m, 2H), 0.90 (s, 9H), 1.38 (s, 8H), 1.79 (d, J=15.4 Hz, 1H), 2.61 (dt, J=18.4, 9.3 Hz, 1H), 2.89-3.20 (m, 2H), 3.34 (s, 2H), 3.54 (dd, J=13.8, 7.6 Hz, 1H), 4.81 (d, J=7.6 Hz, 1H), 4.99 (q, J=11.1 Hz, 3H), 7.27-7.55 (m, 5H).

Step 6: Synthesis of Compound 6

To a 1-L round-bottom flask was added a solution of intermediate 5 (45 g, 75 mmol, 1.00 eq.) in tetrahydrofuran (500 mL) and then Pd/C (10 g, 22.2%/m %) was added. The resulting solution was stirred for 2 h at room temperature in the presence of H$_2$ (1 atm). After the reaction was completed, the solid was filtered off. The resulting filtrate was concentrated under vacuum to give 40 g of crude product 6 in the form of a white solid, m/z (ES+), [M−H]$^+$=510; HPLC tR=1.201 min.

Step 7: Synthesis of Compound 7

To a 500-mL round-bottom flask was added a solution of intermediate 6 (45 g, 75 mmol, 1.00 eq.) in DMF (200 mL), followed by SO$_3$.Py (60 g, 375 mmol, 5.00 eq.) in portions. The resulting solution was stirred for 20 h at room temperature. The resulting mixture was concentrated under vacuum. The crude product was dissolved in 400 mL of a saturated NaH$_2$PO$_4$ solution, followed by the addition of 30 g of tetrabutylammonium hydrogen sulfate. The resulting solution was extracted with ethyl acetate (500 mL×2). The organic phases were combined, dried over Na$_2$SO$_4$, and concentrated under vacuum to give 60 g of crude product 7 in the form of a pale yellow solid, m/z (ES+), [M+H]$^+$=590; HPLC tR=1.702 min. 1H NMR (methanol-d4, 300 MHz): δ (ppm) 0.06 (s, 3H), 0.16 (s, 3H), 0.28-0.60 (m, 2H), 0.69-0.80 (m, 2H), 0.91 (s, 9H), 1.39 (s, 8H), 1.87 (td, J=7.7, 7.2, 3.9 Hz, 2H), 2.82 (s, 3H), 3.01 (d, J=2.6 Hz, 1H), 3.17 (s, 2H), 3.62-3.83 (m, 1H), 4.80 (d, J=7.6 Hz, 1H), 5.02 (dd, J=7.5, 6.0 Hz, 1H)

Step 8: Synthesis of Compound 8

To a 500-mL round-bottom flask was added a solution of intermediate 7 (60 g, 101 mmol, 1.00 eq.) in tetrahydrofuran (300 mL), and then 3HF.Et$_3$N (80 mL, 10.00 eq.) was added dropwise. The resulting solution was stirred for 20 h at room temperature. The reaction mixture was concentrated under vacuum. The crude product was purified by flash column chromatography (under the following conditions: C18 column; Mobile phase: acetonitrile increasing from 0% to 100% within 30 min; Detector: UV 220 nm) to give 40 g of crude product 8 in the form of a yellow oil. m/z (ES+), [M−H]$^+$=474; HPLC tR=1.245 min. 1H NMR (methanol-d4, 300 MHz): δ (ppm) 0.41 (t, J=6.3 Hz, 1H), 0.50 (dd, J=5.7, 2.9, 1.7 Hz, 1H), 0.84 (td, J=10.1, 9.5, 3.9 Hz, 2H), 1.04 (d, J=7.4 Hz, 10H), 1.66 (d, J=4.9 Hz, 2H), 1.82 (d, J=15.4 Hz, 2H), 2.66 (dd, J=15.4, 7.7 Hz, 1H), 3.17-3.25 (m, 3H), 3.48 (d, J=3.5 Hz, 1H), 3.53 (d, J=6.2 Hz, 2H), 4.96 (t, J=6.1 Hz, 1H).

Step 9: Synthesis of Compound JJJ

To a 500-mL round-bottom flask was added a solution of product 8 (40 g, 84 mmol, 1.00 eq.) in dichloromethane (200 mL) and trifluoroacetic acid (TFA) (60 mL) was added dropwise at 0° C. The resulting solution was stirred at 0° C. for 120 min. The resulting mixture was concentrated under vacuum at 0° C. Diethyl ether was added to suspend the product as a solid. The product was collected by centrifugation. The crude product was purified by Prep-HPLC (under the following conditions: Mobile phase A: water (no buffer); Mobile phase B: acetonitrile; Flow rate: 40 mL/min; Gradient: from 0% B to 15% B within 7 min; Detector: 254, 220 nm; tR=3.4 min) to give (1R,4S)-4-(5-((S)-2-amino-1-hydroxyethyl)-1,3,4-oxadiazol-2-yl)-6-oxo-5,7-diazaspiro[bicyclo[3.2.1]octane-2,1'-cyclopropane]-7-yl hydrogen sulfate (5 g, 17.7% over 4 steps) in the form of a white solid, m/z (ES+), [M+H]$^+$=376; HPLC tR=0.838 min. 1H NMR (D$_2$O, 400 MHz): δ (ppm) 0.38 (p, J=5.0 Hz, 1H), 0.42-0.55 (m, 1H), 0.58-0.74 (m, 2H), 1.77 (dd, J=16.1, 4.3 Hz, 1H), 2.29-2.66 (m, 1H), 2.96-3.21 (m, 1H), 3.28 (dt, J=12.4, 4.3 Hz, 1H), 3.43 (qd, J=8.3, 7.4, 4.3 Hz, 2H), 3.47-3.66 (m, 1H), 4.91 (dd, J=7.9, 4.2 Hz, 1H), 5.18-5.37 (m, 1H).

Example 63. Synthesis of Compound KKK

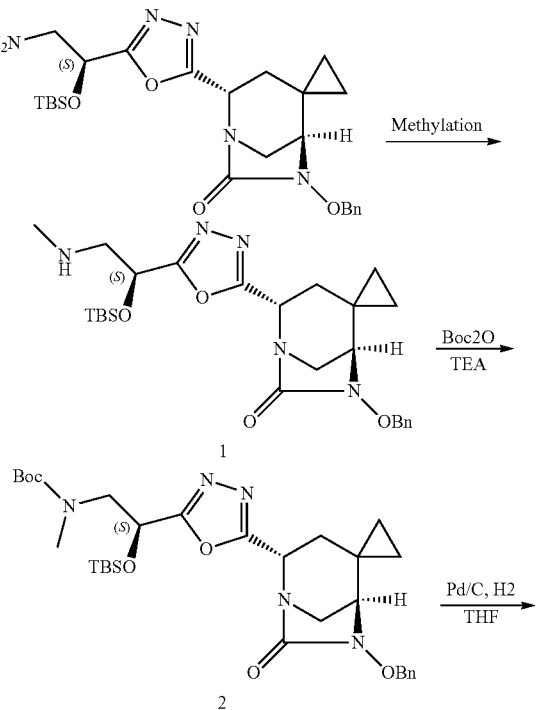

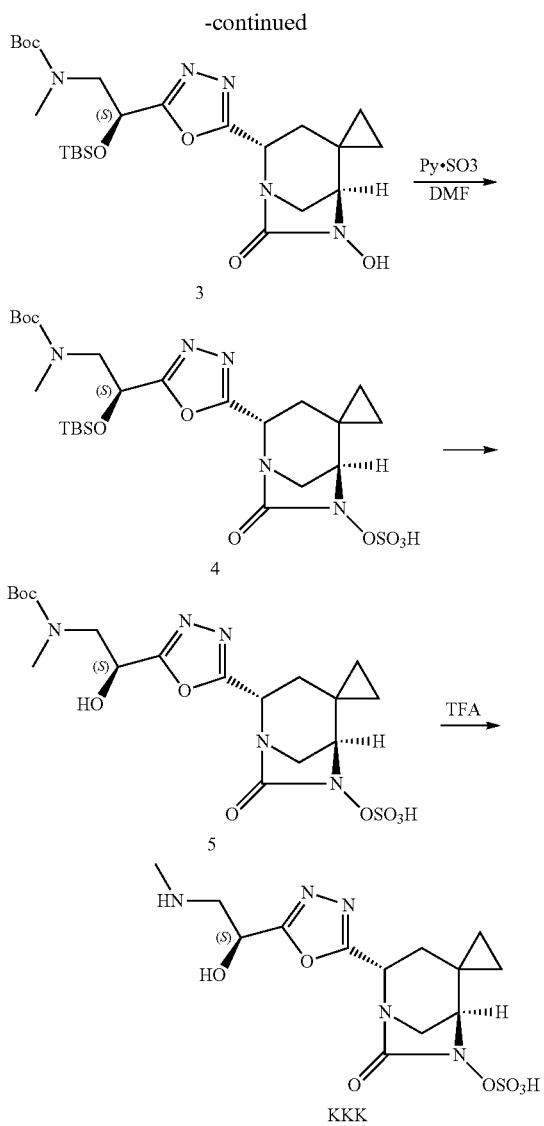

Step 1: Synthesis of Compound 1

To a 250-mL round-bottom flask were added a solution of (1R,4S)-4-(5-((S)-2-amino-1-((tert-butyldimethylsilyl)oxy)ethyl)-1,3,4-oxadiazol-2-yl)-7-(benzyloxy)-5,7-diazaspiro[bicyclo[3.2.1]octane-2,1'-cyclopropan]-6-one (4.0 g, 7.8 mmol, 1.0 eq.) in tetrahydrofuran (80 mL), DIEA (4.0 g, 31.2 mmol, 4.0 eq.), and methyl iodide (CH$_3$I) (1.7 g, 11.7 mmol, 1.5 eq.). The resulting solution was stirred at room temperature for 2 h. The resulting mixture was concentrated under vacuum, and then ethyl acetate (100 mL) was added. The resulting mixture was washed with water (2×80 mL) and brine (2×80 mL), dried over sodium sulfate and concentrated under vacuum to give 4.0 g of crude Compound 1 in the form of a yellow oil. m/z (ES+), [M+H]$^+$=514; HPLC tR=1.469 min.

Step 2: Synthesis of Compound 2

To a 500-mL round-bottom flask were added a solution of (1R,4S)-7-(benzyloxy)-4-(5-((S)-1-((tert-butyldimethylsilyl)oxy)-2-(methylamino)ethyl)-1,3,4-oxadiazol-2-yl)-5,7-diazaspiro[bicyclo[3.2.1]octane-2,1'-cyclopropan]-6-one (4.0 g, the crude product from step 1) in dichloromethane (80 mL), Boc$_2$O (7.0 g, 32 mmol) and triethylamine (3.2 g, 32 mmol). The resulting solution was stirred at room temperature for 2 h. The reaction mixture was concentrated under vacuum. The crude product was purified by flash C-18 column chromatography (under the following conditions: Mobile phase: acetonitrile increasing from 0% to 100% within 30 min; Detector: UV 220 nm) to give tert-butyl ((2S)-2-(5-((1R,4S)-7-(benzyloxy)-6-oxo-5,7-diazaspiro[bicyclo[3.2.1]octane-2,1'-cyclopropan]-4-yl)-1,3,4-oxadiazol-2-yl)-2-((tert-butyldimethylsilyl)oxy)ethyl)(methyl)carbamate (300 mg) in the form of a yellow oil. m/z (ES+), [M+Na]$^+$=636; HPLC tR=3.092 min.

Step 3: Synthesis of Compound 3

To a 25-mL round-bottom flask were added a solution of tert-butyl ((2S)-2-(5-((1R,4S)-7-(benzyloxy)-6-oxo-5,7-diazaspiro[bicyclo[3.2.1]octane-2,1'-cyclopropan]-4-yl)-1,3,4-oxadiazol-2-yl)-2-((tert-butyldimethylsilyl)oxy)ethyl)(methyl)carbamate (300 mg, 0.489 mmol, 1.0 eq.) in tetrahydrofuran (10 mL), and Pd/C (0.1 g). The resulting solution was stirred at room temperature in the presence of H$_2$ (atmospheric pressure) for 2 h. The solid was filtered off. The filtrate was concentrated under vacuum to give 200 mg of crude tert-butyl ((2S)-2-((tert-butyldimethylsilyl)oxy)-2-(5-((1R,4S)-7-hydroxy-6-oxo-5,7-diazaspiro[bicyclo[3.2.1]octane-2,1'-cyclopropan]-4-yl)-1,3,4-oxadiazol-2-yl)ethyl)(methyl)carbamate in the form of a white solid, m/z (ES+), [M+Na]$^+$=546; HPLC tR=3.026 min.

Step 4: Synthesis of Compound 4

To a 25-mL round-bottom flask was added a solution of tert-butyl (2S)-2-((tert-butyldimethylsilyl)oxy)-2-(5-((1R,4S)-7-hydroxy-6-oxo-5,7-diazaspiro[bicyclo[3.2.1]octane-2,1'-cyclopropan]-4-yl)-1,3,4-oxadiazol-2-yl)ethyl)(methyl)carbamate (200 mg, 0.38 mmol, 1.0 eq.) in DMF (5 mL), followed by SO$_3$.Py (112 mg, 1.9 mmol, 5.00 eq.) in portions. The resulting solution was stirred for 20 h at room temperature. The resulting mixture was concentrated under vacuum. To the crude product was added 10 mL of a saturated NaH$_2$PO$_4$ solution. Then 150 mg of tetrabutylammonium hydrogen sulfate was added. The solution was then extracted with ethyl acetate (2×10 mL). The organic phases were combined, dried over sodium sulfate, and concentrated under vacuum to give 100 mg of crude (1R,4S)-4-(5-((S)-2,2,3,3,7,10,10-heptamethyl-8-oxo-4,9-dioxa-7-aza-3-silaundecan-5-yl)-1,3,4-oxadiazol-2-yl)-6-oxo-5,7-diazaspiro[bicyclo[3.2.1]octane-2,1'-cyclopropan]-7-yl hydrogen sulfate in the form a pale yellow solid, m/z (ES+), [M−H]$^+$=602; HPLC tR=2.027 min.

Step 5: Synthesis of Compound 5

To a 25-mL round-bottom flask was added a solution of (1R,4S)-4-(5-((S)-2,2,3,3,7,10,10-heptamethyl-8-oxo-4,9-dioxa-7-aza-3-silaundecan-5-yl)-1,3,4-oxadiazol-2-yl)-6-oxo-5,7-diazaspiro[bicyclo[3.2.1]octane-2,1'-cyclopropan]-7-yl hydrogen sulfate (100 mg, 0.165 mmol, 1.0 eq.) in THF (2 mL), followed by 3HF.Et$_3$N (0.5 mL). The resulting solution was stirred for 20 h at room temperature. The reaction mixture was concentrated under vacuum. The crude product was purified by a flash C-18 column (under the following conditions: Mobile phase: acetonitrile increasing from 0% to 100% within 30 min; Detector: UV 220 nm) to give 50 mg of crude (1R,4S)-4-(5-((S)-2-((tert-butoxycarbonyl)(methyl)amino)-1-hydroxyethyl)-1,3,4-oxadiazol-2-yl)-6-oxo-5,7-diazaspiro[bicyclo[3.2.1]octane-2,1'-cyclopropan]-7-yl hydrogen sulfate in the form of a yellow oil. m/z (ES+), [M−H]$^+$=474; HPLC tR=1.261 min.

Step 6: Synthesis of Compound KKK

To a 7-mL round-bottom flask was added a solution of Compound 6 (50 mg, 0.10 mmol, 1.00 eq.) in dichloromethane (1 mL), and then TFA (0.25 mL, 10.00 eq.) was added dropwise at 0° C. The resulting solution was stirred at 0° C.

for 120 min. The resulting mixture was concentrated under vacuum at 0° C. Diethyl ether was added to suspend the product as a solid. The product was collected by centrifugation. The crude product was purified by Prep-HPLC (under the following conditions: Mobile phase A: water (0.1% formic acid); Mobile phase B: acetonitrile; Flow rate: 60 mL/min; Gradient: from 20% B to 31% B over 7 min; Detector: 254/220 nm; tR=5.43 min) to give (1R,4S)-4-(5-((S)-1-hydroxy-2-(methylamino)ethyl)-1,3,4-oxadiazol-2-yl)-6-oxo-5,7-diazaspiro[bicyclo[3.2.1]octane-2,1'-cyclopropan]-7-yl hydrogen sulfate (20.6 mg, 10.84% over four steps) in the form of a white solid. m/z (ES+), [M−H]$^+$=390; HPLC tR=0.746 min. 1H NMR (D$_2$O, 400 MHz): δ (ppm) 0.35-0.66 (m, 2H), 0.68-0.85 (m, 2H), 1.86 (d, J=16.0 Hz, 1H), 2.64 (ddd, J=16.1, 7.8, 1.4 Hz, 1H), 2.85 (s, 3H), 3.19 (d, J=12.2 Hz, 1H), 3.36 (dd, J=12.2, 3.8 Hz, 1H), 3.52 (d, J=3.7 Hz, 1H), 3.59-3.71 (m, 2H), 4.99 (d, J=7.6 Hz, 1H), 5.43 (dd, J=8.2, 4.3 Hz, 1H).

Example 64. Synthesis of Compound LLL

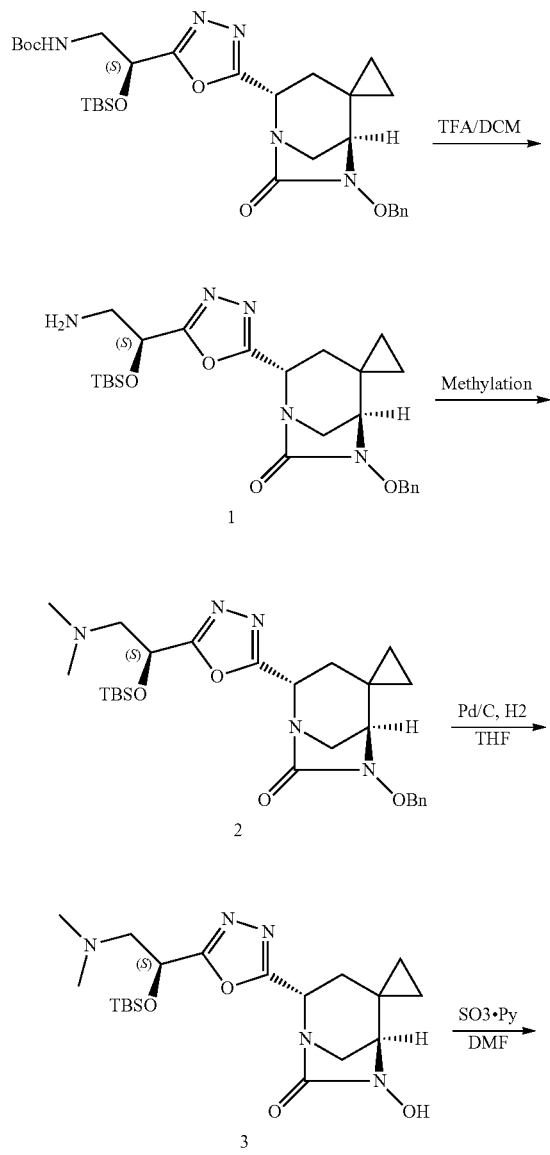

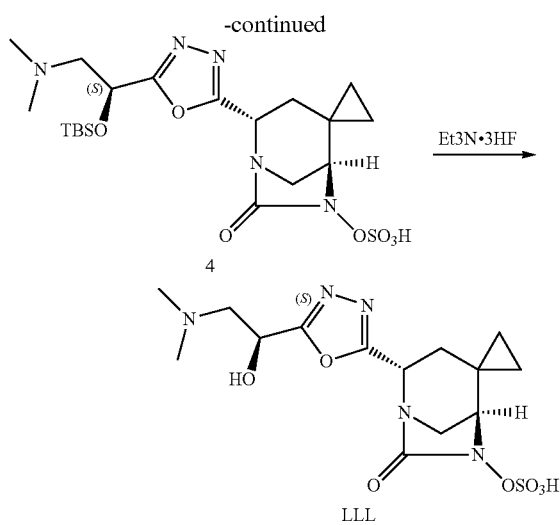

Step 1: Synthesis of Compound 1

To a 250-mL round-bottom flask was added a solution of tert-butyl ((2S)-2-(5-((1R,4S)-7-(benzyloxy)-6-oxo-5,7-diazaspiro[bicyclo[3.2.1]octane-2,1'-cyclopropan]-4-yl)-1,3,4-oxadiazol-2-yl)-2-((tert-butyldimethylsilyl)oxy)ethyl)carbamate (4.0 g, 8.3 mmol, 1.0 eq.) in dichloromethane (40 mL), and then trifluoroacetic acid (20 mL, 18.0 eq.) was added. The resulting solution was stirred at room temperature for 2 h. The resulting mixture was concentrated under vacuum, added with dichloromethane (50 mL), washed with sodium bicarbonate (2×30 mL) and brine (30 mL), dried over sodium sulfate and concentrated under vacuum again to give 4.0 g of crude (1R,4S)-4-(5-((S)-2-amino-1-((tert-butyldimethylsilyl) oxy)ethyl)-1,3,4-oxadiazol-2-yl-7-(benzyloxy)-5,7-diazaspiro[bicyclo[3.2.1]octane-2,1'-cyclopropan]-6-one in the form of a yellow solid, m/z (ES+), [M+H]$^+$=500; HPLC tR=1.061 min.

Step 2: Synthesis of Compound 2

To a 250-mL round-bottom flask was added a solution of (1R,4S)-4-(5-((S)-2-amino-1-((tert-butyldimethylsilyl)oxy)ethyl)-1,3,4-oxadiazol-2-yl)-7-(benzyloxy)-5,7-diazaspiro[bicyclo[3.2.1]octane-2,1'-cyclopropan]-6-one (2.0 g, 3.9 mmol, 1.0 eq.) in tetrahydrofuran (40 mL), and then DIEA (2.0 g, 15.6 mmol, 4.0 eq.) and CH$_3$I (1.14 g, 7.8 mmol, 2.0 eq.) were added. The resulting solution was stirred at room temperature for 2 h. The resulting mixture was concentrated under vacuum, and then ethyl acetate (100 mL) was added. The resulting mixture was washed with water (2×40 mL) and brine (2×40 mL). The organic phase was dried over sodium sulfate and concentrated under vacuum. The crude product was purified by TLC (ethyl acetate) to give (1R,4S)-7-(benzyloxy)-4-(5-((S)-1-((tert-butyldimethylsilyl) oxy)-2-(dimethylamino)ethyl)-1,3,4-oxadiazol-2-yl)-5,7-diazaspiro[bicyclo[3.2.1]octane-2,1'-cyclopropan]-6-one (380 mg, 21.6% over two steps) in the form of a yellow oil. m/z (ES+), [M+H]$^+$=528; HPLC tR=1.561 min.

Step 3: Synthesis of Compound 3

To a 25-mL round-bottom flask were added a solution of (1R,4S)-7-(benzyloxy)-4-(5-((S)-1-((tert-butyldimethylsilyl)oxy)-2-(dimethylamino)ethyl)-1,3,4-oxadiazol-2-yl)-5,7-diazaspiro[bicyclo[3.2.1]octane-2,1'-cyclopropan]-6-one (380 mg, 0.489 mmol, 1 eq.) in tetrahydrofuran (10 mL), and Pd/C (0.1 g). The resulting solution was stirred for 2 h at room temperature in the presence of H$_2$ (atmospheric pressure). The solid was filtered off. The filtrate was concentrated under vacuum to give 330 mg of crude (1R,4S)-4-(5-((S)-1-((tert-butyldimethylsilyl)oxy)-2-(dimethylamino)ethyl)-1,3,4-oxadiazol-2-yl)-7-hydroxy-5,7-diazaspiro[bicyclo[3.2.1]octane-2,1'-cyclopropan]-6-one in the form of a white solid, m/z (ES+), [M+Na]$^+$=438; HPLC tR=0.821 min.

Step 4: Synthesis of Compound 4

To a 25-mL round-bottom flask was added a solution of (1R,4S)-4-(5-((S)-1-((tert-butyldimethylsilyl)oxy)-2-(dimethylamino)ethyl)-1,3,4-oxadiazol-2-yl)-7-hydroxy-5,7-diazaspiro[bicyclo[3.2.1]octane-2,1'-cyclopropan]-6-one (330 mg, 0.76 mmol, 1.0 eq.) in DMF (10 mL), followed by $SO_3 \cdot Py$ (221 mg, 3.8 mmol, 5.00 eq.) in portions. The resulting solution was stirred for 20 h at room temperature. The resulting mixture was concentrated under vacuum. To the crude product was added 10 mL of a saturated $NaH_2PO_4$ solution, followed by 250 mg of tetrabutyl sodium hydrogen sulfate. Then the solution was extracted with 2×15 mL ethyl acetate. The organic phases were combined, dried over sodium sulfate and concentrated under vacuum to give 100 mg of crude (1R,4S)-4-(5-((S)-1-((tert-butyldimethylsilyl)oxy)-2-(dimethylamino)ethyl)-1,3,4-oxadiazol-2-yl)-6-oxo-5,7-diazaspiro[bicyclo[3.2.1]octane-2,1'-cyclopropan]-7-yl hydrogen sulfate in the form of a pale yellow solid, m/z (ES+), [M−H]$^+$=518; HPLC tR=0.872 min.

Step 5: Synthesis of Compound LLL

To a 25-mL round-bottom flask were added a solution of (1R,4S)-4-(5-((S)-1-((tert-butyldimethylsilyl)oxy)-2-(dimethylamino)ethyl)-1,3,4-oxadiazol-2-yl)-6-oxo-5,7-diazaspiro [bicyclo[3.2.1]octane-2,1'-cyclopropan]-7-yl hydrogen sulfate (100 mg, 0.165 mmol, 1.0 eq.) in tetrahydrofuran (2 mL), and $3HF \cdot Et_3N$ (0.5 mL). The resulting solution was stirred for 20 h at room temperature. The reaction mixture was concentrated under vacuum. The crude product was purified by Prep-HPLC under the following conditions; Mobile phase A: water (0.1% formic acid); Mobile phase B: acetonitrile; Flow rate: 25 mL/min; Gradient; from 5% B to 14% B within 7 min; tR=5.28, 7.24 min, to give (1R,4S)-4-(5-((S)-2-(dimethylamino)-1-hydroxyethyl)-1,3,4-oxadiazol-2-yl)-6-oxo-5,7-diazaspiro[bicyclo[3.2.1]octane-2,1'-cyclopropan]-7-yl hydrogen sulfate (14.8 mg, 19% over three steps) in the form of a yellow oil. m/z (ES+), [M+H]$^+$=404; HPLC tR=1.448 min. 1H NMR ($D_2O$, 400 MHz): δ (ppm) 0.32-0.65 (m, 2H), 0.62-0.87 (m, 2H), 1.85 (d, J=16.0 Hz, 1H), 2.43-2.77 (m, 1H), 3.04 (s, 6H), 3.17 (d, J=12.2 Hz, 1H), 3.36 (dd, J=12.2, 3.8 Hz, 1H), 3.52 (d, J=3.7 Hz, 1H), 3.63-3.90 (m, 2H), 4.99 (d, J=7.6 Hz, 1H), 5.54 (dd, J=10.0, 3.9 Hz, 1H).

Biological Experiments
1. Materials
1.1. Bacteria Strains
1.2. Culture Medium
Trypticase soy agar (TSA) (BD BBL 211043)
Cation-adjusted Mueller Hinton Broth (CAMHB) (BD BBL 212322)
1.3. Reagents and Consumables
Imipenem (U.S. Pat. No. 1,337,809)
Ceftazidime (U.S. Pat. No. 1,098,129)
Ampicillin (U.S. Pat. No. 1,033,000)
3-(N-morpholinyl)propanesulfonic acid 4-morpholinpropanesulfonic acid (MOPS) (Sigma M1254)
Disposable plate, 100 mm (VWR 25384-302)
96-well microtiter plate (Greiner 650162)
2. Methods
2.1. Thawing of Bacteria The bacterial strains used for the minimum inhibitory concentration (MIC) test were frozen in a −80° C. ULT freezer and thawed 2 days before use. A small amount of frozen bacterial strains were scraped using a sterile inoculating loop, streaked onto a TSA solid culture dish for inoculation, and then cultured for 20-24 h at 35±2° C. in a normal atmospheric environment.

5-10 colonies with similar morphology were picked from the culture dish using a sterile inoculating loop and then re-streaked onto a suitable solid culture dish. Then the dish was placed into a normal incubator for culture for 20-24 h at 35±2° C.

2.2. Preparation of Bacterial Inocula

The liquid medium was taken out from a 4° C. refrigerator and left to warm at room temperature.

5-10 single bacterial colonies were picked from the solid culture dish, resuspended in 500 μL of 0.9% NaCl, and adjusted to an OD600 of 0.1-0.15 with a spectrophotometer.

The bacteria were then diluted 300-fold with 1.1× CAMHB.

2.3. Preparation of Test Plates
96-Well Plates for Test

Test compounds of columns A-H: having a highest final test concentration of 64 μg/mL or 32 μg/mL, 2-fold diluted.

Growth control (GC): using 1.1×CAMHB containing bacterial inocula and a compound solvent, no compounds.

Sterile control (SC): using 1.1×CAMHB and a compound solvent, no compounds.

Dilution of test compounds: All test compounds were dissolved and diluted in dimethylsulfoxide (DMSO). 170 μL of 3.2 mg/mL (50*64 μg/mL) compound was transferred to wells (A1-H1) of column 1 of a dilution master plate and then 85 μL of DMSO was transferred to wells of other columns. Each compound was diluted 2-fold in sequence (i.e., 85 μL of compound was pipetted from column 1 into column 2 and mixed uniformly, 85 μL of compound was pipetted from column 2 into column 3 and mixed uniformly,

| | | | MIC (μg/ml) | | |
| --- | --- | --- | --- | --- | --- |
| Bacteria | No. | β-lactamase | Imipenem | Ceftazidime | Ampicillin |
| *Klebsiella pneumoniae* (*K. pneumoniae*) | XNWB 0001 | KPC-1/2 | 64-128 | 64-128 | >32 |
| *Klebsiella pneumoniae* (*K. pneumoniae*) | XNWB 0002 | KPC-2, SHV-5 | 32-64 | 128 | >32 |
| *Klebsiella pneumoniae* (*K. pneumoniae*) | XNWB 0003 | KPC-11, SHV-12 | 8-16 | >128 | >32 |
| *Klebsiella pneumoniae* (*K. pneumoniae*) | XNWB 0004 | KPC-2, SHV-12 | 64 | >128 | >32 |
| *Klebsiella pneumoniae* (*K. pneumoniae*) | XNWB 0005 | KPC-3 | 32-64 | >128 | >32 |
| *Klebsiella pneumoniae* (*K. pneumoniae*) | XNWB 0006 | CTX-M-15, SHV | 0.125-0.5 | >128 | >32 |
| *Acinetobacter baumannii* (*A. baumannii*) | XNWB 0007 | AmpC | 32-64 | 64 | >32 |
| *Pseudomonas aeruginosa* (*P. aeruginosa*) | XNWB 0008 | AmpC | 16-32 | 128 | >32 |
| *Escherichia coli* (*E. coli*) | XNWB 0009 | SHV-5A | 0.125-0.5 | 16-32 | >32 |
| *Escherichia coli* (*E. coli*) | XNWB 0010 | SHV-2 | <=0.125 | 4-16 | >32 |
| *Enterobacter aerogenes* (*E. aerogenes*) | XNWB 0011 | TEM-10 | 0.5-1 | 0.5-1 | >32 | then 85 μL of compound was pipetted from column 3 into column 4 and mixed uniformly, and so on until the dilution was done in column 11).

Preparation of additives of imipenem and ceftazidime: Imipenem and ceftazidime were dissolved in 10 mM MOPS buffer. 110 μL of 50 μg/mL (12.5×4 μg/mL) imipenem or 110 μL of 100 μg/mL (12.5×8 μg/mL) ceftazidime was transferred to columns 1-11 of an additive plate, followed by the addition of 110 μL of MOPS buffer to column 12.

Preparation of an additive of ampicillin: Ampicillin was dissolved in ddH$_2$O. 30 μL of 100 μg/mL (12.5×8 μg/mL) ampicillin was transferred to columns 1-11 of an additive plate, followed by the addition of 30 μL of ddH$_2$O to column 12.

2 μL of each compound in the dilution master plate of the test compounds was transferred to the corresponding well of the assay plates. In the mean time, 2 μL of 100% DMSO was transferred to the compound-free wells (GC and SC wells). (1) 8 μL of imipenem in the additive plate of imipenem was transferred to the corresponding wells of the assay plates; (2) 8 μL of ceftazidime in the additive plate of ceftazidime was transferred to the corresponding wells of the assay plates; (3) 8 μL of ampicillin in the additive plate of ampicillin was transferred to the corresponding wells of the assay plates.

90 μL of corresponding bacterial inocula were added to wells (except for SC wells) of the assay plates.

90 μL of a 1.1×CAMHB medium was added to the SC wells of the assay plates.

After addition, the 6 assay plates were covered by sterile covers. The mixtures in the assay plates were centrifuged by a centrifuge at 1000 rpm for 30 s, and mixed uniformly by oscillating with a microplate oscillator at 800 rpm for 1 min, and then cultured in a common incubator for 16-20 h at 35±2° C.

2.4. Colony Counting

The inoculated bacteria were diluted from $10^{-1}$ to $10^{-7}$ with a liquid medium (such as 100 μL of bacterial inocula+ 900 μL of 1.1×CAMHB).

100 μL of the bacterial dilution described above was spread evenly onto TSA plates, 2 replicates per dilution. After uptake of the culture medium by TSA for 10 min, the plates were incubated in an incubator upside down at 35±2° C. for 24 h.

2.5. Minimum Inhibitory Concentration Recording and Colony Counting

The compound management system was turned on to check whether the barcode and compound assignment of each assay plate were correct or not.

The assay plates were placed on a plate reading device, and the speculum was adjusted to observe and record the growth condition of bacteria in each well. In the mean time, each assay plate was photographed with QCount software.

The minimum inhibitory concentration of each compound was recorded by reference to guidelines from the Clinical and Laboratory Standards Institute.

The colonies formed by different dilutions of bacterial inocula on the TSA plates were counted and the bacterial load was calculated.

3. Results 3.1. The First Part: MIC Assay of Compounds of the Present Invention Against Bacteria The minimum inhibitory concentrations of the compounds of the present invention and antibiotics (imipenem, ceftazidime, and ampicillin) against 11 strains of bacteria were tested in this study by reference to the medium microdilution method as indicated by the Clinical and Laboratory Standards Institute. The effect of the test compounds in combination with imipenem, ceftazidime, and ampicillin was also tested. Compounds were diluted two-fold in 96-well plates from the highest detection concentration of 64 μg/mL. The test compounds were tested in combination with a fixed concentration of imipenem (4 μg/mL), ceftazidime (8 μg/mL), and ampicillin (8 μg/mL). The bacterial inocula in the assay plates were resuscitated from TSA and diluted in CAMHB, while growth controls (GC wells) and sterile controls (SC wells) were set up in the assay plates. The minimum inhibitory concentration of each compound combination against different bacteria was observed and recorded after the assay plates were incubated in a common incubator at 35±2° C. for 16-20 h, and the results are shown in Tables 1-3.

TABLE 1

The minimum concentration (μg/mL) of test compounds combined with ceftazidime (8 μg/mL) for bacteriostasis

| Test compounds | Klebsiella pneumoniae | | | | | | Acinetobacter baumannii | Pseudomonas aeruginosa |
| --- | --- | --- | --- | --- | --- | --- | --- | --- |
| | XNWB 0001 | XNWB 0002 | XNWB 0003 | XNWB 0004 | XNWB 0005 | XNWB 0006 | XNWB 0007 | XNWB 0008 |
| Avibactam | A | A | A | A | A | A | C | A |
| Relebactam | A | A | A | A | A | A | C | A |
| Example 1 | A | A | A | B | A | A | C | C |
| Example 2 | A | A | A | B | A | A | C | C |
| Example 3 | B | A | B | B | B | A | C | C |
| Example 4 | A | A | A | A | A | A | C | C |
| Example 5 | A | A | A | B | B | A | C | C |
| Example 6 | A | A | B | B | B | A | C | C |
| Example 7 | B | A | B | B | B | A | C | C |
| Example 8 | A | A | A | A | A | A | C | B |
| Example 9 | A | A | A | A | A | A | C | B |
| Example 10 | A | A | A | A | A | A | C | B |
| Example 11 | A | A | A | A | A | A | C | C |
| Example 12 | B | A | A | B | A | A | C | C |
| Example 13 | A | A | A | B | A | A | B | B |
| Example 14 | A | A | B | B | B | A | C | C |
| Example 54 | B | A | B | C | C | A | C | C |
| Example 34 | A | A | A | B | B | A | C | C |
| Example 33 | B | A | C | C | B | A | C | C |

TABLE 1-continued

The minimum concentration (µg/mL) of test compounds combined with ceftazidime (8 µg/mL) for bacteriostasis

| Test compounds | Klebsiella pneumoniae | | | | | | Acinetobacter baumannii | Pseudomonas aeruginosa |
|---|---|---|---|---|---|---|---|---|
| | XNWB 0001 | XNWB 0002 | XNWB 0003 | XNWB 0004 | XNWB 0005 | XNWB 0006 | XNWB 0007 | XNWB 0008 |
| Example 35 | A | A | A | A | A | A | C | C |
| Example 32 | B | A | B | C | C | B | C | C |
| Example 36 | A | A | A | B | A | A | C | B |
| Example 37 | A | A | B | B | A | A | C | C |
| Example 38 | A | A | A | A | A | A | C | B |
| Example 39 | A | A | A | A | A | A | C | B |
| Example 40 | A | A | A | A | A | A | C | B |
| Example 41 | A | A | A | B | A | A | C | C |
| Example 42 | A | A | A | B | A | A | C | C |
| Example 43 | A | A | B | B | A | A | C | B |
| Example 44 | A | A | A | B | A | A | C | B |
| Example 45 | A | A | A | B | A | A | C | B |
| Example 47 | B | A | C | C | C | B | C | C |
| Example 15 | A | A | A | B | A | A | C | C |
| Example 16 | A | A | A | B | A | A | C | B |
| Example 17 | A | A | A | A | A | A | C | B |
| Example 18 | A | A | A | B | A | A | C | B |
| Example 19 | A | A | A | A | A | A | C | B |
| Example 20 | A | A | A | A | A | A | C | B |
| Example 21 | A | A | A | B | B | A | C | C |
| Example 22 | B | A | B | C | B | A | C | C |
| Example 23 | A | A | A | A | A | A | C | B |
| Example 24 | A | A | A | A | A | A | C | C |
| Example 48 | A | A | A | B | A | A | C | B |
| Example 49 | A | A | A | B | A | A | C | B |
| Example 50 | A | A | A | B | A | A | C | B |
| Example 51 | A | A | B | C | B | A | C | B |
| Example 52 | A | A | B | B | B | A | C | C |
| Example 25 | A | A | A | B | A | A | C | B |
| Example 26 | A | A | A | A | A | A | C | B |
| Example 53 | A | A | A | B | A | A | C | B |
| Example 27 | A | A | B | B | A | A | C | A |
| Example 28 | A | A | A | B | A | A | C | A |
| Example 29 | A | A | A | A | A | A | C | B |
| Example 30 | B | A | A | B | B | A | C | C |
| Example 31 | A | A | A | B | A | A | C | C |
| Example 55 | A | A | A | A | A | A | C | B |
| Example 56 | A | A | A | A | A | A | C | B |

A: <8 µg/mL;
B: 8-16 µg/mL;
C: 16-128 µg/mL

TABLE 2

The minimum concentration (µg/mL) of test compounds combined with imipenem (4 µg/mL) for bacteriostasis

| Test compounds | Klebsiella pneumoniae | | | | | | Acinetobacter baumannii | Pseudomonas aeruginosa |
|---|---|---|---|---|---|---|---|---|
| | XNWB 0001 | XNWB 0002 | XNWB 0003 | XNWB 0004 | XNWB 0005 | XNWB 0006 | XNWB 0007 | XNWB 0008 |
| Avibactam | A | A | A | A | A | A | C | A |
| Relebactam | A | A | A | A | A | A | C | A |
| Example 1 | A | A | A | A | A | A | C | C |
| Example 2 | A | A | A | A | A | A | C | C |
| Example 3 | B | A | A | A | A | A | C | C |
| Example 4 | A | A | A | A | A | A | B | A |
| Example 5 | A | A | A | A | A | A | B | B |
| Example 6 | A | A | A | A | A | A | B | B |
| Example 7 | A | A | A | A | A | A | B | B |
| Example 8 | A | A | A | A | A | A | A | A |
| Example 9 | A | A | A | A | A | A | A | A |
| Example 10 | A | A | A | A | A | A | A | A |
| Example 11 | A | A | A | A | A | A | B | B |
| Example 12 | A | A | A | A | A | A | B | B |
| Example 13 | A | A | A | A | A | A | C | A |

TABLE 2-continued

The minimum concentration (μg/mL) of test compounds combined with imipenem (4 μg/mL) for bacteriostasis

| Test compounds | Klebsiella pneumoniae | | | | | | Acinetobacter baumannii | Pseudomonas aeruginosa |
|---|---|---|---|---|---|---|---|---|
| | XNWB 0001 | XNWB 0002 | XNWB 0003 | XNWB 0004 | XNWB 0005 | XNWB 0006 | XNWB 0007 | XNWB 0008 |
| Example 14 | A | A | A | A | A | A | C | B |
| Example 54 | A | A | A | A | A | A | C | C |
| Example 34 | A | A | A | A | A | A | B | B |
| Example 33 | A | A | A | A | A | A | C | B |
| Example 35 | A | A | A | A | A | A | C | B |
| Example 32 | A | A | A | A | A | A | C | C |
| Example 36 | A | A | A | A | A | A | C | A |
| Example 37 | A | A | A | A | A | A | C | B |
| Example 38 | A | A | A | A | A | A | C | A |
| Example 39 | A | A | A | A | A | A | B | A |
| Example 40 | A | A | A | A | A | A | C | A |
| Example 41 | A | A | A | A | A | A | C | A |
| Example 42 | A | A | A | A | A | A | C | B |
| Example 43 | A | A | A | A | A | A | C | A |
| Example 44 | A | A | A | A | A | A | C | A |
| Example 45 | A | A | A | A | A | A | C | A |
| Example 47 | A | A | A | A | A | A | C | A |
| Example 15 | A | A | A | A | A | A | C | B |
| Example 16 | A | A | A | A | A | A | B | A |
| Example 17 | A | A | A | A | A | A | B | A |
| Example 18 | A | A | A | A | A | A | B | A |
| Example 19 | A | A | A | A | A | A | B | B |
| Example 20 | A | A | A | A | A | A | B | A |
| Example 21 | A | A | A | A | A | A | C | C |
| Example 22 | A | A | A | A | A | A | C | C |
| Example 23 | A | A | A | A | A | A | B | A |
| Example 24 | A | A | A | A | A | A | A | B |
| Example 48 | A | A | A | A | A | A | C | A |
| Example 49 | A | A | A | A | A | A | C | A |
| Example 50 | A | A | A | A | A | A | C | A |
| Example 51 | A | A | A | A | A | A | C | A |
| Example 52 | A | A | A | A | A | A | C | A |
| Example 25 | A | A | A | A | A | A | C | A |
| Example 26 | A | A | A | A | A | A | C | A |
| Example 53 | A | A | A | A | A | A | C | A |
| Example 27 | A | A | A | A | A | A | C | A |
| Example 28 | A | A | A | A | A | A | C | A |
| Example 29 | A | A | A | A | A | A | C | A |
| Example 30 | A | A | A | A | A | A | B | C |
| Example 31 | A | A | A | A | A | A | B | B |
| Example 55 | A | A | A | A | A | A | A | A |
| Example 56 | A | A | A | A | A | A | B | B |
| Example 61 | A | A | A | A | A | A | B | B |
| Example 62 | A | A | A | A | A | A | A | B |

A: <8 μg/mL;
B: 8-16 μg/mL;
C: 16-128 μg/mL

TABLE 3

The minimum concentration (μg/mL) of test compounds combined with ampicillin (8 μg/mL) for bacteriostasis

| Test compounds | Escherichia coli XNWB 0009 | Escherichia coli XNWB 0010 | Enterobacter aerogenes XNWB 0011 |
|---|---|---|---|
| Example 2 | A | A | A |
| Example 3 | A | B | C |
| Example 4 | A | A | B |
| Example 13 | A | A | A |
| Example 14 | A | 4 | B |
| Example 41 | A | A | B |
| Example 43 | A | A | B |
| Example 45 | A | A | A |

A: <8 μg/mL;
B: 8-16 μg/mL;
C: 16-128 μg/mL

The result shows that all the β-lactamase inhibitors have no antibacterial activity (MIC >64 μg/mL) when tested independently, and the combination of the test compounds and imipenem, ceftazidime, or ampicillin can improve the antibacterial effect of imipenem, ceftazidime, or ampicillin on β-lactamase-containing drug-resistant strains to different degrees.

The invention claimed is:
1. A compound of formula (I), or an ester, a stereoisomer, or a pharmaceutically acceptable salt thereof:

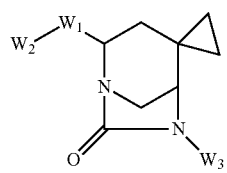

wherein $W_1$ is selected from an optionally substituted 5- or 6-membered heteroaromatic ring containing O, N, and/or S, and —C(O)—; (i) when $W_1$ is the optionally substituted 5- or 6-membered heteroaromatic ring containing O, N, and/or S, $W_1$ is optionally substituted with $C_1$-$C_{12}$ alkyl,
$W_2$ is selected from:
(a) H
(b)

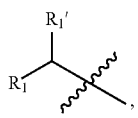

wherein $R_1$ is selected from

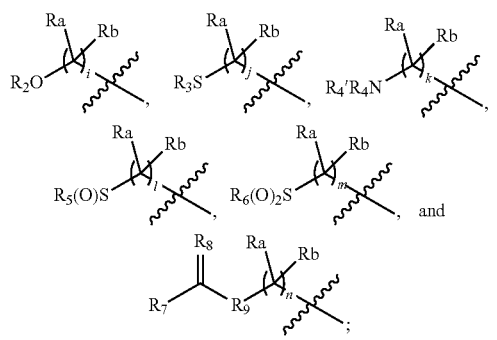

$R_2$, $R_3$, $R_4$, $R_4'$, $R_5$, and $R_6$ are each independently selected from H, $C_1$-$C_{12}$ alkyl, amino $C_1$-$C_{12}$ alkyl, $C_1$-$C_{12}$ alkylamino $C_1$-$C_{12}$ alkyl,

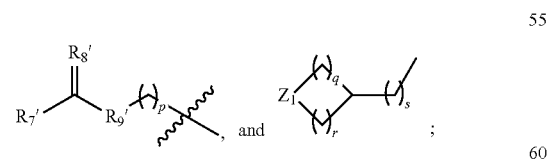

Ra and Rb are each independently selected from H, $C_1$-$C_{12}$ alkyl, $C_3$-$C_8$ cycloalkyl, OH, —O$C_1$-$C_{12}$ alkyl, —NH$_2$, —NHC$_1$-$C_{12}$ alkyl, —N($C_1$-$C_{12}$ alkyl)$_2$, —SH, —S$C_1$-$C_{12}$ alkyl, —S(O)$C_1$-$C_{12}$ alkyl, —S(O$_2$)$C_1$-$C_{12}$ alkyl, and —SO$_3$H; $R_7$ and $R_7'$ are each independently selected from —NH$_2$, —NHC$_1$-$C_{12}$ alkyl, —N($C_1$-$C_{12}$ alkyl)$_2$, —O$C_1$-$C_{12}$ alkyl, and —S$C_1$-$C_{12}$ alkyl; $R_8$ and $R_8'$ are each independently selected from NH, —N($C_1$-$C_{12}$ alkyl), O, and S; $R_9$ and $R_9'$ are each independently selected from —NH—, —N($C_1$-$C_{12}$ alkyl)-, —O—, and —S—; $Z_1$ is selected from $CR_{10}R_{11}$, and $NR_{12}$; $R_{10}$, $R_{11}$, and $R_{12}$ are each independently selected from H, NH$_2$,

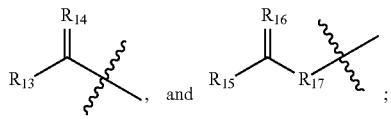

$R_{13}$ and $R_{15}$ are each independently selected from —NH$_2$, —NHC$_1$-$C_{12}$ alkyl, —N($C_1$-$C_{12}$ alkyl)$_2$, —O$C_1$-$C_{12}$ alkyl, and —S$C_1$-$C_{12}$ alkyl; $R_{14}$ and $R_{16}$ are each independently selected from NH, N$C_1$-$C_{12}$ alkyl, O, and S; $R_{17}$ is selected from —NH—, —N($C_1$-$C_{12}$ alkyl)-, —O—, and —S—; i, j, k, l, m, n, p, q, r, and s are each independently selected from 0, 1, 2, 3, 4, 5, and 6, provided that q and r are not both 0; $R_1'$ is selected from H, $C_1$-$C_{12}$ alkyl, $C_3$-$C_8$ cycloalkyl, OH, —O$C_1$-$C_{12}$ alkyl, —NH$_2$, —NHC$_1$-$C_{12}$ alkyl, —N($C_1$-$C_{12}$ alkyl)$_2$, —SH, —S$C_1$-$C_{12}$ alkyl, —S(O)$C_1$-$C_{12}$ alkyl, —S(O$_2$)$C_1$-$C_{12}$ alkyl, and —SO$_3$H;

(c)

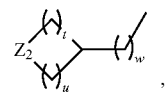

wherein $Z_2$ is selected from $CR_{18}R_{19}$, and $NR_{20}$; $R_{18}$, $R_{19}$ and $R_{20}$ are each independently selected from H, NH$_2$, and

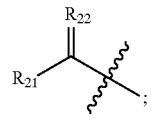

$R_{21}$ is selected from —NH$_2$, —NHC$_1$-$C_{12}$ alkyl, —N($C_1$-$C_{12}$ alkyl)$_2$, —O$C_1$-$C_{12}$ alkyl, and —S$C_1$-$C_{12}$ alkyl; $R_{22}$ is selected from NH, N$C_1$-$C_{12}$ alkyl, O, and S; t, u and w are each independently selected from 0, 1, 2, 3, 4, 5, and 6, provided that t and u are not both 0;

(d)

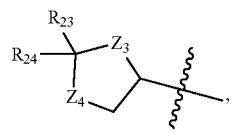

wherein $Z_3$ and $Z_4$ are each independently selected from —NR$_{25}$—, and —O—; $R_{23}$ and $R_{24}$ are each independently selected from H and $C_1$-$C_{12}$ alkyl, or $R_{23}$ and $R_{24}$ together form =O or =NH; $R_{25}$ is selected from H, amino $C_1$-$C_{12}$ alkyl, and $C_1$-$C_{12}$ alkylamino $C_1$-$C_{12}$ alkyl;

(ii) when $W_1$ is selected from —C(O)—,
$W_2$ is selected from —OR$_{26}$ and —NHR$_{27}$, wherein $R_{26}$ and $R_{27}$ are each independently selected from H, $C_1$-$C_{12}$ alkyl, and

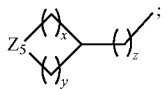;

$Z_5$ is selected from CR$_{28}$R$_{29}$, and NR$_{30}$; $R_{28}$, $R_{29}$, and $R_{30}$ are each independently selected from H, NH$_2$, and

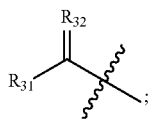;

$R_{31}$ is selected from —NH$_2$, —NHC$_1$-C$_{12}$ alkyl, —N(C$_1$-C$_{12}$ alkyl)$_2$, —OC$_1$-C$_{12}$ alkyl, and —SC$_1$-C$_{12}$ alkyl; $R_{32}$ is selected from NH, NC$_1$-C$_{12}$ alkyl, O, and S; x, y and z are each independently selected from 0, 1, 2, 3, 4, 5, and 6, provided that x and y are not both 0;

$W_3$ is selected from —SO$_3$M, —OSO$_3$M, —OSO$_2$NH$_2$, —OPO$_3$M, —OCR$_{33}$R$_{34}$CO$_2$M, —OCR$_{35}$R$_{36}$SO$_3$M, and —OCR$_{37}$R$_{38}$PO$_3$M; wherein M is selected from H and a pharmaceutically acceptable cation; $R_{33}$, $R_{34}$, $R_{35}$, $R_{36}$, $R_{37}$, and $R_{38}$ are each independently selected from H, C$_1$-C$_{12}$ alkyl, and halogen.

2. The compound, or the ester, the stereoisomer, or the pharmaceutically acceptable salt thereof according to claim 1, wherein the compound of formula (I) is:

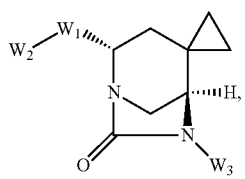
(Ia)

wherein $W_1$, $W_2$, and $W_3$ are defined in formula (I).

3. The compound, or the ester, the stereoisomer, or the pharmaceutically acceptable salt thereof according to claim 2, wherein,
$W_1$ is selected from an optionally substituted 5- or 6-membered heteroaromatic ring containing O, N, and/or S;
$W_2$ is selected from:
(a) H
(b)

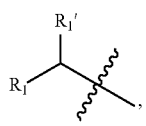, wherein $R_1$ is selected from

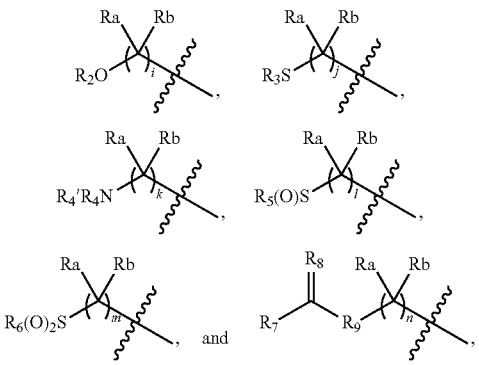

$R_2$, $R_3$, $R_4$, $R_4'$, $R_5$, and $R_6$ are each independently selected from H, C$_1$-C$_{12}$ alkyl, amino C$_1$-C$_{12}$ alkyl, C$_1$-C$_{12}$ alkylamino C$_1$-C$_{12}$ alkyl,

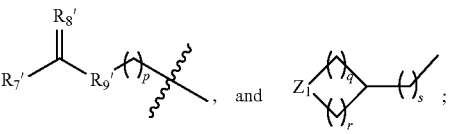;

Ra and Rb are each independently selected from H, C$_1$-C$_{12}$ alkyl, OH, —OC$_1$-C$_{12}$ alkyl, —NH$_2$, —NHC$_1$-C$_{12}$ alkyl, —N(C$_1$-C$_{12}$ alkyl)$_2$, —SH, —SC$_1$-C$_{12}$ alkyl, —S(O)C$_1$-C$_{12}$ alkyl, —S(O$_2$)C$_1$-C$_{12}$ alkyl, and —SO$_3$H; $R_7$ and $R_7'$ are each independently selected from —NH$_2$, —NHC$_1$-C$_{12}$ alkyl, —N(C$_1$-C$_{12}$ alkyl)$_2$, —OC$_1$-C$_{12}$ alkyl, and —SC$_1$-C$_{12}$ alkyl; $R_8$ and $R_8'$ are each independently selected from NH, —NC$_1$-C$_{12}$ alkyl, O, and S; $R_9$ and $R_9'$ are each independently selected from —NH—, —N(C$_1$-C$_{12}$ alkyl)-, —O—, and —S—; $Z_1$ is selected from CR$_{10}$R$_{11}$ and NR$_{12}$; $R_{10}$, $R_{11}$ and $R_{12}$ are each independently selected from H, NH$_2$,

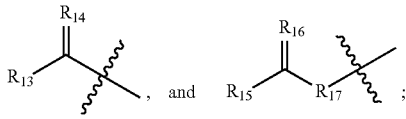;

$R_{13}$ and $R_{15}$ are each independently selected from —NH$_2$, —NHC$_1$-C$_{12}$ alkyl, —N(C$_1$-C$_{12}$ alkyl)$_2$, —OC$_1$-C$_{12}$ alkyl, and —SC$_1$-C$_{12}$ alkyl; $R_{14}$ and $R_{16}$ are each independently selected from NH, NC$_1$-C$_{12}$ alkyl, O, and S; $R_{17}$ is selected from —NH—, —N(C$_1$-C$_{12}$ alkyl)-, —O—, and —S—; and i, j, k, l, m, n, p, q, r, and s are each independently selected from 0, 1, 2, 3, 4, 5, and 6, provided that q and r are not both 0;

$R_1'$ is selected from H, C$_1$-C$_{12}$ alkyl, C$_3$-C$_8$ cycloalkyl, OH, —OC$_1$-C$_{12}$ alkyl, —NH$_2$, —NHC$_1$-C$_{12}$ alkyl, —N(C$_1$-C$_{12}$ alkyl)$_2$, —SH, —SC$_1$-C$_{12}$ alkyl, —S(O) C$_1$-C$_{12}$ alkyl, —S(O$_2$)C$_1$-C$_{12}$ alkyl, and —SO$_3$H;

(c)

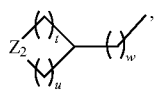

wherein $Z_2$ is selected from $CR_{18}R_{19}$, and $NR_{20}$; $R_{18}$, $R_{19}$ and $R_{20}$ are each independently selected from H, $NH_2$, and

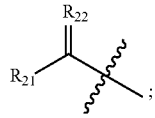

$R_{21}$ is selected from $-NH_2$, $-NHC_1$-$C_{12}$ alkyl, $-N(C_1$-$C_{12}$ alkyl$)_2$, $-OC_1$-$C_{12}$ alkyl, and $-SC_1$-$C_{12}$ alkyl; $R_{22}$ is selected from NH, $NC_1$-$C_{12}$ alkyl, O, and S; t, u and w are each independently selected from 0, 1, 2, 3, 4, 5, and 6, provided that t and u are not both 0;

(d)

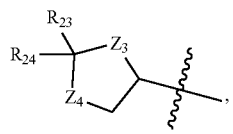

wherein $Z_3$ and $Z_4$ are each independently selected from $-NR_{25}-$, and $-O-$; $R_{23}$ and $R_{24}$ are each independently selected from H and $C_1$-$C_{12}$ alkyl, or $R_{23}$ and $R_{24}$ together form $=O$ or $=NH$; $R_{25}$ is selected from H, amino $C_1$-$C_{12}$ alkyl, and $C_1$-$C_{12}$ alkylamino $C_1$-$C_{12}$ alkyl.

4. The compound, or the ester, the stereoisomer, or the pharmaceutically acceptable salt thereof according to claim 2, wherein,
$W_1$ is $-C(O)-$;
$W_2$ is selected from $-OR_{26}$, and $-NHR_{27}$, wherein $R_{26}$ and $R_{27}$ are each independently selected from H, $C_1$-$C_{12}$ alkyl, and

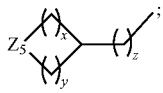

$Z_5$ is selected from $CR_{28}R_{29}$, and $NR_{30}$; $R_{28}$, $R_{29}$, and $R_{30}$ are each independently selected from H, $NH_2$, and

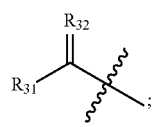

$R_{31}$ is selected from $-NH_2$, $-NHC_1$-$C_{12}$ alkyl, $-N(C_1$-$C_{12}$ alkyl$)_2$, $-OC_1$-$C_{12}$ alky, and $-SC_1$-$C_{12}$ alkyl; $R_{32}$ is selected from NH, $NC_1$-$C_{12}$ alkyl, O, and S; and x, y and z are each independently selected from 0, 1, 2, 3, 4, 5, and 6, provided that x and y are not both 0.

5. The compound, or the ester, the stereoisomer, or the pharmaceutically acceptable salt thereof according to claim 1, wherein $W_1$ is selected from:

X is selected from O, S, and NH; Y and Z are each independently selected from CH and N; and $W_1$ is optionally substituted with $C_1$-$C_{12}$ alkyl.

6. The compound, or the ester, the stereoisomer, or the pharmaceutically acceptable salt thereof according to claim 1, wherein $W_1$ is selected from a furan ring, a pyrrole ring, a pyrazole ring, an imidazole ring, a triazole ring, a thiophene ring, a thiazole ring, an isothiazole ring, an oxazole ring, an isoxazole ring, a 1,2,4-oxadiazole ring, a 1,3,4-oxadiazole ring, a pyridine ring, pyrimidyl, a triazine ring, a pyrazine ring, a tetrazole ring, a pyridazine ring, and a thiadiazole ring;
M is selected from H, sodium ion, potassium ion, calcium ion, magnesium ion, $NH_4^+$, and $N(C_1$-$C_{12}$ alkyl$)_4^+$.

7. The compound or the pharmaceutically acceptable salt thereof according to claim 6, wherein $W_1$ is selected from an oxazole ring, an isoxazole ring, a 1,2,4-oxadiazole ring, and a 1,3,4-oxadiazole ring.

8. The compound or the pharmaceutically acceptable salt thereof according to claim 7, wherein $W_1$ is selected from

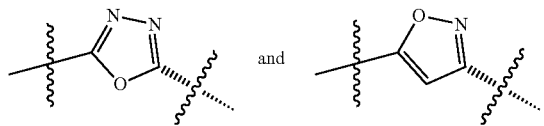

9. The compound or the pharmaceutically acceptable salt thereof according to claim 1, which is selected from:
(1R,4S)-4-(1,3,4-oxadiazol-2-yl)-6-oxo-5,7-diazaspiro [bicyclo[3.2.1]octane-2,1'-cyclopropan]-7-yl sulfate;
(1R,4S)-4-(5-(aminomethyl)-1,3,4-oxadiazol-2-yl)-6-oxo-5,7-diazaspiro[bicyclo[3.2.1]octane-2,1'-cyclopropan]-7-yl sulfate;
(1R,4S)-4-(5-(guanidinomethyl)-1,3,4-oxadiazol-2-yl)-6-oxo-5,7-diazaspiro[bicyclo[3.2.1]octane-2,1'-cyclopropan]-7-yl sulfate;
(1R,4S)-4-(5-(2-aminoethyl)-1,3,4-oxadiazol-2-yl)-6-oxo-5,7-diazaspiro[bicyclo[3.2.1]octane-2,1'-cyclopropan]-7-yl sulfate;
(1R,4S)-4-(5-(2-guanidinoethyl)-1,3,4-oxadiazol-2-yl)-6-oxo-5,7-diazaspiro[bicyclo[3.2.1]octane-2,1'-cyclopropan]-7-yl sulfate;
sodium (1R,4S)-4-(5-(3-aminopropyl)-1,3,4-oxadiazol-2-yl)-6-oxo-5,7-diazaspiro[bicyclo[3.2.1]octane-2,1'-cyclopropan]-7-yl sulfate;
(1R,4S)-4-(5-(4-aminobutyl)-1,3,4-oxadiazol-2-yl)-6-oxo-5,7-diazaspiro[bicyclo[3.2.1]octane-2,1'-cyclopropan]-7-yl sulfate;
(1R,4S)-4-(5-(2-iminoimidazolidin-4-yl)-1,3,4-oxadiazol-2-yl)-6-oxo-5,7-diazaspiro [bicyclo[3.2.1]octane-2,1'-cyclopropan]-7-yl sulfate;

(1R,4S)-4-(5-(2-amino-1-hydroxyethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(2-guanidyl-1-hydroxyethyl)-1,3,4-oxadiazol-2-yl)-6-oxo-5,7-diazaspiro [bicyclo[3.2.1]octane-2,1'-cyclopropan]-7-yl sulfate;

(1R,4S)-4-(5-((R)-2-guanidyl-1-hydroxyethyl)-1,3,4-oxadiazol-2-yl)-6-oxo-5,7-diazaspiro [bicyclo[3.2.1]octane-2,1'-cyclopropan]-7-yl sulfate;

(1R,4S)-4-(5-((S)-2-guanidyl-1-hydroxyethyl)-1,3,4-oxadiazol-2-yl)-6-oxo-5,7-diazaspiro [bicyclo[3.2.1]octane-2,1'-cyclopropan]-7-yl sulfate;

(1R,4S)-4-(5-(1-(guanidinomethyl)cyclopropyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-((azetidin-3-ylamino)methyl)-1,3,4-oxadiazol-2-yl)-6-oxo-5,7-diazaspiro [bicyclo[3.2.1]octane-2,1'-cyclopropan]-7-yl sulfate;

(1R,4S)-4-(isoxazol-3-yl)-6-oxo-5,7-diazaspiro[bicyclo[3.2.1]octane-2,1'-cyclopropan]-7-yl sulfate;

(1R,4S)-4-(5-(guanidinomethyl)isoxazol-3-yl)-6-oxo-5,7-diazaspiro[bicyclo[3.2.1]octane-2,1'-cyclopropan]-7-yl sulfate;

(1R,4S)-4-(5-((1-methylguanidino)methyl)isoxazol-3-yl)-6-oxo-5,7-diazaspiro[bicycle [3.2.1]octane-2,1'-cyclopropan]-7-yl sulfate;

(1R,4S)-4-(5-(aminomethyl)-isoxazol-3-yl)-6-oxo-5,7-diazaspiro[bicyclo[3.2.1]octane-2,1'-cyclopropan]-7-yl sulfate;

(1R,4S)-4-(5-((methylamino)methyl)isoxazol-3-yl)-6-oxo-5,7-diazaspiro[bicyclo[3.2.1]octane-2,1'-cyclopropan]-7-yl sulfate;

(1R,4S)-4-(5-(2-guanidinoethyl)isoxazol-3-yl)-6-oxo-5,7-diazaspiro[bicyclo[3.2.1]octane-2,1'-cyclopropan]-7-yl sulfate;

(1R,4S)-4-(5-(2-(1-methylguanidino)ethyl)isoxazol-3-yl)-6-oxo-5,7-diazaspiro[bicycle [3.2.1]octane-2,1'-cyclopropan]-7-yl sulfate;

(1R,4S)-4-(5-(2-guanidyl-1-hydroxyethyl)isoxazol-3-yl)-6-oxo-5,7-diazaspiro[bicycle [3.2.1]octane-2,1'-cyclopropan]-7-yl sulfate;

(1R,4S)-4-(5-((S)-2-guanidyl-1-hydroxyethyl)isoxazol-3-yl)-6-oxo-5,7-diazaspiro[bicycle [3.2.1]octane-2,1'-cyclopropan]-7-yl sulfate;

(1R,4S)-4-(5-((R)-2-guanidyl-1-hydroxyethyl)isoxazol-3-yl)-6-oxo-5,7-diazaspiro[bicycle [3.2.1]octane-2,1'-cyclopropan]-7-yl sulfate;

(1R,4S)-4-(5-(2-aminoethyl)isoxazol-3-yl)-6-oxo-5,7-diazaspiro[bicyclo[3.2.1]octane-2,1'-cyclopropan]-7-yl sulfate;

(1R,4S)-4-(5-(2-(methylamino)ethyl)isoxazol-3-yl)-6-oxo-5,7-diazaspiro[bicyclo[3.2.1]octane-2,1'-cyclopropan]-7-yl sulfate;

(1R,4S)-6-oxo-4-(5-(piperidin-4-yl)isoxazol-3-yl)-5,7-diazaspiro[bicyclo[3.2.1]octane-2,1'-cyclopropan]-7-yl sulfate;

(1R,4S)-6-oxo-4-(5-(piperidin-3-yl)isoxazol-3-yl)-5,7-diazaspiro[bicyclo[3.2.1]octane-2,1'-cyclopropan]-7-yl sulfate;

(1R,4S)-6-oxo-4-(5-(pyrrolidin-3-yl)isoxazol-3-yl)-5,7-diazaspiro[bicyclo[3.2.1]octane-2,1'-cyclopropan]-7-yl sulfate;

(1R,4S)-6-oxo-4-(5-(2-(piperidin-4-ylamino)ethyl)isoxazol-3-yl)-5,7-diazaspiro[bicycle [3.2.1]octane-2,1'-cyclopropan]-7-yl sulfate;

(1R,4S)-4-(5-(2-((1-amidinopiperidin-4-yl)amino)ethyl)isoxazol-3-yl)-6-oxo-5,7-diazaspiro[bicyclo[3.2.1]octane-2,1'-cyclopropan]-7-yl sulfate;

(1R,4S)-4-(5-((1S,3R)-3-aminocyclobutyl)-1,3,4-oxadiazol-2-yl)-6-oxo-5,7-diazaspiro [bicyclo[3.2.1]octane-2,1'-cyclopropan]-7-yl sulfate;

(1R,4S)-4-(5-((1R,3S)-3-aminocyclobutyl)-1,3,4-oxadiazol-2-yl)-6-oxo-5,7-diazaspiro [bicyclo[3.2.1]octane-2,1'-cyclopropan]-7-yl sulfate;

(1R,4S)-4-(5-((1R,3S)-3-aminocyclopentyl)-1,3,4-oxadiazol-2-yl)-6-oxo-5,7-diazaspiro [bicyclo[3.2.1]octane-2,1'-cyclopropan]-7-yl sulfate;

(1R,4S)-4-(5-((1R,3R)-3-aminocyclopentyl)-1,3,4-oxadiazol-2-yl)-6-oxo-5,7-diazaspiro [bicyclo[3.2.1]octane-2,1'-cyclopropan]-7-yl sulfate;

(1R,4S)-4-(5-(((1R,3R)-3-aminocyclobutyl)methyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(((1S,3S)-3-aminocyclobutyl)methyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-((1-aminocyclopropyl)methyl)-1,3,4-oxadiazol-2-yl)-6-oxo-5,7-diazaspiro [bicyclo[3.2.1]octane-2,1'-cyclopropan]-7-yl sulfate;

(1R,4S)-4-(5-((1-(methylamino)cyclopropyl)methyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(azetidin-3-ylmethyl)-1,3,4-oxadiazol-2-yl)-6-oxo-5,7-diazaspiro[bicycle [3.2.1]octane-2,1'-cyclopropan]-7-yl sulfate;

(1R,4S)-4-(5-(2-(methylamino)ethyl)-1,3,4-oxadiazol-2-yl)-6-oxo-5,7-diazaspiro[bicycle [3.2.1]octane-2,1'-cyclopropan]-7-yl sulfate;

(1R,4S)-4-(5-((azetidin-3-ylamino)methyl)isoxazol-3-yl)-6-oxo-5,7-diazaspiro[bicycle [3.2.1]octane-2,1'-cyclopropan]-7-yl sulfate;

(1R,4S)-4-(5-(azetidin-3-ylmethyl)isoxazol-3-yl)-6-oxo-5,7-diazaspiro[bicyclo[3.2.1]octane-2,1'-cyclopropan]-7-yl sulfate;

(1R,4S)-4-(5-((azetidin-3-yloxy)methyl)isoxazol-3-yl)-6-oxo-5,7-diazaspiro[bicyclo[3.2.1]octane-2,1'-cyclopropan]-7-yl sulfate;

(1R,4S)-4-(5-(((1-amidinoazetidin-3-yl)amino)methyl)isoxazol-3-yl)-6-oxo-5,7-diazaspiro [bicyclo[3.2.1]octane-2,1'-cyclopropan]-7-yl sulfate;

(1R,4S)-4-(5-(3-aminocyclobutyl)isoxazol-3-yl)-6-oxo-5,7-diazaspiro[bicyclo[3.2.1]octane-2,1'-cyclopropan]-7-yl sulfate;

(1R,4S)-4-(5-((1S,3S)-3-aminocyclobutyl)isoxazol-3-yl)-6-oxo-5,7-diazaspiro[bicycle [3.2.1]octane-2,1'-cyclopropan]-7-yl sulfate;

(1R,4S)-4-(5-((1R,3R)-3-aminocyclobutyl)isoxazol-3-yl)-6-oxo-5,7-diazaspiro[bicycle [3.2.1]octane-2,1'-cyclopropan]-7-yl sulfate;

(1R,4S)-4-(5-(2-((2-guanidinoethyl)amino)ethyl)isoxazol-3-yl)-6-oxo-5,7-diazaspiro [bicyclo[3.2.1]octane-2,1'-cyclopropan]-7-yl sulfate;

(1R,4S)-6-oxo-4-(piperidin-4-ylaminoformyl)-5,7-diazaspiro[bicyclo[3.2.1]octane-2,1'-cyclopropan]-7-yl sulfate;

(1R,4S)-6-oxo-4-(pyrrolidin-3-ylaminoformyl)-5,7-diazaspiro[bicyclo[3.2.1]octane-2,1'-cyclopropan]-7-yl sulfate;

(1R,4S)-4-(azetidin-3-ylaminoformyl)-6-oxo-5,7-diazaspiro[bicyclo[3.2.1]octane-2,1'-cyclopropan]-7-yl sulfate;

(1R,4S)-4-(5-((S)-1-hydroxy-2-((2-(methylamino)ethyl)amino)ethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-((S)-2-((2-aminoethyl)amino)-1-hydroxyethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-((S)-2-iminoimidazolidin-4-yl)-1,3,4-oxadiazol-2-yl)-6-oxo-5,7-diazaspiro [bicyclo[3.2.1]octane-2,1'-cyclopropan]-7-yl sulfate;

(1R,4S)-4-(5-((R)-2-iminoimidazolidin-4-yl)-1,3,4-oxadiazol-2-yl)-6-oxo-5,7-diazaspiro [bicyclo[3.2.1]octane-2,1'-cyclopropan]-7-yl sulfate;

2-(((1R,4S)-4-(5-(aminomethyl)-1,3,4-oxadiazol-2-yl)-6-oxo-5,7-diazaspiro[bicyclo[3.2.1]octane-2,1'-cyclopropan]-7-yl)oxy)acetate;

2-(((1R,4S)-4-(5-(((tert-butoxycarbonyl)amino)methyl)isoxazol-3-yl)-6-oxo-5,7-diazaspiro[bicyclo[3.2.1]octane-2,1'-cyclopropan]-7-yl)oxy)acetate;

2-(((1R,4S)-4-(5-(aminomethyl)-1,3,4-oxadiazol-2-yl)-6-oxo-5,7-diazaspiro[bicyclo[3.2.1]octane-2,1'-cyclopropan]-7-yl)oxy)-2,2-difluoroacetate;

2-(((1R,4S)-4-(5-(((tert-butoxycarbonyl)amino)methyl)isoxazol-3-yl)-6-oxo-5,7-diazaspiro[bicyclo[3.2.1]octane-2,1'-cyclopropan]-7-yl)oxy)-2,2-difluoroacetate;

(1R,4S)-4-(5-((1S,3R)-3-guanidinocyclobutyl)isoxazol-3-yl)-6-oxo-5,7-diazaspiro[bicycle [3.2.1]octane-2,1'-cyclopropan]-7-yl sulfate;

(1R,4S)-4-(5-(1-hydroxy-2-((2-(methylamino)ethyl)amino)ethyl)isoxazol-3-yl)-6-oxo-5,7-diazaspiro[bicyclo[3.2.1]octane-2,1'-cyclopropan]-7-yl sulfate;

(1R,4S)-4-(5-((S)-1-hydroxy-2-((2-(methylamino)ethyl)amino)ethyl)isoxazol-3-yl)-6-oxo-5,7-diazaspiro[bicyclo[3.2.1]octane-2,1'-cyclopropan]-7-yl sulfate;

(1R,4S)-4-(5-((R)-1-hydroxy-2-((2-(methylamino)ethyl)amino)ethyl)isoxazol-3-yl)-6-oxo-5,7-diazaspiro[bicyclo[3.2.1]octane-2,1'-cyclopropan]-7-yl sulfate;

(1R,4S)-4-(5-(2-((2-aminoethyl)amino)-1-hydroxyethyl)isoxazol-3-yl)-6-oxo-5,7-diazaspiro[bicyclo[3.2.1]octane-2,1'-cyclopropan]-7-yl sulfate;

(1R,4S)-4-(5-((S)-2-((2-aminoethyl)amino)-1-hydroxyethyl)isoxazol-3-yl)-6-oxo-5,7-diazaspiro[bicyclo[3.2.1]octane-2,1'-cyclopropan]-7-yl sulfate;

(1R,4S)-4-(5-((R)-2-((2-aminoethyl)amino)-1-hydroxyethyl)isoxazol-3-yl)-6-oxo-5,7-diazaspiro[bicyclo[3.2.1]octane-2,1'-cyclopropan]-7-yl sulfate;

(1R,4S)-4-(5-(2-((2-guanidinoethyl)amino)-1-hydroxyethyl)isoxazol-3-yl)-6-oxo-5,7-diazaspiro[bicyclo[3.2.1]octane-2,1'-cyclopropan]-7-yl sulfate;

(1R,4S)-4-(5-((S)-2-((2-guanidinoethyl)amino)-1-hydroxyethyl)isoxazol-3-yl)-6-oxo-5,7-diazaspiro[bicyclo[3.2.1]octane-2,1'-cyclopropan]-7-yl sulfate;

(1R,4S)-4-(5-((R)-2-((2-guanidinoethyl)amino)-1-hydroxyethyl)isoxazol-3-yl)-6-oxo-5,7-diazaspiro[bicyclo[3.2.1]octane-2,1'-cyclopropan]-7-yl sulfate;

(1R,4S)-4-(5-((1-hydroxy-2-((2-methylamino)ethyl)amino)ethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-((R)-1-hydroxy-2-((2-(methylamino)ethyl)amino)ethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(2-((2-aminoethyl)amino)-1-hydroxyethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-((R)-2-((2-aminoethyl)amino)-1-hydroxyethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(2-((2-guanidinoethyl)amino)-1-hydroxyethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-((S)-2-((2-guanidinoethyl)amino)-1-hydroxyethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-((R)-2-((2-guanidinoethyl)amino)-1-hydroxyethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(2-(azetidin-3-ylamino)-1-hydroxyethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(1-hydroxy-2-(methylamino)ethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(1-hydroxy-2-(pyrrolidin-3-ylamino)ethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(2-(dimethylamino)-1-hydroxyethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(hydroxy(pyrrolidin-2-yl)methyl)-1,3,4-oxadiazol-2-yl)-6-oxo-5,7-diazaspiro [bicyclo[3.2.1]octane-2,1'-cyclopropan]-7-yl sulfate;

2-hydroxy-N,N,N-trimethyl-2-(5-((1R,4S)-6-oxo-7-(sulfooxy)-5,7-diazaspiro[bicycle [3.2.1]octane-2,1'-cyclopropane]-4-yl)-1,3,4-oxadiazol-2-yl)ethan-1-ammonium;

(1R,4S)-4-(5-(1-hydroxy-2-(piperidin-4-ylamino)ethyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-(4-hydroxypiperidin-4-yl)isoxazol-3-yl)-6-oxo-5,7-diazaspiro[bicyclo[3.2.1]octane-2,1'-cyclopropan]-7-yl sulfate;

(1R,4S)-4-(5-(1-amidinopiperidin-4-yl)isoxazol-3-yl)-6-oxo-5,7-diazaspiro[bicyclo[3.2.1]octane-2,1'-cyclopropan]-7-yl sulfate;

(1R,4S)-6-oxo-4-(5-(piperazin-1-yl)isoxazol-3-yl)-5,7-diazaspiro[bicyclo[3.2.1]octane-2,1'-cyclopropan]-7-yl sulfate;

(1R,4S)-6-oxo-4-(5-(2-oxopiperazine-1-yl)isoxazol-3-yl)-5,7-diazaspiro[bicyclo[3.2.1]octane-2,1'-cyclopropan]-7-yl sulfate;

(1R,4S)-4-(5-(L-prolyl)-1,3,4-oxadiazol-2-yl)-6-oxo-5,7-diazaspiro[bicyclo[3.2.1]octane-2,1'-cyclopropan]-7-yl sulfate;

(1R,4S)-4-(5-((S)-2-((2-(dimethylamino)ethyl)amino)-1-hydroxyethyl)-1,3,4-oxadiazol-2-yl)-6-oxo-5,7-diazaspiro[bicyclo[3.2.1]octane-2,1'-cyclopropan]-7-yl sulfate;

2-(((2S)-2-hydroxy-2-(5-((1R,4S)-6-oxo-7-(sulfooxy)-5,7-diazaspiro[bicyclo[3.2.1]octane-2,1'-cyclopropane]-4-yl)-1,3,4-oxadiazol-2-yl)ethyl)amino)-N,N,N-trimethylethan-1-ammonium;

(1R,4S)-6-oxo-4-(5-(2-oxoimidazolidine-4-yl)-1,3,4-oxadiazol-2-yl)-5,7-diazaspiro[bicyclo[3.2.1]octane-2,1'-cyclopropan]-7-yl sulfate;

(1R,4S)-6-oxo-4-(5-(2-oxooxazolidine-5-yl)-1,3,4-oxadiazol-2-yl)-5,7-diazaspiro[bicycle [3.2.1]octane-2,1'-cyclopropan]-7-yl sulfate;

(1R,4S)-6-oxo-4-(5-(2-oxooxazolidine-4-yl)-1,3,4-oxadi-azol-2-yl)-5,7-diazaspiro[bicycle [3.2.1]octane-2,1'-cyclopropan]-7-yl sulfate;
(1R,4S)-4-(5-(2-imino-1-((methylamino)methyl)imida-zolidin-4-yl)-1,3,4-oxadiazol-2-yl)-6-oxo-5,7-diaz-aspiro[bicyclo[3.2.1]octane-2,1'-cyclopropan]-7-yl sulfate;
(1R,4S)-4-(5-(1-(((dimethylamino)methyl)-2-iminoimida-zolidin-4-yl)-1,3,4-oxadiazol-2-yl)-6-oxo-5,7-diaz-aspiro[bicyclo[3.2.1]octane-2,1'-cyclopropan]-7-yl sulfate;
1-(2-imino-4-(5-((1R,4S)-6-oxo-7-(sulfooxy)-5,7-diaz-aspiro[bicyclo[3.2.1]octane-2,1'-cyclopropane]-4-yl)-1,3,4-oxadiazol-2-yl)imidazolidin-1-yl)-N,N,N-trim-ethylmethylammonium;
(1R,4S)-4-(5-(2-imino-1-((methylamino)methyl)-5-oxo-imidazolidin-4-yl)-1,3,4-oxadiazol-2-yl)-6-oxo-5,7-di-azaspiro[bicyclo[3.2.1]octane-2,1'-cyclopropane]-7-yl sulfate;
(1R,4S)-4-(5-(5-hydroxy-2-imino-1-((methylamino) methyl)imidazolidin-4-yl)-1,3,4-oxadiazol-2-yl)-6-oxo-5,7-diazaspiro[bicyclo[3.2.1]octane-2,1'-cyclo-propane]-7-yl sulfate;
(1R,4S)-4-(5-(3-((methylamino)methyl)-2-oxooxazoli-dine-4-yl)-1,3,4-oxadiazol-2-yl)-6-oxo-5,7-diazaspiro [bicyclo[3.2.1]octane-2,1'-cyclopropane]-7-yl sulfate;
(1R,4S)-4-(5-(1-(aminomethyl)-2-iminoimidazolidin-4-yl)-1,3,4-oxadiazol-2-yl)-6-oxo-5,7-diazaspiro[bicyclo [3.2.1]octane-2,1'-cyclopropane]-7-yl sulfate;
(1R,4S)-4-(5-(5-amino-2-iminoimidazolidin-4-yl)-1,3,4-oxadiazol-2-yl)-6-oxo-5,7-diazaspiro[bicyclo[3.2.1] octane-2,1'-cyclopropane]-7-yl sulfate;
(1R,4S)-4-(5-(2-imino-5-(methylamino)imidazolidin-4-yl)-1,3,4-oxadiazol-2-yl)-6-oxo-5,7-diazaspiro[bicyclo [3.2.1]octane-2,1'-cyclopropane]-7-yl sulfate;
(1R,4S)-4-(5-(5-(dimethylamino)-2-iminoimidazolidin-4-yl)-1,3,4-oxadiazol-2-yl)-6-oxo-5,7-diazaspiro[bicy-clo[3.2.1]octane-2,1'-cyclopropan]-7-yl sulfate;
(1R,4S)-4-(5-((R)-2-amino-1-hydroxyethyl)-1,3,4-oxadi-azol-2-yl)-6-oxo-5,7-diazaspiro [bicyclo[3.2.1]octane-2,1'-cyclopropane]-7-yl sulfate;
(1R,4S)-4-(5-((S)-2-amino-1-hydroxyethyl)-1,3,4-oxadi-azol-2-yl)-6-oxo-5,7-diazaspiro [bicyclo[3.2.1]octane-2,1'-cyclopropane]-7-yl sulfate;
(1R,4S)-4-(5-((S)-1-hydroxy-2-(methylamino)ethyl)-1,3,4-oxadiazol-2-yl)-6-oxo-5,7-diazaspiro[bicyclo[3.2.1] octane-2,1'-cyclopropane]-7-yl sulfate;
(1R,4S)-4-(5-((S)-2-(dimethylamino)-1-hydroxyethyl)-1,3,4-oxadiazol-2-yl)-6-oxo-5,7-diazaspiro[bicyclo [3.2.1]octane-2,1'-cyclopropane]-7-yl sulfate;
2-(((1R,4S)-4-(5-(aminomethyl)-1,3,4-oxadiazol-2-yl)-6-oxo-5,7-diazaspiro[bicyclo[3.2.1]octane-2,1'-cyclo-propan]-7-yl)oxy)acetate;
2-(((1R,4S)-4-(5-(((tert-butoxycarbonyl)amino)methyl) isoxazol-3-yl)-6-oxo-5,7-diazaspiro[bicyclo[3.2.1]oc-tane-2,1'-cyclopropan]-7-yl)oxy)acetate;
2-(((1R,4S)-4-(5-(aminomethyl)-1,3,4-oxadiazol-2-yl)-6-oxo-5,7-diazaspiro[bicyclo[3.2.1]octane-2,1'-cyclo-propan]-7-yl)oxy)-2,2-difluoroacetate;
2-(((1R,4S)-4-(5-(((tert-butoxycarbonyl)amino)methyl) isoxazol-3-yl)-6-oxo-5,7-diazaspiro[bicyclo[3.2.1]oc-tane-2,1'-cyclopropan]-7-yl)oxy)-2,2-difluoroacetate.

10. A method of preparation for the compound of formula (I) of claim 1, wherein $W_1$ in the compound of formula (I) is selected from a 1,3,4-oxadiazole ring; the method comprising:

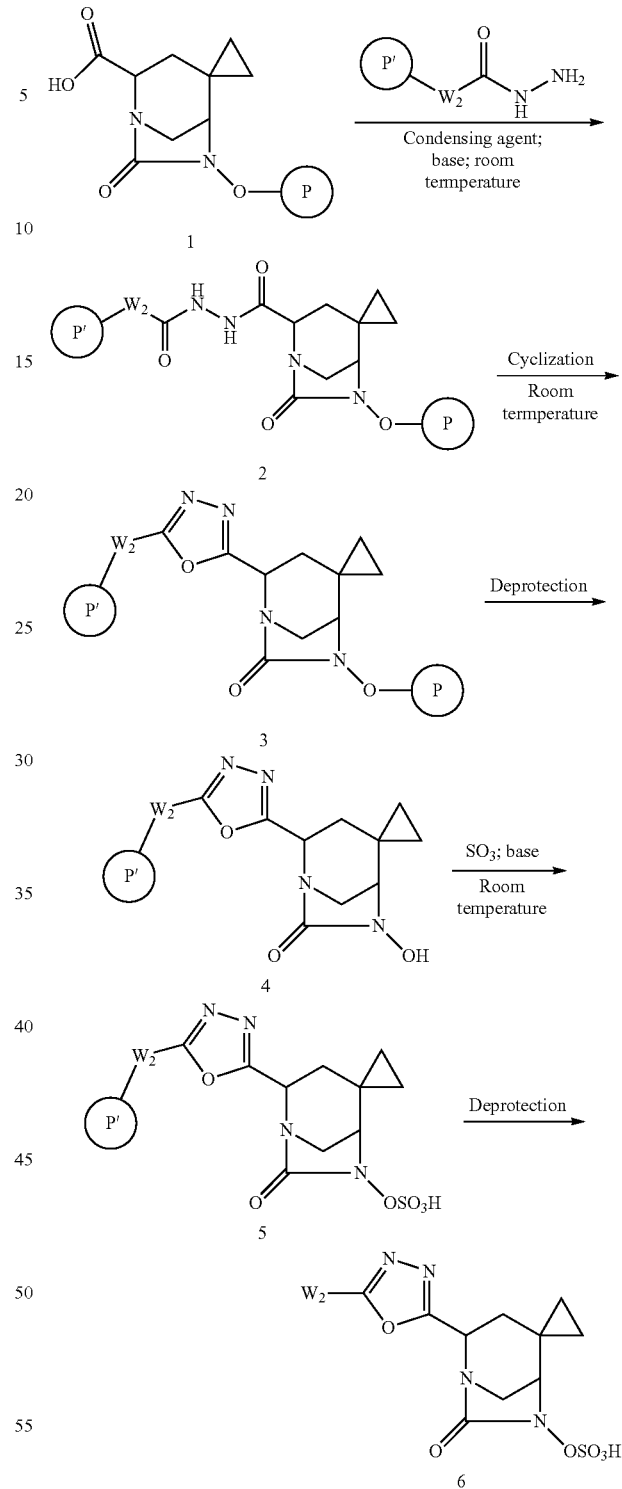

step 1: the intermediate 1 and hydrazide are subjected to condensation under a basic condition to give the intermediate 2;

Step 2: the intermediate 2 is subjected to cyclization to give the intermediate 3;

step 3: the protecting group P in the intermediate 3 is selectively removed to give the intermediate 4;

step 4: the intermediate 4 reacts with SO$_3$ under a basic condition to give the intermediate 5;

step 5: the protecting group P' in the intermediate 5 is removed to give the product 6;

wherein, P is a hydroxyl protecting group, P' is a hydroxyl or amine protecting group, and W$_2$ is defined in formula (I).

11. A pharmaceutical composition comprising the compound according to claim 1, and a pharmaceutically acceptable excipient.

12. The pharmaceutical composition according to claim 11, further comprising one or more β-lactam antibiotics.

13. The pharmaceutical composition according to claim 12, wherein the β-lactam antibiotic is selected from a penicillin antibiotic, a cephalosporin antibiotic, a monobactam antibiotic, a carbapenem antibiotic, and a penemase inhibitor.

14. A method of treating a disease caused by a bacterial infection in a subject, comprising administration of a therapeutically effective amount of the compound according to claim 1.

15. The method according to claim 14, wherein the method further comprises administration of a β-lactam antibiotic.

16. The method according to claim 14, wherein the bacterium is selected from one or more of *Citrobacter* spp., *Citrobacter freundii, Enterobacter cloacae, Klebsiella pneumoniae, Escherichia coli, Proteus vulgaris, Salmonella* spp., *Serratia marcescens, Shigella* spp., *Pseudomonas aeruginosa, Moraxella mucositis, Neisseria gonorrhoeae, Neisseria meningitidis, Acinetobacter* spp., *Burkholderia* spp., *Campylobacter* spp., *Helicobacter pylori, Vibrio cholerae, Klebsiella pneumoniae, Haemophilus influenzae, Mycobacterium avium* complex, *Mycobacterium abscessus, Mycobacterium kansasii, Mycobacterium ulcerosa, Chlamydophila pneumoniae, Chlamydia trachomatis*, β-hemolytic *Streptococcus, Acinetobacter baumannii, Pseudomonas pyocyaneum, Pseudomonas aeruginosa, Bacteroides fragilis, Bacillus cereus,* and *Stenotrophomonas maltophilia*.

17. The method according to claim 14, wherein the disease is selected from one or more of respiratory tract infection, urinary tract infection, central nervous system infection, ear infection, *pleuropneumoniae* and bronchial infection, intra-abdominal infection, cardiovascular infection, skin or soft tissue infections, bone and joint infections, genital infection, eye infection, pharyngeal infection, and oral infection.

18. The method according to claim 17, wherein the disease is selected from one or more of upper respiratory tract infection, lower respiratory tract infection, tracheitis, bronchitis, pneumonia, pulmonary tuberculosis, pharyngitis, complicated urinary tract infection, non-complicated urinary tract infections, cystitis, pyelonephritis, encephalitis, meningitis, brain abscess, otitis externa, otitis media, blood infection, endocarditis, myocarditis, pericarditis, arthritis, osteomyelitis, genital ulceration, vaginitis, cervicitis, conjunctivitis, keratitis, endophthalmitis, pharyngitis, and gingivitis.

19. The method according to claim 18, wherein the blood infection is sepsis or bacteremia.

* * * * *